US008628777B2

(12) United States Patent
Goddard et al.

(10) Patent No.: US 8,628,777 B2
(45) Date of Patent: Jan. 14, 2014

(54) ANTIBODIES BINDING IL-1 RELATED POLYPEPTIDES

(75) Inventors: Audrey Goddard, San Francisco, CA (US); Guohua James Pan, Etobicoke (CA)

(73) Assignee: Genentech, Inc., South San Francisco, CA (US)

( * ) Notice: Subject to any disclaimer, the term of this patent is extended or adjusted under 35 U.S.C. 154(b) by 639 days.

(21) Appl. No.: 12/495,633

(22) Filed: Jun. 30, 2009

(65) Prior Publication Data

US 2009/0304701 A1  Dec. 10, 2009

Related U.S. Application Data

(60) Division of application No. 11/548,249, filed on Oct. 10, 2006, now abandoned, which is a continuation of application No. 09/869,566, filed as application No. PCT/US99/30720 on Dec. 22, 1999, now abandoned.

(60) Provisional application No. 60/113,430, filed on Dec. 23, 1998, provisional application No. 60/116,843, filed on Jan. 22, 1999, provisional application No. 60/129,122, filed on Apr. 13, 1999.

(51) Int. Cl.
*A61K 39/395* (2006.01)

(52) U.S. Cl.
USPC ............... 424/145.1; 530/389.2; 530/388.1; 530/351

(58) Field of Classification Search
None
See application file for complete search history.

(56) References Cited

U.S. PATENT DOCUMENTS

| 6,294,655 B1 | 9/2001 | Ford et al. |
| 6,680,380 B1 | 1/2004 | Timans |
| 7,033,783 B2 | 4/2006 | Sims et al. |

FOREIGN PATENT DOCUMENTS

| EP | 855404 | 7/1998 |
| WO | WO 95/10298 | 4/1995 |
| WO | WO 98/47921 A1 | 10/1998 |
| WO | WO 99/06426 | 2/1999 |
| WO | WO 99/35268 | 7/1999 |
| WO | WO 99/51744 | 10/1999 |
| WO | WO 00/08045 | 2/2000 |
| WO | WO 00/17363 | 3/2000 |
| WO | WO 00/20595 | 4/2000 |
| WO | WO 00/24899 | 5/2000 |
| WO | WO 00/36108 A | 6/2000 |
| WO | WO 00/56889 A2 | 9/2000 |
| WO | 01/40247 A1 | 6/2001 |
| WO | 01/42304 A1 | 6/2001 |

OTHER PUBLICATIONS

Altschul et al., "Gapped BLAST and PST-BLAST: A New Generation of Protein Database Search Programs" *Nucleic Acids Research.* 25(17):3389-3402 (1997).
Bazan et al., "A Newly Defined Interleukin-1?" *Nature.* 379:591 (Feb. 15, 1996).
Dinarello et al., "Induction of Interleukin-1 and Interleukin-1 Receptor Antagonist" *Seminars in Oncology* (Suppl. 9, XP000864695) 24(3):S9-81-S9-93 (Jun. 1997).
Dinarello et al., "Overview of Interleukin-18: More Than an Interferon-γ Inducing Factor." *J. Leukocyte Biol.* 63:658-664 (Jun. 1998).
Dinarello, C.A., "Biologic Basis for Interleukin-1 in Disease." *Blood.* 87(6):2095-2147 (Mar. 15, 1996).
Eisenberg et al., "Interleukin-1 Receptor Antagonist is a Member of the Interleukin-1 Gene Family: Evolution of a Cytokine Control Mechanism." *Proc. Natl. Acad. Sci. (USA)* 88:5232-5236 (Jun. 1991).
Eisenberg et al., "Primary Structure and Functional Expression From Complementary DNA of a Human Interleukin-1 Receptor Antagonist." *Nature.* 343:341-346 (Jan. 1990).
Haskill et al., "cDNA Cloning of an Intracellular Form of the Human Interleukin 1 Receptor Antagonist Associated With Epithelium." *Proc. Natl. Acad. Sci. (USA)* 88: 3681-3685 (May 1991).
Matsushime et al., "Cloning and Expression of Murine Interleukin-1 Receptor Antagonist in Macrophages Stimulated by Colony-Stimulating Factor 1." *Blood.* 78(3):616-623 (Aug. 1991).
Pan et al., "The Receptor for the Cytotoxic Ligand TRAIL" *Science* 276:111-113 (Apr. 4, 1997).
Shuck et al., "Cloning, Heterologous Expression and Characterization of Murine Interleukin-1 Receptor Antagonist Protein." *European Journal of Immunology* 21:2775-2780 (1991).
Zahedi et al., "Mouse IL-1 Receptor Antagonist Protein: Molecular Characterization, Gene Mapping, and Expression of mRNA in Vitro and in Vivo." *J. Immunol.* 146(12):4228-4233 (Jun. 1991).
Zahedi et al., "The Mouse Interleukin 1 Receptor Antagonist Protein: Gene Structure and Regulation In Vitro." *Cytokine.* 6(1):1-9 (Jan. 1994).

*Primary Examiner* — Dong Jiang
(74) *Attorney, Agent, or Firm* — Elinor K. Shin

(57) ABSTRACT

The present invention is directed to novel polypeptides having homology to the IL-1-like family of proteins and to nucleic acid molecules encoding those polypeptides. Also provided herein are vectors and host cells comprising those nucleic acid sequences, chimeric polypeptide molecules comprising the polypeptides of the present invention fused to heterologous polypeptide sequences, antibodies which bind to the polypeptides of the present invention, and methods for producing the polypeptides of the present invention.

4 Claims, 24 Drawing Sheets

FIG. 1A

```
701  TGAAGCTGGC TGCCCAAAAG GAATCAGCAC GCCGGGCCCT CATCTTTTAT AGGGCTCAGG TGGGCTCCTG GAACATGCTG GAGTCGGGGG CTCACCCCGG
     ACTTCGACCG ACGGGTTTTC CTTAGTCGTG CGGCCCGGGA GTAGAAAATA TCCCGAGTCC ACCGAGGAC CTTGTACGAC CTCAGCCGCC GAGTGGGGCC
 91   K  L  A    A  Q  K    E  S  A  R    R  P  F    I  F  Y    R  A  Q  V    G  S  W    N  M  L    E  S  A  A    H  P  G

801  ATGGTTCATC TGCACCTCCT GCAATTGTAA TGAGCCTGTT GGGGTGACAG ATAAATTTGA GAACAGGAAA CACATTGAAT TTTCATTTCA ACCAGTTTGC
     TACCAAGTAG ACGTGGAGGA CGTTAACATT ACTCGGACAA CCCCACTGTC TATTTAAACT CTTGTCCTTT GTGTAACTTA AAAGTAAAGT TGGTCAAACG
124   W  F  I    C  T  S    C  N  L  *    *  P  V    G  V  T  D    K  F  E    N  R  K    H  I  E  F    S  F  Q    P  V  C

901  AAAGCTGAAA TGAGCCCCAG TGAGGTCAGC GATTAGAAAA CTGCCCCATT GAACGCCTTC CTCGCTAATT TGAACTAATT GTATAAAAAC ACCAAACCTG
     TTTCGACTTT ACTCGGGGTC ACTCCAGTCG CTAATCTTTT GACGGGGTAA CTTGCGGAAG GAGCGATTAA ACTTGATTAA CATATTTTTG TGGTTTGGAC
157   K  A  E  M    S  P  S    E  V  S    D  *

^85066.AH1283.r
               ^85066.AH1285.Not.r, 5'Tag: TTTCCCTTTGCGGCCGCTTA

1001 CTCACT
     GAGTGA
```

FIG. 1B

```
  1 TAATTCACCA TGTCTGCACT TCTGATCCTA GCTCTTGTTG GAGCTGCAGT TGCTGACTAC AAAGACGATG ACGACAAGCT TGCGGCCGCG AATTCAGCTC
    ATTAAGTGGT ACAGACGTGA AGACTAGGAT CGAGAACAAC CTCGACGTCA ACGACTGATG TTTCTGCTAC TGCTGTTCGA ACGCCGGCGC TTAAGTCGAG
  1              M  S  A  L  L  I  L  A  L  V  G  A  A  V  A  D  Y  K  D  D  D  D  K  L  A  A  A  N  S  A  L
                 ^orf                                             ^flag                                  insert st 101 TTTGCAGAGG TCCAAAGGTG AAGAACTTAA ACCCGAAGAA ATTCAGCATT CATGACCAGG ATCACAAAGT ACTGGTCCTG GACTCTGGGA ATCTCATAGC
    AAACGTCTCC AGGTTTCCAC TTCTTGAATT TGGGCTTCTT TAAGTCGTAA GTACTGGTCC TAGTGTTTCA TGACCAGGAC CTGAGACCCT TAGAGTATCG
 32 C  R  G    P  K  V    K  N  L  N    P  K  K    F  S  I    H  D  Q  D    H  K  V    L  V  L    D  S  G  N    L  I  A 201 AGTTCCAGAT AAAAACTACA TTTTTGATGT GCATTAGCCT CATCCTTGAG CTCAGCCTCT GCGGAGAAAG GAAGTCCGAT TCTCCTGGGG
    TCAAGGTCTA TTTTTGATGT AAAAACTACA CGTAATCGGA GTAGGAACTC GAGTCGGAGA CGCCTCTTTC CTTCAGGCTA AGAGGACCCC
 65 V  P  D    K  N  Y  I    R  P  E    I  F  F    A  L  A  S    S  L  S    S  A  S    A  E  K  G    S  P  I  L  L  G 301 GTCTCTAAAG GGGAGTTTTG TCTCTACTGT GACAAGGATA AAGGACAAAG TCATCCATCC CTTCAGTGGA AGAAGGAGAA ACTGATGAAG CTGGCTGCCC
    CAGAGATTTC CCCTCAAAAC AGAGATGACA CTGTTCCTAT TTCCTGTTTC AGTAGGTAGG GAAGTCACCT TCTTCCTCTT TGACTACTTC GACCGACGGG
 98 V  S  K  G    E  F  C    L  Y  C    D  K  D  K    G  Q  S    H  P  S    L  Q  L  K    K  E  K    L  M  K    L  A  A  Q 401 AAAAGGAATC AGCACGCCGG TCGTGCGGCC CCCTTCATCT TTTATAGGGC TCAGGTGGGC TCCTGGAACA TGCTGGAGTC GGCGGCTCAC CCCGGATGGT TCATCTGCAC
    TTTTCCTTAG TCGTGCGGCC AGCACGCCGG GGGAAGTAGA AAATATCCCG AGTCCACCCG AGGACCTTGT ACGACCTCAG CCGCCGAGTG GGGCCTACCA AGTAGACGTG
132 K  E  S    A  R  R    P  F  I  F    Y  R  A    Q  V  G    S  W  N  M    L  E  S    A  A  H    P  G  W  F    I  C  T 501 CTCCTGCAAT TGTAATGAGC CTGTTGGGGT GACAGGGAAA GGGAAACACAT TTTCAACCAG TTTCAAAAGC TGAAATGAGC
    GAGGACGTTA ACATTACTCG GACAACCCCA CTGTCCCTTT CCCTTTGTGTA AAAGTTGGTC AAACGTTTCG ACTTTACTCG
165 S  C  N    C  N  E  P    V  G  V    T  D  K    F  E  N  R    K  H  I    E  F  S    F  Q  P  V    C  K  A    E  M  S 601 CCCAGTGAGG TCAGCGGATTA GGGTACCAGT CGACTCTAGA GGATCCCGGG
    GGGTCACTCC AGTCGCCTAAT CCCATGGTCA GCTGAGATCT CCTAGGGCCC
198 P  S  E  V    S  D  Q                                    ^inserts ends
```

FIG. 2

```
  1 GGCACGAGGC AAGCCTTCCA GGTTATCGTG ACGGCACCTTG AAAGTCTGAG AGCTACTGCC CTACAGAAAG TTACTAGTGC CCTAAAGCTG GCGCTGGCAC
    CCGTGCTCCG TTCGGAAGGT CCAATAGCAC TGCCGTGGAAC TTTCAGACTC TCGATGACGG GATGTCTTTC AATGATCACG GGATTTCGAC CGCGACCGTG

101 TGATGTTACT GCTGCTGTTG GAGTACAAACT TCCCTATAGA AAACAACTGC CAGCACCTTA AGACCACTCA CCACCTTCAGA GTGAAGAACT TAAACCCGAA
    ACTACAATGA CGACGACAAC CTCATGTTGA AGGGATATCT TTTGTTGACG GTCGTGGAAT TCTGGTGAGT GTGGAAGTCT CACTTCTTGA ATTTGGGCTT
  1 M  L  L     L  L  L    E  Y  N  F    P  I  E    N  N  C    Q  H  L  K    T  T  H    T  F  R    V  K  N  L    N  P  K
    ^Met

201 GAAATTCAGC ATTCATGACC AGGATCACAA AGTACTGGTC CTGGACTCTG GGAATCTCAT AGCAGTTCCA GATAAAAACT ACATACGCCC AGAGATCTTC
    CTTTAAGTCG TAAGTACTGG TCCTAGTGTT TCATGACCAG GACCTGAGAC CCTTAGAGTA TCGTCAAGGT CTATTTTTGA TGTATGCGGG TCTCTAGAAG
 34 K  F  S    I  H  D  Q    D  H  K    V  L  V    L  D  S  G    N  L  I    A  V  P    D  K  N  Y    I  R  P    E  I  F

301 TTTGCATTAG CCTCATCCTT GAGCTCAGCC TCTGCGGAGA AAGGAAGTCC GATTCTCCTG AAGGGGAGTT TTGTCTCTAC TGTGACAAGG
    AAACGTAAATC GGAGTAGGAA CTCGAGTCGG AGACGCCTCT TTCCTTCAGG CTAAGAGGAC TTCCCCTCAA AACAGAGATG ACACTGTTCC
 67 F  A  L  A    S  S  L    S  S  A    S  A  E  K    G  S  P    I  L  L    G  V  S  K    G  E  F    C  L  Y    C  D  K  D

401 ATAAAGGACA AAGTCATCCA TCCCCTTCAGC TGAAGAAGGA CCCAAAAGGA ATCAGCACGC CGGCCCTTCA TCTTTTATAG
    TATTTCCTGT TTCAGTAGGT AGGGAAGTCG ACTTCTTCCT CTTTGACTAC TTCGACCGAC AGTCGTGCG GCCGGGAAGT AGAAAATATC
101 K  G  Q    S  H  P    S  L  Q  L    K  K  E    K  L  M    K  L  A  A    Q  K  E    S  A  R    R  P  F  I    F  Y  R

501 GGCTCAGGTG GGCTCCTGGA ACATGCTGGA GTCGGCGCCA CACCCCCGAT GGTTCATCTG CACCTCCTGC AATTGTAATG AGCCTGTTGG GGTGACAGAT
    CCGAGTCCAC CCGAGGACCT TGTACGACCT CAGCCGCGGT GTGGGGGCTA CCAAGTAGAC GTGGAGGACG TTAACATTAC TCGGACAACC CCACTGTCTA
134 A  Q  V    G  S  W  N    M  L  E    S  A  A    H  P  G  W    F  I  C    T  S  C    N  C  N  E    P  V  G    V  T  D

601 AAATTTGAGA ACAGGAAACA CATTGAATTT TCATTTCAAC CAGTTTGCAA AGCTGAAATG TCGACTTTAC AGGTCAGCGA TTAGGAAACT GCCCATTGA
    TTTAAACTCT TGTCCTTTGT GTAACTTAAA AGTAAAGTTG GTCAAACGTT TCGACTTTAC AGCTGAAATG TCCAGTCGCT AATCCTTTGA CGGGGTAACT
167 K  F  E  N    R  K  H    I  E  F    S  F  Q  P    V  C  K    A  E  M    S  P  S  E    V  S  D    Q

701 ACGCCTTCCT CGCTAATTTG AACTAATTGT ATAAAAACAC CAAACCTGCT CACT
    TGCCGGAAGGA GCGATTAAAC TTGATTAACA TATTTTTGTG GTTTGGACGA GTGA
```

FIG. 3

```
  1 CCAGGCCCAA GCNTCCCCAC CATGAATTTT GTTCACACAA GTCGAAAGGT GAAGAGCTTA AACCCGAAGA AATTCAGCAT TCATGACCAG GATCACAAAG
    GGTCCGGGTT CGNAGGGGTG GTACTTAAAA CAAGTGTGTT CAGCTTTCCA CTTCTCGAAT TTGGGCTTCT TTAAGTCGTA AGTACTGGTC CTAGTGTTTC

101 TACTGGCCTG GACTCTGGGA ATCTCATAGC AGTTCCAGAT AAAAACTACA GATCTTCTTT GCATTAGCCT CATCCTTGAG CTTCAGCCTCT
    ATGACCGGAC CTGAGACCCT TAGAGTATCG TCAAGGTCTA TTTTTGATGT CTAGAAGAAA CGTAATCGGA GTAGGAACTC GAGTCGGAGA

201 GCGGAGAAAG GAAGTCCGAT TCTCCTGGGG GTCTCTAAAG GGGAGTTTTG TCTCTACTGT GACAAGGATA AAGGACAAAG TCATCCATCC CTTCAGCTGA
    CGCCCTTTTC CTTCAGGCTA AGAGGACCCC CAGAGATTTC CCCTCAAAAC AGAGATGACA CTGTTCCTAT TTCCTGTTTC AGTAGGTAGG GAAGTCGACT
  1                     I L L G   V S K G   E F C   D K D K   L Y C     ^84664.p1
                          ^orf
                          ^84664.f1

301 AGAAGGAGAA ACTGATGAAG CTGGCTGCCC AAAAGGAATC AGCACGCCGG CCCTTCATCT TTTATAGGGC TCAGGTGGGC TCCTGGAACA TGCTGGAGTC
    TCTTCCTCTT TGACTACTTC GACCGACGGG TTTTCCTTAG TCGTGCGGCC GGGAAGTAGA AAATATCCCG AGTCCACCCG AGGACCTTGT ACGACCTCAG
 29   K E K     L M K     L A A Q     K E S     A R R     P F I F     Y R A     Q V G     S W N M   L E S

401 GGGGCTCAC CCGGATGGT TCATCTGCAC AGTAGACGTG GAGGACGTTA ACATTACTCG CCCAGTGAGG TCAGCGATTA GGAAACTGCC CCATTGAACG
    CCGCCGAGTG GGCCTACCA AGTAGACGTG TCATCTGCAC CTCCTGCAAT TGTAATGAGC GGGTCACTCC AGTCGCTAAT CCTTTGACGG GGTAACTTGC
 62   A A H     P G W F     I C T     S C N     N E P     V G V     T D K     F E N R     K H I E   F S

501 TTTCAACCAG TTTGCAAAGC TGAAATGAGC CCAGTGAGG TCAGCGATTA GGAAACTGCC CCTTCCTCGC TAATTTGAAC TAATTGTATA
    AAAGTTGGTC AAACGTTTCG ACTTTACTCG GGTCACTCC AGTCGCTAAT CCTTTGACGG GGAAGGAGCG ATTAAACTTG ATTAACATAT
 95   F Q P V     C K A     E M S     P S E V   S D Q
                                      ^84664.r1

601 AAAAACCCCAA ACCTGCTCAC TAAAAAAAAA
    TTTTGGGGTT TGGACGAGTG ATTTTTTTTT
```

FIG. 4

```
  1 GTCGACCCAC GCGTCCGAAG CTGCTGGAGC CACGATTCAG TCCCCTGGAC TGTAGATAAA GACCCTTTCT TGCCAGGTGC TGAGACAACC ACACTATGAG
    CAGCTGGGTG CGCAGGCTTC GACGACCTCG GTGCTAAGTC AGGGGACCTG ACATCTATTT CTGGGAAAGA ACGGTCCACG ACTCTGTTGG TGTGATACTC
  1                                                                                                      M  R
                                                                                                        ^MET

^insert starts                       92929.AH1421.Asc.f, 5'Tag: AAAGGGAAAGGCGCGCC^

101 AGGCACTCCA GGAGACGCTG ATGGTGGAGG AAGGGCCGTC TATCAATCAA TCACTGTTGC TGTTATCACA CAGAGCTCT TGAGCAAGGC
    TCCGTGAGGT CCTCTGCGAC TACCACCTCC TTCCCGGCAG ATAGTTAGTT AGTGACAACG ACAATAGTGT AGTTCATAG GTCTCCGAGA ACTCGTTCCG
  3  G  T  P  G  D  A  D   G  G  G   R  A  V     Y  Q  S  I     T  V  A  V  I  T     C  K  Y  P    E  A  L  E  Q  G

201 AGAGGGGATC CCATTTATTT GGGAATCCAG AATCCAGAAA TGTGTTTGTA TTGTGAGAAG AACACTCTTC AGCCCACATT GCAGCTAAAA GAGCAGAAGA
    TCTCCCCTAG GGTAAATAAA CCCTTAGGTC TTAGGTCTTT ACACAAACAT AACACTCTTC TTGTGAGAAG TCGGGTGTAA CGTCGATTTT CTCGTCTTCT
 36  R  G  D  P   I  Y  L   G  I  Q  N  P  E  M    C  L  Y    C  E  K   V  G  E  Q    P  F  L    Q  L  K  E  Q  K  I

301 TCATGGATCT GTATGGCCAA CCCGAGCCCG TGAAACCCTT CCTTTTCTAC CGTGCCAAGA CTGGTAGGAC CTCCACCCTT GAGTCTGTGG CCTTCCCGGA
    AGTACCTAGA CATACCGGTT GGGCTCGGGC ACTTTGGGAA GGAAAAGATG GCACGGTTCT GACCATCCTG GAGGTGGGAA CTCAGACACC GGAAGGGCCT
 70   M  D  L   Y  G  Q    P  E  P  V   K  P  F    L  F  Y    R  A  K  T    G  R  T    S  T  L    E  S  V  A    F  P  D

401 CTGGTTCATT GCCTCCTCCA AGAGAGACCA GCCCATCATT CTGACTTCAG AACTTGGGAA GTCATACAAC ACTGCCTTTG AATTAAATAT TTACTGACT
    GACCAAGTAA CGGAGGAGGT TCTCTCTGGT CGGGTAGTAA GACTGAAGTC TTGAACCCTT CAGTAGTTG TGACGAAAC TTAATTATA ATGACTGA
103   W  F  I    A  S  S  K   R  D  Q    P  I  I    L  T  S   E  L  G  K    S  Y  N    T  A  F   E  L  N  I   N  D  O
                                                                                                            92929.AH1

501 ACTCAGCCTA GAGGTGGCAG CTTGGTCTTT GTCTTAAAGT TTCTGGTTCC CAATGTGTTT TCGTCTACAT TTTCTTAGTG TCAATTCAC GCTGGTGCTG
    TGAGTCGGAT CTCCACCGTC GAACCAGAAA CAGAATTTCA AAGACCAAGG GTTACACAAA AGCAGATGTA AAAGAATCAC AGTAAAAGTG CGACCACGAC
136

601 AGACAGGAGC AAGGCTGCTG TTATCATCTC ATTTATAATT GAAGAAGAAG CAATTACTTC ATAGCAACTG AAGAACAGGA TATGGCCTCA GAAGCAGGAG
    TCTGTCCTCG TTCCGACGAC AATAGTAGAG TAAAATATTA CTTCTTCTC GTTAATGAAG TATCGTTGAC TTCTTGTCCT ACACCGGAGT CTTCGTCCTC

701 AGCTGGGTGG TATAAGGCTG TCCCTCTCAAG CTGGTGCTGT GTAGGCCACA AGGCATCGC ATGAGTGACT TTAAGACTCA AAGACCAAAC ACTGAGCTTT
    TCGACCCACC ATATTCCGAC AGGAGAGTTC GACCACGACA CATCCGGTGT TCCGTAGACG TACTCACTGA AATTCTGAGT TTCTGTTTG TGACTCGAAA
```

FIG. 5A

```
 801 CTTCTAGGGG TGGGTATGAA GATGCTTCAG AGCTCATGCG CGTTACCCAC GATGGCATGA CTAGCACAGA GCTGATCTCT GTTTCTGTTT TGCTTTATTC
     GAAGATCCCC ACCCATACTT CTACGAAGTC TCGAGTACGC GCAATGGGTG CTACCGTACT GATCGTGTCT CGACTAGAGA CAAAGACAAA ACGAAATAAG
 901 CCCTCTGGGA TGATATCATC CAGTCTTTAT ATGTTGCCAA TATACCTTCAT TGTGTGTAAT AGAACCTTCT TAGCATTAAG ACCTTGTAAA CAAAATAAT
     GGAGAACCCT ACTATAGTAG GTCAGAAATA TACAACGGTT ATATGGAGTA ACACACATTA TCTTGGAAGA ATCGTAATTC TGGAACATTT GTTTTATTA
1001 TCTTGGGGTG GGTATGAAGA TGCTTCAGAG CTCATGCGCG TTACCCACGA TGGCATGACT AGCACAGAGC TGATCTCTGT TTCTGTTTTG CTTTATTCCC
     AGAACCCCAC CCATACTTCT ACGAAGTCTC GAGTACGCGC AATGGGTGCT ACCGTACTGA TCGTGTCTCG ACTAGAGACA AAGACAAAAC GAAATAAGGG
1101 TCTTGGGATG ATATCATCCA GTCTTTATAT GTTGCCAATA TACCTCATTG TGTAATAG AACCTTCTTA GCATTAAGAC CTTGTAAACA AAATAATTC
     AGAACCCTAC TATAGTAGGT CAGAAATATA CAACGGTTAT ATGGAGTAAC ACATTATC TTGGAAGAAT CGTAATTCTG GAACATTTGT TTTATTAAG
1201 TTGTGTTAAG TTAAATCATT TTTGTCCTAA TTGTAATGTG GTTAAATAAA CTTTGTGTAT TTATATAATA ATAAAGCTAA AACTGATATA
     AACACAATTC AATTTAGTAA AAACAGATT ATTAGAATT CAATTATT GAAACACATA AATATATTAT TATTTCGATT TTGACTATAT
1301 AAATAAAGAA AGAGTAAACT G
     TTTATTTCTT TCTCATTTGA C
```

FIG. 5B

```
  1 AAGCTGCTGG AGCCACGATT CAGTCCCCTG GACTGTAGAT AAAGACCCTT TCTTGCCAGG TGCTGAGACA ACCACACTAT GAGAGGCACT CCAGGAGACG
    TTCGACGACC TCGGTGCTAA GTCAGGGGAC CTGACATCTA TTTCTGGGAA AGAACGGTCC ACGACTCTGT TGGTGTGATA CTCTCCGTGA GGTCCTCTGC

101 CTGATGGTGG AGGAAGGGCC GTCTATCAAT CAATCACTGT TGCTGTTATC ACATGCAAGT ATCCAGAGGC TCTTGAGCAA GGCAGAGGGG ATCCCATTTA
    GACTACCACC TCCTTCCCGG CAGATAGTTA GTTAGTGACA ACGACAATAG TGTACGTTCA TAGGTCTCCG AGAACTCGTT CCGTCTCCCC TAGGGTAAAT

201 TTTGGGAATC CAGAATCCAG AAATGTGTTT GTATTGTGAG AAGGTTGGA
    AAACCCTTAG GTCTTAGGTC TTTACACAAA CATAACACTC TTCCAACCT
```

FIG. 6

```
  1 ATGGTCCTGA GTGGGGCGCT GTGCTTCCGA ATGAAGGACT ATGAAGGACT CGGCATTGAA GGTGCTTTAT CTGCATAATA ACCAGCTTCT AGCTGGAGGG CTGCATGCAG
    TACCAGGACT CACCCCGCGA CACGAAGGCT TACTTCCTGA TACTTCCTGA GCCGTAACTT CCACGAAATA GACGTATTAT TGGTCGAAGA TCGACCTCCC GACGTACGTC
  1  M  V  L   S  G  A    L  C  F  R   M  K  D      S   A  L  K    V  L  Y   L  H  N  N   Q  L  L   A  G  G    L  H  A  G

101 GGAAGGTCAT TAAAGGTGAA ATTTCCAGTA ATTTCCACTT CTCTAGTCGC TGGTCCCCAA TCGGTGGCTG GATGCCAGCC TGTCCCCCGT CATCCTGGGT GTCCAGGGTG GAAGCCAGTG
    CCTTCCAGTA ATTTCCACTT CTCTAGTCGC TGGTCCCCAA ACCAGGGGTT AGCCACCGAC CTACGGTCGG ACAGGGGCA GTAGGACCCA CAGGTCCCAC CTTCGGTCAC
 35  K  V  I   K  G  E    E  I  S  V    V  P  N    R  W  L   D  A  S  L    S  P  V    I  L  G    V  Q  G  G    S  Q  C

201 CCTGTCATGT GGGGTGGGGC AGGAGCCGAC TCTAACACTA GAGCCAGTGA ACATCATGGA GCTCTATCTT GGTGCCAAGG AATCCAAGAG CTTCACCTTC
    GGACAGTACA CCCCACCCCG TCCTCGGCTG AGATTGTGAT CTCGGTCACT TGTAGTACCT CGAGATAGAA CCACGGTTCC TTAGGTTCTC GAAGTGGAAG
 68  L  S  C   G  V  G    Q  E  P  T   L  T  L    E  P  V  N    I  M  E   L  Y  L    G  A  K  E   S  K  S    F  T  F

301 TACCGGCGGG ACATGGGGCT CACCTCCAGC TTCGAGTCGG CTGCCTACCC GGGCTGGTTC CTGTGCACGG TGCCTGAAGC CGATCAGCCT GTCAGACTCA
    ATGGCCGCCC TGTACCCCGA GTGGAGGTCG AAGCTCAGCT GACGGATGGG CCCGACCAAG GACACGTGCC ACGGACTTCG GCTAGTCGGA CAGTCTGAGT
101  Y  R  R   D  M  G    L  T  S  S    F  E  S  A   A  Y  P   G  W  F    L  C  T   V  P  E  A    D  Q  P    V  R  L  T

401 CCCAGCTTCC CGAGAATGGT GGCTGGAATG CCCCCATCAC AGACTTCTAC TTCCAGCAGT GTGACTAG
    GGGTCGAAGG GCTCTTACCA CCGACCTTAC GGGGTAGTG TCTGAAGATG AAGGTCGTCA CACTGATC
135  Q  L  P   E  N  G    G  W  N  A   P  I  T    D  F  Y  F   Q  Q  C    D  O
```

FIG. 7

```
  1 GCTCCCGCCA GGAGAAAGGA ACATTCTGAG GGGAGTCTAC ACCCTGTGGA GCTCAAGATG GTCCTGAGTG GGGGCGCTGTG CTTCCGAATG AAGGACTCGG
    CGAGGGCGGT CCTCTTTCCT TGTAAGACTC CCCTCAGATC CGAGTTCTAC CAGGACTCAC TGGGACACCT CGAGTTCTAC CAGGACTCAC GAAGGCTTAC TTCCTGAGCC
  1  A  P  A  R  R  K  E  H  S  E  H  S  E  G  S  L  H  P  V  E  L  K  M  V  L  S  G  A  L  C  F  R  M  K  D  S  A

101 CATTGAAGGT GCTTATCTG CATAATAACC AGCTTCTAGC TGGAGGGCTG CATGCAGGGA AGTGCATTAA ATCAGCGTGG TCCCCAATCG
    GTAACTTCCA CGAATAGAC GTATTATTGG TCGAAGATCG ACCTCCCGAC GTACGTCCCT TCCAGTAATT TCCACTTCTC TAGTCGCACC AGGGGTTAGC
 35  L  K  V  L  Y  L  H  N  N  Q  L  L  A  G  G  L  H  A  G  K  V  I  K  G  E  E  I  S  V  V  P  N  R

201 GTGGCTGGAT GCCAGCCTGT CCCCCGTCAT CCTGGGTGTC CAGGGTGGAA GCCAGTGCCT GTCATGTGGG GTGGGGCAGG AGNCGACTCT AACAT
    CACCGACCTA CGGTCGGACA GGGGGCAGTA GGACCCACAG GTCCCACCTT CGGTCACGGA CAGTACACCC CACCCCGTCC TCNGCTGAGA TTGTA
 68  W  L  D  A  S  L  S  P  V  I  L  G  V  Q  G  G  S  Q  C  L  S  C  G  V  G  Q  E  X  T  L  T
```

FIG. 8

```
  1 ATAGGGAATT TGGCCCTCGA GGCCAAGAAT TCGGCACGAG GGGAGCCTGC TTTCTACTTA GGTCTCAAAT TTTCCAGCCT TGTCTCTTGCC TAAAATTTCC
    TATCCCTTAA ACCGGGAGCT CCGGTTCTTA AGCCGTGCTC CCCTCGGACG AAAGATGAAT CCAGAGTTTA AAAGGTCGGA ACAGAAACGG ATTTTAAAGG
                                                     ^insert starts
101 TGCTGTTTAT TTCAAAATAG GGTCTACATA CTGTGGAGCT CATGATGGTT CTGAGTGGGG CACTATGCTT CCGAATGAAG GATTCAGCCT TGAAGGTACT
    ACGACAAATA AAGTTTTATC CCAGATGTAT GACACCTCGA GTACTACCAA GACTCACCCC GTGATACGAA GGCTTACTTC CTAAGTCGGA ACTTCCATGA
                                                  M  V                L  S  G  A  L  C  F  R  M  K  D  S  A  L  K  V  L
                                                  ^orf
  1
201 GTATCTGCAC AATAACCAGC CTGTCATCCT GGGCGTTCAA GGAGGAAGCC AGAGACTGCAC TCATTAAAGG GCAGAGAAGG AGTGTTGTCC CAAATCGGGC ACTGGATGCC
    CATAGACGTG TTATTGGTCG GACAGTAGGA CCCGCAAGTT CCTCCTTCGG TCACGACTG AGTAATTTCC CGTCTCTTCC TCACAACAGG GTTTAGCCCG TGACCTACGG
     Y  L  H  N  N  Q  L   A  V  I  L   G  V  Q   G  G  S  Q   C  L  S   E  K  V  L   S  V  V  P   N  R  A   L  D  A
  20
301 AGTCTGTCCC CTGTCATCCT GGGCGTTCAA GGAGGAAGCC AGTGCCTATC TTGTGGGACA GAGAAAGGGC CAATTCTGAA ACTTGAGCCA GTGAACATCA
    TCAGACAGGG GACAGTAGGA CCCGCAAGTT CCTCCTTCGG TCACGGATAG AACACCCTGT CTCTTTCCCG GTTAAGACTT TGAACTCGGT CACTTGTAGT
     S  L  S  P   V  I  L   G  V  Q   G  G  S  Q   C  L  S   C  G  T   E  K  G  P   I  L  K   L  E  P   V  N  I  M
  53
401 TGGAGCTCTA CCCTCGGGCC AAGGAATCAA AGAGCTTCAC CGGGATATGG GTCTTACCTC CAGCTTCGAA TCCGCTGCCT ACCCAGGCTG
    ACCTCGAGAT GGGAGCCCGG TTCCTTAGTT TCTCGAAGTG GCCCTATACC CAGAATGGAG GTCGAAGCTT AGGCGACGGA TGGGTCCGAC
     E  L  Y   L  G  A   K  E  S  K   S  F  T   F  Y  R   R  D  M  G   L  T  S   S  F  E  S   S  A  A  Y   P  G  W
  87
501 GTTCCTCTGC ACCTCACCGG AAGCTGACCA GCCTGTCAGG GCCGTGTCAA TCCCTGAGGA CCCCGCCTGG GATGCTCCCA TCACAGACTT CTACTTTCAG
    CAAGGAGACG TGGAGTGGCC TTCGACTGGT CGGACAGTCC CGGCAGTTCT GGGACTGCCT GGGGCGGACC CTACGAGGGT AGTGTCTGAA GATGAAAGTC
     F  L  C   T  S  P  E   A  D  Q   P  V  R   A  V  S   S  L  R   D  A  P  I   T  D  F   Y  F  Q
  120
601 CAGTGTGACT AGGGCTGCGT GGTCCCCAAA ACTCCATAAG CAGAGGCAGA GTAGGCAGTG GCGGCTCCTG ATAGAGGATA GAGAGACAGA GGAGCTCCAC
    GTCACACTGA TCCCGACGCA CCAGGGGTTT TGAGGTATTC GTCTCCGTCT CATCCGTCAC CGCCGAGGAC TATCTCCTAT CTCTCTGTCT CCTCGAGGTG
     Q  C  D  *
  153
701 AGTAGGTGGC TTACTCCTCT CCTTCCCTAC CTTCTGACCT AAGGCACACA GACACTCTCT TCTCCTGCAT CCCAGTGCTG GTAAATCTTC
    TCATCCACCG AATGAGGAGA GGAAGGGATG GAAGACTGGA TTCCGTGTGT CTGTGAGAGA AGAGGACGTA GGGTCACGAC CATTTAGAAG
```

FIG. 9A

```
 801  TGGTATTTGG AGCTCAATGT GTAGATTCTT TCAGATTGGA TGGTACTACC TCTGGTGTGG AACCCAATAG TGGTACTACC AGAGCAACAT
      ACCATAAACC TCGAGTTACA CATCTAAGAA AGTCTAACCT ACCATGATGG AGACCACACC TTGGGTTATC CCTGGTTGTT TCTCGTTGTA

901  AAAGATTCT  TGGGTGAAGA AGAGGTGGGA ACTGTTCATA TCTGACACAG TCTTCAGAA  TACCTCAGAA GTCCTGCCAT TCCTTATGTT CTGGAGAAAG
      TTTTCTAAGA ACCCACTTCT TCTCCACCCT TGACAAGTAT AGACTGTGTC AGAAGTCTT  ATGGAGTCTT CAGGACGGTA AGGAATACAA GACCTCTTTC

1001  TGGAGGGGGG GTCACCAAGA CTTTCTCTGG CTGGCTGGGC CCTTTCCCTC AACCTTTCTG ACATCTGCAG CCTCTCTCAT TCTTGCCTTC ATTCTCTGGC
      ACCTCCCCCC CAGTGGTTCT GAAAGAGACC GACCGACCCG GGAAAGGGAG TTGGAAAGAC TGTAGACGTC GGAGAGAGTA AGAACGGAAG TAAGAGACCG

1101  CCTGAACCGA GAGGGTGATA TCAGGATAGC TGACAGGAGA CACTGTCCTG GTTGAAACC  AGAGGGGACA ATAAAAAACC CTGATTCTGG
      GGACTTGGCT CTCCCACTAT AGTCCTATCG ACTGTCTTCT GTGACAGGAC CAAACTTTGG TCTCCCCTGT TATTTTTTGG GACTAAGACC

1201  TCTCTACTCA CATAAAAAGA AGCTTGTGAA CATTAAGTGG GAAGAGATTG CTACTAAATA ACATACCTTG TAATTTCATC TTAATTAAAA TATACTTCTC
      AGAGATGAGT GTATTTTTCT TCGAACACTT GTAATTCACC CTTCTCTAAC GATGATTTAT TGTATGGAAC ATTAAAGTAG AATTAATTTT ATATGAAGAG

1301  TATATTATAT ATTTTAAAAA AAAAAAAAAA AAAAACATGC GGCCGCAAGC TTATTCCATT TAGGA
      ATATAATATA TAAAATTTTT TTTTTTTTTT TTTTTGTACG CCGGCGTTCG AATAAGGTAA ATCCT
                                                      ^insert ends
```

FIG. 9B

```
  1 GGAGCCTGCT TTCTACTTAG GTCTCAAATT TTCCAGCCCT GTCTTTGCCT AAAATTCCT  GCTGTTTATT TCAAAATAGG GTCTACATAC TGTGGAGCTC
    CCTCGGACGA AAGATGAATC CAGAGTTTAA AAGGTCGGGA CAGAAACGGA TTTTAAGGA  CGACAAATAA AGTTTTATCC CAGATGTATG ACACCTCGAG

101 ATGATGGTTC TGAGTGGGGC ACTATGCTTC CGAATGAAGG ATTCAGCCTT GAAGGTACTG TATCTGCACA ATAACCAGCT GCTGGCTGGA GGACTGCACG
    TACTACCAAG ACTCACCCCG TGATACGAAG GCTTACTTCC TAAGTCGGAA CTTCCATGAC ATAGACGTGT TATTGGTCGA CGACCGACCT CCTGACGTGC
  1  M  M  V  L  S  G  A  L  C  F  R  M  K  D  S  A  L  K  V  L  Y  L  H  N  N  Q  L  L  A  G  G  L  H  A
     ^orf 201 CAGAGAAGGT CATTAAAGGT GAGGAGATCA CTCCTCTAGT GTGTTGTCCC AAATCGGGCA GTCTGTCCCC TGTCATCCTG GGCGTTCAAG GGAGAAGCCA
    GTCTCTTCCA GTAATTTCCA CTCCTCTAGT GAGGAGATCA CACAACAGGG TTTAGCCCGT CAGACAGGGG ACAGTAGGAC CCGCAAGTTC CTCCTTCGGT
 35  E  K  V  I  K  G  E  E  I  S  V  V  P  N  R  A  L  D  A  S  L  S  P  V  I  L  G  V  Q  G  G  S  Q 301 GTGCCTATCT TGTGGGACAG AGAAAGGGCC AATTCTGAAA CTTGAGCCAG TGAACATCAT GGAGCTCTAC CTCGGGGCCA AG
    CACGGATAGA ACACCCTGTC TCTTTCCCGG TTAAGACTTT GAACTCGGTC ACTTGTAGTA CCTCGAGATG GAGCCCCGGT TC
 68  C  L  S  C  G  T  E  K  G  P  I  L  K  L  E  P  V  N  I  M  E  L  Y  L  G  A  K
```

| | | | | |
|---|---|---|---|---|
| hIL1Ra | 155 | P V S L T N M P D E G - - - - - - - V M V T K F Y F Q E D E - - - - - - - - - - - - - - - - - - - - - - - - - - - - - - |
| hIL1Rabeta | 148 | P I I L T S E L G K S - - - - - - - - - - - Y N T A F E L N I N D - - - - - - - - - - - - - - - - - - - - - - - - |
| tango77 | 135 | P V G V T D K F E N R - - - - - - - - - - - - - K H I E F S F Q P V C K A E M S P S E V S D |
| hIL1Ra1S | 135 | P V G V T D K F E N R - - - - - - - - - - - - - K H I E F S F Q P V C K A E M S P S E V S D |
| hIL1Ra1L | 175 | P V G V T D K F E N R - - - - - - - - - - - - - K H I E F S F Q P V C K A E M S P S E V S D |
| hIL1Ra1V | 186 | P V G V T D K F E N R - - - - - - - - - - - - - K H I E F S F Q P V C K A E M S P S E V S D |
| hIL1Ra2 | 113 | P I I L T S E L G K S - - - - - - - - - - - Y N T A F E L N I N D - - - - - - - - - - - - - - - - - - - - - - - - |
| hIL1Ra3 | 130 | P V R L T Q L P E N G G W N A P I T D F Y F Q Q C D - - - - - - - - - - - - - - - - - - - - - - - - - - - - - |

FIG. 12C

```
  1 AAAATGGGCT CTGAGGACTG GGAAAAAGAT GAACCCCAGT GCTGCTTAGA AGACCCGGCT GTAAGCCCCC TGGAACCAGG CCCAAGCCTC CCCGCCATGA
    TTTTACCCGA GACTCCTGAC CCTTTTTCTA CTTGGGGTCA CGACGAATCT TCTGGGGCCGA CATTCGGGGG ACCTTGGTCC GGGTTCGGAG GGGCGGTACT
  1  M  G  S  E  D  W  E  K  D  E  P  Q  C  L  E  D  P  A  V  S  P  L  E  P  G  P  S  L  P  A  M  N
     ^insert starts
     ^orf 101 ATTTGTTCA CACAAGTCCA AAGGTGAAGA ACTTAAACCC GAAGAAATTC AGCATTCATG ACCAGGATCA CAAAGTACTG GTCCTGGACT CTGGGAATCT
    TAAACAAGT GTGTTCAGGT TTCCACTTCT TGAATTTGGG CTTCTTTAAG TCGTAAGTAC TGGTCCTAGT GTTTCATGAC CAGGACCTGA GACCCTTAGA
 34  F  V  H  T  S  P  K  V  K  N  L  N  P  K  K  F  S  I  H  D  Q  D  H  K  V  L  V  L  D  S  G  N  L 201 CATAGCAGTT CCAGATAAAA ACTACATACG TTCTTTGCAT TAGCCTCATC CTTGAGCTCA GCCTCTGCGG AGAAAGGAAG TCCGATTCTC
    GTATCGTCAA GGTCTATTTT TGATGTATGC AAGAAACGTA ATCGGAGTAG GAACTCGAGT CGGAGACGCC TCTTTCCTTC AGGCTAAGAG
 67  I  A  V  P  D  K  N  Y  I  R  P  E  I  F  F  A  L  A  S  S  L  S  S  A  S  A  E  K  G  S  P  I  L 301 CTGGGGGTCT CTAAAGGGGA GTTTTGTCTC TACTGTGACA AGGATAAAGG ACAAAGTCAT CCATCCCTTC AGTGAAGAA GGAGAAACTG ATGAAGCTGG
    GACCCCCAGA GATTTCCCCT CAAAACAGAG ATGACACTGT TCCTATTTCC TGTTTCAGTA GGTAGGGAAG TCACTTCTT CCTCTTTGAC TACTTCGACC
100  L  G  V  S  K  G  E  F  C  L  Y  C  D  K  D  K  G  Q  S  H  P  S  L  Q  L  K  K  E  K  L  M  K  L  A 401 CTGCCCAAAA GGAATCAGCA CGCGGCCTCC GCGGCCGTGT ATCCCGAGTC CACCCGAGGA GTGGGCTCT GGAACATGCT GGAGTCGGCC GCTCACCCCG GATGGTTCAT
    GACGGGTTTT CCTTAGTCGT GCGCCGGAGG CGCCGGCACA TAGGGCTCAG GTGGGCTCCT CACCCGAGA CCTTGTACGA CCTCAGCCGC CGAGTGGGGC CTACCAAGTA
134  A  Q  K  E  S  A  R  R  P  F  I  F  Y  R  A  Q  V  G  S  W  N  M  L  E  S  A  A  H  P  G  W  F  I 501 CTGCCACTCC TGCAATTGTA ATGAGCCTGT TGGGGTGACA ACCCCACTGT GATAAATTTG AGAACAGGAA TTTTCATTTC AACCAGTTTG CAAAGCTGAA
    GACGGTGAGG ACGTTAACAT TACTCGGACA ACCCCACTGT GGGGTGACA CTATTTAAAC TCTTGTCCTT AAAAGTAAAC TTGGTCAAAC GTTTCGACTT
167  C  T  S  C  N  C  N  E  P  V  G  V  T  D  K  F  E  N  R  K  H  I  E  F  S  F  Q  P  V  C  K  A  E 601 ATGAGCCCCA GTGAGGTCAG CGATTA
    TACTCGGGGT CACTCCAGTC GCTAAT
200  M  S  P  S  E  V  S  D
```

FIG. 15

```
  1 AAAATGGGCT CTGAGGACTG GGAAAAAGAT GAACCCCAGT GCTGCTTAGA AGACCCGGCT GTAAGCCCCC TGGAACCAGG CCCAAGCCTC CCCGCCATGA
    TTTTACCCGA GACTCCTGAC CCTTTTTCTA CTTGGGGTCA CGACGAATCT TCTGGGCCGA CATTCGGGGG ACCTTGGTCC GGGTTCGGAG GGGCGGTACT
  1  M  G  S  E  D  W  E  K  D  E  P  Q  C  L  E  D  P  A  V  S  P  L  E  P  G  P  S  L  P  A  M  N
     ^insert starts
     ^orf 101 ATTTGTTCA  CACAAAGATC TTCCTTTGCAT TAGCCTCATC CTTGAGCTCA GCCTCTGCGG AGAAAGGAAG TCCGATTCTC CTGGGGGTCT CTAAAGGGGA
    TAAACAAGT  GTGTTTCTAG AAGAAACGTA ATCGGAGTAG GAACTCGAGT CGGAGACGCC TCTTTCCTTC AGGCTAAGAG GACCCCCAGA GATTTCCCCT
 34  F  V  H   T  K  I   F  F  A  L   A  S  S   L  S  S   A  S  A  E   K  G  S   P  I  L   L  G  V  S   K  G  E 201 GTTTTGTCTC TACTGTGACA AGGATAAAGG TCCTATTTCC ACAAAGTCAT CCATCCCTTC AGCTGAAGAA GGAGAAACTG ATGAAGCTGG CTGCCCAAAA GGAATCAGCA
    CAAAACAGAG ATGACACTGT TCCTATTTCC AGGATAAAGG TGTTTCAGTA GGTAGGGAAG TCGACTTCTT CCTCTTTGAC TACTTCGACC GACGGGTTTT CCTTAGTCGT
 67  F  C  L   Y  C  D  K   D  K  G   Q  S  H   P  S  L  Q   L  K  K   E  K  L   M  K  L  A   A  Q  K   E  S  A 301 CGCCGGCCCT TCATCTTTTA TAGGGCTCCA GTGGGGTCCT GGAACATGCT CCTTGTACGA CCCCAGCCGC GAGTGGGGGC CTACCAAGTA CTGCACCTCC TGCAATTGTA
    GCGGCCGGGA AGTAGAAAAT ATCCCGAGTC CACCCAGGA CCTTGTACGA GGAACATGCT GGGGTCGGCG CTCACCCCCG GATGGTTCAT GACGTGGAGG ACGTTAACAT
100  R  R  P  F  I  F  Y   R  A  Q  V  G  S  W   N  M  L   E  S  A  A  H  P  G  W  F  I  C  T  S  C  N  C  N 401 ATGAGCCTGT TGGGGTGACA GATAAATTTG AGAACAGGAA TCTTGTCCTT AAAAGTAACT AAAAGTAAAG TTGGTCAAAC CAAAGCTGAA GTTTCGACTT CAAAGCCTGAA ATGAGCCCCA GTGAGGTCAG
    TACTCGGACA ACCCCACTGT CTATTTAAAC TCTTGTCCTT AGAACAGGAA ACACATTGAA TGTGTAACTT TTGTCAAAC CAAAGTAAAG GTTTCGACTT CAAAGTCAAAC TACTCGGGGT CACTCCAGTC
134  E  P  V   G  V  T   D  K  F  E   N  R  K   H  I  E   F  S  F  Q   P  V  C   K  A  E   M  S  P  S   E  V  S

501 CGATTA
    GCTAAT
167  D
```

FIG. 16

```
  1 AACCCGAAGA AATTCAGCAT TCATGACCAG GATCACAAAG TACTGGTCCT GGACTCTGGG AATCTCATAG CAGTTCCAGA TAAAAACTAC ATACGCCCAG
    TTGGGCTTCT TTAAGTCGTA AGTACTGGTC CTAGTGTTTC ATGACCAGGA CCTGAGACCC TTAGAGTATC GTCAAGGTCT ATTTTTGATG TATGCGGGTC
  1 N  P  K  K  F  S  I  H  D  Q  D  H  K  V  L  V  L  D  S  G  N  L  I  A  V  P  D  K  N  Y  I  R  P  E

101 AGATCTTCTT TGCATTAGCC TCATCCTTGA GCTCAGCCTC TGCGGAGAAA GGAAGTCCGA TTCTCCCTGGG GGTCTCTAAA GGGGAGTTTT GTCTCTACTG
    TCTAGAAGAA ACGTAATCGG AGTAGGAACT CGAGTCGGAG ACGCCTCTTT CCTTCAGGCT AAGAGGACCC CCAGAGATTT CCCCTCAAAA CAGAGATGAC
 35 I  F  F  A  L  A  S  S  L  S  S  A  S  A  E  K  G  S  P  I  L  L  G  V  S  K  G  E  F  C  L  Y  C

201 TGACAAGGAT AAAGGACAAA TTTCCTGTTT CAGTAGGTAG GGAAGTCGAC TTGACTACTT CGACCGACGG GTTTTCCTTA GTCGTGCGGC CGGAAGTAG
    ACTGTTCCTA TTTCCTGTTT CAGTAGGTAG GGAAGTCGAC TTGACTACTT CGACCGACGG GTTTTCCTTA GTCGTGCGGC CGGAAGTAG
 68 D  K  D  K  G  Q  S  H  P  S  L  Q  L  K  K  E  K  L  M  K  L  A  A  Q  K  E  S  A  R  R  P  F  I

301 TTTTATAGGG CTCAGGTGAG ATGCTGGAGT CTCCTGGAAC CCCCCGATGG TTCATCTGCA CCTCCTGCAA TTGTAATGAG CCTGTTGGGG
    AAAATATCCC GAGTCCACCT TACGACCTTG GGGCGCCGAGT AAGTAGACGT GGAGGACGTT AACATTACTC GGACAACCCC
101 F  Y  R  A  Q  V  G  S  W  N  M  L  E  S  A  A  H  P  G  W  F  I  C  T  S  C  N  E  P  V  G  V

401 TGACAGATAA ATTTGAGAAC AGGAAACACA TTGAATTTTC ATTTCAACCA GTTTGCAAAG CTGAAATGAG CCCCAGTGAG GTCAGCGATT AGGAAACTGC
    ACTGTCTATT TAAACTCTTG TCCTTTGTGT AACTTAAAAG TAAAGTTGGT CAAACGTTTC GACTTTACTC GGGTCACTC CAGTCGCTAA TCCTTTGACG
135 T  D  K  F  E  N  R  K  H  I  E  F  S  F  Q  P  V  C  K  A  E  M  S  P  S  E  V  S  D  Q

501 CCCATTGAAC GCCTTCCCTCG CTAATTGTAT AAAAACACCA AACCTGCTCA C
    GGGTAACTTG CGGAAGGAGC GATTAACATA TTTTTGTGGT TTGGACGAGT G
```

```
  1 GGCCCCTGAG GCCAAGAATT CGGCACGAGG CTTCATTCCA TTTTCTGTTG AGTAATAAAC TCAACGTTGA AAATGTCCTT TGTGGGGGAG AACTCAGGAG
    CCGGGGACTC CGGTTCTTAA GCCGTGCTCC GAAGTAAGGT AAAAGACAAC TCATTATTTG AGTTGCAACT TTTACAGAAA ACACCCCCTC TTGAGTCCTC
  1                                                                                         M  S  F  V  G  E  N  S  G  V

101 TGAAAATGGG CTCTGAGGAC TGGGAAAAAG ATGAACCCCA GTGCTGCTTA GAAGACCCGG CCTGGAACCA GGCCCAAGCC TCCCACCAT
    ACTTTTACCC GAGACTCCTG ACCCTTTTTC TACTTGGGGT CACGACGAAT CTTCTGGGCC GGACCTTGGT CCGGGTTCGG AGGGTGGTA
 11    K  M  G  S  E  D  W  E  K  D  E  P  Q  C  C  L  E  D  P  A  G  S  P  L  E  P  G  P  S  L  P  T  M

201 GAATTTTGTT CACACAAGTC CAAAGGTGAA GAACTTAAAC CCGAAGAAAT TCAGCATTCA TGACCAGGAT CACAAAGTAC TGGTCCTGGA CTCTGGGAAT
    CTTAAAACAA GTGTGTTCAG GTTTCCACTT CTTGAATTTG GGCTTCTTTA AGTCGTAAGT ACTGGTCCTA GTGTTTCATG ACCAGGACCT GAGACCCTTA
 44  N  F  V  H  T  S  P  K  V  K  N  L  N  P  K  K  F  S  I  H  D  Q  D  H  K  V  L  V  L  D  S  G  N

301 CTCATAGCAG TTCCAGATAA AAACTACATA TTTGATGTAT GCGGGTCTCT AGAAGAAACG TCTTCTTTGC ATTAGCCTCA CAGCCCTCTGC AGTCCGATTC
    GAGTATCGTC AAGGTCTATT TTTGATGTAT CGCCCAGAGA TCTTCTTTGC TTCTTTTGCG AGAAGAAACG TAATCGGAGT GTCGGAGACG TCAGGCTAAG
 77  L  I  A  V  P  D  K  N  Y  I  F  D  V  C  R  P  E  I  F  F  A  L  A  S  S  L  S  S  A  S  A  E  K  G  S  P  I  L

401 TCCTGGGGGT CTCTAAAGGG GAGTTTTGTC TCTACTGTGA CAAGGATAAA GTTCCTATTT TATAGGGCTC AGGTGGGCTC CTGGAACATG TGATGAAGCT
    AGGACCCCCA GAGATTTCCC CTCAAAACAG AGATGACACT GTTCCTATTT CAAGGATAAA ATATCCCGAG TCCACCCGAG GACCTTGTAC ACTACTTCGA
111    L  G  V  S  K  G  E  F  C  L  Y  C  D  K  D  K  V  P  I  L  Y  R  A  Q  V  G  S  W  N  M  L

501 GGCTGCCCAA AAGGAATCAG CACGCCCGCC CTTCATCTTT TATAGGGCTC AGGTGGGCTC CTGGAACATG CTGGCTCACCC CGGATGGTTC
    CCGACGGGTT TTCCTTAGTC GTGCGGGCGG GAAGTAGAAA ATATCCCGAG TCCACCCGAG GACCTTGTAC GACCTCAGCC GCCTACCAAG
144  A  A  Q  K  E  S  A  R  R  R  P  F  I  F  Y  R  A  Q  V  G  S  W  N  M  L  E  S  A  H  P  G  W  F

601 ATCTGCACCT CCTGCAATTG TAATGAGCCC GTTGGGGTGA CAGATAAATT TGAGAACAGG AAACACATTG AATTTCATT TCAACCAGTT TGCAAGCTG
    TAGACGTGGA GGACGTTAAC ATTACTCGGA CAACCCCACT GTCTATTTAA ACTCTTGTCC TTTGTGTAA TTAAAAGTAA AGTTGGTCAA ACGTTTGAC
177  I  C  T  S  C  N  C  N  E  P  V  G  V  T  D  K  F  E  N  R  K  H  I  E  F  S  F  Q  P  V  C  K  A  E

701 AAATGAGCCC CAGTGAGGTC AGCGATTAGG AAACTGCCCC ATTGAACGCC TTCCTCGCTA ATTGAACTA ATTGTATAAA AACACCAAAC CTGCTCACTA
    TTTACTCGGG GTCACTCCAG TCGCTAATCC TTTGACGGGG TAACGTGCGG AAGGAGCGAT TAAACTTGAT TAACATATTT TTGTGGTTTG GACGAGTGAT
211  M  S  P  S  E  V  S  D  O

801 AAAAAAAAAA AAAAAAAACGT TTGCGGCCGC AAGCTTATT
    TTTTTTTTTT TTTTTTTGCA AACGCCGGCG TTCGAATAA
```

FIG. 19

ANTIBODIES BINDING IL-1 RELATED POLYPEPTIDES

RELATED APPLICATIONS

This is a divisional application of U.S. Ser. No. 11/548,249, which is a continuation of U.S. Ser. No. 09/869,566 filed Feb. 19, 2002, which is a national phase application of PCT/US99/30720, filed Dec. 22, 1999, which claims the benefit of: (i) U.S. Ser. No. 60/113,430, filed 23 Dec. 1998, (ii) U.S. Ser. No. 60/116,843, filed 22 Jan. 1999 and (iii) U.S. Ser. No. 60/129,122, filed 13 Apr. 1999; all of which are herein incorporated by reference.

FIELD OF THE INVENTION

The present invention relates generally to the identification and isolation of novel DNAs having homology to interleukin-1 (IL-1) or interleukin-1 receptor antagonist (IL-1Ra) polypeptides, and to the recombinant production of novel polypeptides, designated herein as interleukin-1-like polypeptides ("IL-1lp").

BACKGROUND OF THE INVENTION

Interleukin-1 refers to two proteins (IL-1α and IL-1β) which play a key role early in the inflammatory response (for a review, see Dinarello, *Blood*, 87: 2095-2147 (1996) and references therein). both proteins are made as intracellular precursor proteins which are cleaved upon secretion to yield mature carboxy-terminal 17 kDa fragments which are biologically active. In the case of IL-1β this cleavage involves an intracellular cysteine protease, known as ICE, which is required to release the active fragment from the inactive precursor. The precursor of IL-1α is active.

These two proteins act by binding to cell surface receptors found on almost all cell types and triggering a range of responses either alone or in concert with other secreted factors. These range from effects on proliferation (e.g. fibroblasts, T cells) apoptosis (e.g. A375 melanoma cells), cytokine induction (e.g. of TNF, IL-1, IL-8), receptor activation (e.g. E-selectin), eicosanoid production (e.g. PGE2) and the secretion of degradative enzymes (e.g. collagenase). To achieve these effects, IL-1 activates transcription factors such as NF-KB and AP-1. Several of the activities of IL-1 action on target cells are believed to be mediated through activation of kinase cascades that have also been associated with cellular stresses, such as the stress activated MAP kinase JNK/SAPK and p38.

A third member of the IL-1 family was subsequently discovered which acts as a natural antagonist of IL-1α and IL-1β by binding to the IL-1 receptor but not transducing an intracellular signal or a biological response. The protein is called IL-1Ra (for IL-1 receptor antagonist) or IRAP (for IL-1 receptor antagonist protein). At least three alternatively spliced forms of IL-1Ra exist: one encodes a secreted protein, also known as secretory IL-1Ra ("sIL-1Ra") (described in Eisenberg et al., *Nature*, 343: 341-346 (1990)), and the other two encode intracellular proteins. IL-1α, IL-1β and IL-1Ra exhibit approximately 25-30% sequence identity with each other and share a similar three dimensional structure consisting of twelve β-strands folded into a β-barrel, with an internal thrice repeated structural motif.

There are three known IL-1 receptor subunits. The active receptor complex consists of the type I receptor and IL-1 accessory protein (IL-1RAcP). The type I receptor is responsible for binding of the IL-1α, IL-1β and IL-1Ra ligands, and is able to do so in the absence of the IL-1RAcP. However, signal transduction requires the interaction of IL-1α or IL-1β with the IL-1RAcP. IL-1Ra does not interact with the IL-1RAcP and hence cannot induce signal transduction. A third receptor subunit, the type II receptor, binds IL-1α and IL-1β but cannot transduce signal due its lack of an intracellular domain. Instead, the type II receptor either acts as a decoy in its membrane bound form or as an IL-1 antagonist in a processed, secreted form, and hence inhibits IL-1 activity. The type II receptor weakly binds to IL-1Ra.

Many studies using IL-1Ra, soluble IL-1R derived from the extracellular domain of the type I IL-1 receptor, antibodies to IL-1α or IL-1β, and transgenic knockout mice for these genes have shown that IL-1 plays a role in a number of pathophysiologies (for a review, see Dinarello, *Blood*, 87: 2095-2147 (1996)). For example, IL-1Ra has been shown to be effective in animal models of septic shock, rheumatoid arthritis, graft-versus-host disease (GVHD), stroke, cardiac ischemia, psoriasis, inflammatory bowel disease, and asthma. In addition, IL-1Ra has demonstrated efficacy in clinical trials for rheumatoid arthritis and GVHD, and is also in clinical trials for inflammatory bowel disease, asthma and psoriasis.

More recently, interleukin-18 (IL-18) was placed in the IL-1 family (for a review, see Dinarello et al, *J. Leukocyte Biol.*, 63: 658-664 (1998)). IL-18 shares the β-pleated, barrel-like form of IL-1α and IL-1β. In addition, IL-18 is the natural ligand for the IL-1 receptor family member formerly known as IL-1R-related protein (IL-1Rrp) (now known as the IL-18 receptor (IL-18R)). IL-18 has been shown to initiate the inflammatory cytokine cascade in a mixed population of peripheral blood mononuclear cells (PBMCs) by triggering the constitutive IL-18 receptors on lymphocytes and NK cells, inducing TNF production in the activated cells. TNF, in turn, stimulates IL-1 and IL-8 production in CD14+ cells. Because of its ability to induce TNF, IL-1, and both C-C and C-X-C chemokines, and because IL-18 induces Fas ligand as well as nuclear translocation of nuclear factor κB (NF-κB), IL-18 ranks with other pro-inflammatory cytokines as a likely contributor to systemic and local inflammation.

SUMMARY OF THE INVENTION

A family of cDNA clones (DNA85066, DNA96786, DNA94618, DNA102043, DNA114876, DNA102044, DNA92929, DNA96787, and DNA92505) has been identified, having homology to interleukin-1, that encode novel polypeptides. The novel polypeptides and variants thereof are collectively designated in the present application as "interleukin-1-like polypeptides" or "IL-1lp", as further defined herein. Accordingly, one aspect of the invention is an isolated IL-1lp polypeptide.

In another embodiment, the invention provides an isolated nucleic acid molecule encoding an IL-1lp polypeptide.

In another embodiment, the invention provides a method for producing an IL-1lp comprising culturing a host cell comprising a heterologous nucleic acid sequence encoding an IL-1lp polypeptide, under conditions wherein the IL-1lp polypeptide is expressed, and recovering the IL-1lp polypeptide from the host cell.

In another embodiment, the invention provides an anti-IL-1lp antibody.

In another embodiment, the invention provides chimeric molecules comprising an IL-1lp polypeptide fused to a heterologous polypeptide or amino acid sequence. An example of such a chimeric molecule comprises an IL-1lp polypeptide fused to an epitope tag sequence or a Fc region of an immunoglobulin.

In another embodiment, the invention provides an antibody which specifically binds to an IL-1lp polypeptide. Optionally, the antibody is a monoclonal antibody.

In yet another embodiment, the invention concerns agonists and antagonists of a native IL-1lp polypeptide. In a particular embodiment, the agonist or antagonist is an anti-IL-1lp antibody.

In a further embodiment, the invention concerns a method of identifying agonists or antagonists of a native IL-1lp polypeptide, by contacting the native IL-1lp polypeptide with a candidate molecule and monitoring a biological activity mediated by said polypeptide.

In a still further embodiment, the invention concerns a composition comprising an IL-1lp polypeptide, or an agonist or antagonist as hereinabove defined, in combination with a pharmaceutically acceptable carrier.

BRIEF DESCRIPTION OF THE DRAWINGS

FIG. 1 shows a nucleotide sequence (SEQ ID NO:1) and derived amino acid sequences (SEQ ID NOS:2-3) related to a native sequence hIL-1Ra1. The nucleotide sequence (SEQ ID NO:1) contains an intron believed to extend from nucleotide positions 181 to 432, with a splice donor site at nucleotide positions 181 to 186 and splice acceptor site at nucleotide positions 430 to 432. The amino acid sequences (SEQ ID NOS:2 and 3) are derived from the exonic sequences that are believed to make up the processed (intron-free) coding sequence.

FIG. 2 shows the nucleotide sequence (SEQ ID NO:4) and derived amino acid sequence (SEQ ID NO:5) of a native sequence hIL-1Ra1 polypeptide fused at its N-terminus to a heterologous signal peptide (amino acid positions 1-15), flag peptide affinity handle (amino acid positions 16-23) and peptide linker (amino acid positions 24-36).

FIG. 3 shows the nucleotide sequence (SEQ ID NO:6) and derived amino acid sequence (SEQ ID NO:7) of a native sequence hIL-1Ra1 polypeptide. The nucleotide sequence (SEQ ID NO:6) and derived amino acid sequence (SEQ ID NO:7) are believed to represent the processed (intron-free) form and intact hIL-1Ra1 polypeptide, respectively, of the nucleotide sequence (SEQ ID NO:1) and amino acid sequences (SEQ ID NOS:2-3) of FIG. 1. The start and stop codons in the coding sequence are located at nucleotide positions 103-105 and 682-684, respectively. The putative signal sequence extends from amino acid positions 1 to 14. A putative cAMP- and cGMP-dependent protein kinase phosphorylation site is located at amino acid positions 33-36. Putative N-myristoylation sites are located at amino acid positions 50-55 and 87-92.

FIG. 4 shows the nucleotide sequence (SEQ ID NO:8) of which nucleotides 145-629 correspond EST AI014548.

FIG. 5 shows the nucleotide sequence (SEQ ID NO:9) and derived amino acid sequence (SEQ ID NO:10) of a native sequence hIL-1Ra2 polypeptide. The start and stop codons in the coding sequence are located at nucleotide positions 96-98 and 498-500, respectively. The putative signal sequence extends from amino acid positions 1-26.

FIG. 6 shows the nucleotide sequence (SEQ ID NO:11) of EST 1433156.

FIG. 7 shows the nucleotide sequence (SEQ ID NO:12) and derived amino acid sequence (SEQ ID NO:13) of a native sequence hIL-1Ra3 polypeptide. The start and stop codons in the coding sequence are located at nucleotide positions 1-3 and 466-468, respectively. The putative signal sequence extends from amino acid positions 1-33. Putative N-myristoylation sites are located at amino acid positions 29-34, 30-35, 60-65, 63-68, 73-78, 91-96 and 106-111. An interleukin-1-like sequence is located at amino acid positions 111-131.

FIG. 8 shows the nucleotide sequence (SEQ ID NO:14) of EST 5120028.

FIG. 9 shows the nucleotide sequence (SEQ ID NO:15) and derived amino acid sequence (SEQ ID NO:16) of a native sequence mIL-1Ra3 polypeptide. The start and stop codons in the coding sequence are located at nucleotide positions 145-147 and 610-612, respectively. The putative signal sequence extends from amino acid positions 1-33. Putative N-myristoylation sites are located at amino acid positions 29-34, 60-65, 63-68, 91-96 and 106-111. An interleukin-1-like sequence is located at amino acid positions 111-131.

FIG. 10 shows the nucleotide sequence (SEQ ID NO:17) of EST WO8205.

Figure 12A:
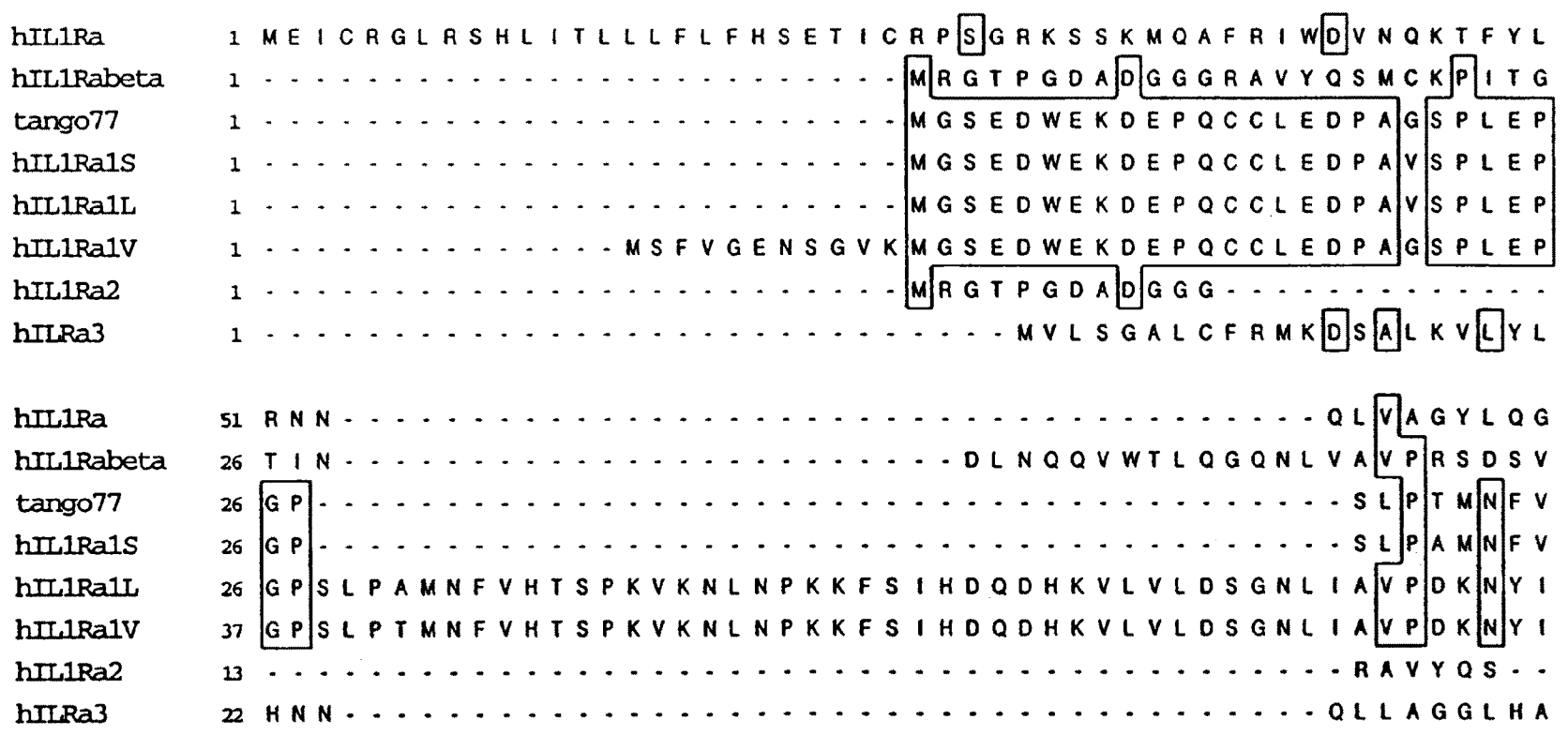
Figure 12B:
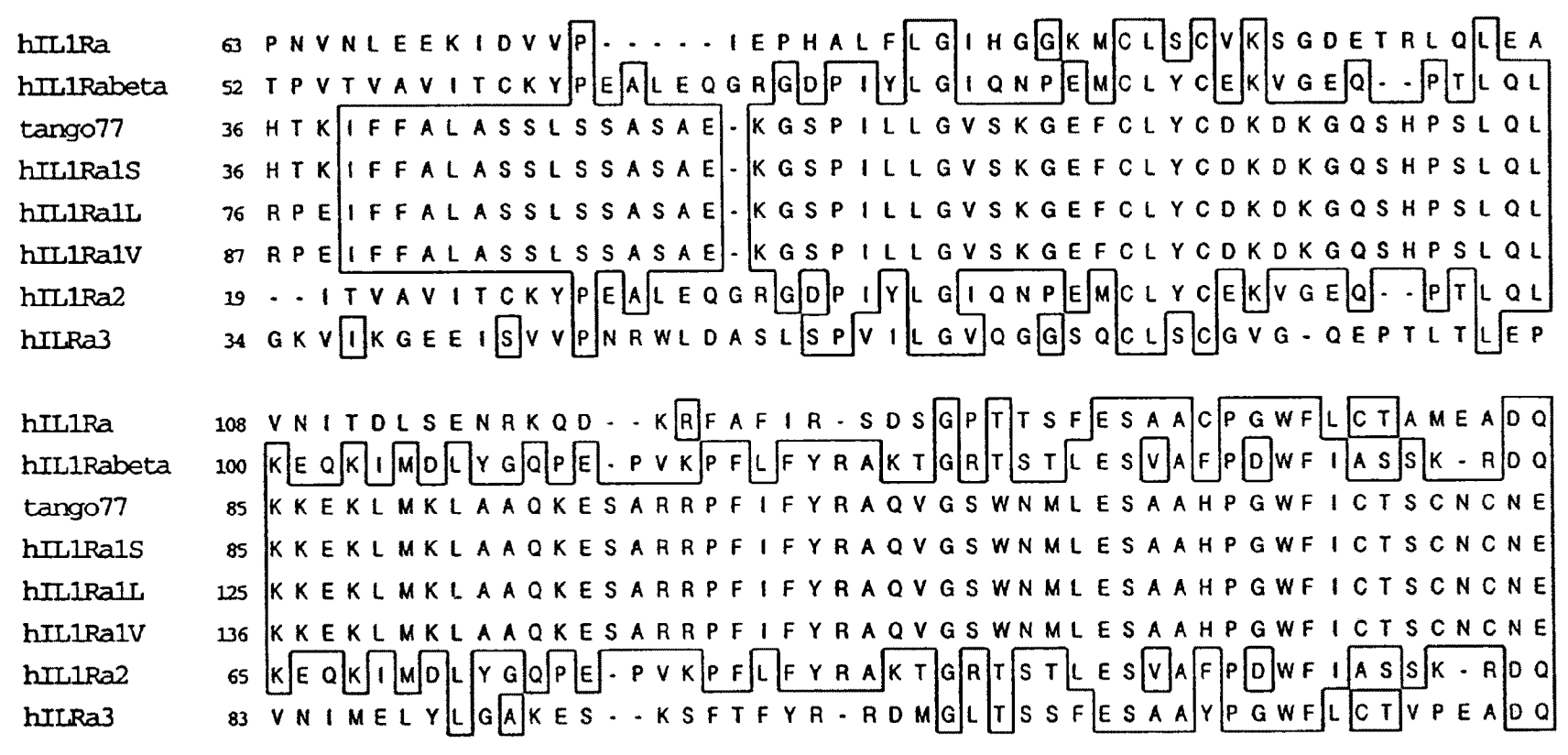

FIG. 12 is an amino acid sequence alignment of native sequence hIL-1Ra1L (SEQ ID NO:19), hIL-1Ra1V (SEQ ID NO:25), hIL-1Ra1S (SEQ ID NO:21), hIL-1Ra2 (SEQ ID NO:10), hIL-1Ra3 (SEQ ID NO:13) and mIL-1Ra3 (SEQ ID NO:16) polypeptides with secretory hIL-1Ra (also referred to as "sIL-1Ra" and "hIL-1Ra") (SEQ ID NO:26), hIL-1Raβ (SEQ ID NO:27) and TANGO-77 (SEQ ID NO:28).

FIG. 15 shows the nucleotide sequence (SEQ ID NO:18) and derived amino acid sequence (SEQ ID NO:19) of a native sequence hIL-1RaL polypeptide. The start and stop codons in the coding sequence are located at nucleotide positions 4-6 and 625-627, respectively. The putative signal sequence extends from amino acid positions 1 to 34. A putative cAMP- and cGMP-dependent protein kinase phosphorylation site is located at amino acid positions 47-50. Putative N-myristoylation sites are located at amino acid positions 64-69 and 101-106.

FIG. 16 shows the nucleotide sequence (SEQ ID NO:20) and derived amino acid sequence (SEQ ID NO:21) of a native sequence hIL-1Ra1S polypeptide. The start and stop codons in the coding sequence are located at nucleotide positions 4-6 and 505-507, respectively. A putative signal sequence extends from amino acid positions 1 to 46. A putative N-myristoylation site is located at amino acid positions 61-66.

FIG. 17 shows the single stranded nucleotide sequence (SEQ ID NO:23) of EST AI343258 (lower strand) along with its complementary nucleotide sequence (SEQ ID NO:22) (upper strand).

Figure 18:
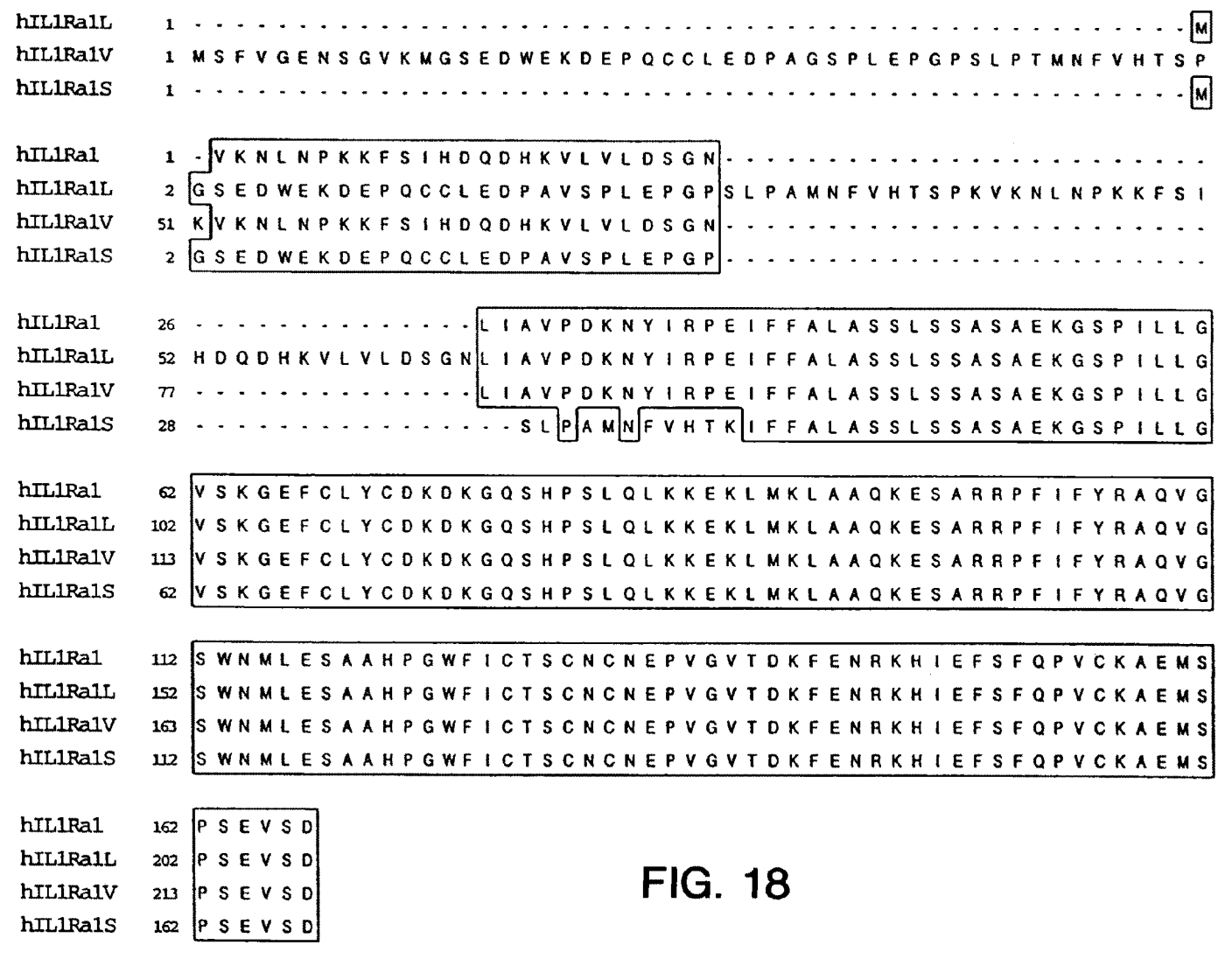

FIG. 18 is an amino acid sequence alignment of native sequence hIL-1Ra1 (SEQ ID NO:3), hIL-1Ra1L (SEQ ID NO:19), hIL-1Ra1V (SEQ ID NO:25) and hIL-1Ra1S (SEQ ID NO:21) polypeptides.

FIG. 19 shows the nucleotide sequence (SEQ ID NO:24) and derived amino acid sequence (SEQ ID NO:25) of a native sequence hIL-1Ra1V polypeptide. The start and stop codons in the coding sequence are located at nucleotide positions 73-75 and 727-729, respectively. An alternate start codon is located at nucleotide positions 106-108. A putative signal sequence extends from amino acid positions 1 to 48.

DETAILED DESCRIPTION OF THE PREFERRED EMBODIMENTS

I. Definitions

Figure 11A:
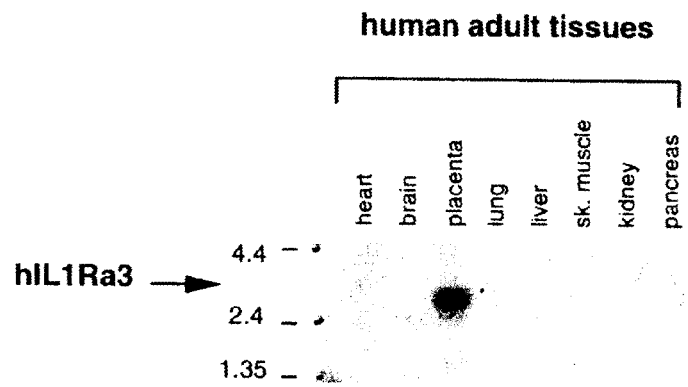
FIG. 11 is an autoradiograph of Northern blots depicting expression of hIL-1Ra3 mRNA in placental tissue and expression of mIL-1Ra3 mRNA in day-17 mouse embryo tissue.

The terms "interleukin-1-like polypeptide", "interleukin-1-like protein", "IL-1lp", "IL-1lp polypeptide", and "IL-1lp protein" encompass any native sequence IL-1lp, and further encompass IL-1lp variants (which are further defined herein). The IL-1lp may be isolated from a variety of sources, such as from human tissue types or from another source, or prepared by recombinant and/or synthetic methods.

A "native sequence IL-1lp" comprises a polypeptide having the same amino acid sequence as a native sequence hIL-1Ra1, hIL-1Ra1L, hIL-1Ra1V, hIL-1Ra1S, hIL-1Ra2, hIL-1Ra3, or mIL-1Ra3, (which are further defined herein). Such native sequence IL-1lp can be isolated from nature or can be produced by recombinant and/or synthetic means. The term "native sequence IL-1lp" specifically encompasses naturally-occurring truncated or secreted forms (e.g., a processed, mature sequence) and naturally-occurring allelic variants of the IL-1lp.

The terms "naturally-occurring amino acid sequence" and "native amino acid sequence" mean any amino acid sequence found in a polypeptide existing in nature, i.e. present in a naturally-occurring polypeptide.

The terms "non-naturally-occurring amino acid sequence" and "non-native amino acid sequence" mean any amino acid sequence not found in a polypeptide existing in nature, i.e. not present in a naturally-occurring polypeptide.

"IL-1lp variant" is defined as any polypeptide that comprises a variant of hIL-1Ra1, hIL-1Ra1L, hIL-1Ra1V, hIL-1Ra1S, hIL-1Ra2, hIL-1Ra3, or mIL-1Ra3 (which are further defined herein).

Human interleukin-1 receptor antagonist analog 1 ("hIL-1Ra1"), hIL-1Ra1 polypeptide, and hIL-1Ra1 protein are defined as any native sequence hIL-1Ra1 or variant hIL-1Ra1.

A "native sequence hIL-1Ra1" means a polypeptide comprising a naturally-occurring amino acid sequence selected from the group consisting of: (1) the amino acid sequence of amino acid residues from at or about 37 to at or about 63 of FIG. 2 (SEQ ID NO:5); (2) the amino acid sequence of amino acid residues from at or about 37 to at or about 203 of FIG. 2 (SEQ ID NO:5); (3) the amino acid sequence of amino acid residues from at or about 15 to about 53 of FIG. 3 (SEQ ID NO:7); (4) the amino acid sequence of amino acid residues from at or about 15 to at or about 193 of FIG. 3 (SEQ ID NO:7); and (5) the amino acid sequence of any naturally-occurring truncated or secreted form or any naturally-occurring allelic variant of a polypeptide comprising the amino acid sequence of (1) or (2) or (3) or (4). In one embodiment of the invention, the native sequence hIL-1Ra1 comprises amino acids from at or about 37 to at or about 203 of FIG. 2 (SEQ ID NO:5) or amino acids from at or about 15 to at or about 193 of FIG. 3 (SEQ ID NO:7).

"hIL-1Ra1 variant" is defined as any hIL-1Ra1 N-terminal variant or hIL-1Ra1 full sequence variant (which are further defined herein).

"hIL-1Ra1 N-terminal variant" means any hIL-1Ra1 other than a native sequence hIL-1Ra1, which variant is an active hIL-1Ra1, as defined below, having at least about 80% amino acid sequence identity with an amino acid sequence selected from the group consisting of: (1) the amino acid sequence of amino acid residues from at or about 37 to at or about 63 of FIG. 2 (SEQ ID NO:5); and (2) the amino acid sequence of amino acid residues from at or about 15 to at or about 53 of FIG. 3 (SEQ ID NO:7). Such hIL-1Ra1 N-terminal variants include, for instance, hIL-1Ra1 polypeptides wherein one or more amino acid residues are added, or deleted, internally or at the N- or C-terminus, in the sequence of amino acid residues from at or about 37 to at or about 63 of FIG. 2 (SEQ ID NO:5) or in the sequence of amino acid residues from at or about 15 to at or about 53 of FIG. 3 (SEQ ID NO:7). Ordinarily, an hIL-1Ra1 N-terminal variant will have at least about 80% amino acid sequence identity, or at least about 85% amino acid sequence identity, or at least about 90% amino acid sequence identity, or at least about 95% amino acid sequence identity with an amino acid sequence selected from the group consisting of: (1) the amino acid sequence of amino acid residues from at or about 37 to at or about 63 of FIG. 2 (SEQ ID NO:5); and (2) the amino acid sequence of amino acid residues from at or about 15 to at or about 53 of FIG. 3 (SEQ ID NO:7).

"hIL-1Ra1 full sequence variant" means any hIL-1Ra1 other than a native sequence hIL-1Ra1, which variant retains at least one biologic activity of a native sequence hIL-1Ra1, such as the ability to bind IL-18R, and which variant has at least about 80% amino acid sequence identity, or at least about 85% amino acid sequence identity, or at least about 90% amino acid sequence identity, or at least about 95% amino acid sequence identity with an amino acid sequence selected from the group consisting of: (1) the amino acid sequence of amino acid residues from at or about 37 to at or about 203 of FIG. 2 (SEQ ID NO:5); and (2) the amino acid sequence of amino acid residues from at or about 15 to at or about 193 of FIG. 3 (SEQ ID NO:7). Such hIL-1Ra1 full sequence variants include, for instance, hIL-1Ra1 polypeptides wherein one or more amino acid residues are added, or deleted, internally or at the N- or C-terminus, in the sequence of amino acid residues from at or about 37 to at or about 203 of FIG. 2 (SEQ ID NO:5) or in the sequence of amino acid residues from at or about 15 to at or about 193 of FIG. 3 (SEQ ID NO:7).

Human interleukin-1 receptor antagonist analog 1 long ("hIL-1Ra1L"), hIL-1Ra1L polypeptide, and hIL-1Ra1L protein are defined as any native sequence hIL-1Ra1L or hIL-1Ra1L variant (which are further defined herein).

A "native sequence hIL-1Ra1L" means a polypeptide comprising a naturally-occurring amino acid sequence selected from the group consisting of: (1) the amino acid sequence of amino acid residues from at or about 26 to at or about 44 of FIG. 15 (SEQ ID NO:19); (2) the amino acid sequence of amino acid residues from at or about 26 to at or about 207 of FIG. 15 (SEQ ID NO:19); and (3) the amino acid sequence of any naturally-occurring truncated or secreted form or any naturally-occurring allelic variant of a polypeptide comprising the amino acid sequence of (1) or (2). In one embodiment of the invention, the native sequence hIL-1Ra1L comprises amino acids from at or about 26 to at or about 207 of FIG. 15 (SEQ ID NO:19).

"hIL-1Ra1L variant" is defined as any hIL-1Ra1L N-terminal variant or hIL-1Ra1L full sequence variant or hIL-1Ra1L fusion variant (which are further defined herein).

"hIL-1Ra1L N-terminal variant" means any hIL-1Ra1L other than a native sequence hIL-1Ra1L, which variant is an active hIL-1Ra1L, as defined below, having at least about 80% amino acid sequence identity with the amino acid sequence of amino acid residues from at or about 26 to at or about 44 of FIG. 15 (SEQ ID NO:19). Such hIL-1Ra1L N-terminal variants include, for instance, hIL-1Ra1L polypeptides wherein one or more amino acid residues are added, or deleted, internally or at the N- or C-terminus, in the sequence of amino acid residues from at or about 26 to at or about 44 of FIG. 15 (SEQ ID NO:19). Ordinarily, an hIL-1Ra1L N-terminal variant will have at least about 80% amino acid sequence identity, or at least about 85% amino acid sequence identity, or at least about 90% amino acid sequence identity, or at least about 95% amino acid sequence identity with the amino acid sequence of amino acid residues from at or about 26 to at or about 44 of FIG. 15 (SEQ ID NO:19).

"hIL-1Ra1L full sequence variant" means any hIL-1Ra1L other than a native sequence hIL-1Ra1L, which variant retains at least one biologic activity of a native sequence hIL-1Ra1L, such as the ability to bind IL-18R, and which variant has at least about 80% amino acid sequence identity, or at least about 85% amino acid sequence identity, or at least about 90% amino acid sequence identity, or at least about 95% amino acid sequence identity with the amino acid sequence of amino acid residues from at or about 26 to at or about 207 of FIG. 15 (SEQ ID NO:19). Such hIL-1Ra1L full sequence variants include, for instance, hIL-1Ra1L polypeptides wherein one or more amino acid residues are added, or deleted, internally or at the N- or C-terminus, in the sequence of amino acid residues from at or about 26 to at or about 207 of FIG. 15 (SEQ ID NO:19).

"hIL-1Ra1L fusion variant" means a chimeric hIL-1Ra1L consisting of a native sequence hIL-1Ra1L fused at its N- or C-terminus to a heterologous amino acid or amino acid sequence. In one embodiment, the hIL-1Ra1L fusion variant polypeptide consists of a native sequence of hIL-1Ra1L fused at its N-terminus or C-terminus to a heterologous amino acid or amino acid sequence, wherein the heterologous amino acid or amino acid sequence is heterologous to the native sequence, i.e. the resulting chimeric sequence is non-naturally occurring. In another embodiment, the hIL-1Ra1L fusion variant consists of the amino acid sequence of amino acids from at or about 26 to at or about 207, inclusive of FIG. 15 (SEQ ID NO:19), or the amino acid sequence of amino acid residues from at or about 1 to at or about 207, inclusive of FIG. 15 (SEQ ID NO:19), fused at its N-terminus or C-terminus to a heterologous amino acid or amino acid sequence to form a non-naturally occurring fusion protein. Such hIL-1Ra1L fusion variants include, for instance, hIL-1Ra1L polypeptides wherein a heterologous secretion leader sequence is fused to the N-terminus of the sequence of amino acid residues from at or about 26 to at or about 207 of FIG. 15 (SEQ ID NO:19), or amino acid residues from at or about 1 to at or about 207 of FIG. 15 (SEQ ID NO:19).

Human interleukin-1 receptor antagonist analog 1 long allelic variant ("hIL-1Ra1V"), hIL-1Ra1V polypeptide, and hIL-1Ra1V protein are defined as any native sequence hIL-1Ra1V or hIL-1Ra1V variant (which are further defined herein).

A "native sequence hIL-1Ra1V" means a polypeptide comprising a naturally-occurring amino acid sequence selected from the group consisting of: (1) the amino acid sequence of amino acid residues from at or about 46 to at or about 55 of FIG. 19 (SEQ ID NO:25); (2) the amino acid sequence of amino acid residues from at or about 46 to at or about 218 of FIG. 19 (SEQ ID NO:25); (3) the amino acid sequence of amino acid residues from at or about 37 to at or about 218 of FIG. 19 (SEQ ID NO:25); (4) the amino acid sequence of amino acid residues from at or about 12 to at or about 218 of FIG. 19 (SEQ ID NO:25); and (5) the amino acid sequence of any naturally-occurring truncated or secreted form or any naturally-occurring allelic variant of a polypeptide comprising the amino acid sequence of (1) or (2) or (3) or (4). In one embodiment of the invention, the native sequence hIL-1Ra1V comprises amino acids from at or about 46 to at or about 218 of FIG. 19 (SEQ ID NO:25), or amino acids from at or about 37 to at or about 218 of FIG. 19 (SEQ ID NO:25), or amino acids from at or about 12 to at or about 218 of FIG. 19 (SEQ ID NO:25), or amino acids from at or about 1 to at or about 218 of FIG. 19 (SEQ ID NO:25).

"hIL-1Ra1V variant" is defined as any hIL-1Ra1V N-terminal variant or hIL-1Ra1V full sequence variant or hIL-1Ra1V fusion variant (which are further defined herein).

"hIL-Ra1V N-terminal variant" is defined as any hIL-1Ra1V other than a native sequence hIL-1Ra1V, which variant is an active hIL-1 Ra1V, as defined below, having at least about 80% amino acid sequence identity with the amino acid sequence of amino acid residues from at or about 46 to at or about 89 of FIG. 19 (SEQ ID NO:25). Such hIL-1Ra1V N-terminal variants include, for instance, hIL-1Ra1V polypeptides wherein one or more amino acid residues are added, internally or at the N- or C-terminus, in the sequence of amino acid residues from at or about 46 to at or about 89 of FIG. 19 (SEQ ID NO:25). Ordinarily, an hIL-1Ra1V N-terminal variant will have at least about 80% amino acid sequence identity, or at least about 85% amino acid sequence identity, or at least about 90% amino acid sequence identity, or at least about 95% amino acid sequence identity with the sequence of amino acid residues from at or about 46 to at or about 89 of FIG. 19 (SEQ ID NO:25).

"hIL-1Ra1V full sequence variant" means any hIL-1Ra1V other than a native sequence hIL-1Ra1V, which variant retains at least one biologic activity of a native sequence hIL-1Ra1V, such as the ability to bind IL-18R, and which variant has at least about 80% amino acid sequence identity, or at least about 85% amino acid sequence identity, or at least about 90% amino acid sequence identity, or at least about 95% amino acid sequence identity with the sequence of amino acid residues from at or about 46 to at or about 218 of FIG. 19 (SEQ ID NO:25).

"hIL-1Ra1V fusion variant" means a chimeric hIL-1Ra1V consisting of a native sequence hIL-1Ra1V fused at its N- or C-terminus to a heterologous amino acid or amino acid sequence. In one embodiment, the hIL-1Ra1V fusion variant polypeptide consists of a native sequence of hIL-1Ra1V fused at its N-terminus or C-terminus to a heterologous amino acid or amino acid sequence, wherein the heterologous amino acid or amino acid sequence is heterologous to the native sequence, i.e. the resulting chimeric sequence is non-naturally occurring. In another embodiment, the hIL-1Ra1V fusion variant consists of the amino acid sequence of amino acids from at or about 46 to at or about 218 of FIG. 19 (SEQ ID NO:25), or the amino acid sequence of amino acids from at or about 37 to at or about 218 of FIG. 19 (SEQ ID NO:25), or the amino acid sequence of amino acids from at or about 12 to at or about 218 of FIG. 19 (SEQ ID NO:25), or the amino acid sequence of amino acids from at or about 1 to at or about 218 of FIG. 19 (SEQ ID NO:25), fused at its N-terminus or C-terminus to a heterologous amino acid sequence to form a non-naturally occurring fusion protein. Such hIL-1Ra1V fusion variants include, for instance, hIL-1Ra1V polypeptides wherein a heterologous secretion leader sequence is fused to the N-terminus of the sequence of amino acid residues from at or about 46 to at or about 218 of FIG. 19 (SEQ ID NO:25), or amino acid residues from at or about 37 to at or about 218 of FIG. 19 (SEQ ID NO:25), or amino acid residues from at or about 12 to at or about 218 of FIG. 19 (SEQ ID NO:25), or amino acid residues from at or about 1 to at or about 218 of FIG. 19 (SEQ ID NO:25).

Human interleukin-1 receptor antagonist analog 1 short ("hIL-1Ra1S"), hIL-1Ra1S polypeptide, and hIL-1Ra1S protein are defined as any native sequence hIL-1Ra1S or hIL-1Ra1S variant (which are further defined herein).

A "native sequence hIL-1Ra1S" means a polypeptide comprising a naturally-occurring amino acid sequence selected from the group consisting of: (1) the amino acid sequence of amino acid residues from at or about 1 to at or about 38 of FIG. 16 (SEQ ID NO:21); (2) the amino acid sequence of amino acid residues from at or about 26 to at or about 167 of FIG. 16 (SEQ ID NO:21); (3) the amino acid sequence of amino acid residues from at or about 39 to at or about 167 of FIG. 16 (SEQ ID NO:21); (4) the amino acid sequence of amino acid residues from at or about 47 to at or about 167 of FIG. 16 (SEQ ID NO:21); and (5) the amino acid sequence of any naturally-occurring truncated or secreted form or any naturally-occurring allelic variant of a polypeptide comprising the amino acid sequence of (1) or (2) or (3) or (4). In one embodiment of the invention, the native sequence hIL-1Ra1S comprises amino acids from at or about 26 to at or about 167 of FIG. 16 (SEQ ID NO:21), or amino acids from at or about 1 to at or about 167 of FIG. 16 (SEQ ID NO:21). In another embodiment, the native sequence hIL-1Ra1S consists of amino acids from at or about 47 to at or about 167 of FIG. 16 (SEQ ID NO:21) or amino acids from at or about 39 to at or about 167 of FIG. 16 (SEQ ID NO:21).

"hIL-1Ra1S fusion variant" and "hIL-1Ra1S variant" mean a chimeric hIL-1Ra1S consisting of a native sequence hIL-1Ra1S fused at its N-terminus or C-terminus to a heterologous amino acid or amino acid sequence. In one embodiment, the hIL-1Ra1S fusion variant polypeptide consists of a native sequence of hIL-1Ra1S fused at its N-terminus or C-terminus to a heterologous amino acid or amino acid sequence, wherein the heterologous amino acid or amino acid sequence is heterologous to the native sequence, i.e. the resulting chimeric sequence is non-naturally occurring. In another embodiment, the hIL-1Ra1S fusion variant consists of the amino acid sequence of amino acids from at or about 47 to at or about 167 of FIG. 16 (SEQ ID NO:21), or the amino acid sequence of amino acids from at or about 39 to at or about 167 of FIG. 16 (SEQ ID NO:21), fused at its N-terminus or C-terminus to a heterologous amino acid or amino acid sequence to form a non-naturally occurring fusion protein. Such hIL-1Ra1S fusion variants include, for instance, hIL-1Ra1S polypeptides wherein a heterologous secretion leader sequence is fused to the N-terminus of the sequence of amino acid residues from at or about 47 to at or about 167 of FIG. 16 (SEQ ID NO:21), or amino acid residues from at or about 39 to at or about 167 of FIG. 16 (SEQ ID NO:21).

Human interleukin-1 receptor antagonist analog 2 ("hIL-1Ra2"), hIL-1Ra2 polypeptide, and hIL-1Ra2 protein are defined as any native sequence hIL-1Ra2 or hIL-1Ra2 fusion variant (which are further defined herein).

A "native sequence hIL-1Ra2" means (1) a polypeptide comprising the amino acid sequence of amino acid residues from at or about 1 to at or about 134 of FIG. 5 (SEQ ID NO:10) or (2) a polypeptide consisting of a naturally-occurring truncated or secreted form of the polypeptide of (1). In one embodiment of the invention, the native sequence hIL-1Ra2 consists of amino acids from at or about 27 to at or about 134 of FIG. 5 (SEQ ID NO:10), or amino acids from at or about 1 to at or about 134 of FIG. 5 (SEQ ID NO:10).

"hIL-1Ra2 fusion variant" and "hIL-1Ra2 variant" mean a chimeric hIL-1Ra2 consisting of a native sequence hIL-1Ra2 fused at its N-terminus or C-terminus to a heterologous amino acid or amino acid sequence. In one embodiment, the hIL-1Ra2 fusion variant polypeptide consists of a native sequence of hIL-1Ra2 fused at its N-terminus or C-terminus to a heterologous amino acid or amino acid sequence, wherein the heterologous amino acid or amino acid sequence is heterologous to the native sequence, i.e. the resulting chimeric sequence is non-naturally occurring. In another embodiment, the hIL-1Ra2 variant consists of the amino acid sequence of amino acids from at or about 27 to at or about 134 of FIG. 5 (SEQ ID NO:10), or amino acids from at or about 1 to at or about 134 of FIG. 5 (SEQ ID NO:10), fused at its N-terminus or C-terminus to a heterologous amino acid or amino acid sequence to form a non-naturally occurring fusion protein. Such hIL-1Ra2 fusion variants include, for instance, hIL-1Ra2 polypeptides wherein a heterologous secretion leader sequence is fused to the N-terminus of the sequence of amino acids from at or about 27 to at or about 134 of FIG. 5 (SEQ ID NO:10), or amino acids from at or about 1 to at or about 134 of FIG. 5 (SEQ ID NO:10).

Human interleukin-1 receptor antagonist analog 3 ("hIL-1Ra3"), hIL-1Ra3 polypeptide, and hIL-1Ra3 protein are defined as any native sequence hIL-1Ra3 or variant hIL-1Ra3 (which are further defined herein).

A "native sequence hIL-1Ra3" means a polypeptide comprising an amino acid sequence selected from the group consisting of: (1) the amino acid sequence of amino acid residues from at or about 95 to at or about 134 of FIG. 7 (SEQ ID NO:13); (2) the amino acid sequence of amino acid residues from at or about 34 to at or about 155 of FIG. 7 (SEQ ID NO:13); and (3) the amino acid sequence of any naturally-occurring truncated or secreted form or any naturally-occurring allelic variant of a polypeptide comprising the amino acid sequence of (1) or (2). In one embodiment of the invention, the native sequence hIL-1Ra3 comprises amino acids from at or about 34 to at or about 155 of FIG. 7 (SEQ ID NO:13), or amino acids from at or about 2 to at or about 155 of FIG. 7 (SEQ ID NO:13).

"hIL-1Ra3 variant" is defined as any hIL-1Ra3 C-terminal variant or hIL-1Ra3 full sequence variant (which are further defined herein).

"hIL-1Ra3 C-terminal variant" means any hIL-1Ra3 other than a native sequence hIL-1Ra3, which variant is an active hIL-1Ra3, as defined below, having at least about 80% amino acid sequence identity with the amino acid sequence of amino acid residues from at or about 95 to at or about 134 of FIG. 7 (SEQ ID NO:13) or the amino acid sequence of amino acid residues from at or about 80 to at or about 155 of FIG. 7 (SEQ ID NO:13). Such hIL-1Ra3 C-terminal variants include, for instance, hIL-1Ra3 polypeptides wherein one or more amino acid residues are added, or deleted, internally or at the N- or C-terminus, in the sequence of amino acid residues from at or about 95 to at or about 134 of FIG. 7 (SEQ ID NO:13) or in the sequence of amino acid residues from at or about 80 to at or about 155 of FIG. 7 (SEQ ID NO:13). Ordinarily, an hIL-1Ra3 C-terminal variant will have at least about 80% amino acid sequence identity, or at least about 85% amino acid sequence identity, or at least about 90% amino acid sequence identity, or at least about 95% amino acid sequence identity with the amino acid sequence of amino acid residues from at or about 95 to at or about 134 of FIG. 7 (SEQ ID NO:13) or the amino acid sequence of amino acid residues from at or about 80 to at or about 155 of FIG. 7 (SEQ ID NO:13).

"hIL-1Ra3 full sequence variant" means any hIL-1Ra3 other than a native sequence hIL-1Ra3, which variant retains at least one biologic activity of a native sequence hIL-1Ra3, such as the ability to bind IL-1R, and which variant has at least about 80% amino acid sequence identity, or at least about 85% amino acid sequence identity, or at least about 90% amino acid sequence identity, or at least about 95% amino acid sequence identity with the amino acid sequence of amino acid residues from at or about 34 to at or about 155 of FIG. 7 (SEQ ID NO:13) or the amino acid sequence of amino acid residues from at or about 2 to at or about 155 of FIG. 7 (SEQ ID NO:13). Such hIL-1Ra3 full sequence variants include, for instance, hIL-1Ra3 polypeptides wherein one or more amino acid residues are added, or deleted, internally or at the N- or C-terminus, in the sequence of amino acid residues from at or about 34 to at or about 155 of FIG. 7 (SEQ ID NO:13) or the amino acid sequence of amino acid residues from at or about 2 to at or about 155 of FIG. 7 (SEQ ID NO:13).

Murine interleukin-1 receptor antagonist analog 3 ("mIL-1Ra3"), mIL-1Ra3 polypeptide, and mIL-1Ra3 protein are defined as any native sequence mIL-1Ra3 or variant mIL-1Ra3.

A "native sequence mIL-1Ra3" means a polypeptide comprising an amino acid sequence selected from the group consisting of: (1) the amino acid sequence of amino acid residues from at or about 95 to at or about 134 of FIG. 9 (SEQ ID NO:16); (2) the amino acid sequence of amino acid residues from at or about 34 to at or about 155 of FIG. 9 (SEQ ID NO:16); and (3) the amino acid sequence of any naturally-occurring truncated or secreted form or naturally-occurring allelic variant of a polypeptide comprising the amino acid sequence of (1) or (2). In one embodiment of the invention, the native sequence mIL-1Ra3 comprises amino acids from at or about 34 to at or about 155 of FIG. 9 (SEQ ID NO:16).

"mIL-1Ra3 variant" is defined as any mIL-1Ra3 C-terminal variant or mIL-1Ra3 full sequence variant (which are further defined herein).

"mIL-1Ra3 C-terminal variant" means any mIL-1Ra3 other than a native sequence mIL-1Ra3, which variant is an active mIL-1Ra3, as defined below, having at least about 80% amino acid sequence identity with the amino acid sequence of amino acids from at or about 95 to at or about 134 of FIG. 9 (SEQ ID NO:16). Such mIL-1Ra3 C-terminal variants include, for instance, mIL-1Ra3 polypeptides wherein one or more amino acid residues are added, or deleted, internally or at the N- or C-terminus, in the sequence of amino acids from at or about 95 to at or about 134 of FIG. 9 (SEQ ID NO:16). Ordinarily, an mIL-1Ra3 C-terminal variant will have at least about 80% amino acid sequence identity, or at least about 85% amino acid sequence identity, or at least about 90% amino acid sequence identity, and or at least about 95% amino acid sequence identity with the amino acid sequence of amino acids 95 to 134 of FIG. 9 (SEQ ID NO:16).

"mIL-1Ra3 full sequence variant" means any mIL-1Ra3 other than a native sequence mIL-1Ra3, which variant retains at least one biologic activity of a native sequence mIL-1Ra3, such as the ability to bind IL-1R, and which variant has at least about 85% amino acid sequence identity, or at least about 90% amino acid sequence identity, or at least about 95% sequence identity with the amino acid sequence of amino acid residues from at or about 34 to at or about 155 of FIG. 9 (SEQ ID NO:16) or the amino acid sequence of amino acid residues from at or about 2 to at or about 155 of FIG. 9 (SEQ ID NO:16). Such mIL-1Ra3 full sequence variants include, for instance, mIL-1Ra3 polypeptides wherein one or more amino acid residues are added, or deleted, internally or at the N- or C-terminus, in the sequence of amino acid residues from at or about 34 to at or about 155 of FIG. 9 (SEQ ID NO:16) or in the sequence of amino acid residues from at or about 2 to at or about 155 of FIG. 9 (SEQ ID NO:16).

"Human interleukin-1-like polypeptide", "hIL-1lp", "hIL-1lp polypeptide", "hIL-1lp protein", "human interleukin-1 receptor antagonist analog", "hIL-1Raa", "hIL-1Raa polypeptide", and "hIL-1Raa protein" are defined as any hIL-1Ra1, hIL-1Ra2 or hIL-1Ra3 polypeptide.

"Native sequence hIL-1lp" and "native sequence hIL-1Raa" are defined as any polypeptide that comprises a native sequence hIL-1Ra1, hIL-1Ra2, or hIL-1Ra3.

"hIL-1lp variant" is defined as any polypeptide that comprises a variant of hIL-1Ra1, hIL-1Ra2, or hIL-1Ra3.

"Interleukin-1 receptor", "interleukin-1 receptor polypeptide", "interleukin-1 receptor protein", "IL-1 receptor", "IL-1R", "IL-1R polypeptide", and "IL-1R protein", are defined as the family of cell surface proteins that bind to interleukin-1 (IL-1) and/or function in IL-1-induced signal transduction in a given species, such as human or mouse. IL-1R includes the human T cell-expressed IL-1 receptor disclosed in Sims, et al., *Proc. Natl. Acad. Sci.* (*USA*), 86: 8946-8950 (1989).

"Interleukin-18 receptor", "interleukin-18 receptor polypeptide", "interleukin-18 receptor protein", "IL-18 receptor", "IL-18R", "IL-18R polypeptide", and "IL-18R protein", are defined as the family of cell surface proteins that bind to interleukin-18 (IL-18) and/or function in IL-18-induced signal transduction in a given species, such as human or mouse. IL-18R includes the IL-1 receptor related protein (IL-1Rrp) described in Torigoe et al., *J. Biol. Chem.*, 272:

25737-25742 (1997) and the IL-18 receptor accessory protein-like molecule (IL-18RAcPL) described in Born et al., *J. Biol. Chem.*, 273: 29445-29450 (1998).

"Interleukin-1-like family" and "IL-1-like family" are used to indicate the family of polypeptides related to the ligands of IL-1R or IL-18R. The IL-1-like family includes IL-1 receptor agonists and antagonists and related polypeptides such as IL-1α (described in Bazan et al., *Nature*, 379: 591 (1996), IL-1β (Bazan et al.), IL-18 (interferon-γ inducing factor)(IGIF)(Bazan et al.), IL-1 receptor antagonist polypeptides such as secretory IL-1Ra (sIL-1Ra)(described in Eisenberg et al., *Nature*, 343: 341-346 (1990)) and intracellular IL-1Ra (icIL-1Ra) (described in Haskill et al., *Proc. Natl. Acad. Sci.* (*USA*), 88: 3681-3685 (1991)), and the IL-1lp polypeptides of the invention.

"Percent (%) amino acid sequence identity" with respect to the IL-1lp sequences identified herein is defined as the percentage of amino acid residues in a candidate sequence that are identical with the amino acid residues in an IL-1lp sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For purposes herein, however, % amino acid sequence identity values are obtained as described below by using the sequence comparison computer program ALIGN-2, wherein the complete source code for the ALIGN-2 program is provided in Tables 3A-3Q. The ALIGN-2 sequence comparison computer program was authored by Genentech, Inc. and the source code shown in Tables 3A-3Q has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Tables 3A-3Q. The ALIGN-2 program should be compiled for use on a UNIX operating system, preferably digital UNIX V4.0D. All sequence comparison parameters are set by the ALIGN-2 program and do not vary.

For purposes herein, the % amino acid sequence identity of a given amino acid sequence A to, with, or against a given amino acid sequence B (which also can be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. As examples of % amino acid sequence identity calculations, Tables 2A-2B demonstrate how to calculate the % amino acid sequence identity of the amino acid sequence designated "Comparison Protein" to the amino acid sequence designated "PRO".

Unless specifically stated otherwise, all % amino acid sequence identity values used herein are obtained as described above using the ALIGN-2 sequence comparison computer program. However, % amino acid sequence identity may also be determined using the sequence comparison program NCBI-BLAST2 (Altschul et al., *Nucleic Acids Res.* 25:3389-3402 (1997)). The NCBI-BLAST2 sequence comparison program may be downloaded from http://www.ncbi.nlm.nih.gov. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for amino acid sequence comparisons, the % amino acid sequence identity of a given amino acid sequence A to, with, or against a given amino acid sequence B (which also can be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program NCBI-BLAST2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

"Percent (%) nucleic acid sequence identity" with respect to the IL-1lp polypeptide-encoding nucleic acid sequences identified herein is defined as the percentage of nucleotides in a candidate sequence that are identical with the nucleotides in an IL-1lp polypeptide-encoding nucleic acid sequence, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For purposes herein, however, % nucleic acid sequence identity values are obtained as described below by using the sequence comparison computer program ALIGN-2, wherein the complete source code for the ALIGN-2 program is provided in Tables 3A-3Q. The ALIGN-2 sequence comparison computer program was authored by Genentech, Inc. and the source code shown in Tables 3A-3Q has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Tables 3A-3Q. The ALIGN-2 program should be compiled for use on a UNIX operating system, preferably digital UNIX V4.0D. All sequence comparison parameters are set by the ALIGN-2 program and do not vary.

For purposes herein, the % nucleic acid sequence identity of a given nucleic acid sequence C to, with, or against a given nucleic acid sequence D (which also can be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program ALIGN-2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C. As examples of % nucleic acid sequence identity calculations, Tables 2C-2D demonstrate how to calculate the % nucleic acid sequence identity of the nucleic acid sequence designated "Comparison DNA" to the nucleic acid sequence designated "PRO-DNA".

Unless specifically stated otherwise, all % nucleic acid sequence identity values used herein are obtained as described above using the ALIGN-2 sequence comparison computer program. However, % nucleic acid sequence identity may also be determined using the sequence comparison program NCBI-BLAST2 (Altschul et al., *Nucleic Acids Res.* 25:3389-3402 (1997)). The NCBI-BLAST2 sequence comparison program may be downloaded from http://www.ncbi.nlm.nih.gov. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for sequence comparisons, the % nucleic acid sequence identity of a given nucleic acid sequence C to, with, or against a given nucleic acid sequence D (which also can be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program NCBI-BLAST2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

The term "positives", in the context of the amino acid sequence identity comparisons performed as described above, includes amino acid residues in the sequences compared that are not only identical, but also those that have similar properties. Amino acid residues that score a positive value to an amino acid residue of interest are those that are either identical to the amino acid residue of interest or are a preferred substitution (as defined in Table 1 below) of the amino acid residue of interest.

For purposes herein, the % value of positives of a given amino acid sequence A to, with, or against a given amino acid sequence B (which also can be phrased as a given amino acid sequence A that has or comprises a certain % positives to, with, or against a given amino acid sequence B) is calculated as follows:

100 times the fraction X/Y where X is the number of amino acid residues scoring a positive value as defined above by the sequence alignment program ALIGN-2 in that program's alignment of A and B, and where Y is the total number of amino acid residues in B. It will be appreciated that where the length of amino acid sequence A is not equal to the length of amino acid sequence B, the % positives of A to B will not equal the % positives of B to A.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the IL-11p natural environment will not be present. Ordinarily, however, isolated polypeptide will be prepared by at least one purification step.

An "isolated" nucleic acid molecule encoding a IL-11p polypeptide is a nucleic acid molecule that is identified and separated from at least one contaminant nucleic acid molecule with which it is ordinarily associated in the natural source of the IL-11p-encoding nucleic acid. An isolated IL-11p-encoding nucleic acid molecule is other than in the form or setting in which it is found in nature. Isolated nucleic acid molecules therefore are distinguished from the IL-11p-encoding nucleic acid molecule as it exists in natural cells. However, an isolated nucleic acid molecule encoding a IL-11p polypeptide includes IL-11p-encoding nucleic acid molecules contained in cells that ordinarily express IL-11p where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "antibody" is used in the broadest sense and specifically covers single anti-IL-11p monoclonal antibodies (including agonist, antagonist, and neutralizing antibodies) and anti-IL-11p antibody compositions with polyepitopic specificity. The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50% (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml),0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "epitope tagged" when used herein refers to a chimeric polypeptide comprising an IL-1lp polypeptide fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or igG-4 subtypes, IgA (including IgA-1 and IgA-2), IgE, IgD or IgM.

"Active" or "activity" for the purposes herein refers to form(s) of IL-1lp which retain one or more of the biologic activities of native or naturally-occurring IL-1lp, or which exhibit immunological cross-reactivity with a native or naturally-occurring IL-1lp.

As used herein, a "biologic activity" or "biological activity" of an IL-1lp means any effector function exhibited by the IL-1lp in the physiology or pathophysiology of a mammal, excluding any immunogenic or antigenic functions of the IL-1lp. Immunogenic and antigenic functions of an IL-1lp refer to the ability of the IL-1lp to generate a humoral or cell-mediated immune response specific to the IL-1lp, and the ability of the IL-1lp to specifically recognize and interact with anti-IL-1lp antibodies, B cells or T cells, respectively, in a mammal.

As used herein, "immunological cross-reactivity" with an IL-1lp means that the candidate polypeptide is capable of competitively inhibiting the binding of the IL-1lp to polyclonal or monoclonal antibodies raised against the IL-1lp.

In one embodiment, IL-1lp activity includes the ability to agonize or antagonize one or more biological activities of any IL-1-like family member, e.g. an IL-1lp activity that antagonizes an IL-1-mediated or IL-18-mediated inflammatory response. In another embodiment, IL-1lp activity includes the ability to bind to the IL-18 receptor and/or IL-1 receptor.

The term "antagonist" is used in the broadest sense, and includes any molecule that partially or fully blocks, inhibits, or neutralizes a biological activity of a native IL-1lp polypeptide disclosed herein. In a similar manner, the term "agonist" is used in the broadest sense and includes any molecule that mimics a biological activity of a native IL-1lp polypeptide disclosed herein. Suitable agonist or antagonist molecules specifically include agonist or antagonist antibodies or antibody fragments, fragments or amino acid sequence variants of native IL-1lp polypeptides, peptides, small organic molecules, etc.

"Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Mammal" for purposes of treatment refers to any animal classified as a mammal, including humans, domestic and farm animals, and zoo, sports, or pet animals, such as dogs, cats, cattle, horses, sheep, pigs, etc. Preferably, the mammal is human.

Administration "in combination with" one or more further therapeutic agents includes simultaneous (concurrent) and consecutive administration in any order.

The terms "inflammatory disorders" and "inflammatory diseases" are used interchangeably herein and refer to pathological states resulting in inflammation. Examples of such disorders include inflammatory skin diseases such as psoriasis and atopic dermatitis; systemic scleroderma and sclerosis; responses associated with inflammatory bowel disease (such as Crohn's disease and ulcerative colitis); ischemic reperfusion disorders including surgical tissue reperfusion injury, myocardial ischemic conditions such as myocardial infarction, cardiac arrest, reperfusion after cardiac surgery and constriction after percutaneous transluminal coronary angioplasty, stroke, and abdominal aortic aneurysms; cerebral edema secondary to stroke; cranial trauma; hypovolemic shock; asphyxia; adult respiratory distress syndrome; acute lung injury; Behcet's Disease; dermatomyositis; polymyositis; multiple sclerosis; dermatitis; meningitis; encephalitis; uveitis; osteoarthritis; autoimmune diseases such as rheumatoid arthritis, Sjorgen's syndrome, vasculitis, and insulin-dependent diabetes mellitus (IDDM); diseases involving leukocyte diapedesis; central nervous system (CNS) inflammatory disorder; meningitis; multiple organ injury syndrome secondary to septicaemia or trauma; inflammatory diseases of the liver, including alcoholic hepatitis and hepatic fibrosis; pathologic host responses to infection, including pathologic inflammation in granulomatous diseases, hepatitis, and bacterial pneumonia; antigen-antibody complex mediated diseases including glomerulonephritis; sepsis; sarcoidosis; immunopathologic responses to tissue/organ transplantation, including graft-versus host disease (GVHD); inflammations of the lung, including pleurisy, alveolitis, vasculitis, pneumonia, chronic bronchitis, bronchiectasis, diffuse panbronchiolitis, hypersensitivity pneumonitis, idiopathic pulmonary fibrosis (IPF), and cystic fibrosis; inflammation in renal diseases, including acute or chronic nephritic conditions such as lupus nephritis; pancreatitis; etc. The preferred indications include rheumatoid arthritis, osteoarthritis, sepsis, acute lung injury, adult respiratory distress syndrome, idiopathic pulmonary fibrosis, ischemic reperfusion (including surgical tissue reperfusion injury, stroke, myocardial ischemia, and acute myocardial infarction), asthma, psoriasis, graft-versus-host disease (GVHD), and inflammatory bowel disease such as ulcerative colitis.

As used herein, the terms "asthma", "asthmatic disorder", "asthmatic disease", and "bronchial asthma" refer to a condition of the lungs in which there is widespread narrowing of lower airways. "Atopic asthma" and "allergic asthma" refer to asthma that is a manifestation of an IgE-mediated hypersensitivity reaction in the lower airways, including, e.g., moderate or severe chronic asthma, such as conditions requiring the frequent or constant use of inhaled or systemic steroids to control the asthma symptoms. A preferred indication is allergic asthma.

II. Detailed Description of the Invention

The present invention provides newly identified and isolated nucleotide sequences encoding polypeptides referred to in the present application as IL-1lp. In particular, cDNAs encoding IL-1lp polypeptides have been identified and isolated, as disclosed in further detail in the Examples below.

Using NCBI-BLAST2 sequence alignment computer programs, it has been found that a full-length native sequence hIL-1Ra1 (shown in FIG. 3 and SEQ ID NO:7) has some amino acid sequence identity with human IL-1 receptor antagonist beta (hIL-1Raβ) and TANGO-77 protein, a full-length native sequence hIL-1Ra1L (shown in FIG. 15 and SEQ ID NO:19) has some amino acid sequence identity with human IL-1 receptor antagonist beta (hIL-1Raβ) and TANGO-77 protein, a full-length native sequence hIL-1Ra1V (shown in FIG. 19 and SEQ ID NO:25) has some amino acid sequence identity with human IL-1 receptor antagonist beta (hIL-1Raβ) and TANGO-77 protein, a full-length native sequence hIL-1Ra1S (shown in FIG. 16 and SEQ ID NO:21) appears to be an allelic variant of TANGO-77 protein and has some amino acid sequence identity with human IL-1 receptor antagonist beta (hIL-1Raβ), a full-length native sequence hIL-1Ra2 (shown in FIG. 5 and SEQ ID NO:10) has some amino acid sequence identity with hIL-1Raβ, a full-length native sequence hIL-1Ra3 (shown in FIG. 7 and SEQ ID NO:13) has some amino acid sequence identity with human intracellular IL-1 receptor antagonist (hicIL-1Ra), and a full-length native sequence mIL-1Ra3 (shown in FIG. 9 and SEQ ID NO:16) has some amino acid sequence identity with mouse IL-1 receptor antagonist (mIL-1Ra) and has some amino acid sequence identity with hicIL-1Ra. hIL-1Raβ is described in EP 0855404 published Jul. 29, 1998. TANGO-77 protein is described in WO 99/06426 published Feb. 11, 1999. hicIL-1Ra is described in WO 95/10298 published Apr. 20, 1995 and in Haskill et al., *Proc. Natl. Acad. Sci.* (*USA*), 88: 3681-3685 (1991). mIL-1Ra is described in Zahedi et al., *J. Immunol.*, 146: 4228-4233 (1991), Matsushime et al., *Blood,* 78: 616-623 (1991), Zahedi et al., *Cytokine,* 6: 1-9 (1994), Eisenberg et al., *Proc. Natl. Acad. Sci.* (*USA*), 88: 5232-5236 (1991) and Shuck et al., *Eur. J. Immunol.,* 21: 2775-2780 (1991). Accordingly, it is presently believed that the IL-1lp polypeptides disclosed in the present application are newly identified members of the interleukin-1-like family and possess inflammatory or anti-inflammatory activities, or other cellular response activating or inhibiting activities, typical of the IL-1-like family.

In addition to the full-length native sequence IL-1lp polypeptides described herein, it is contemplated that IL-1lp variants can be prepared. Such embodiments of the invention include all IL-1lp polypeptides that are IL-1lp variants as defined herein, such as hIL-1Ra1 variants, hIL-1Ra1L variants, hIL-1Ra1S variants, hIL-1Ra2 variants, hIL-1Ra3 variants, and mIL-1Ra3 variants.

IL-1lp variants can be prepared by introducing appropriate nucleotide changes into the IL-1lp DNA, and/or by synthesis of the desired IL-1lp polypeptide. Those skilled in the art will appreciate that amino acid changes may alter post-translational processes of the IL-1lp, such as changing the number or position of glycosylation sites or altering the membrane anchoring characteristics.

Variations in the native full-length sequence IL-1lp or in various domains of the IL-1lp described herein, can be made, for example, using any of the techniques and guidelines for conservative and non-conservative mutations set forth, for instance, in U.S. Pat. No. 5,364,934. Variations may be a substitution, deletion or insertion of one or more codons encoding the IL-1lp that results in a change in the amino acid sequence of the IL-1lp as compared with the native sequence IL-1lp. Optionally the variation is by substitution of at least one amino acid with any other amino acid in one or more of the domains of the IL-1lp. Guidance in determining which amino acid residue may be inserted, substituted or deleted without adversely affecting the desired activity may be found by comparing the sequence of the IL-1lp with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of 1 to 5 amino acids. The variation allowed may be determined by systematically making insertions, deletions or substitutions of amino acids in the sequence and testing the resulting variants for activity in the in vitro assay described in the Examples below.

Table 1 below lists conservative amino acid substitutions (under the heading of "Preferred Substitutions") that are useful in generating variants of the native sequence IL-1lp. If such substitutions result in alteration of biological activity, it is useful to introduce more substantial changes, such as the "Exemplary Substitutions" denoted in Table 1 or the substantial changes described below in reference to amino acid classes, at the active site in question.

TABLE 1

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in function or immunological identity of the IL-1lp polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis (Carter et al., *Nucl. Acids Res.*, 13:4331 (1986); Zoller et al., *Nucl. Acids Res.*, 10:6487 (1987)), cassette mutagenesis (Wells et al., *Gene*, 34:315 (1985)), restriction selection mutagenesis [Wells et al., *Philos. Trans. R. Soc. London SerA,* 317:415 (1986)] or other known techniques can be performed on the cloned DNA to produce the IL-1lp variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, *Science*, 244: 1081-1085 (1989)]. Alanine is also typically preferred because it is the most common amino acid. Further, it is frequently found in both buried and exposed positions [Creighton, *The Proteins*, (W.H. Freeman & Co., N.Y.); Chothia, *J. Mol. Biol.*, 150:1 (1976)]. If alanine substitution does not yield adequate amounts of variant, an isoteric amino acid can be used.

Covalent modifications of IL-1lp are included within the scope of this invention. One type of covalent modification includes reacting targeted amino acid residues of an IL-1lp polypeptide with an organic derivatizing agent that is capable of reacting with selected side chains or the N- or C-terminal residues of the IL-1lp. Derivatization with bifunctional agents is useful, for instance, for crosslinking IL-1lp to a water-insoluble support matrix or surface for use in the method for purifying anti-IL-1lp antibodies, and vice-versa. Commonly used crosslinking agents include, e.g., 1,1-bis (diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio] propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties*, W.H. Freeman & Co., San Francisco, pp. 79-86 (1983)], acetylation of the N-terminal amine, and amidation of any C-terminal carboxyl group.

Another type of covalent modification of the IL-1lp polypeptide included within the scope of this invention comprises altering the native glycosylation pattern of the polypeptide. "Altering the native glycosylation pattern" is intended for purposes herein to mean deleting one or more carbohydrate moieties found in native sequence IL-1lp (either by removing the underlying glycosylation site or by deleting the glycosylation by chemical and/or enzymatic means), and/or adding one or more glycosylation sites that are not present in the native sequence IL-1lp. In addition, the phrase includes qualitative changes in the glycosylation of the native proteins, involving a change in the nature and proportions of the various carbohydrate moieties present.

Addition of glycosylation sites to the IL-1lp polypeptide may be accomplished by altering the amino acid sequence. The alteration may be made, for example, by the addition of, or substitution by, one or more serine or threonine residues to the native sequence IL-1lp (for O-linked glycosylation sites). The IL-1lp amino acid sequence may optionally be altered through changes at the DNA level, particularly by mutating the DNA encoding the IL-1lp polypeptide at preselected bases such that codons are generated that will translate into the desired amino acids.

Another means of increasing the number of carbohydrate moieties on the IL-1lp polypeptide is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem.*, pp. 259-306 (1981).

Removal of carbohydrate moieties present on the IL-1lp polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Another type of covalent modification of IL-1lp comprises linking the IL-1lp polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The IL-1lp of the present invention may also be modified in a way to form a chimeric molecule comprising IL-1lp fused to another, heterologous polypeptide or amino acid sequence.

In one embodiment, such a chimeric molecule comprises a fusion of the IL-1lp with a tag polypeptide which provides an epitope to which an anti-tag antibody can selectively bind. The epitope tag is generally placed at the amino- or carboxyl-terminus of the IL-1lp. The presence of such epitope-tagged forms of the IL-1lp can be detected using an antibody against the tag polypeptide. Also, provision of the epitope tag enables the IL-1lp to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159-2165 (1988)]; the c-myc tag and the 8F9, 3C7, 6E10, G4, B7 and 9E10 antibodies thereto [Evan et al., *Molecular and Cellular Biology*, 5:3610-3616 (1985)]; and the Herpes Simplex virus glycoprotein D (gD) tag and its antibody [Paborsky et al., *Protein Engineering*, 3(6):547-553 (1990)]. Other tag polypeptides include the Flag-peptide [Hopp et al., *BioTechnology*, 6:1204-1210 (1988)]; the KT3 epitope peptide [Martin et al., *Science*, 255:192-194 (1992)]; an α-tubulin epitope peptide [Skinner et al., *J. Biol. Chem.*, 266:15163-15166 (1991)]; and the T7 gene 10 protein peptide tag [Lutz-Freyermuth et al., *Proc. Natl. Acad. Sci. USA*, 87:6393-6397 (1990)].

In an alternative embodiment, the chimeric molecule may comprise a fusion of the IL-1lp with an immunoglobulin or a particular region of an immunoglobulin. For a bivalent form of the chimeric molecule (also referred to as an immunoadhesin), such a fusion could be to the Fc region of an IgG molecule. The Ig fusions preferably include the substitution of a soluble form of an IL-1lp polypeptide in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995.

In one aspect, the invention provides an isolated nucleic acid comprising DNA encoding an IL-1lp polypeptide that retains at least one biologic activity of a native sequence IL-1lp, such as the IL-1R binding activity of a native sequence hIL-1Ra3 or mIL-1Ra3, or the IL-18R binding activity of a native sequence hIL-1Ra1, hIL-1Ra1L, or hIL-1Ra1V, which DNA has at least at or about 80% sequence identity, or at least at or about 85% sequence identity, or at least at or about 90% sequence identity, or at least at or about 95% sequence identity to (a) a DNA molecule selected from the group consisting of: (1) a DNA molecule encoding an IL-1lp polypeptide comprising amino acid residues from at or about 37 to at or about 203, inclusive of FIG. 2 (SEQ ID NO:5), (2) a DNA molecule encoding an IL-1lp polypeptide comprising amino acid residues from at or about 15 to at or about 193, inclusive of FIG. 3 (SEQ ID NO:7), (3) a DNA molecule encoding an IL-1lp polypeptide comprising amino acid residues from at or about 34 to at or about 155, inclusive of FIG. 7 (SEQ ID NO:13), (4) a DNA molecule encoding an IL-1lp polypeptide comprising amino acid residues from at or about 34 to at or about 155, inclusive of FIG. 9 (SEQ ID NO:16), (5) a DNA molecule encoding an IL-1lp polypeptide comprising amino acid residues from at or about 26 to at or about 207, inclusive of FIG. 15 (SEQ ID NO:19), and (6) a DNA molecule encoding an IL-1lp polypeptide comprising amino acid residues from at or about 46 to at or about 218 of FIG. 19 (SEQ ID NO:25), or (b) the complement of the DNA molecule of (a).

In another aspect, the invention provides an isolated nucleic acid comprising DNA encoding an IL-1lp polypeptide that retains at least one biologic activity of a native sequence IL-1lp, such as the IL-18R binding activity of a native sequence hIL-1Ra1, hIL-1Ra1L, or hIL-1Ra1V, which DNA has at least at or about 80% sequence identity, or at least at or about 85% sequence identity, or at least at or about 90% sequence identity, or at least at or about 95% sequence identity to (a) a DNA molecule selected from the group consisting of: (1) a DNA molecule encoding an IL-1lp polypeptide comprising amino acid residues from at or about 1 to at or about 207, inclusive of FIG. 15 (SEQ ID NO:19), and (2) a DNA molecule encoding an IL-1lp polypeptide comprising amino acid residues from at or about 1 to at or about 218 of FIG. 19 (SEQ ID NO:25), or (b) the complement of the DNA molecule of (a).

In another aspect, the invention provides an isolated nucleic acid comprising DNA encoding an IL-1lp polypeptide that retains at least one biologic activity of a native sequence IL-1lp, such as the IL-18R binding activity of a native sequence hIL-1Ra1, or the IL-1R binding activity of a native sequence hIL-1Ra3 or mIL-1Ra3, which DNA has at least at or about 80% sequence identity, or at least at or about 85% sequence identity, or at least at or about 90% sequence identity, or at least at or about 95% sequence identity to (a) a DNA molecule selected from the group consisting of: (1) a DNA molecule encoding an IL-1lp polypeptide comprising amino acid residues from at or about 95 to at or about 134, inclusive of FIG. 7 (SEQ ID NO:13), and (2) a DNA molecule encoding an IL-1lp polypeptide comprising amino acid residues from at or about 95 to at or about 134, inclusive of FIG. 9 (SEQ ID NO:16), or (b) the complement of the DNA molecule of (a).

In another aspect, the invention provides an isolated nucleic acid comprising DNA encoding an IL-1lp polypeptide that retains at least one biologic activity of a native sequence IL-1lp, such as the IL-18R binding activity of a native sequence hIL-1Ra1, or the IL-1R binding activity of a native sequence hIL-1Ra3 or mIL-1Ra3, which DNA has at least at or about 80% sequence identity, or at least at or about 85% sequence identity, or at least at or about 90% sequence identity, or at least at or about 95% sequence identity to (a) a DNA molecule encoding an IL-1lp polypeptide comprising amino acid residues from at or about 80 to at or about 155, inclusive of FIG. 7 (SEQ ID NO:13), or (b) the complement of the DNA molecule of (a).

In another aspect, the invention provides an isolated nucleic acid comprising DNA encoding an IL-1lp polypeptide that retains at least one biologic activity of a native sequence IL-1lp, such as the IL-18R binding activity of a native sequence hIL-1Ra1, or the IL-1R binding activity of a native sequence hIL-1Ra3 or mIL-1Ra3, which DNA has at least at or about 80% sequence identity, or at least at or about 85% sequence identity, or at least at or about 90% sequence identity, or at least at or about 95% sequence identity to (a) a DNA molecule selected from the group consisting of: (1) a DNA molecule encoding an IL-1lp polypeptide comprising amino acid residues from at or about 2 to at or about 155, inclusive of FIG. 7 (SEQ ID NO:13), and (2) a DNA molecule encoding an IL-1lp polypeptide comprising amino acid residues from at or about 2 to at or about 155, inclusive of FIG. 9 (SEQ ID NO:16), or (b) the complement of the DNA molecule of (a).

In another aspect, the invention provides an isolated nucleic acid comprising DNA having at least at or about 80% sequence identity, or at least at or about 85% sequence identity, or at least at or about 90% sequence identity, or at least at or about 95% sequence identity to (a) a DNA molecule selected from the group consisting of: (1) a DNA molecule encoding an IL-1lp polypeptide comprising amino acid residues from at or about 95 to at or about 134, inclusive of FIG. 7 (SEQ ID NO:13), and (2) a DNA molecule encoding an IL-1lp polypeptide comprising amino acid residues from at or about 95 to at or about 134, inclusive of FIG. 9 (SEQ ID NO:16), or (b) the complement of the DNA molecule of (a).

In another aspect, the invention provides an isolated nucleic acid comprising DNA having at least at or about 80% sequence identity, or at least at or about 85% sequence identity, or at least at or about 90% sequence identity, or at least at or about 95% sequence identity to (a) a DNA molecule encoding an IL-1lp polypeptide comprising amino acid residues from at or about 80 to at or about 155, inclusive of FIG. 7 (SEQ ID NO:13), or (b) the complement of the DNA molecule of (a).

In another aspect, the invention provides an isolated nucleic acid comprising DNA having at least at or about 80% sequence identity, or at least at or about 85% sequence identity, or at least at or about 90% sequence identity, or at least at or about 95% sequence identity to (a) a DNA molecule selected from the group consisting of: (1) a DNA molecule encoding an IL-1lp polypeptide comprising amino acid residues from at or about 2 to at or about 155, inclusive of FIG. 7 (SEQ ID NO: 13), and (2) a DNA molecule encoding an IL-1lp polypeptide comprising amino acid residues from at or about 2 to at or about 155, inclusive of FIG. 9 (SEQ ID NO:16), or (b) the complement of the DNA molecule of (a).

In another aspect, the invention concerns an isolated nucleic acid molecule encoding an IL-1lp polypeptide, comprising DNA hybridizing to the complement of a nucleic acid sequence selected from the group consisting of: (1) the nucleic acid sequence consisting of nucleotide positions from at or about 238 to at or about 465 in the sense strand of FIG. 7 (SEQ ID NO:12); (2) the nucleic acid sequence consisting of nucleotide positions from at or about 427 to at or about 609 in the sense strand of FIG. 9 (SEQ ID NO:15); and (3) the nucleic acid sequence consisting of nucleotide positions from at or about 79 to at or about 135 in the sense strand of FIG. 15 (SEQ ID NO:18). Preferably, hybridization occurs under stringent hybridization and wash conditions.

In another aspect, the invention concerns an isolated nucleic acid molecule, comprising DNA that is at least 90 nucleotides in length and that hybridizes to the complement of a nucleic acid sequence selected from the group consisting of: (1) the nucleic acid sequence consisting of nucleotide positions from at or about 238 to at or about 465 in the sense strand of FIG. 7 (SEQ ID NO:12); (2) the nucleic acid sequence consisting of nucleotide positions from at or about 427 to at or about 609 in the sense strand of FIG. 9 (SEQ ID NO:15); and (3) the nucleic acid sequence consisting of nucleotide positions from at or about 115 to at or about 135 in the sense strand of FIG. 15 (SEQ ID NO:18). Preferably, hybridization occurs under stringent hybridization and wash conditions.

In another aspect, the invention concerns an isolated nucleic acid molecule comprising DNA encoding an IL-1lp polypeptide that retains at least one biologic activity of a native sequence IL-1lp, such as the IL-1R binding activity of a native sequence hIL-1Ra3 or mIL-1Ra3, or the IL-18R binding activity of a native sequence hIL-1Ra1, hIL-1Ra1L, or hIL-1Ra1V, which DNA hybridizes to the complement of a nucleic acid sequence selected from the group consisting of: (1) the nucleic acid sequence consisting of nucleotide positions from at or about 118 to at or about 231 in the sense strand of FIG. 2 (SEQ ID NO:4); (2) the nucleic acid sequence consisting of nucleotide positions from at or about 100 to at or about 465 in the sense strand of FIG. 7 (SEQ ID NO:12); (3) the nucleic acid sequence consisting of nucleotide positions from at or about 244 to at or about 609 in the sense strand of FIG. 9 (SEQ ID NO:15); and (4) the nucleic acid sequence consisting of nucleotide positions from at or about 208 to at or about 339 in the sense strand of FIG. 19 (SEQ ID NO:24). Preferably, hybridization occurs under stringent hybridization and wash conditions.

In another aspect, the invention concerns an isolated nucleic acid molecule comprising DNA encoding an IL-1lp polypeptide that retains at least one biologic activity of a native sequence IL-1lp, such as the IL-1R binding activity of a native sequence hIL-1Ra3 or mIL-1Ra3, which DNA hybridizes to the complement of a nucleic acid sequence selected from the group consisting of: (1) the nucleic acid sequence consisting of nucleotide positions from at or about 4 to at or about 465 in the sense strand of FIG. 7 (SEQ ID NO:12); and (2) the nucleic acid sequence consisting of nucleotide positions from at or about 148 to at or about 609 in the sense strand of FIG. 9 (SEQ ID NO:15). Preferably, hybridization occurs under stringent hybridization and wash conditions.

In a further aspect, the invention concerns an isolated nucleic acid molecule comprising DNA encoding an IL-1lp polypeptide that retains at least one biologic activity of a native sequence IL-1lp, such as the IL-1R binding activity of a native sequence hIL-1Ra3 or mIL-1Ra3, or the IL-18R binding activity of a native sequence hIL-1Ra1, hIL-1Ra1L, or hIL-1Ra1V, which DNA has at least at or about 80% sequence identity, or at least at or about 85% sequence identity, or at least at or about 90% sequence identity, or at least at or about 95% sequence identity to (a) a DNA encoding an IL-1lp, such as a mature IL-1lp polypeptide, encoded by the cDNA insert in the vector deposited as ATCC Deposit No. 203588 (DNA85066-2534), ATCC Deposit No. 203587 (DNA96786-2534), ATCC Deposit No. 203589 (DNA96787-2534), ATCC Deposit No. 203590 (DNA92505-2534), ATCC Deposit No. 203846 (DNA102043-2534), or ATCC Deposit No. 203973 (DNA114876-2534), or (b) the complement of the DNA molecule of (a). In a preferred embodiment, the nucleic acid comprises a DNA encoding an IL-1lp polypeptide, such as a mature IL-1lp polypeptide, encoded by the cDNA insert in the vector deposited as ATCC Deposit No. 203588 (DNA85066-2534), ATCC Deposit No. 203587 (DNA96786-2534), ATCC Deposit No. 203586 (DNA92929-2534), ATCC Deposit No. 203589 (DNA96787-2534), ATCC Deposit No. 203590 (DNA92505-2534), ATCC Deposit No. 203846 (DNA102043-2534), ATCC Deposit No. 203973 (DNA114876-2534), or ATCC Deposit No. 203855 (DNA102044-2534).

In a further aspect, the invention concerns an isolated nucleic acid molecule comprising DNA encoding an IL-1lp polypeptide that retains at least one biologic activity of a native sequence IL-1lp, such as the IL-1R binding activity of a native sequence hIL-1Ra3 or mIL-1Ra3, or the IL-18R binding activity of a native sequence hIL-1Ra1, hIL-1Ra1L, or hIL-1Ra1V, which DNA has at least at or about 80% sequence identity, or at least at or about 85% sequence identity, or at least at or about 90% sequence identity, or at least at or about 95% sequence identity to (a) a DNA encoding the entire amino acid sequence encoded by the longest open reading frame in the cDNA insert of a vector selected from the group consisting of the vectors deposited as ATCC Deposit No. 203588 (DNA85066-2534), ATCC Deposit No. 203587 (DNA96786-2534), ATCC Deposit No. 203589 (DNA96787-2534), ATCC Deposit No. 203590 (DNA92505-2534), ATCC Deposit No. 203846 (DNA102043-2534), and ATCC Deposit No. 203973 (DNA114876-2534), or (b) the complement of the DNA molecule of (a). In a preferred embodiment, the nucleic acid comprises (a) DNA encoding the entire amino acid sequence encoded by the longest open reading frame in the cDNA insert of a vector selected from the group consisting of the vectors deposited as ATCC Deposit No. 203588 (DNA85066-2534), ATCC Deposit No. 203587 (DNA96786-2534), ATCC Deposit No. 203586 (DNA92929-2534), ATCC Deposit No. 203589 (DNA96787-2534), and ATCC Deposit No. 203590 (DNA92505-2534), or (b) the complement of the DNA of (a). In another preferred embodiment, the nucleic acid comprises (a) DNA encoding the entire amino acid sequence encoded by the longest open reading frame in the cDNA insert of a vector selected from the group consisting of the vectors deposited as ATCC Deposit No. 203846 (DNA102043-2534), ATCC Deposit No. 203855 (DNA102044-2534), and ATCC Deposit No. 203973 (DNA114876-2534), or (b) the complement of the DNA of (a).

In another aspect, the invention concerns an isolated nucleic acid molecule comprising DNA encoding an IL-1lp polypeptide that retains at least one biologic activity of a native sequence IL-1lp, such as the IL-1R binding activity of a native sequence IL-1Ra3 or mIL-1Ra3, or the IL-18R binding activity of a native sequence hIL-1Ra1, hIL-1Ra1L, or hIL-1Ra1V, which DNA has at least at or about 80% sequence identity, or at least at or about 85% sequence identity, or at least at or about 90% sequence identity, or at least at or about 95% sequence identity to (a) DNA encoding an amino acid sequence selected from the group consisting of: (1) the entire amino acid sequence encoded by the longest open reading frame in the cDNA insert in the vector deposited as ATCC Deposit No. 203588, (2) the entire amino acid sequence, or the entire amino acid sequence excluding the 36 N-terminal amino acid residues of such sequence, encoded by the longest open reading frame in the cDNA insert in the vector deposited as ATCC Deposit No. 203587, (3) the entire amino acid sequence, or the entire amino acid sequence excluding the N-terminal amino acid residue of such sequence, encoded by the longest open reading frame in the cDNA insert in the vector deposited as ATCC Deposit No. 203589, (4) the entire amino acid sequence, or the entire amino acid sequence excluding the N-terminal amino acid residue of such sequence, encoded by the longest open reading frame in the cDNA insert in the vector deposited as ATCC Deposit No. 203590, (5) the entire amino acid sequence, or the entire amino acid sequence excluding the N-terminal amino acid residue of such sequence, or the entire amino acid sequence excluding the 34 N-terminal amino acid residues of such sequence, encoded by the longest open reading frame in the cDNA insert in the vector deposited as ATCC Deposit No. 203846, and (6) the entire amino acid sequence, or the entire amino acid sequence excluding the N-terminal amino acid residue of such sequence, or the entire amino acid sequence excluding the 45 N-terminal amino acid residues of such sequence, encoded by the longest open reading frame in the cDNA insert in the vector deposited as ATCC Deposit No. 203973, or (b) the complement of the DNA of (a).

In a preferred embodiment, the nucleic acid comprises (a) DNA encoding an amino acid sequence selected from the group consisting of: (1) the entire amino acid sequence encoded by the longest open reading frame in the cDNA insert in the vector deposited as ATCC Deposit No. 203588, (2) the entire amino acid sequence, or the entire amino acid sequence excluding the 36 N-terminal amino acid residues of such sequence, encoded by the longest open reading frame in the cDNA insert in the vector deposited as ATCC Deposit No. 203587, (3) the entire amino acid sequence, or the entire amino acid sequence excluding the N-terminal amino acid residue of such sequence, encoded by the longest open reading frame in the cDNA insert in the vector deposited as ATCC Deposit No. 203589, (4) the entire amino acid sequence, or the entire amino acid sequence excluding the N-terminal amino acid residue of such sequence, encoded by the longest open reading frame in the cDNA insert in the vector deposited as ATCC Deposit No. 203590, (5) the entire amino acid sequence, or the entire amino acid sequence excluding the N-terminal amino acid residue of such sequence, or the entire amino acid sequence excluding the 34 N-terminal amino acid residues of such sequence, encoded by the longest open reading frame in the cDNA insert in the vector deposited as ATCC Deposit No. 203846, and (6) the entire amino acid sequence, or the entire amino acid sequence excluding the N-terminal amino acid residue of such sequence, or the entire amino acid sequence excluding the 45 N-terminal amino acid residues of such sequence, encoded by the longest open reading frame in the cDNA insert in the vector deposited as ATCC Deposit No. 203973, or (b) the complement of the DNA of (a).

In a still further aspect, the invention concerns an isolated nucleic acid molecule comprising (a) DNA encoding an IL-1lp polypeptide that retains at least one biologic activity of a native sequence IL-1lp, such as the IL-18R binding activity of a native sequence hIL-1Ra1, or the IL-1R binding activity of a native sequence hIL-1Ra3 or mIL-1Ra3, and which IL-1lp polypeptide has at least at or about 80% sequence identity, or at least at or about 85% sequence identity, or at least at or about 90% sequence identity, or at least at or about 95% sequence identity to an amino acid sequence selected from the group consisting of: (1) amino acid residues from at or about 37 to at or about 203, inclusive of FIG. 2 (SEQ ID NO:5), (2) amino acid residues from at or about 15 to at or about 193, inclusive of FIG. 3 (SEQ ID NO:7), (3) amino acid residues from at or about 34 to at or about 155, inclusive of FIG. 7 (SEQ ID NO:13), (4) amino acid residues from at or about 34 to at or about 155, inclusive of FIG. 9 (SEQ ID NO:16), (5) amino acid residues from at or about 26 to at or about 207, inclusive of FIG. 15 (SEQ ID NO:19), and (6) amino acid residues from at or about 46 to at or about 218, inclusive of FIG. 19 (SEQ ID NO:25), or (b) the complement of the DNA of (a).

In a still further aspect, the invention concerns an isolated nucleic acid molecule comprising (a) DNA encoding an IL-1lp polypeptide that retains at least one biologic activity of a native sequence IL-1lp, such as the IL-18R binding activity of a native sequence hIL-1Ra1, or the IL-1R binding activity of a native sequence hIL-1Ra3 or mIL-1Ra3, and which IL-1lp polypeptide has at least at or about 80% sequence identity, or at least at or about 85% sequence identity, or at least at or about 90% sequence identity, or at least at or about 95% sequence identity to an amino acid sequence selected from the group consisting of: (1) amino acid residues from at or about 95 to at or about 134, inclusive of FIG. 7 (SEQ ID NO:13), and (2) amino acid residues from at or about 95 to at or about 134, inclusive of FIG. 9 (SEQ ID NO:16), or (b) the complement of the DNA of (a).

In a still further aspect, the invention concerns an isolated nucleic acid molecule comprising (a) DNA encoding an IL-1lp polypeptide that retains at least one biologic activity of a native sequence IL-1lp, such as the IL-18R binding activity of a native sequence hIL-1Ra1, or the IL-1R binding activity of a native sequence hIL-1Ra3 or mIL-1Ra3, and which IL-1lp polypeptide has at least at or about 80% sequence identity, or at least at or about 85% sequence identity, or at least at or about 90% sequence identity, or at least at or about 95% sequence identity to the amino acid sequence of amino acid residues from at or about 80 to at or about 155, inclusive of FIG. 7 (SEQ ID NO:13), or (b) the complement of the DNA of (a).

In a still further aspect, the invention concerns an isolated nucleic acid molecule comprising (a) DNA encoding an IL-1lp polypeptide that retains at least one biologic activity of a native sequence IL-1lp, such as the IL-18R binding activity of a native sequence hIL-1Ra1, or the IL-1R binding activity of a native sequence hIL-1Ra3 or mIL-1Ra3, and which IL-1lp polypeptide has at least at or about 80% sequence identity, or at least at or about 85% sequence identity, or at least at or about 90% sequence identity, or at least at or about 95% sequence identity to an amino acid sequence selected from the group consisting of: (1) amino acid residues from at or about 2 to at or about 155, inclusive of FIG. 7 (SEQ ID NO:13), and (2) amino acid residues from at or about 2 to at or about 155, inclusive of FIG. 9 (SEQ ID NO:16), or (b) the complement of the DNA of (a).

In a still further aspect, the invention concerns an isolated nucleic acid molecule comprising (a) DNA encoding an IL-1lp polypeptide having at least at or about 80% sequence identity, or at least at or about 85% sequence identity, or at least at or about 90% sequence identity, or at least at or about 95% sequence identity to an amino acid sequence selected from the group consisting of: (1) amino acid residues from at or about 95 to at or about 134, inclusive of FIG. 7 (SEQ ID NO:13), and (2) amino acid residues from at or about 95 to at or about 134, inclusive of FIG. 9 (SEQ ID NO:16), or (b) the complement of the DNA of (a).

In a still further aspect, the invention concerns an isolated nucleic acid molecule comprising (a) DNA encoding an IL-1lp polypeptide having at least at or about 80% sequence identity, or at least at or about 85% sequence identity, or at least at or about 90% sequence identity, or at least at or about 95% sequence identity to the amino acid sequence of amino acid residues from at or about 80 to at or about 155, inclusive of FIG. 7 (SEQ ID NO:13), or (b) the complement of the DNA of (a).

In a still further aspect, the invention concerns an isolated nucleic acid molecule comprising (a) DNA encoding an IL-1lp polypeptide having at least at or about 80% sequence identity, or at least at or about 85% sequence identity, or at least at or about 90% sequence identity, or at least at or about 95% sequence identity to an amino acid sequence selected from the group consisting of: (1) amino acid residues from at or about 2 to at or about 155, inclusive of FIG. 7 (SEQ ID NO:13), and (2) amino acid residues from at or about 2 to at or about 155, inclusive of FIG. 9 (SEQ ID NO:16), or (b) the complement of the DNA of (a).

In a still further aspect, the invention concerns an isolated nucleic acid molecule comprising (a) DNA encoding an IL-1lp polypeptide that retains at least one biologic activity of a native sequence IL-1lp, such as the IL-18R binding activity of a native sequence hIL-1Ra1, hIL-1Ra1L, or hIL-1Ra1V, and which IL-1lp polypeptide has at least at or about 80% sequence identity, or at least at or about 85% sequence identity, or at least at or about 90% sequence identity, or at least at or about 95% sequence identity to an amino acid sequence selected from the group consisting of: (1) amino acid residues from at or about 1 to at or about 207, inclusive of FIG. 15 (SEQ ID NO:19), and (2) amino acid residues from at or about 1 to at or about 218, inclusive of FIG. 19 (SEQ ID NO:25), or (b) the complement of the DNA of (a).

In a further aspect, the invention concerns an isolated nucleic acid molecule comprising DNA encoding an IL-1lp that retains at least one biologic activity of a native sequence IL-1lp, such as the IL-1R binding activity of a native sequence hIL-1Ra3 or mIL-1Ra3, or the IL-18R binding activity of a native sequence hIL-1Ra1, hIL-1Ra1L, hIL-1Ra1S, or hIL-1Ra1V, which DNA is produced by hybridizing a test DNA molecule under stringent conditions with (a) a DNA molecule encoding an IL-1lp polypeptide selected from the group consisting of: (1) an IL-1lp polypeptide comprising the sequence of amino acid residues from at or about 37 to at or about 203, inclusive of FIG. 2 (SEQ ID NO:5), (2) an IL-1lp polypeptide comprising the sequence of amino acid residues from at or about 15 to at or about 193, inclusive of FIG. 3 (SEQ ID NO:7), (3) an IL-1lp polypeptide comprising the sequence of amino acid residues from at or about 34 to at or about 155, inclusive of FIG. 7 (SEQ ID NO:13), (4) an IL-1lp polypeptide comprising the sequence of amino acid residues from at or about 34 to at or about 155, inclusive of FIG. 9 (SEQ ID NO:16), (5) an IL-1lp polypeptide comprising the sequence of amino acid residues from at or about 26 to at or about 207, inclusive of FIG. 15 (SEQ ID NO:19), and (6) an IL-1lp polypeptide comprising the sequence of amino acid residues from at or about 46 to at or about 218, inclusive of FIG. 19 (SEQ ID NO:25), or (b) the complement of the DNA molecule of (a), and, if the test DNA molecule encodes an IL-1lp that retains at least one biologic activity of a native sequence IL-1lp, such as the IL-1R binding activity of a native sequence hIL-1Ra3 or mIL-1Ra3, or the IL-18R binding activity of a native sequence hIL-1Ra1, hIL-1Ra1L, or hIL-1Ra1V, and if the test DNA molecule has at least at or about an 80% sequence identity, or at least at or about an 85% sequence identity, or at least at or about a 90% sequence identity, or at least at or about a 95% sequence identity to the DNA molecule of (a) or (b), isolating the test DNA molecule.

In another aspect, the invention provides an isolated nucleic acid molecule comprising (a) DNA encoding an a polypeptide, such as IL-1lp polypeptide, selected from the group consisting of: (1) a polypeptide, such as an hIL-1Ra1 polypeptide, comprising amino acid residues from at or about 37 to at or about 63, inclusive of FIG. 2 (SEQ ID NO:5); (2) a polypeptide, such as an hIL-1Ra1 polypeptide, comprising amino acid residues from at or about 15 to at or about 53, inclusive of FIG. 3 (SEQ ID NO:7); (3) a polypeptide, such as an hIL-1Ra2 polypeptide, comprising amino acid residues from at or about 1 to at or about 134, inclusive of FIG. 5 (SEQ ID NO:10); (4) a polypeptide comprising amino acid residues from at or about 10 to at or about 134, inclusive of FIG. 5 (SEQ ID NO:10); (5) a polypeptide, such as an hIL-1Ra2 polypeptide, consisting of amino acid residues from at or about 27 to at or about 134, inclusive of FIG. 5 (SEQ ID NO:10); (6) a polypeptide, such as an hIL-1Ra2 fusion variant polypeptide, consisting of a native amino acid sequence of hIL-1Ra2 consisting of amino acid residues from at or about 27 to at or about 134, inclusive of FIG. 5 (SEQ ID NO:10) fused at its N-terminus or C-terminus to a heterologous amino acid or amino acid sequence; (7) a polypeptide, such as an hIL-1Ra3 polypeptide, comprising amino acid residues from at or about 95 to at or about 134, inclusive of FIG. 7 (SEQ ID NO:13); and (8) a polypeptide, such as a mIL-1Ra3 polypeptide, comprising amino acid residues from at or about 95 to at or about 134, inclusive of FIG. 9 (SEQ ID NO:16); or (b) the complement of the DNA of (a).

In another aspect, the invention provides an isolated nucleic acid molecule comprising (a) DNA encoding a polypeptide, such as an IL-1lp polypeptide, selected from the group consisting of: (1) a polypeptide, such as an hIL-1Ra1L polypeptide, comprising amino acid residues from at or about 26 to at or about 44, inclusive of FIG. 15 (SEQ ID NO:19); (2) a polypeptide, such as an hIL-1Ra1L polypeptide, comprising amino acid residues from at or about 1 to at or about 44, inclusive of FIG. 15 (SEQ ID NO:19); (3) a polypeptide, such as an hIL-1Ra1L polypeptide, comprising amino acid residues from at or about 26 to at or about 78, inclusive of FIG. 15 (SEQ ID NO:19); (4) a polypeptide, such as an hIL-1Ra1L polypeptide, comprising amino acid residues from at or about 1 to at or about 78, inclusive of FIG. 15 (SEQ ID NO:19); (5) a polypeptide, such as an hIL-1Ra1S polypeptide, comprising amino acid residues from at or about 1 to at or about 38, inclusive of FIG. 16 (SEQ ID NO:21); (6) a polypeptide, such as an hIL-1Ra1V polypeptide, comprising amino acid residues from at or about 37 to at or about 55, inclusive of FIG. 19 (SEQ ID NO:25); (7) a polypeptide, such as an hIL-1Ra1V polypeptide, comprising amino acid residues from at or about 12 to at or about 55, inclusive of FIG. 19 (SEQ ID NO:25); (8) a polypeptide, such as an hIL-1Ra1V polypeptide, comprising amino acid residues from at or about 1 to at or about 55, inclusive of FIG. 19 (SEQ ID NO:25); (9) a polypeptide, such as an hIL-1Ra1V polypeptide, comprising amino acid residues from at or about 46 to at or about 55, inclusive of FIG. 19 (SEQ ID NO:25); (10) a polypeptide, such as an hIL-1Ra1V polypeptide, comprising amino acid residues from at or about 46 to at or about 89, inclusive of FIG. 19 (SEQ ID NO:25); (11) a polypeptide, such as an hIL-1Ra1V polypeptide, comprising amino acid residues from at or about 37 to at or about 89, inclusive of FIG. 19 (SEQ ID NO:25); (12) a polypeptide, such as an hIL-1Ra1V polypeptide, comprising amino acid residues from at or about 12 to at or about 89, inclusive of FIG. 19 (SEQ ID NO:25); and (13) a polypeptide, such as an hIL-1Ra1V polypeptide, comprising amino acid residues from at or about 1 to at or about 89, inclusive of FIG. 19 (SEQ ID NO:25); or (b) the complement of the DNA of (a).

In another aspect, the invention provides an isolated nucleic acid molecule comprising (a) DNA encoding a polypeptide, such as an hIL-1lp polypeptide, selected from the group consisting of: (1) a polypeptide, such as an hIL-1Ra1L polypeptide, consisting of a native amino acid sequence of hIL-1Ra1L consisting of amino acid residues from at or about 26 to at or about 207, inclusive of FIG. 15 (SEQ ID NO:19) fused at its N-terminus or C-terminus to a heterologous amino acid or amino acid sequence; (2) a polypeptide, such as an hIL-1Ra1L polypeptide, consisting of a native amino acid sequence of hIL-1Ra1L consisting of amino acid residues from at or about 1 to at or about 207, inclusive of FIG. 15 (SEQ ID NO:19) fused at its N-terminus or C-terminus to a heterologous amino acid or amino acid sequence; (3) a polypeptide, such as an hIL-1Ra1L polypeptide, consisting of amino acid residues from at or about 26 to at or about 207, inclusive of FIG. 15 (SEQ ID NO:19); (4) a polypeptide, such as an hIL-1Ra1L polypeptide, consisting of amino acid residues from at or about 1 to at or about 207, inclusive of FIG. 15 (SEQ ID NO:19); (5) a polypeptide, such as an hIL-1Ra1S fusion variant polypeptide, consisting of a native amino acid sequence of hIL-1Ra1S consisting of amino acid residues from at or about 26 to at or about 167, inclusive of FIG. 16 (SEQ ID NO:21) fused at its N-terminus or C-terminus to a heterologous amino acid or amino acid sequence; (6) a polypeptide, such as an hIL-1Ra1S polypeptide, consisting of amino acid residues from at or about 26 to at or about 167, inclusive of FIG. 16 (SEQ ID NO:21); (7) a polypeptide, such as an hIL-1Ra1S fusion variant polypeptide, consisting of a native amino acid sequence of hIL-1Ra1S consisting of amino acid residues from at or about 1 to at or about 167, inclusive of FIG. 16 (SEQ ID NO:21) fused at its N-terminus or C-terminus to a heterologous amino acid or amino acid sequence; (8) a polypeptide, such as an hIL-1Ra1S polypeptide, consisting of amino acid residues from at or about 1 to at or about 167, inclusive of FIG. 16 (SEQ ID NO:21); (9) a polypeptide, such as an hIL-1Ra1S fusion variant polypeptide, consisting of a native amino acid sequence of hIL-1Ra1S consisting of amino acid residues from at or about 39 to at or about 167, inclusive of FIG. 16 (SEQ ID NO:21) fused at its N-terminus or C-terminus to a heterologous amino acid or amino acid sequence; (10) a polypeptide, such as an hIL-1Ra1S fusion variant polypeptide, consisting of a native amino acid sequence of hIL-1Ra1S consisting of amino acid residues from at or about 47 to at or about 167, inclusive of FIG. 16 (SEQ ID NO:21) fused at its N-terminus or C-terminus to a heterologous amino acid or amino acid sequence; (11) a polypeptide, such as an hIL-1Ra1S polypeptide, consisting of amino acid residues from at or about 39 to at or about 167, inclusive of FIG. 16 (SEQ ID NO:21); (12) a polypeptide, such as an hIL-1Ra1S polypeptide, consisting of amino acid residues from at or about 47 to at or about 167, inclusive of FIG. 16 (SEQ ID NO:21); (13) a polypeptide, such as an hIL-1Ra1V polypeptide, consisting of a native amino acid sequence of hIL-1Ra1V consisting of amino acid residues from at or about 1 to at or about 218, inclusive of FIG. 19 (SEQ ID NO:25) fused at its N-terminus or C-terminus to a heterologous amino acid or amino acid sequence; (14) a polypeptide, such as an hIL-1Ra1V polypeptide, consisting of amino acid residues from at or about 1 to at or about 218, inclusive of FIG. 19 (SEQ ID NO:25); (15) a polypeptide, such as an hIL-1Ra1V polypeptide, consisting of a native amino acid sequence of hIL-1Ra1V consisting of amino acid residues from at or about 12 to at or about 218, inclusive of FIG. 19 (SEQ ID NO:25) fused at its N-terminus or C-terminus to a heterologous amino acid or amino acid sequence; (16) a polypeptide, such as an hIL-1Ra1V polypeptide, consisting of amino acid residues from at or about 12 to at or about 218, inclusive of FIG. 19 (SEQ ID NO:25); (17) a polypeptide, such as an hIL-1Ra1V fusion variant polypeptide, consisting of a native amino acid sequence of hIL-1Ra1V consisting of amino acid residues from at or about 37 to at or about 218, inclusive of FIG. 19 (SEQ ID NO:25) fused at its N-terminus or C-terminus to a heterologous amino acid or amino acid sequence; (18) a polypeptide, such as an hIL-1Ra1V fusion variant polypeptide, consisting of a native amino acid sequence of hIL-1Ra1V consisting of amino acid residues from at or about 46 to at or about 218, inclusive of FIG. 19 (SEQ ID NO:25) fused at its N-terminus or C-terminus to a heterologous amino acid or amino acid sequence; (19) a polypeptide, such as an hIL-1Ra1V polypeptide, consisting of amino acid residues from at or about 37 to at or about 218, inclusive of FIG. 19 (SEQ ID NO:25); and (20) a polypeptide, such as an hIL-1Ra1V polypeptide, consisting of amino acid residues from at or about 46 to at or about 218, inclusive of FIG. 19 (SEQ ID NO:25); or (b) the complement of the DNA of (a).

In another aspect, the invention provides an isolated DNA molecule selected from the group consisting of: (1) a DNA molecule encoding a polypeptide, such as an hIL-1Ra1 polypeptide, comprising the amino acid sequence of amino acid residues from at or about 37 to at or about 203, inclusive of FIG. 2 (SEQ ID NO:5); (2) a DNA molecule encoding a polypeptide, such as an hIL-1Ra1 polypeptide, comprising the amino acid sequence of amino acid residues from at or about 15 to at or about 193, inclusive of FIG. 3 (SEQ ID NO:7); (3) a DNA molecule encoding a polypeptide, such as an hIL-1Ra2 polypeptide, comprising the amino acid sequence of amino acid residues from at or about 1 to at or about 134, inclusive of FIG. 5 (SEQ ID NO:10); (4) a DNA molecule encoding a polypeptide comprising the amino acid sequence of amino acid residues from at or about 10 to at or about 134, inclusive of FIG. 5 (SEQ ID NO:10); (5) a DNA molecule encoding a polypeptide, such as an hIL-1Ra2 fusion variant polypeptide, consisting of a native amino acid sequence of hIL-1Ra2 consisting of amino acid residues from at or about 27 to at or about 134, inclusive of FIG. 5 (SEQ ID NO:10) fused at its N-terminus or C-terminus to a heterologous amino acid or amino acid sequence; (6) a DNA molecule encoding a polypeptide, such as an hIL-1Ra2 polypeptide, consisting of the amino acid sequence of amino acid residues from at or about 27 to at or about 134, inclusive of FIG. 5 (SEQ ID NO:10); (7) a DNA molecule encoding a polypeptide, such as an hIL-1Ra3 polypeptide, comprising the amino acid sequence of amino acid residues from at or about 95 to at or about 134, inclusive of FIG. 7 (SEQ ID NO:13); (8) a DNA molecule encoding a polypeptide, such as a mIL-1Ra3 polypeptide, comprising the amino acid sequence of amino acid residues from about 95 to at or about 134, inclusive of FIG. 9 (SEQ ID NO:16); and (9) the complement of any of the DNA molecules of (1)-(8).

In another aspect, the invention provides an isolated DNA molecule selected from the group consisting of: (1) a DNA molecule encoding a polypeptide, such as an hIL-1Ra1L polypeptide, comprising the amino acid sequence of amino acid residues from at or about 26 to at or about 207, inclusive of FIG. 15 (SEQ ID NO:19); (2) a DNA molecule encoding a polypeptide, such as an hIL-1Ra1S polypeptide, comprising the amino acid sequence of amino acid residues from at or about 26 to at or about 167, inclusive of FIG. 16 (SEQ ID NO:21); (3) a DNA molecule encoding a polypeptide, such as an hIL-1Ra1V polypeptide, comprising the amino acid sequence of amino acid residues from at or about 37 to at or about 218, inclusive of FIG. 19 (SEQ ID NO:25); (4) a DNA molecule encoding a polypeptide, such as an hIL-1Ra1V polypeptide, comprising the amino acid sequence of amino acid residues from at or about 46 to at or about 218, inclusive of FIG. 19 (SEQ ID NO:25); and (5) the complement of any of the DNA molecules of (1)-(4).

In another aspect, the invention provides an isolated DNA molecule selected from the group consisting of: (1) a DNA molecule encoding a polypeptide, such as an hIL-1Ra1L polypeptide, comprising the amino acid sequence of amino acid residues from at or about 1 to at or about 207, inclusive of FIG. 15 (SEQ ID NO:19); (2) a DNA molecule encoding a polypeptide, such as an hIL-1Ra1S polypeptide, comprising the amino acid sequence of amino acid residues from at or about 1 to at or about 167, inclusive of FIG. 16 (SEQ ID NO:21); (3) a DNA molecule encoding a polypeptide, such as an hIL-1Ra1V polypeptide, comprising the amino acid sequence of amino acid residues from at or about 12 to at or about 218, inclusive of FIG. 19 (SEQ ID NO:25); (4) a DNA molecule encoding a polypeptide, such as an hIL-1Ra1V polypeptide, comprising the amino acid sequence of amino acid residues from at or about 1 to at or about 218, inclusive of FIG. 19 (SEQ ID NO:25); and (5) the complement of any of the DNA molecules of (1)-(4).

In another aspect, the invention provides an isolated DNA molecule selected from the group consisting of: (1) a DNA molecule encoding a polypeptide, such as an hIL-1Ra3 polypeptide, comprising amino acid residues from at or about 80 to at or about 155, inclusive of FIG. 7 (SEQ ID NO:13); and (2) the complement of the DNA molecule of (1).

In another aspect, the invention provides an isolated DNA molecule selected from the group consisting of: (1) a DNA molecule encoding a polypeptide, such as an hIL-1Ra1 polypeptide, comprising the amino acid sequence of amino acid residues from at or about 1 to at or about 203, inclusive of FIG. 2 (SEQ ID NO:5); (2) a DNA molecule encoding a polypeptide, such as an hIL-1Ra1 polypeptide, comprising the amino acid sequence of amino acid residues from at or about 1 to at or about 193, inclusive of FIG. 3 (SEQ ID NO:7); (3) a DNA molecule encoding a polypeptide, such as an hIL-1Ra3 polypeptide, comprising the amino acid sequence of amino acid residues from at or about 34 to at or about 155, inclusive of FIG. 7 (SEQ ID NO:13); (4) a DNA molecule encoding a polypeptide, such as a mIL-1Ra3 polypeptide, comprising the amino acid sequence of amino acid residues from at or about 34 to at or about 155, inclusive of FIG. 9 (SEQ ID NO:16); and (5) the complement of any of the DNA molecules of (1)-(4).

In another aspect, the invention provides an isolated DNA molecule selected from the group consisting of: (1) a DNA molecule encoding a polypeptide, such as an hIL-1Ra3 polypeptide, comprising the amino acid sequence of amino acid residues from at or about 1 to at or about 155, inclusive of FIG. 7 (SEQ ID NO:13); (2) a DNA molecule encoding a polypeptide, such as a mIL-1Ra3 polypeptide, comprising the amino acid sequence of amino acid residues from at or about 1 to at or about 155, inclusive of FIG. 9 (SEQ ID NO:16); and (3) the complement of any of the DNA molecules of (1)-(2).

In another aspect, the invention provides an isolated DNA molecule selected from the group consisting of: (1) a DNA molecule encoding a polypeptide, such as an hIL-1Ra3 polypeptide, comprising the amino acid sequence of amino acid residues from at or about 2 to at or about 155, inclusive of FIG. 7 (SEQ ID NO:13); (2) a DNA molecule encoding a polypeptide, such as a mIL-1Ra3 polypeptide, comprising the amino acid sequence of amino acid residues from at or about 2 to at or about 155, inclusive of FIG. 9 (SEQ ID NO:16); and (3) the complement of any of the DNA molecules of (1)-(2).

In another aspect, the invention provides an isolated nucleic acid molecule comprising (a) a DNA molecule encoding a polypeptide selected from the group consisting of: (1) a polypeptide comprising an hIL-1Ra1 polypeptide, such as a mature hIL-1Ra1 polypeptide, encoded by the cDNA insert in the vector deposited as ATCC Deposit No. 203588; (2) a polypeptide comprising an hIL-1Ra1 polypeptide, such as a mature hIL-1Ra1 polypeptide, encoded by the cDNA insert in the vector deposited as ATCC Deposit No. 203587; (3) a polypeptide consisting of an hIL-1Ra2 polypeptide, such as a mature hIL-1Ra2 polypeptide, encoded by the cDNA insert in the vector deposited as ATCC Deposit No. 203586, which hIL-1Ra2 polypeptide is fused at its N-terminus or C-terminus to a heterologous amino acid or amino acid sequence; (4) a polypeptide consisting of an hIL-1Ra2 polypeptide, such as a mature hIL-1Ra2 polypeptide, encoded by the cDNA insert in the vector deposited as ATCC Deposit No. 203586; (5) a polypeptide comprising an hIL-1Ra3 polypeptide, such as a mature hIL-1Ra3 polypeptide, encoded by the cDNA insert in the vector deposited as ATCC Deposit No. 203589; and (6) a polypeptide comprising a mIL-1Ra3 polypeptide, such as a mature mIL-1Ra3 polypeptide, encoded by the cDNA insert in the vector deposited as ATCC Deposit No. 203590; or (b) the complement of the DNA molecule of (a).

In another aspect, the invention provides an isolated nucleic acid molecule comprising (a) a DNA molecule encoding a polypeptide selected from the group consisting of: (1) a polypeptide comprising an hIL-1Ra1L polypeptide, such as a mature hIL-1Ra1L polypeptide, encoded by the cDNA insert in the vector deposited as ATCC Deposit No. 203846; (2) a polypeptide consisting of an hIL-1Ra1S polypeptide, such as a mature hIL-1Ra1S polypeptide, encoded by the cDNA insert in the vector deposited as ATCC Deposit No. 203855, which hIL-1Ra1S polypeptide is fused at its N-terminus or C-terminus to a heterologous amino acid or amino acid sequence; (3) a polypeptide consisting of an hIL-1Ra1S polypeptide, such as a mature hIL-1Ra1S polypeptide, encoded by the cDNA insert in the vector deposited as ATCC Deposit No. 203855; (4) a polypeptide comprising an hIL-1Ra1V polypeptide, such as a mature hIL-1Ra1V polypeptide, encoded by the cDNA insert in the vector deposited as ATCC Deposit No. 203973; or (b) the complement of the DNA molecule of (a).

In another aspect, the invention provides an isolated nucleic acid molecule comprising (a) a DNA molecule encoding a polypeptide comprising an hIL-1Ra1S polypeptide, such as a mature hIL-1Ra1S polypeptide, encoded by the cDNA insert in the vector deposited as ATCC Deposit No. 203855; or (b) the complement of the DNA molecule of (a).

In another aspect, the invention provides an isolated nucleic acid molecule comprising (a) a DNA encoding a polypeptide selected from the group consisting of: (1) a polypeptide comprising the entire amino acid sequence encoded by the longest open reading frame in the cDNA insert in the vector deposited as ATCC Deposit No. 203588; (2) a polypeptide comprising the entire amino acid sequence, or the entire amino acid sequence excluding the 36 N-terminal amino acid residues of such sequence, encoded by the longest open reading frame in the cDNA insert in the vector deposited as ATCC Deposit No. 203587; (3) a polypeptide comprising the entire amino acid sequence, or the entire amino acid sequence excluding the N-terminal amino acid residue of such sequence, or the entire amino acid sequence excluding the 9 N-terminal amino acid residues of such sequence, encoded by the longest open reading frame in the cDNA insert in the vector deposited as ATCC Deposit No. 203586; (4) a polypeptide comprising the entire amino acid sequence, or the entire amino acid sequence excluding the N-terminal amino acid residue of such sequence, encoded by the longest open reading frame in the cDNA insert in the vector deposited as ATCC Deposit No. 203589; and (5) a polypeptide comprising the entire amino acid sequence, or the entire amino acid sequence excluding the N-terminal amino acid residue of such sequence, encoded by the longest open reading frame in the cDNA insert in the vector deposited as ATCC Deposit No. 203590; or (b) the complement of the DNA of (a).

In another aspect, the invention provides an isolated nucleic acid molecule comprising (a) a DNA encoding a polypeptide comprising the entire amino acid sequence encoded by the longest open reading frame in the cDNA insert of a vector selected from the group consisting of the vectors deposited as ATCC Deposit Nos. 203588, 203586, 203589, 203590, and 203973, or (b) the complement of the DNA of (a).

In another aspect, the invention provides an isolated nucleic acid molecule comprising (a) a DNA encoding a polypeptide selected from the group consisting of: (1) a polypeptide comprising the entire amino acid sequence, or the entire amino acid sequence excluding the N-terminal amino acid residue of such sequence, or the entire amino acid sequence excluding the 34 N-terminal amino acid residues of such sequence, encoded by the longest open reading frame in the cDNA insert in the vector deposited as ATCC Deposit No. 203846; (2) a polypeptide comprising the entire amino acid sequence, or the entire amino acid sequence excluding the N-terminal amino acid residue of such sequence, or the entire amino acid sequence excluding the 25 N-terminal amino acid residues of such sequence, encoded by the longest open reading frame in the cDNA insert in the vector deposited as ATCC Deposit No. 204855; and (3) a polypeptide comprising the entire amino acid sequence, or the entire amino acid sequence excluding the N-terminal amino acid residue of such sequence, or the entire amino acid sequence excluding the 11 N-terminal amino acid residues of such sequence, or the entire amino acid sequence excluding the 36 N-terminal amino acid residues of such sequence, or the entire amino acid sequence excluding the 45 N-terminal amino acid residues of such sequence, encoded by the longest open reading frame in the cDNA insert in the vector deposited as ATCC Deposit No. 203973; or (b) the complement of the DNA of (a).

In another aspect, the invention provides an isolated nucleic acid molecule comprising (a) a DNA encoding a non-naturally occurring, chimeric polypeptide formed by fusing the entire amino acid sequence excluding the 38 N-terminal amino acid residues of such sequence, or the entire amino acid sequence excluding the 46 N-terminal amino acid residues of such sequence, encoded by the longest open reading frame in the cDNA insert in the vector deposited as ATCC Deposit No. 203855, at its N-terminus or C-terminus to a heterologous amino acid or amino acid sequence; or (b) the complement of the DNA of (a).

In another aspect, the invention provides an isolated nucleic acid molecule comprising (a) a DNA encoding a polypeptide consisting of the entire amino acid sequence excluding the 38 N-terminal amino acid residues of such sequence, or the entire amino acid sequence excluding the 46 N-terminal amino acid residues of such sequence, encoded by the longest open reading frame in the cDNA insert in the vector deposited as ATCC Deposit No. 203855; or (b) the complement of the DNA of (a).

In another aspect, the invention provides an isolated nucleic acid molecule comprising (a) a DNA molecule encoding a polypeptide comprising the entire amino acid sequence encoded by the longest open reading frame in the cDNA insert of a vector selected from the group consisting of the vectors deposited as ATCC Deposit Nos. 203846, 203855 and 203973, or (b) the complement of the DNA of (a).

In another aspect, the invention provides an isolated DNA molecule selected from the group consisting of: (1) a DNA molecule which encodes a polypeptide, such as an hIL-1Ra1V fusion variant polypeptide, consisting of a native amino acid sequence of hIL-1Ra1V consisting of amino acid residues from at or about 37 to at or about 218, inclusive of FIG. 19 (SEQ ID NO:25) fused at its N-terminus or C-terminus to a heterologous amino acid or amino acid sequence, and which DNA molecule comprises the nucleic acid sequence in the sense strand of FIG. 19 (SEQ ID NO:24) that encodes the native amino acid sequence; (2) a DNA molecule which encodes a polypeptide, such as an hIL-1Ra1V fusion variant polypeptide, consisting of a native amino acid sequence of hIL-1Ra1V consisting of amino acid residues from at or about 46 to at or about 218, inclusive of FIG. 19 (SEQ ID NO:25) fused at its N-terminus or C-terminus to a heterologous amino acid or amino acid sequence, and which DNA molecule comprises the nucleic acid sequence in the sense strand of FIG. 19 (SEQ ID NO:24) that encodes the native amino acid sequence; (3) a DNA molecule which encodes a polypeptide, such as an hIL-1Ra1V polypeptide, consisting of a native amino acid sequence of hIL-1Ra1V consisting of amino acid residues from at or about 37 to at or about 218, inclusive of FIG. 19 (SEQ ID NO:25), and which DNA molecule comprises the nucleic acid sequence in the sense strand of FIG. 19 (SEQ ID NO:24) that encodes the native amino acid sequence; (4) a DNA molecule which encodes a polypeptide, such as an hIL-1Ra1V polypeptide, consisting of a native amino acid sequence of hIL-1Ra1V consisting of amino acid residues from at or about 46 to at or about 218, inclusive of FIG. 19 (SEQ ID NO:25), and which DNA molecule comprises the nucleic acid sequence in the sense strand of FIG. 19 (SEQ ID NO:24) that encodes the native amino acid sequence; and (5) the complement of any of the DNA molecules of (1)-(4).

In another aspect, the invention provides an isolated DNA molecule selected from the group consisting of: (1) a DNA molecule which encodes a polypeptide, such as an hIL-1Ra1 polypeptide, and which DNA molecule comprises the nucleic acid sequence of nucleotide positions from at or about 118 to at or about 618, inclusive in the sense strand of FIG. 2 (SEQ ID NO:4); (2) a DNA molecule which encodes a polypeptide, such as an hIL-1Ra1 polypeptide, and which DNA molecule comprises the nucleic acid sequence of nucleotide positions from at or about 145 to at or about 681, inclusive in the sense strand of FIG. 3 (SEQ ID NO:6); (3) a DNA molecule which encodes a polypeptide, such as an hIL-1Ra2 polypeptide, and which DNA molecule comprises the nucleic acid sequence of nucleotide positions from at or about 96 to at or about 497, inclusive in the sense strand of FIG. 5 (SEQ ID NO:9); (4) a DNA molecule which comprises the nucleic acid sequence of nucleotide positions from at or about 123 to at or about 497, inclusive in the sense strand of FIG. 5 (SEQ ID NO:9); (5) a DNA molecule which encodes a polypeptide, such as an hIL-1Ra2 fusion variant polypeptide, consisting of a native amino acid sequence of hIL-1Ra2 consisting of amino acid residues from at or about 27 to at or about 134, inclusive of FIG. 5 (SEQ ID NO:10) fused at its N-terminus or C-terminus to a heterologous amino acid or amino acid sequence, and which DNA molecule comprises the nucleic acid sequence in the sense strand of FIG. 5 (SEQ ID NO:9) that encodes the native amino acid sequence; (6) a DNA molecule which encodes a polypeptide, such as an hIL-1Ra2 polypeptide, consisting of a native amino acid sequence of hIL-1Ra2 consisting of amino acid residues from at or about 27 to at or about 134, inclusive of FIG. 5 (SEQ ID NO:10), and which DNA molecule comprises the nucleic acid sequence in the sense strand of FIG. 5 (SEQ ID NO:9) that encodes the native amino acid sequence; (7) a DNA molecule which encodes a polypeptide, such as an hIL-1Ra3 polypeptide, and which DNA molecule comprises the nucleic acid sequence of nucleotide positions from at or about 283 to at or about 402, inclusive in the sense strand of FIG. 7 (SEQ ID NO:12); (8) a DNA molecule which encodes a polypeptide, such as a mIL-1Ra3 polypeptide, and which DNA molecule comprises the nucleic acid sequence of nucleotide positions from at or about 427 to at or about 546, inclusive in the sense strand of FIG. 9 (SEQ ID NO:15); and (9) the complement of any of the DNA molecules of (1)-(8).

In another aspect, the invention provides an isolated DNA molecule selected from the group consisting of: (1) a DNA molecule which encodes a polypeptide, such as an hIL-1Ra1L polypeptide, and which DNA molecule comprises the nucleic acid sequence of nucleotide positions from at or about 79 to at or about 624, inclusive in the sense strand of FIG. 15 (SEQ ID NO:18); (2) a DNA molecule which encodes a polypeptide, such as an hIL-1Ra1S polypeptide, and which DNA molecule comprises the nucleic acid sequence of nucleotide positions from at or about 79 to at or about 504, inclusive in the sense strand of FIG. 16 (SEQ ID NO:20); (3) a DNA molecule which encodes a polypeptide, such as an hIL-1Ra1S fusion variant polypeptide, consisting of a native amino acid sequence of hIL-1Ra1S consisting of amino acid residues from at or about 39 to at or about 167, inclusive of FIG. 16 (SEQ ID NO:21) fused at its N-terminus or C-terminus to a heterologous amino acid or amino acid sequence, and which DNA molecule comprises the nucleic acid sequence in the sense strand of FIG. 16 (SEQ ID NO:20) that encodes the native amino acid sequence; (4) a DNA molecule which encodes a polypeptide, such as an hIL-1Ra1S fusion variant polypeptide, consisting of a native amino acid sequence of hIL-1Ra1S consisting of amino acid residues from at or about 47 to at or about 167, inclusive of FIG. 16 (SEQ ID NO:21) fused at its N-terminus or C-terminus to a heterologous amino acid or amino acid sequence, and which DNA molecule comprises the nucleic acid sequence in the sense strand of FIG. 16 (SEQ ID NO:20) that encodes the native amino acid sequence; (5) a DNA molecule which encodes a polypeptide, such as an hIL-1Ra1S polypeptide, consisting of a native amino acid sequence of hIL-1Ra1S consisting of amino acid residues from at or about 39 to at or about 167, inclusive of FIG. 16 (SEQ ID NO:21), and which DNA molecule comprises the nucleic acid sequence in the sense strand of FIG. 16 (SEQ ID NO:20) that encodes the native amino acid sequence; (6) a DNA molecule which encodes a polypeptide, such as an hIL-1Ra1S polypeptide, consisting of a native amino acid sequence of hIL-1Ra1S consisting of amino acid residues from at or about 47 to at or about 167, inclusive of FIG. 16 (SEQ ID NO:21), and which DNA molecule comprises the nucleic acid sequence in the sense strand of FIG. 16 (SEQ ID NO:20) that encodes the native amino acid sequence; (7) a DNA molecule which encodes a polypeptide, such as an hIL-1Ra1V polypeptide, and which DNA molecule comprises the nucleic acid sequence of nucleotide positions from at or about 181 to at or about 729, inclusive in the sense strand of FIG. 19 (SEQ ID NO:24); (8) a DNA molecule which encodes a polypeptide, such as an hIL-1Ra1V polypeptide, and which DNA molecule comprises the nucleic acid sequence of nucleotide positions from at or about 208 to at or about 729, inclusive in the sense strand of FIG. 19 (SEQ ID NO:24); and (9) the complement of any of the DNA molecules of (1)-(8).

In another aspect, the invention provides an isolated DNA molecule selected from the group consisting of: (1) a DNA molecule which encodes a polypeptide, such as an hIL-1Ra1L polypeptide, and which DNA molecule comprises the nucleic acid sequence of nucleotide positions from at or about 4 to at or about 624, inclusive in the sense strand of FIG. 15 (SEQ ID NO:18); (2) a DNA molecule which encodes a polypeptide, such as an hIL-1Ra1S polypeptide, and which DNA molecule comprises the nucleic acid sequence of nucleotide positions from at or about 4 to at or about 504, inclusive in the sense strand of FIG. 16 (SEQ ID NO:20); (3) a DNA molecule which encodes a polypeptide, such as an hIL-1Ra1V polypeptide, and which DNA molecule comprises the nucleic acid sequence of nucleotide positions from at or about 106 to at or about 729, inclusive in the sense strand of FIG. 19 (SEQ ID NO:24); (4) a DNA molecule which encodes a polypeptide, such as an hIL-1Ra1V polypeptide, and which comprises the nucleic acid sequence of nucleotide positions from at or about 73 to at or about 729, inclusive in the sense strand of FIG. 19 (SEQ ID NO:24); and (5) the complement of any of the DNA molecules of (1)-(4).

In another aspect, the invention provides an isolated DNA molecule selected from the group consisting of: (1) a DNA molecule comprising the nucleic acid sequence of nucleotide positions from at or about 103 to at or about 681, inclusive in the sense strand of FIG. 3 (SEQ ID NO:6); (2) a DNA molecule comprising the nucleic acid sequence of nucleotide positions from at or about 100 to at or about 465, inclusive in the sense strand of FIG. 7 (SEQ ID NO:12); (3) a DNA molecule comprising the nucleic acid sequence of nucleotide positions from at or about 244 to at or about 609, inclusive in the sense strand of FIG. 9 (SEQ ID NO:15); and (4) the complement of any of the DNA molecules of (1)-(3).

In another aspect, the invention provides an isolated DNA molecule comprising (a) the complete DNA sequence in the sense strand of FIG. 2 (SEQ ID NO:4), FIG. 3 (SEQ ID NO:6), FIG. 5 (SEQ ID NO:9), FIG. 7 (SEQ ID NO:12), or FIG. 9 (SEQ ID NO:15), or (b) the complement of (a).

In another aspect, the invention provides an isolated DNA molecule comprising (a) the complete DNA sequence in the sense strand of FIG. 15 (SEQ ID NO:18), FIG. 16 (SEQ ID NO:20), or FIG. 19 (SEQ ID NO:24), or (b) the complement of (a).

In a specific aspect, the invention provides an isolated nucleic acid molecule comprising DNA encoding an IL-1lp polypeptide, with or without the N-terminal signal sequence and/or the initiating methionine, or is complementary to such IL-1lp encoding nucleic acid molecule. The signal peptide has been tentatively identified as extending from amino acid position 1 to at or about amino acid position 14 in the IL-1lp sequence of FIG. 3 (SEQ ID NO:7), from amino acid position 1 to at or about amino acid position 26 in the IL-1lp sequence of FIG. 5 (SEQ ID NO:10), from amino acid position 1 to at or about amino acid position 33 in the IL-1lp sequence of FIG. 7 (SEQ ID NO:13), and from amino acid position 1 to at or about amino acid position 33 in the IL-1lp sequence of FIG. 9 (SEQ ID NO:16).

The IL-1lp sequence of amino acids from at or about 1 to at or about 207 of FIG. 15 (SEQ ID NO:19) is believed to behave as a mature sequence (without a presequence that is removed in post-translational processing) in certain animal cells. In addition, it is believed that other animal cells recognize and remove in post-translational processing one or more signal peptide(s) contained in the sequence of amino acid positions 1 to about 34 of FIG. 15 (SEQ ID NO:19).

The IL-1lp sequence of amino acids from at or about 1 to at or about 167 of FIG. 16 (SEQ ID NO:21) is believed to behave as a mature sequence (without a presequence that is removed in post-translational processing) in certain animal cells. In addition, it is believed that other animal cells recognize and remove in post-translational processing one or more signal peptide(s) contained in the sequence of amino acid positions 1 to about 46 in the IL-1lp sequence of FIG. 16 (SEQ ID NO:21).

The IL-1lp sequence of amino acids from at or about 1 to at or about 218 of FIG. 19 (SEQ ID NO:25) is believed to behave as a mature sequence (without a presequence that is removable in post-translational processing) in certain animal cells. The IL-1lp sequence of amino acids from at or about 12 to at or about 218 of FIG. 19 (SEQ ID NO:25) that results from initiation of translation at the start codon occurring at nucleotide positions 106-108 is also believed to behave as mature sequence in certain animal cells. It is further believed that other animal cells recognize and remove in post-translational processing one or more signal peptide(s) contained in the sequence of amino acid positions 1 to 45 in the IL-1lp polypeptide of amino acid positions 1 to 218 of FIG. 19 (SEQ ID NO:25) or contained in the sequence of amino acid positions 12 to 45 in the IL-1lp polypeptide of amino acid positions 12 to 218 of FIG. 19 (SEQ ID NO:25).

In a still further aspect, the invention concerns an isolated nucleic acid molecule comprising (a) DNA encoding an IL-1lp polypeptide that retains at least one biologic activity of a native sequence IL-1lp, such as the IL-18R binding activity of a native sequence hIL-1Ra1, or the IL-1R binding activity of a native sequence hIL-1Ra3 or mIL-1Ra3, and which IL-1lp polypeptide has at least at or about 80% positives, or at least at or about 85% positives, or at least at or about 90% positives, or at least at or about 95% positives to an amino acid sequence selected from the group consisting of: (1) amino acid residues from at or about 37 to at or about 203, inclusive of FIG. 2 (SEQ ID NO:5), (2) amino acid residues from at or about 15 to at or about 193, inclusive of FIG. 3 (SEQ ID NO:7), (3) amino acid residues from at or about 34 to at or about 155, inclusive of FIG. 7 (SEQ ID NO:13), (4) amino acid residues from at or about 34 to at or about 155, inclusive of FIG. 9 (SEQ ID NO:16), (5) amino acid residues from at or about 26 to at or about 207, inclusive of FIG. 15 (SEQ ID NO:19), and (6) amino acid residues from at or about 46 to at or about 218, inclusive of FIG. 19 (SEQ ID NO:25), or (b) the complement of the DNA of (a).

In a still further aspect, the invention concerns an isolated nucleic acid molecule comprising (a) DNA encoding an IL-1lp polypeptide that retains at least one biologic activity of a native sequence IL-1lp, such as the IL-18R binding activity of a native sequence hIL-1Ra1, or the IL-1R binding activity of a native sequence hIL-1Ra3 or mIL-1Ra3, and which IL-1lp polypeptide has at least at or about 80% positives, or at least at or about 85% positives, or at least at or about 90% positives, or at least at or about 95% positives to an amino acid sequence selected from the group consisting of: (1) amino acid residues from at or about 95 to at or about 134, inclusive of FIG. 7 (SEQ ID NO:13), and (2) amino acid residues from at or about 95 to at or about 134, inclusive of FIG. 9 (SEQ ID NO:16), or (b) the complement of the DNA of (a).

In a still further aspect, the invention concerns an isolated nucleic acid molecule comprising (a) DNA encoding an IL-1lp polypeptide that retains at least one biologic activity of a native sequence IL-1lp, such as the IL-18R binding activity of a native sequence hIL-1Ra1, or the IL-1R binding activity of a native sequence hIL-1Ra3 or mIL-1Ra3, and which IL-1lp polypeptide has at least at or about 80% positives, or at least at or about 85% positives, or at least at or about 90% positives, or at least at or about 95% positives to the amino acid sequence of amino acid residues from at or about 80 to at or about 155, inclusive of FIG. 7 (SEQ ID NO:13), or (b) the complement of the DNA of (a).

In a still further aspect, the invention concerns an isolated nucleic acid molecule comprising (a) DNA encoding an IL-1lp polypeptide that retains at least one biologic activity of a native sequence IL-1lp, such as the IL-18R binding activity of a native sequence hIL-1Ra1, or the IL-1R binding activity of a native sequence hIL-1Ra3 or mIL-1Ra3, and which IL-1lp polypeptide has at least at or about 80% positives, or at least at or about 85% positives, or at least at or about 90% positives, or at least at or about 95% positives to an amino acid sequence selected from the group consisting of: (1) amino acid residues from at or about 2 to at or about 155, inclusive of FIG. 7 (SEQ ID NO:13), and (2) amino acid residues from at or about 2 to at or about 155, inclusive of FIG. 9 (SEQ ID NO:16), or (b) the complement of the DNA of (a).

In a still further aspect, the invention concerns an isolated nucleic acid molecule comprising (a) DNA encoding an IL-1lp polypeptide having at least at or about 80% positives, or at least at or about 85% positives, or at least at or about 90% positives, or at least at or about 95% positives to an amino acid sequence selected from the group consisting of: (1) amino acid residues from at or about 95 to at or about 134, inclusive of FIG. 7 (SEQ ID NO:13), and (2) amino acid residues from at or about 95 to at or about 134, inclusive of FIG. 9 (SEQ ID NO:16), or (b) the complement of the DNA of (a).

In a still further aspect, the invention concerns an isolated nucleic acid molecule comprising (a) DNA encoding an IL-1lp polypeptide having at least at or about 80% positives, or at least at or about 85% positives, or at least at or about 90% positives, or at least at or about 95% positives to the amino acid sequence of amino acid residues from at or about 80 to at or about 155, inclusive of FIG. 7 (SEQ ID NO:13), or (b) the complement of the DNA of (a).

In a still further aspect, the invention concerns an isolated nucleic acid molecule comprising (a) DNA encoding an IL-1lp polypeptide having at least at or about 80% positives, or at least at or about 85% positives, or at least at or about 90% positives, or at least at or about 95% positives to an amino acid sequence selected from the group consisting of: (1) amino acid residues from at or about 2 to at or about 155, inclusive of FIG. 7 (SEQ ID NO:13), and (2) amino acid residues from at or about 2 to at or about 155, inclusive of FIG. 9 (SEQ ID NO:16), or (b) the complement of the DNA of (a).

In a still further aspect, the invention concerns an isolated nucleic acid molecule comprising (a) DNA encoding an IL-1lp polypeptide that retains at least one biologic activity of a native sequence IL-1lp, such as the IL-18R binding activity of a native sequence hIL-1Ra1, hIL-1Ra1L, or hIL-1Ra1V, and which IL-1lp polypeptide has at least at or about 80% positives, or at least at or about 85% positives, or at least at or about 90% positives, or at least at or about 95% positives to an amino acid sequence selected from the group consisting of: (1) amino acid residues from at or about 1 to at or about 207, inclusive of FIG. 15 (SEQ ID NO:19), and (2) amino acid residues from at or about 1 to at or about 218, inclusive of FIG. 19 (SEQ ID NO:25), or (b) the complement of the DNA of (a).

In another embodiment, the invention provides a vector comprising DNA encoding IL-1lp or its variants. The vector may comprise any of the isolated nucleic acid molecules hereinabove defined.

A host cell comprising such a vector is also provided. By way of example, the host cells may be CHO cells, *E. coli*, or yeast. A process for producing IL-1lp polypeptides is further provided and comprises culturing host cells under conditions suitable for expression of IL-1lp and recovering IL-1lp from the cell culture.

In another embodiment, the invention provides isolated IL-1lp polypeptide encoded by any of the isolated nucleic acid sequences hereinabove defined.

In another aspect, the invention provides isolated native sequence IL-1lp polypeptide, which in one embodiment, comprises an amino acid sequence selected from the group consisting of: (1) the amino acid sequence of residues from at or about 37 to at or about 203, inclusive of FIG. 2 (SEQ ID NO:5), (2) the amino acid sequence of residues from at or about 15 to at or about 193, inclusive of FIG. 3 (SEQ ID NO:7), (3) the amino acid sequence of residues from at or about 34 to at or about 155, inclusive of FIG. 7 (SEQ ID NO:13), and (4) the amino acid sequence of residues from at or about 34 to at or about 155, inclusive of FIG. 9 (SEQ ID NO:16).

In another aspect, the invention provides isolated native sequence IL-1lp polypeptide, which in one embodiment, comprises an amino acid sequence selected from the group consisting of: (1) the amino acid sequence of residues from at or about 1 to at or about 207, inclusive of FIG. 15 (SEQ ID NO:19), (2) the amino acid sequence of residues from at or about 26 to at or about 207, inclusive of FIG. 15 (SEQ ID NO:19), (3) the amino acid sequence of residues from at or about 1 to at or about 167, inclusive of FIG. 16 (SEQ ID NO:21), (4) the amino acid sequence of residues from at or about 26 to at or about 167, inclusive of FIG. 16 (SEQ ID NO:21), (5) the amino acid sequence of residues from at or about 1 to at or about 218, inclusive of FIG. 19 (SEQ ID NO:25), (6) the amino acid sequence of residues from at or about 12 to at or about 218, inclusive of FIG. 19 (SEQ ID NO:25), (7) the amino acid sequence of residues from at or about 37 to at or about 218, inclusive of FIG. 19 (SEQ ID NO:25), and (8) the amino acid sequence of residues from at or about 46 to at or about 218, inclusive of FIG. 19 (SEQ ID NO:25).

In another aspect, the invention concerns an isolated IL-1lp polypeptide that retains at least one biologic activity of a native sequence IL-1lp, such as the IL-1R binding activity of a native sequence hIL-1Ra3 or mIL-1Ra3, or the IL18R binding activity of a native sequencer hIL-1Ra1V, hIL-1Ra1L, hIL-1Ra1V, and that consists of an amino acid sequence having at least at or about 80% sequence identity, or at least at or about 85% sequence identity, or at least at or about 90% sequence identity, or at least at or about 95% sequence identity to the sequence of amino acid residues from at or about 37 to at or about 203, inclusive of FIG. 2 (SEQ ID NO:5), the sequence of amino acid residues from at or about 15 to at or about 193, inclusive of FIG. 3 (SEQ ID NO:7), the sequence of amino acid residues from at or about 34 to at or about 155, inclusive of FIG. 7 (SEQ ID NO:13), the sequence of amino acid residues from at or about 34 to at or about 155, inclusive of FIG. 9 (SEQ ID NO:16), the sequence of amino acid residues from at or about 26 to at or about 207, inclusive of FIG. 15 (SEQ ID NO:19), or the sequence of amino acid residues from at or about 46 to at or about 218, inclusive of FIG. 19 (SEQ ID NO:25).

In another aspect, the invention concerns an isolated IL-1lp polypeptide that retains at least one biologic activity of a native sequence IL-1lp, such as the IL-18R binding activity of a native sequence hIL-1Ra1, hIL-1Ra1L, or hIL-1Ra1V, and that consists of an amino acid sequence having at least at or about 80% sequence identity, or at least at or about 85% sequence identity, or at least at or about 90% sequence identity, or at least at or about 95% sequence identity to the sequence of amino acid residues from at or about 1 to at or about 207, inclusive of FIG. 15 (SEQ ID NO:19), or the sequence of amino acid residues from at or about 1 to at or about 218, inclusive of FIG. 19 (SEQ ID NO:25).

In another aspect, the invention provides an isolated IL-1lp selected from the group consisting of: (1) a polypeptide, such as an hIL-1Ra1 polypeptide, consisting of an amino acid sequence having a sequence identity of at least at or about 80%, or at least at or about 85%, or at least at or about 90%, or at least at or about 95%, to the sequence of amino acid residues from at or about 37 to at or about 63, inclusive of FIG. 2 (SEQ ID NO:5); (2) a polypeptide, such as an hIL-1Ra1 polypeptide, consisting of an amino acid sequence having a sequence identity of at least at or about 80%, or at least at or about 85%, or at least at or about 90%, or at least at or about 95%, to the sequence of amino acid residues from at or about 15 to at or about 53, inclusive of FIG. 3 (SEQ ID NO:7); (3) a polypeptide, such as an hIL-1Ra2 polypeptide, comprising the amino acid sequence of amino acid residues from at or about 1 to at or about 134, inclusive of FIG. 5 (SEQ ID NO:10); (4) a polypeptide comprising the amino acid sequence of amino acid residues from at or about 10 to at or about 134, inclusive of FIG. 5 (SEQ ID NO:10); (5) a polypeptide, such as an hIL-1Ra2 polypeptide, consisting of the amino acid sequence of amino acid residues from at or about 27 to at or about 134, inclusive of FIG. 5 (SEQ ID NO:10); (6) a polypeptide, such as an hIL-1Ra2 fusion variant polypeptide, consisting of a native amino acid sequence of hIL-1Ra2 consisting of amino acid residues from at or about 27 to at or about 134, inclusive of FIG. 5 (SEQ ID NO:10) fused at its N-terminus or C-terminus to a heterologous amino acid or amino acid sequence; (7) a polypeptide, such as an hIL-1Ra3 polypeptide, consisting of an amino acid sequence having a sequence identity of at least at or about 80%, or at least at or about 85%, or at least at or about 90%, or at least at or about 95%, to the sequence of amino acid residues from at or about 95 to at or about 134, inclusive of FIG. 7 (SEQ ID NO:13); and (8) a polypeptide, such as a mIL-1Ra3 polypeptide, consisting of an amino acid sequence having a sequence identity of at least at or about 80%, or at least at or about 85%, or at least at or about 90%, or at least at or about 95%, to the sequence of amino acid residues from at or about 95 to at or about 134, inclusive of FIG. 9 (SEQ ID NO:16).

In another aspect, the invention provides an isolated IL-1lp selected from the group consisting of: (1) a polypeptide, such as an hIL-1Ra1L polypeptide, consisting of an amino acid sequence having a sequence identity of at least at or about 80%, or at least at or about 85%, or at least at or about 90%, or at least at or about 95%, to the sequence of amino acid residues from at or about 27 to at or about 44, inclusive of FIG. 15 (SEQ ID NO:19); (2) a polypeptide, such as an hIL-1Ra1S fusion variant polypeptide, consisting of a native amino acid sequence of hIL-1Ra1S consisting of amino acid residues from at or about 39 to at or about 167, inclusive of FIG. 16 (SEQ ID NO:21) fused at its N-terminus or C-terminus to a heterologous amino acid or amino acid sequence; (3) a polypeptide, such as an hIL-1Ra1S fusion variant polypeptide, consisting of a native amino acid sequence of hIL-1Ra1S consisting of amino acid residues from at or about 47 to at or about 167, inclusive of FIG. 16 (SEQ ID NO:21) fused at its N-terminus or C-terminus to a heterologous amino acid or amino acid sequence; (4) a polypeptide, such as an hIL-1Ra1S polypeptide, consisting of amino acid residues from at or about 39 to at or about 167, inclusive of FIG. 16 (SEQ ID NO:21); (5) a polypeptide, such as an hIL-1Ra1S polypeptide, consisting of amino acid residues from at or about 47 to at or about 167, inclusive of FIG. 16 (SEQ ID NO:21); and (6) a polypeptide, such as an hIL-1Ra1V polypeptide, consisting of an amino acid sequence having a sequence identity of at least at or about 80%, or at least at or about 85%, or at least at or about 90%, or at least at or about 95%, to the sequence of amino acid residues from at or about 37 to at or about 55, inclusive of FIG. 19 (SEQ ID NO:25).

In another aspect, the invention concerns an isolated IL-1lp polypeptide that consists of an amino acid sequence having at least at or about 80% sequence identity, or at least at or about 85% sequence identity, or at least at or about 90% sequence identity, or at least at or about 95% sequence identity to the sequence of amino acid residues from at or about 37 to at or about 203, inclusive of FIG. 2 (SEQ ID NO:5), the sequence of amino acid residues from at or about 15 to at or about 193, inclusive of FIG. 3 (SEQ ID NO:7), the sequence of amino acid residues from at or about 34 to at or about 155, inclusive of FIG. 7 (SEQ ID NO:13), the sequence of amino acid residues from at or about 34 to at or about 155, inclusive of FIG. 9 (SEQ ID NO:16), the sequence of amino acid residues from at or about 26 to at or about 207, inclusive of FIG. 15 (SEQ ID NO:19), or the sequence of amino acid residues from at or about 46 to at or about 218, inclusive of FIG. 19 (SEQ ID NO:25).

In another aspect, the invention concerns an isolated IL-1lp polypeptide that consists of an amino acid sequence having at least at or about 80% sequence identity, or at least at or about 85% sequence identity, or at least at or about 90% sequence identity, or at least at or about 95% sequence identity to the sequence of amino acid residues from at or about 1 to at or about 207, inclusive of FIG. 15 (SEQ ID NO:19), or the sequence of amino acid residues from at or about 1 to at or about 218, inclusive of FIG. 19 (SEQ ID NO:25).

In another aspect, the invention provides an isolated polypeptide, such as an hIL-1Ra3 polypeptide, consisting of an amino acid sequence having a sequence identity of at least at or about 80%, or at least at or about 85%, or at least at or about 90%, or at least at or about 95%, to the sequence of amino acid residues from at or about 80 to at or about 155, inclusive of FIG. 7 (SEQ ID NO:13).

In a further aspect, the invention concerns an isolated IL-1lp polypeptide that retains at least one biologic activity of a native sequence IL-1lp, such as the IL-1R binding activity of a native sequence hIL-1Ra3 or mIL-1Ra3, or the IL-18R binding activity of a native sequence hIL-1Ra1, hIL-1Ra1L, or hIL-1Ra1V, and that consists of an amino acid sequence having at least at or about 80% sequence identity, or at least at or about 85% sequence identity, or at least at or about 90% sequence identity, or at least at or about 95% sequence identity to the amino acid sequence of an IL-1lp, such as a mature IL-1lp polypeptide, encoded by the cDNA insert in the vector deposited as ATCC Deposit No. 203588 (DNA85066-2534), ATCC Deposit No. 203587 (DNA96786-2534), ATCC Deposit No. 203589 (DNA96787-2534), ATCC Deposit No. 203590 (DNA92505-2534), ATCC Deposit No. 203846 (DNA102043-2534), or ATCC Deposit No. 203973 (DNA114876-2534). In a preferred embodiment, the IL-1lp polypeptide comprises the amino acid sequence of an IL-1lp, such as a mature IL-1lp polypeptide, encoded by the cDNA insert in the vector deposited as ATCC Deposit No. 203588

(DNA85066-2534), ATCC Deposit No. 203587 (DNA96786-2534), ATCC Deposit No. 203586 (DNA92929-2534), ATCC Deposit No. 203589 (DNA96787-2534), ATCC Deposit No. 203590 (DNA92505-2534), ATCC Deposit No. 203846 (DNA102043-2534), ATCC Deposit No. 203973 (DNA114876-2534), or ATCC Deposit No. 203855 (DNA 102044-2534).

In a further aspect, the invention concerns an isolated IL-1lp polypeptide that retains at least one biologic activity of a native sequence IL-1lp, such as the IL-1R binding activity of a native sequence hIL-1Ra3 or mIL-1Ra3, or the IL-18R binding activity of a native sequence hIL-1Ra1, hIL-1Ra1L, or hIL-1Ra1V, and that consists of an amino acid sequence having at least at or about 80% sequence identity, or at least at or about 85% sequence identity, or at least at or about 90% sequence identity, or at least at or about 95% sequence identity to the entire amino acid sequence encoded by the longest open reading frame in the cDNA insert of a vector selected from the group consisting of the vectors deposited as ATCC Deposit No. 203588 (DNA85066-2534), ATCC Deposit No. 203587 (DNA96786-2534), ATCC Deposit No. 203589 (DNA96787-2534), ATCC Deposit No. 203590 (DNA92505-2534), ATCC Deposit No. 203846 (DNA102043-2534), and ATCC Deposit No. 203973 (DNA114876-2534). In a preferred embodiment, the IL-1lp polypeptide comprises the entire amino acid sequence encoded by the longest open reading frame in the cDNA insert of a vector selected from the group consisting of the vectors deposited as ATCC Deposit No. 203588 (DNA85066-2534), ATCC Deposit No. 203587 (DNA96786-2534), ATCC Deposit No. 203586 (DNA92929-2534), ATCC Deposit No. 203589 (DNA96787-2534), and ATCC Deposit No. 203590 (DNA92505-2534). In another preferred embodiment, the IL-1lp polypeptide comprises the entire amino acid sequence encoded by the longest open reading frame in the cDNA insert of a vector selected from the group consisting of the vectors deposited as ATCC Deposit No. 203846 (DNA102043-2534), ATCC Deposit No. 203855 (DNA102044-2534), and ATCC Deposit No. 203973 (DNA114876-2534).

In another aspect, the invention concerns an isolated IL-1lp polypeptide that retains at least one biologic activity of a native sequence IL-1lp, such as the IL-1R binding activity of a native sequence IL-1Ra3 or mIL-1Ra3, or the IL-18R binding activity of a native sequence hIL-1Ra1, hIL-1Ra1L, or hIL-1Ra1V, and that consists of an amino acid sequence having at least at or about 80% sequence identity, or at least at or about 85% sequence identity, or at least at or about 90% sequence identity, or at least at or about 95% sequence identity to an amino acid sequence selected from the group consisting of: (1) the entire amino acid sequence encoded by the longest open reading frame in the cDNA insert in the vector deposited as ATCC Deposit No. 203588, (2) the entire amino acid sequence, or the entire amino acid sequence excluding the 36 N-terminal amino acid residues of such sequence, encoded by the longest open reading frame in the cDNA insert in the vector deposited as ATCC Deposit No. 203587, (3) the entire amino acid sequence, or the entire amino acid sequence excluding the N-terminal amino acid residue of such sequence, encoded by the longest open reading frame in the cDNA insert in the vector deposited as ATCC Deposit No. 203589, (4) the entire amino acid sequence, or the entire amino acid sequence excluding the N-terminal amino acid residue of such sequence, encoded by the longest open reading frame in the cDNA insert in the vector deposited as ATCC Deposit No. 203590, (5) the entire amino acid sequence, or the entire amino acid sequence excluding the N-terminal amino acid residue of such sequence, or the entire amino acid sequence excluding the 34 N-terminal amino acid residues of such sequence, encoded by the longest open reading frame in the cDNA insert in the vector deposited as ATCC Deposit No. 203846, and (6) the entire amino acid sequence, or the entire amino acid sequence excluding the N-terminal amino acid residue of such sequence, or the entire amino acid sequence excluding the 45 N-terminal amino acid residues of such sequence, encoded by the longest open reading frame in the cDNA insert in the vector deposited as ATCC Deposit No. 203973.

In a further aspect, the invention concerns an isolated IL-1lp polypeptide that consists of an amino acid sequence having at least at or about 80% sequence identity, or at least at or about 85% sequence identity, or at least at or about 90% sequence identity, or at least at or about 95% sequence identity to the amino acid sequence of an IL-1lp, such as a mature IL-1lp polypeptide, encoded by the cDNA insert in the vector deposited as ATCC Deposit No. 203588 (DNA85066-2534), ATCC Deposit No. 203587 (DNA96786-2534), ATCC Deposit No. 203589 (DNA96787-2534), ATCC Deposit No. 203590 (DNA92505-2534), ATCC Deposit No. 203846 (DNA102043-2534), or ATCC Deposit No. 203973 (DNA114876-2534).

In a further aspect, the invention concerns an isolated IL-1lp polypeptide that consists of an amino acid sequence having at least at or about 80% sequence identity, or at least at or about 85% sequence identity, or at least at or about 90% sequence identity, or at least at or about 95% sequence identity to the entire amino acid sequence encoded by the longest open reading frame in the cDNA insert of a vector selected from the group consisting of the vectors deposited as ATCC Deposit No. 203588 (DNA85066-2534), ATCC Deposit No. 203587 (DNA96786-2534), ATCC Deposit No. 203589 (DNA96787-2534), ATCC Deposit No. 203590 (DNA92505-2534), ATCC Deposit No. 203846 (DNA102043-2534), and ATCC Deposit No. 203973 (DNA114876-2534).

In another aspect, the invention concerns an isolated IL-1lp polypeptide that consists of an amino acid sequence having at least at or about 80% sequence identity, or at least at or about 85% sequence identity, or at least at or about 90% sequence identity, or at least at or about 95% sequence identity to an amino acid sequence selected from the group consisting of: (1) the entire amino acid sequence encoded by the longest open reading frame in the cDNA insert in the vector deposited as ATCC Deposit No. 203588, (2) the entire amino acid sequence, or the entire amino acid sequence excluding the 36 N-terminal amino acid residues of such sequence, encoded by the longest open reading frame in the cDNA insert in the vector deposited as ATCC Deposit No. 203587, (3) the entire amino acid sequence, or the entire amino acid sequence excluding the N-terminal amino acid residue of such sequence, encoded by the longest open reading frame in the cDNA insert in the vector deposited as ATCC Deposit No. 203589, (4) the entire amino acid sequence, or the entire amino acid sequence excluding the N-terminal amino acid residue of such sequence, encoded by the longest open reading frame in the cDNA insert in the vector deposited as ATCC Deposit No. 203590, (5) the entire amino acid sequence, or the entire amino acid sequence excluding the N-terminal amino acid residue of such sequence, or the entire amino acid sequence excluding the 34 N-terminal amino acid residues of such sequence, encoded by the longest open reading frame in the cDNA insert in the vector deposited as ATCC Deposit No. 203846, and (6) the entire amino acid sequence, or the entire amino acid sequence excluding the N-terminal amino acid residue of such sequence, or the entire amino acid sequence excluding the 45 N-terminal amino acid residues of such sequence, encoded by the longest open reading frame in the cDNA insert in the vector deposited as ATCC Deposit No. 203973.

In a preferred embodiment, the IL-1lp polypeptide comprises an amino acid sequence selected from the group consisting of: (1) the entire amino acid sequence encoded by the longest open reading frame in the cDNA insert in the vector deposited as ATCC Deposit No. 203588, (2) the entire amino acid sequence, or the entire amino acid sequence excluding the 36 N-terminal amino acid residues of such sequence, encoded by the longest open reading frame in the cDNA insert in the vector deposited as ATCC Deposit No. 203587, (3) the entire amino acid sequence, or the entire amino acid sequence excluding the N-terminal amino acid residue of such sequence, encoded by the longest open reading frame in the cDNA insert in the vector deposited as ATCC Deposit No. 203589, (4) the entire amino acid sequence, or the entire amino acid sequence excluding the N-terminal amino acid residue of such sequence, encoded by the longest open reading frame in the cDNA insert in the vector deposited as ATCC Deposit No. 203590, (5) the entire amino acid sequence, or the entire amino acid sequence excluding the N-terminal amino acid residue of such sequence, or the entire amino acid sequence excluding the 34 N-terminal amino acid residues of such sequence, encoded by the longest open reading frame in the cDNA insert in the vector deposited as ATCC Deposit No. 203846, and (6) the entire amino acid sequence, or the entire amino acid sequence excluding the N-terminal amino acid residue of such sequence, or the entire amino acid sequence excluding the 45 N-terminal amino acid residues of such sequence, encoded by the longest open reading frame in the cDNA insert in the vector deposited as ATCC Deposit No. 203973.

In another aspect, the invention concerns an isolated IL-1lp polypeptide that retains at least one biologic activity of a native sequence IL-1lp, such as the IL-1R binding activity of a native sequence hIL-1Ra3 or mIL-1Ra3, or the IL-18R binding activity of a native sequence hIL-1Ra1, hIL-1Ra1L, or hIL-1Ra1V, and that consists of an amino acid sequence having at least at or about 80% positives, or at least at or about 85% positives, or at least at or about 90% positives, or at least at or about 95% positives to the sequence of amino acid residues from at or about 37 to at or about 203, inclusive of FIG. 2 (SEQ ID NO:5), the sequence of amino acid residues from at or about 15 to at or about 193, inclusive of FIG. 3 (SEQ ID NO:7), the sequence of amino acid residues from at or about 34 to at or about 155, inclusive of FIG. 7 (SEQ ID NO:13), the sequence of amino acid residues from at or about 34 to at or about 155, inclusive of FIG. 9 (SEQ ID NO:16), or the sequence of amino acid residues from at or about 46 to at or about 218, inclusive of FIG. 19 (SEQ ID NO:25).

In another aspect, the invention concerns an isolated IL-1lp polypeptide that retains at least one biologic activity of a native sequence IL-1lp, such as the IL-18R binding activity of a native sequence hIL-1Ra1, hIL-1Ra1L, or hIL-1Ra1V, and that consists of an amino acid sequence having at least at or about 80% positives, or at least at or about 85% positives, or at least at or about 90% positives, or at least at or about 95% positives to the sequence of amino acid residues from at or about 1 to at or about 207, inclusive of FIG. 15 (SEQ ID NO:19), or the sequence of amino acid residues from at or about 1 to at or about 218, inclusive of FIG. 19 (SEQ ID NO:25).

In another aspect, the invention provides an isolated IL-1lp selected from the group consisting of: (1) a polypeptide, such as an hIL-1Ra1 polypeptide, consisting of an amino acid sequence having a % positives value of at least at or about 80%, or at least at or about 85%, or at least at or about 90%, or at least at or about 95%, to the sequence of amino acid residues from at or about 37 to at or about 63, inclusive of FIG. 2 (SEQ ID NO:5); (2) a polypeptide, such as an hIL-1Ra1 polypeptide, consisting of an amino acid sequence having a % positives value of at least at or about 80%, or at least at or about 85%, or at least at or about 90%, or at least at or about 95%, to the sequence of amino acid residues from at or about 15 to at or about 53, inclusive of FIG. 3 (SEQ ID NO:7); (3) a polypeptide, such as an hIL-1Ra2 polypeptide, comprising the amino acid sequence of amino acid residues from at or about 1 to at or about 134, inclusive of FIG. 5 (SEQ ID NO:10); (4) a polypeptide comprising the amino acid sequence of amino acid residues from at or about 10 to at or about 134, inclusive of FIG. 5 (SEQ ID NO:10); (5) a polypeptide, such as an hIL-1Ra2 polypeptide, consisting of the amino acid sequence of amino acid residues from at or about 27 to at or about 134, inclusive of FIG. 5 (SEQ ID NO:10); (6) a polypeptide, such as an hIL-1Ra2 fusion variant polypeptide, consisting of a native amino acid sequence of hIL-1Ra2 consisting of amino acid residues from at or about 27 to at or about 134, inclusive of FIG. 5 (SEQ ID NO:10) fused at its N-terminus or C-terminus to a heterologous amino acid or amino acid sequence; (7) a polypeptide, such as an hIL-1Ra3 polypeptide, consisting of an amino acid sequence having a % positives value of at least at or about 80%, or at least at or about 85%, or at least at or about 90%, or at least at or about 95%, to the sequence of amino acid residues from at or about 95 to at or about 134, inclusive of FIG. 7 (SEQ ID NO:13); and (8) a polypeptide, such as a mIL-1Ra3 polypeptide, consisting of an amino acid sequence having a % positives value of at least at or about 80%, or at least at or about 85%, or at least at or about 90%, or at least at or about 95%, to the sequence of amino acid residues from at or about 95 to at or about 134, inclusive of FIG. 9 (SEQ ID NO:16).

In another aspect, the invention provides an isolated IL-1lp selected from the group consisting of: (1) a polypeptide, such as an hIL-1Ra1L polypeptide, consisting of an amino acid sequence having a % positives value of at least at or about 80%, or at least at or about 85%, or at least at or about 90%, or at least at or about 95%, to the sequence of amino acid residues from at or about 27 to at or about 44, inclusive of FIG. 15 (SEQ ID NO:19); (2) a polypeptide, such as an hIL-1Ra1S fusion variant polypeptide, consisting of a native amino acid sequence of hIL-1Ra1S consisting of amino acid residues from at or about 39 to at or about 167, inclusive of FIG. 16 (SEQ ID NO:21) fused at its N-terminus or C-terminus to a heterologous amino acid or amino acid sequence; (3) a polypeptide, such as an hIL-1Ra1S fusion variant polypeptide, consisting of a native amino acid sequence of hIL-1Ra1S consisting of amino acid residues from at or about 47 to at or about 167, inclusive of FIG. 16 (SEQ ID NO:21) fused at its N-terminus or C-terminus to a heterologous amino acid or amino acid sequence; (4) a polypeptide, such as an hIL-1Ra1S polypeptide, consisting of amino acid residues from at or about 39 to at or about 167, inclusive of FIG. 16 (SEQ ID NO:21); (5) a polypeptide, such as an hIL-1Ra1S polypeptide, consisting of amino acid residues from at or about 47 to at or about 167, inclusive of FIG. 16 (SEQ ID NO:21); and (6) a polypeptide, such as an hIL-1Ra1V polypeptide, consisting of an amino acid sequence having a % positives value of at least at or about 80%, or at least at or about 85%, or at least at or about 90%, or at least at or about 95%, to the sequence of amino acid residues from at or about 37 to at or about 55, inclusive of FIG. 19 (SEQ ID NO:25).

In another aspect, the invention concerns an isolated IL-1lp polypeptide that consists of an amino acid sequence having at least at or about 80% positives, or at least at or about 85% positives, or at least at or about 90% positives, or at least at or about 95% positives to the sequence of amino acid residues from at or about 37 to at or about 203, inclusive of FIG. 2 (SEQ ID NO:5), the sequence of amino acid residues from at or about 15 to at or about 193, inclusive of FIG. 3 (SEQ ID NO:7), the sequence of amino acid residues from at or about 34 to at or about 155, inclusive of FIG. 7 (SEQ ID NO:13), the sequence of amino acid residues from at or about 34 to at or about 155, inclusive of FIG. 9 (SEQ ID NO:16), or the sequence of amino acid residues from at or about 46 to at or about 218, inclusive of FIG. 19 (SEQ ID NO:25).

In another aspect, the invention concerns an isolated IL-1lp polypeptide that consists of an amino acid sequence having at least at or about 80% positives, or at least at or about 85% positives, or at least at or about 90% positives, or at least at or about 95% positives to the sequence of amino acid residues from at or about 1 to at or about 207, inclusive of FIG. 15 (SEQ ID NO:19), or the sequence of amino acid residues from at or about 1 to at or about 218, inclusive of FIG. 19 (SEQ ID NO:25).

In a further aspect, the invention concerns an isolated IL-1lp polypeptide that retains at least one biologic activity of a native sequence IL-1lp, such as the IL-1R binding activity of a native sequence hIL-1Ra3 or mIL-1Ra3, or the IL-18R binding activity of a native sequence hIL-1Ra1, hIL-1Ra1L, or hIL-1Ra1V, and that consists of an amino acid sequence that has at least at or about 80% positives, or at least at or about 85% positives, or at least at or about 90% positives, or at least at or about 95% positives to the amino acid sequence of an IL-1lp, such as a mature IL-1lp polypeptide, encoded by the cDNA insert in the vector deposited as ATCC Deposit No. 203588 (DNA85066-2534), ATCC Deposit No. 203587 (DNA96786-2534), ATCC Deposit No. 203589 (DNA96787-2534), ATCC Deposit No. 203590 (DNA92505-2534), ATCC Deposit No. 203846 (DNA102043-2534), or ATCC Deposit No. 203973 (DNA114876-2534).

In a further aspect, the invention concerns an isolated IL-1lp polypeptide that retains at least one biologic activity of a native sequence IL-1lp, such as the IL-1R binding activity of a native sequence hIL-1Ra3 or mIL-1Ra3, or the IL-18R binding activity of a native sequence hIL-1Ra1, hIL-1Ra1L, or hIL-1Ra1V, and that consists of an amino acid sequence that has at least at or about 80% positives, or at least at or about 85% positives, or at least at or about 90% positives, or at least at or about 95% positives to the entire amino acid sequence encoded by the longest open reading frame in the cDNA insert of a vector selected from the group consisting of the vectors deposited as ATCC Deposit No. 203588 (DNA85066-2534), ATCC Deposit No. 203587 (DNA96786-2534), ATCC Deposit No. 203589 (DNA96787-2534), ATCC Deposit No. 203590 (DNA92505-2534), ATCC Deposit No. 203846 (DNA102043-2534), and ATCC Deposit No. 203973 (DNA114876-2534).

In another aspect, the invention concerns an isolated IL-1lp polypeptide that retains at least one biologic activity of a native sequence IL-1lp, such as the IL-1R binding activity of a native sequence IL-1Ra3 or mIL-1Ra3, or the IL-18R binding activity of a native sequence hIL-1Ra1, hIL-1Ra1L, or hIL-1Ra1V, and that consists of an amino acid sequence having at least at or about 80% positives, or at least at or about 85% positives, or at least at or about 90% positives, or at least at or about 95% positives to an amino acid sequence selected from the group consisting of: (1) the entire amino acid sequence encoded by the longest open reading frame in the cDNA insert in the vector deposited as ATCC Deposit No. 203588, (2) the entire amino acid sequence, or the entire amino acid sequence excluding the 36 N-terminal amino acid residues of such sequence, encoded by the longest open reading frame in the cDNA insert in the vector deposited as ATCC Deposit No. 203587, (3) the entire amino acid sequence, or the entire amino acid sequence excluding the N-terminal amino acid residue of such sequence, encoded by the longest open reading frame in the cDNA insert in the vector deposited as ATCC Deposit No. 203589, (4) the entire amino acid sequence, or the entire amino acid sequence excluding the N-terminal amino acid residue of such sequence, encoded by the longest open reading frame in the cDNA insert in the vector deposited as ATCC Deposit No. 203590, (5) the entire amino acid sequence, or the entire amino acid sequence excluding the N-terminal amino acid residue of such sequence, or the entire amino acid sequence excluding the 34 N-terminal amino acid residues of such sequence, encoded by the longest open reading frame in the cDNA insert in the vector deposited as ATCC Deposit No. 203846, and (6) the entire amino acid sequence, or the entire amino acid sequence excluding the N-terminal amino acid residue of such sequence, or the entire amino acid sequence excluding the 45 N-terminal amino acid residues of such sequence, encoded by the longest open reading frame in the cDNA insert in the vector deposited as ATCC Deposit No. 203973.

In a further aspect, the invention concerns an isolated IL-1lp polypeptide that consists of an amino acid sequence that has at least at or about 80% positives, or at least at or about 85% positives, or at least at or about 90% positives, or at least at or about 95% positives to the amino acid sequence of an IL-1lp, such as a mature IL-1lp polypeptide, encoded by the cDNA insert in the vector deposited as ATCC Deposit No. 203588 (DNA85066-2534), ATCC Deposit No. 203587 (DNA96786-2534), ATCC Deposit No. 203589 (DNA96787-2534), ATCC Deposit No. 203590 (DNA92505-2534), ATCC Deposit No. 203846 (DNA102043-2534), or ATCC Deposit No. 203973 (DNA114876-2534).

In a further aspect, the invention concerns an isolated IL-1lp polypeptide that consists of an amino acid sequence that has at least at or about 80% positives, or at least at or about 85% positives, or at least at or about 90% positives, or at least at or about 95% positives to the entire amino acid sequence encoded by the longest open reading frame in the cDNA insert of a vector selected from the group consisting of the vectors deposited as ATCC Deposit No. 203588 (DNA85066-2534), ATCC Deposit No. 203587 (DNA96786-2534), ATCC Deposit No. 203589 (DNA96787-2534), ATCC Deposit No. 203590 (DNA92505-2534), ATCC Deposit No. 203846 (DNA102043-2534), and ATCC Deposit No. 203973 (DNA114876-2534).

In another aspect, the invention concerns an isolated IL-1lp polypeptide that consists of an amino acid sequence having at least at or about 80% positives, or at least at or about 85% positives, or at least at or about 90% positives, or at least at or about 95% positives to an amino acid sequence selected from the group consisting of: (1) the entire amino acid sequence encoded by the longest open reading frame in the cDNA insert in the vector deposited as ATCC Deposit No. 203588, (2) the entire amino acid sequence, or the entire amino acid sequence excluding the 36 N-terminal amino acid residues of such sequence, encoded by the longest open reading frame in the cDNA insert in the vector deposited as ATCC Deposit No. 203587, (3) the entire amino acid sequence, or the entire amino acid sequence excluding the N-terminal amino acid residue of such sequence, encoded by the longest open reading frame in the cDNA insert in the vector deposited as ATCC Deposit No. 203589, (4) the entire amino acid sequence, or the entire amino acid sequence excluding the N-terminal amino acid residue of such sequence, encoded by the longest open reading frame in the cDNA insert in the vector deposited as ATCC Deposit No. 203590, (5) the entire amino acid sequence, or the entire amino acid sequence excluding the N-terminal amino acid residue of such sequence, or the entire amino acid sequence excluding the 34 N-terminal amino acid residues of such sequence, encoded by the longest open reading frame in the cDNA insert in the vector deposited as ATCC Deposit No. 203846, and (6) the entire amino acid sequence, or the entire amino acid sequence excluding the N-terminal amino acid residue of such sequence, or the entire amino acid sequence excluding the 45 N-terminal amino acid residues of such sequence, encoded by the longest open reading frame in the cDNA insert in the vector deposited as ATCC Deposit No. 203973.

In another aspect, the invention provides an isolated polypeptide, such as an hIL-1Ra3 polypeptide, consisting of an amino acid sequence having a % positives value of at least at or about 80%, or at least at or about 85%, or at least at or about 90%, or at least at or about 95%, to the sequence of amino acid residues from at or about 80 to at or about 155, inclusive of FIG. 7 (SEQ ID NO:13).

In yet another aspect, the invention concerns an isolated IL-11p polypeptide comprising an amino acid sequence selected from the group consisting of: (1) amino acid residues from at or about 37 to at or about 63, inclusive of FIG. 2 (SEQ ID NO:5); (2) amino acid residues from at or about 15 to at or about 53, inclusive of FIG. 3 (SEQ ID NO:7); (3) amino acid residues from at or about 80 to at or about 155, inclusive of FIG. 7 (SEQ ID NO:13); and (4) amino acid residues from at or about 95 to at or about 155, inclusive of FIG. 9 (SEQ ID NO:16), or a fragment of such IL-11p polypeptide that coincides with a stretch of at least about 10 contiguous amino acids in such amino acid sequence, wherein the IL-11p polypeptide or fragment thereof is sufficient to provide a binding site for an anti-IL-11p antibody. Preferably, the IL-11p fragment retains at least one biologic activity of a native sequence IL-11p polypeptide.

In yet another aspect, the invention concerns an isolated IL-11p polypeptide comprising an amino acid sequence selected from the group consisting of: (1) amino acid residues from at or about 26 to at or about 44, inclusive of FIG. 15 (SEQ ID NO:19), (2) amino acid residues from at or about 26 to at or about 78, inclusive of FIG. 19 (SEQ ID NO:25), and (3) amino acid residues from at or about 46 to at or about 89, inclusive of FIG. 19 (SEQ ID NO:25), or a fragment of such IL-11p polypeptide that coincides with a stretch of at least about 10 contiguous amino acids in such amino acid sequence, wherein the IL-11p polypeptide or fragment thereof is sufficient to provide a binding site for an anti-IL-11p antibody. Preferably, the IL-11p fragment retains at least one biologic activity of a native sequence IL-11p polypeptide.

In a further aspect, the invention provides an isolated IL-11p polypeptide selected from the group consisting of: (1) a polypeptide, such as an hIL-1Ra1 polypeptide, comprising amino acid residues from at or about 37 to at or about 63, inclusive of FIG. 2 (SEQ ID NO:5); (2) a polypeptide, such as an hIL-1Ra1 polypeptide, comprising amino acid residues from at or about 15 to at or about 53, inclusive of FIG. 3 (SEQ ID NO:7); (3) a polypeptide, such as an hIL-1Ra3 polypeptide, comprising amino acid residues from at or about 95 to at or about 134, inclusive of FIG. 7 (SEQ ID NO:13); and (4) a polypeptide, such as a mIL-1Ra3 polypeptide, comprising amino acid residues from at or about 95 to at or about 134, inclusive of FIG. 9 (SEQ ID NO:16).

In a further aspect, the invention provides an isolated IL-11p polypeptide selected from the group consisting of: (1) a polypeptide, such as an hIL-1Ra1 polypeptide, comprising amino acid residues from at or about 37 to at or about 203, inclusive of FIG. 2 (SEQ ID NO:5); (2) a polypeptide, such as an hIL-1Ra1 polypeptide, comprising amino acid residues from at or about 15 to at or about 193, inclusive of FIG. 3 (SEQ ID NO:7); (3) a polypeptide, such as an hIL-1Ra3 polypeptide, comprising amino acid residues from at or about 34 to at or about 155, inclusive of FIG. 7 (SEQ ID NO:13); and (3) a polypeptide, such as a mIL-1Ra3 polypeptide, comprising amino acid residues from at or about 34 to at or about 155, inclusive of FIG. 9 (SEQ ID NO:16).

In a further aspect, the invention provides an isolated polypeptide, such as an hIL-1Ra3 polypeptide, comprising amino acid residues from at or about 80 to at or about 155, inclusive of FIG. 7 (SEQ ID NO:13).

In a further aspect, the invention provides an isolated IL-11p polypeptide selected from the group consisting of: (1) a polypeptide, such as an hIL-1Ra1L polypeptide, comprising amino acid residues from at or about 26 to at or about 44, inclusive of FIG. 15 (SEQ ID NO:19); (2) a polypeptide, such as an hIL-1Ra1L polypeptide, comprising amino acid residues from at or about 1 to at or about 44, inclusive of FIG. 15 (SEQ ID NO:19); (3) a polypeptide, such as an hIL-1Ra1S polypeptide, comprising amino acid residues from at or about 1 to at or about 38, inclusive of FIG. 16 (SEQ ID NO:21); (4) a polypeptide, such as an hIL-1Ra1V polypeptide, comprising amino acid residues from at or about 37 to at or about 55, inclusive of FIG. 19 (SEQ ID NO:25); (5) a polypeptide, such as an hIL-1Ra1V polypeptide, comprising amino acid residues from at or about 12 to at or about 55, inclusive of FIG. 19 (SEQ ID NO:25); and (6) a polypeptide, such as an hIL-1Ra1V polypeptide, comprising amino acid residues from at or about 1 to at or about 55, inclusive of FIG. 19 (SEQ ID NO:25).

In a further aspect, the invention provides an isolated IL-11p polypeptide selected from the group consisting of: (1) a polypeptide, such as an hIL-1Ra1L fusion variant polypeptide, consisting of a native amino acid sequence of hIL-1Ra1L consisting of amino acid residues from at or about 1 to at or about 207, inclusive of FIG. 15 (SEQ ID NO:19) fused at its N-terminus or C-terminus to a heterologous amino acid or amino acid sequence; (2) a polypeptide, such as an hIL-1Ra1L fusion variant polypeptide, consisting of a native amino acid sequence of hIL-1Ra1L consisting of amino acid residues from at or about 26 to at or about 207, inclusive of FIG. 15 (SEQ ID NO:19) fused at its N-terminus or C-terminus to a heterologous amino acid or amino acid sequence; (3) a polypeptide, such as an hIL-1Ra1L polypeptide, consisting of amino acid residues from at or about 1 to at or about 207, inclusive of FIG. 15 (SEQ ID NO:19); (4) a polypeptide, such as an hIL-1Ra1L polypeptide, consisting of amino acid residues from at or about 26 to at or about 207, inclusive of FIG. 15 (SEQ ID NO:19); (5) a polypeptide, such as an hIL-1Ra1V fusion variant polypeptide, consisting of a native amino acid sequence of hIL-1Ra1V consisting of amino acid residues from at or about 1 to at or about 218, inclusive of FIG. 19 (SEQ ID NO:25) fused at its N-terminus or C-terminus to a heterologous amino acid or amino acid sequence; (6) a polypeptide, such as an hIL-1Ra1V fusion variant polypeptide, consisting of a native amino acid sequence of hIL-1Ra1V consisting of amino acid residues from at or about 12 to at or about 218, inclusive of FIG. 19 (SEQ ID NO:25) fused at its N-terminus or C-terminus to a heterologous amino acid or amino acid sequence; (7) a polypeptide, such as an hIL-1Ra1V fusion variant polypeptide, consisting of a native amino acid sequence of hIL-1Ra1V consisting of amino acid residues from at or about 37 to at or about 218, inclusive of FIG. 19 (SEQ ID NO:25) fused at its N-terminus or C-terminus to a heterologous amino acid or amino acid sequence; (8) a polypeptide, such as an hIL-1Ra1V fusion variant polypeptide, consisting of a native amino acid sequence of hIL-1Ra1V consisting of amino acid residues from at or about 46 to at or about 218, inclusive of FIG. 19 (SEQ ID NO:25) fused at its N-terminus or C-terminus to a heterologous amino acid or amino acid sequence; (9) a polypeptide, such as an hIL-1Ra1V polypeptide, consisting of the amino acid sequence of amino acid residues from at or about 1 to at or about 218, inclusive of FIG. 19 (SEQ ID NO:25); (10) a polypeptide, such as an hIL-1Ra1V polypeptide, consisting of the amino acid sequence of amino acid residues from at or about 12 to at or about 218, inclusive of FIG. 19 (SEQ ID NO:25); (11) a polypeptide, such as an hIL-1Ra1V polypeptide, consisting of the amino acid sequence of amino acid residues from at or about 37 to at or about 218, inclusive of FIG. 19 (SEQ ID NO:25); and (12) a polypeptide, such as an hIL-1Ra1V polypeptide, consisting of the amino acid sequence of amino acid residues from at or about 46 to at or about 218, inclusive of FIG. 19 (SEQ ID NO:25).

In a further aspect, the invention provides an isolated IL-1lp polypeptide selected from the group consisting of: (1) a polypeptide, such as an hIL-1Ra1L polypeptide, comprising amino acid residues from at or about 1 to at or about 207, inclusive of FIG. 15 (SEQ ID NO:19); (2) a polypeptide, such as an hIL-1Ra1L polypeptide, comprising amino acid residues from at or about 26 to at or about 207, inclusive of FIG. 15 (SEQ ID NO:19); (3) a polypeptide, such as an hIL-1Ra1S polypeptide, comprising amino acid residues from at or about 1 to at or about 167, inclusive of FIG. 16 (SEQ ID NO:21); (4) a polypeptide, such as an hIL-1Ra1S polypeptide, comprising amino acid residues from at or about 26 to at or about 167, inclusive of FIG. 16 (SEQ ID NO:21); (5) a polypeptide, such as an hIL-1Ra1V polypeptide, comprising amino acid residues from at or about 1 to at or about 218, inclusive of FIG. 19 (SEQ ID NO:25); and (6) a polypeptide, such as an hIL-1Ra1V polypeptide, comprising amino acid residues from at or about 12 to at or about 218, inclusive of FIG. 19 (SEQ ID NO:25).

In a further aspect, the invention provides an isolated IL-1lp polypeptide selected from the group consisting of: (1) a polypeptide, such as an hIL-1Ra1V polypeptide, comprising amino acid residues from at or about 37 to at or about 218, inclusive of FIG. 19 (SEQ ID NO:25); and (2) a polypeptide, such as an hIL-1Ra1V polypeptide, comprising amino acid residues from at or about 46 to at or about 218, inclusive of FIG. 19 (SEQ ID NO:25).

In a further aspect, the invention provides an isolated IL-1lp polypeptide selected from the group consisting of: (1) a polypeptide consisting of the amino acid sequence of amino acid residues 10 to 134, inclusive of FIG. 5 (SEQ ID NO:10) fused at its N-terminus or C-terminus to a heterologous amino acid or amino acid sequence; (2) a polypeptide consisting of the amino acid sequence of amino acid residues 10 to 134, inclusive of FIG. 5 (SEQ ID NO:10); (3) a polypeptide, such as an hIL-1Ra3 polypeptide, consisting of a native amino acid sequence of hIL-1Ra3 consisting of amino acid residues 2 to 155, inclusive of FIG. 7 (SEQ ID NO:13) fused at its N-terminus or C-terminus to a heterologous amino acid or amino acid sequence; (4) a polypeptide, such as an hIL-1Ra3 polypeptide, consisting of the amino acid sequence of amino acid residues from 2 to 155, inclusive of FIG. 7 (SEQ ID NO:13); (5) a polypeptide, such as a mIL-1Ra3 polypeptide, consisting of a native amino acid sequence of mIL-1Ra3 consisting of amino acid residues 2 to 155, inclusive of FIG. 9 (SEQ ID NO:16) fused at its N-terminus or C-terminus to a heterologous amino acid or amino acid sequence; (6) a polypeptide, such as a mIL-1Ra3 polypeptide, consisting of the amino acid sequence of amino acid residues 2 to 155, inclusive of FIG. 9 (SEQ ID NO:16).

In a further aspect, the invention provides an isolated IL-1lp polypeptide selected from the group consisting of: (1) a polypeptide comprising the amino acid sequence of amino acid residues 10 to 134, inclusive of FIG. 5 (SEQ ID NO:10); (2) a polypeptide, such as an hIL-1Ra3 polypeptide, comprising the amino acid sequence of amino acid residues 2 to 155, inclusive of FIG. 7 (SEQ ID NO:13); and (3) a polypeptide, such as a mIL-1Ra3 polypeptide, comprising the amino acid sequence of amino acid residues from 2 to 155, inclusive of FIG. 9 (SEQ ID NO:16).

In a still further aspect, the invention provides an isolated IL-1lp polypeptide that is the same as a mature polypeptide encoded by the cDNA insert of a vector selected from the group consisting of the vectors deposited as ATCC Deposit Nos. 203588, 203587, 203586, 203589, and 203590.

In a still further aspect, the invention provides an isolated IL-1lp polypeptide that is the same as a mature polypeptide encoded by the cDNA insert of a vector selected from the group consisting of the vectors deposited as ATCC Deposit Nos. 203846, 203855 and 203973.

In a still further aspect, the invention provides an isolated polypeptide comprising the entire amino acid sequence encoded by the longest open reading frame in the cDNA insert of a vector selected from the group consisting of the vectors deposited as ATCC Deposit Nos. 203588, 203586, 203589 and 203590.

In a still further aspect, the invention provides an isolated polypeptide comprising the entire amino acid sequence encoded by the longest open reading frame in the cDNA insert of a vector selected from the group consisting of the vectors deposited as ATCC Deposit Nos. 203846, 203855 and 203973.

In another aspect, the invention provides a polypeptide that is produced by (i) hybridizing a test DNA molecule under stringent conditions with (a) a DNA molecule encoding an amino acid sequence selected from the group consisting of: (1) amino acid residues from at or about 37 to at or about 203, inclusive of FIG. 2 (SEQ ID NO:5), (2) amino acid residues from at or about 15 to at or about 193, inclusive of FIG. 3 (SEQ ID NO:7), (3) amino acid residues from at or about 2 to at or about 155, inclusive of FIG. 7 (SEQ ID NO:13), and (4) amino acid residues from at or about 2 to at or about 155, inclusive of FIG. 9 (SEQ ID NO:16), or (b) the complement of the DNA molecule of (a), and if the test DNA molecule encodes an IL-1lp polypeptide that retains at least one biologic activity of a native sequence IL-1lp, such as the IL-1R binding activity of a native sequence hIL-1Ra3 or mIL-1Ra3, or the IL-18R binding activity of a native sequence hIL-1Ra1, hIL-1Ra1L, or hIL-1Ra1V, and if the test DNA molecule has at least at or about an 80% sequence identity, or at least at or about an 85% sequence identity, or at least at or about a 90% sequence identity, or at least at or about a 95% sequence identity to the DNA molecule of (a) or (b), (ii) culturing a host cell comprising the test DNA molecule under conditions suitable for expression of the IL-1lp polypeptide, and (iii) recovering the IL-1lp polypeptide from the cell culture.

In a still further aspect, the invention provides a polypeptide that is produced by (i) hybridizing a test DNA molecule under stringent conditions with (a) a DNA molecule encoding an amino acid sequence selected from the group consisting of: (1) amino acid residues from at or about 26 to at or about 207, inclusive of FIG. 15 (SEQ ID NO:19), (2) amino acid residues from at or about 1 to at or about 218, inclusive of FIG. 19 (SEQ ID NO:25), (3) amino acid residues from at or about 12 to at or about 218, inclusive of FIG. 19 (SEQ ID NO:25), (4) amino acid residues from at or about 37 to at or about 218, inclusive of FIG. 19 (SEQ ID NO:25), and (5) amino acid residues from at or about 46 to at or about 218, inclusive of FIG. 19 (SEQ ID NO:25), or (b) the complement of the DNA molecule of (a), and if the test DNA molecule encodes an IL-1lp polypeptide that retains at least one biologic activity of a native sequence IL-1lp, such as the IL-18R binding activity of a native sequence hIL-1Ra1, hIL-1Ra1L, or hIL-1Ra1V, and if the test DNA molecule has at least at or about an 80% sequence identity, or at least at or about an 85% sequence identity, or at least at or about a 90% sequence identity, or at least at or about a 95% sequence identity to the DNA molecule of (a) or (b), (ii) culturing a host cell comprising the test DNA molecule under conditions suitable for expression of the IL-1lp polypeptide, and (iii) recovering the IL-1lp polypeptide from the cell culture.

A. Preparation of IL-1lp

The description below relates primarily to production of IL-1lp by culturing cells transformed or transfected with a vector containing IL-1lp nucleic acid. It is, of course, contemplated that alternative methods, which are well known in the art, may be employed to prepare IL-1lp. For instance, the IL-1lp sequence, or portions thereof, may be produced by direct peptide synthesis using solid-phase techniques [see, e.g., Stewart et al., *Solid-Phase Peptide Synthesis*, W.H. Freeman Co., San Francisco, Calif. (1969); Merrifield, *J. Am. Chem. Soc.*, 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the IL-1lp may be chemically synthesized separately and combined using chemical or enzymatic methods to produce the full-length IL-1lp.

1. Isolation of DNA Encoding IL-1lp

DNA encoding IL-1lp may be obtained from a cDNA library prepared from tissue believed to possess the IL-1lp mRNA and to express it at a detectable level. Accordingly, human IL-1lp DNA can be conveniently obtained from a cDNA library prepared from human tissue, such as described in the Examples. The IL-1lp-encoding gene may also be obtained from a genomic library or by oligonucleotide synthesis.

Libraries can be screened with probes (such as antibodies to the IL-1lp or oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding IL-1lp is to use PCR methodology [Sambrook et al., supra; Dieffenbach et al., *PCR Primer: A Laboratory Manual* (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined through sequence alignment using computer software programs such as BLAST, BLAST2, ALIGN-2, DNAstar, and INHERIT which employ various algorithms to measure homology.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for IL-1lp production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: A Practical Approach*, M. Butler, ed. (IRL Press, 1991) and Sambrook et al., supra.

Methods of transfection are known to the ordinarily skilled artisan, for example, $CaPO_4$ and electroporation. Depending on the host cell used, transformation is performed using standard techniques appropriate to such cells. The calcium treatment employing calcium chloride, as described in Sambrook et al., supra, or electroporation is generally used for prokaryotes or other cells that contain substantial cell-wall barriers. Infection with *Agrobacterium tumefaciens* is used for transformation of certain plant cells, as described by Shaw et al., *Gene*, 23:315 (1983) and WO 89/05859 published 29 Jun. 1989. For mammalian cells without such cell walls, the calcium phosphate precipitation method of Graham and van der Eb, *Virology*, 52:456-457 (1978) can be employed. General aspects of mammalian cell host system transformations have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci.* (*USA*), 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527-537 (1990) and Mansour et al., *Nature*, 336: 348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635).

In addition to prokaryotes, eukaryotic microbes such as filamentous fungi or yeast are suitable cloning or expression hosts for IL-1lp-encoding vectors. *Saccharomyces cerevisiae* is a commonly used lower eukaryotic host microorganism.

Suitable host cells for the expression of glycosylated IL-1lp are derived from multicellular organisms. Examples of invertebrate cells include insect cells such as *Drosophila* S2 and *Spodoptera* Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); Chinese hamster ovary cells/-DHFR (CHO, Urlaub and Chasin, *Proc. Natl. Acad. Sci. USA*, 77:4216 (1980)); mouse sertoli cells (TM4, Mather, *Biol. Reprod.*, 23:243-251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding IL-1lp may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The IL-1lp may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the IL-1lp-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the IL-1lp-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA*, 77:4216 (1980). A suitable selection gene for use in yeast is the trp1 gene present in the yeast plasmid YRp7 [Stinchcomb et al., *Nature*, 282:39 (1979); Kingsman et al., *Gene*, 7:141 (1979); Tschemper et al., *Gene*, 10:157 (1980)]. The trp1 gene provides a selection marker for a mutant strain of yeast lacking the ability to grow in tryptophan, for example, ATCC No. 44076 or PEP4-1 [Jones, *Genetics*, 85:12 (1977)].

Expression and cloning vectors usually contain a promoter operably linked to the IL-1lp-encoding nucleic acid sequence to direct mRNA synthesis. Promoters recognized by a variety of potential host cells are well known. Promoters suitable for use with prokaryotic hosts include the β-lactamase and lactose promoter systems [Chang et al., *Nature*, 275:615 (1978); Goeddel et al., *Nature*, 281:544 (1979)], alkaline phosphatase, a tryptophan (trp) promoter system [Goeddel, *Nucleic Acids Res.*, 8:4057 (1980); EP 36,776], and hybrid promoters such as the tac promoter [deBoer et al., Proc. Natl. Acad. Sci. USA, 80:21-25 (1983)]. Promoters for use in bacterial systems also will contain a Shine-Dalgarno (S.D.) sequence operably linked to the DNA encoding IL-1lp.

Examples of suitable promoting sequences for use with yeast hosts include the promoters for 3-phosphoglycerate kinase [Hitzeman et al., *J. Biol. Chem.*, 255:2073 (1980)] or other glycolytic enzymes [Hess et al., *J. Adv. Enzyme Reg.*, 7:149 (1968); Holland, *Biochemistry*, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

IL-1lp transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the IL-1lp by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the IL-1lp coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding IL-1lp.

Still other methods, vectors, and host cells suitable for adaptation to the synthesis of IL-1lp in recombinant vertebrate cell culture are described in Gething et al., *Nature*, 293:620-625 (1981); Mantei et al., *Nature*, 281:40-46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA*, 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence IL-1lp polypeptide or against a synthetic peptide based on the DNA sequences provided herein or against exogenous sequence fused to IL-1lp DNA and encoding a specific antibody epitope.

5. Purification of Polypeptide

Forms of IL-1lp may be recovered from culture medium or from host cell lysates. If membrane-bound, it can be released from the membrane using a suitable detergent solution (e.g. Triton-X 100) or by enzymatic cleavage. Cells employed in expression of IL-1lp can be disrupted by various physical or chemical means, such as freeze-thaw cycling, sonication, mechanical disruption, or cell lysing agents. It may be desired to purify IL-1lp from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the IL-1lp. Various methods of protein purification may be employed and such methods are known in the art and described for example in Deutscher, *Methods in Enzymology*, 182 (1990); Scopes, *Protein Purification: Principles and Practice*, Springer-Verlag, New York (1982). The purification step(s) selected will depend, for example, on the nature of the production process used and the particular IL-1lp produced.

B. Activity Assays for IL-1lp Variants

The biological activity or activities of a particular IL-1lp variant polypeptide can be characterized using a variety of in vitro assays known in the art. For example, the ability of an hIL-1Ra3 variant polypeptide or a mIL-1Ra3 variant polypeptide to bind IL-1R can be assayed using a radioimmunoprecipitation assay wherein IL-1R extracellular domain (ECD) fused to the Fc region of human immunoglobulin G (IL-1R ECD-Fc) (which can be prepared, e.g., as described in Examples 9 and 10 below) is incubated in solution with radiolabeled hIL-1Ra3 variant polypeptide or mIL-1Ra3 variant polypeptide to form labeled complexes, followed by immunoprecipitation of the labeled complexes with goat anti-human IgG Fc and quantitation of radioactivity in the precipitate. In another example, an hIL-1Ra3 variant polypeptide-FLAG tag fusion protein-encoding DNA and an IL-1R ECD-Fc encoding DNA can be coexpressed in a host cell and secreted into the cell's culture medium, followed by immunoprecipitation of culture supernatant with protein G-sepharose and identification of bound hIL-1Ra3 variant polypeptide-FLAG tag fusion protein by immunoblotting with anti-FLAG monoclonal antibody, essentially as described in Example 9 below.

In another embodiment, the ability of an hIL-1Ra3 variant polypeptide or a mIL-1Ra3 variant polypeptide to inhibit the binding of IL-1 to IL-1R can be assayed using a competitive binding assay. For example, a radioimmunoprecipitation assay can be employed wherein IL-1R ECD-Fc is incubated in solution of radiolabeled IL-1 with or without unlabeled hIL-1Ra3 variant polypeptide or unlabeled mIL-1Ra3 variant polypeptide to form labeled or unlabeled complexes, followed by immunoprecipitation of complexes with anti-human IgG Fc and quantitation of radioactivity in the precipitate. If the presence of unlabeled hIL-1Ra3 variant polypeptide or unlabeled mIL-1Ra3 variant polypeptide in the incubation solution diminishes the radioactivity measured in the resulting immunoprecipitate, the hIL-1Ra3 variant polypeptide or mIL-1Ra3 variant polypeptide in question qualifies as an inhibitor of IL-1 binding to IL-1R. In yet another embodiment, IL-1R ECD-Fc and an hIL-1Ra3 variant-FLAG tag fusion protein or mIL-1Ra3 variant-FLAG tag fusion protein are obtained by recombinant expression in separate cell cultures (essentially as described in Example 10 below), IL-1 and IL-1R ECD-Fc are admixed together with or without the hIL-1Ra3 variant-FLAG tag fusion protein or mIL-1Ra3 variant-FLAG tag fusion protein and incubated in solution, the incubation solution is immunoprecipitated with protein G-sepharose, and the bound hIL-1Ra3 variant-FLAG tag fusion protein or mIL-1Ra3 variant-FLAG tag fusion protein is identified by immunoblotting with anti-FLAG monoclonal antibody. If the presence of IL-1 in the incubation solution diminishes the signal detected by anti-FLAG immunoblotting, the hIL-1Ra3 variant polypeptide or mIL-1Ra3 variant polypeptide in question qualifies as an inhibitor of IL-1 binding to IL-1R.

Similarly, the biological activity or activities of a particular hIL-1Ra1 variant polypeptide can be determined by using a variety of in vitro assays known in the art. For example, the ability of an hIL-1Ra1 variant polypeptide to bind IL-18R can be assayed using a radioimmunoprecipitation assay wherein IL-18R extracellular domain (ECD) fused to the Fc region of human immunoglobulin G (IL-18R ECD-Fc) (which can be prepared, e.g., as described in Examples 9 and 10 below) is incubated in solution with radiolabeled hIL-1Ra1 variant polypeptide to form labeled complex, followed by immunoprecipitation of the labeled complex with goat anti-human IgG Fc and quantitation of radioactivity in the precipitate. In another example, an hIL-1Ra1 variant polypeptide-FLAG tag fusion protein-encoding DNA and an IL-18R ECD-Fc encoding DNA can be coexpressed in a host cell and secreted into the cell's culture medium, followed by immunoprecipitation of culture supernatant with protein G-sepharose and identification of bound hIL-1Ra1 variant polypeptide-FLAG tag fusion protein by immunoblotting with anti-FLAG monoclonal antibody, essentially as described in Example 9 below.

In another embodiment, the ability of an hIL-1Ra1 variant polypeptide to inhibit the binding of IL-18 to IL-18R can be assayed using a competitive binding assay. For example, a radioimmunoprecipitation assay can be employed wherein IL-18R ECD-Fc is incubated in solution of radiolabeled IL-18 with or without unlabeled hIL-1Ra1 variant polypeptide to form labeled or unlabeled complexes, followed by immunoprecipitation of complexes with anti-human IgG Fc and quantitation of radioactivity in the precipitate. If the presence of unlabeled hIL-1Ra1 variant polypeptide in the incubation solution diminishes the radioactivity measured in the resulting immunoprecipitate, the hIL-1Ra1 variant polypeptide in question qualifies as an inhibitor of IL-18 binding to IL-18R. In yet another embodiment, IL-18R ECD-Fc and an hIL-1Ra1 variant-FLAG tag fusion protein are obtained by recombinant expression in separate cell cultures (essentially as described in Example 10 below), IL-18 and IL-18R ECD-Fc are admixed together with or without the hIL-1Ra1 variant-FLAG tag fusion protein and incubated in solution, the incubation solution is immunoprecipitated with protein G-sepharose, and the bound hIL-1Ra1 variant-FLAG tag fusion protein is identified by immunoblotting with anti-FLAG monoclonal antibody. If the presence of IL-18 in the incubation solution diminishes the signal detected by anti-FLAG immunoblotting, the hIL-1Ra1 variant polypeptide in question qualifies as an inhibitor of IL-18 binding to IL-18R.

C. Uses for IL-1lp

Nucleotide sequences (or their complement) encoding IL-1lp have various applications in the art of molecular biology, including uses as hybridization probes, in chromosome and gene mapping and in the generation of anti-sense RNA and DNA. IL-1lp nucleic acid will also be useful for the preparation of IL-1lp polypeptides by the recombinant techniques described herein.

Figure 1A:
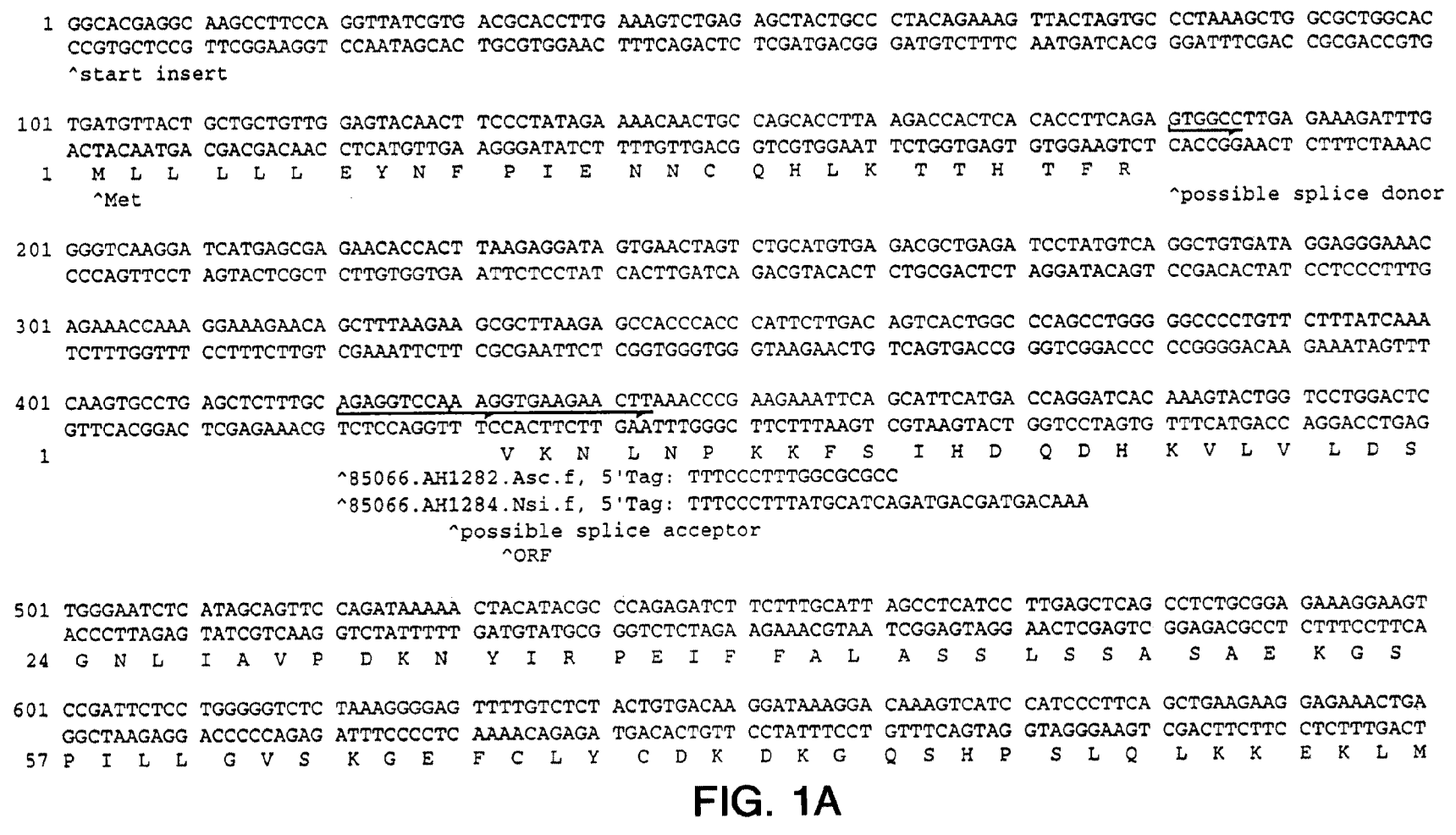

The full-length native sequence IL-1lp genes of FIG. 1 (SEQ ID NO:1), FIG. 2 (SEQ ID NO:4), FIG. 3 (SEQ ID NO:6), FIG. 5 (SEQ ID NO:9), FIG. 7 (SEQ ID NO:12), FIG. 9 (SEQ ID NO:15), FIG. 15 (SEQ ID NO:18), and FIG. 16 (SEQ ID NO:20), and FIG. 19 (SEQ ID NO:24), or portions thereof, may be used as hybridization probes for a cDNA library to isolate the full-length IL-1lp gene or to isolate still other genes (for instance, those encoding naturally-occurring variants of IL-1lp or IL-1lp from other species) which have a desired sequence identity to the IL-1lp sequence disclosed in FIG. 1 (SEQ ID NO:1), FIG. 2 (SEQ ID NO:4), FIG. 3 (SEQ ID NO:6), FIG. 5 (SEQ ID NO:9), FIG. 7 (SEQ ID NO:12), FIG. 9 (SEQ ID NO:15), FIG. 15 (SEQ ID NO:18), FIG. 16 (SEQ ID NO:20), or FIG. 19 (SEQ ID NO:24). Optionally, the length of the probes will be about 20 to about 50 bases. The hybridization probes may be derived from the nucleotide sequence of FIG. 1 (SEQ ID NO:1), FIG. 2 (SEQ ID NO:4), FIG. 3 (SEQ ID NO:6), FIG. 5 (SEQ ID NO:9), FIG. 7 (SEQ ID NO:12), FIG. 9 (SEQ ID NO:15), FIG. 15 (SEQ ID NO:18), FIG. 16 (SEQ ID NO:20) or FIG. 19 (SEQ ID NO:24), or from genomic sequences including promoters, enhancer elements and introns of native sequence IL-1lp. By way of example, a screening method will comprise isolating the coding region of the IL-1lp gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the IL-1lp gene of the present invention can be used to screen libraries of human cDNA, genomic DNA or mRNA to determine which members of such libraries the probe hybridizes to. Hybridization techniques are described in further detail in the Examples below.

The probes may also be employed in PCR techniques to generate a pool of sequences for identification of closely related IL-1lp coding sequences.

Nucleotide sequences encoding an IL-1lp can also be used to construct hybridization probes for mapping the gene which encodes that IL-1lp and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

When the coding sequences for IL-1lp encode a protein which binds to another protein (example, where the IL-1lp binds to an IL-1 receptor or IL-18 receptor), the IL-1lp can be used in assays to identify the other proteins or molecules involved in the binding interaction. By such methods, inhibitors of the receptor/ligand binding interaction can be identified. Proteins involved in such binding interactions can also be used to screen for peptide or small molecule inhibitors or agonists of the binding interaction. Screening assays can be designed to find lead compounds that mimic the biological activity of a native IL-1lp or a receptor for IL-1lp. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein-protein binding assays, biochemical screening assays, immunoassays and cell based assays, which are well characterized in the art.

Nucleic acids which encode IL-1lp or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding IL-1lp can be used to clone genomic DNA encoding IL-1lp in accordance with established techniques and the genomic sequences used to generate transgenic animals that contain cells which express DNA encoding IL-11p. Methods for generating transgenic animals, particularly animals such as mice or rats, have become conventional in the art and are described, for example, in U.S. Pat. Nos. 4,736,866 and 4,870,009. Typically, particular cells would be targeted for IL-11p transgene incorporation with tissue-specific enhancers. Transgenic animals that include a copy of a transgene encoding IL-11p introduced into the germ line of the animal at an embryonic stage can be used to examine the effect of increased expression of DNA encoding IL-11p. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of IL-11p can be used to construct an IL-11p "knock out" animal which has a defective or altered gene encoding IL-11p as a result of homologous recombination between the endogenous gene encoding IL-11p and altered genomic DNA encoding IL-11p introduced into an embryonic cell of the animal. For example, cDNA encoding IL-11p can be used to clone genomic DNA encoding IL-11p in accordance with established techniques. A portion of the genomic DNA encoding IL-11p can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell,* 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell,* 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach,* E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the IL-11p polypeptide.

Nucleic acid encoding the IL-11p polypeptides may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. USA* 83, 4143-4146 [1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology* 11, 205-210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., J. Biol. Chem. 262, 4429-4432 (1987); and Wagner et al., *Proc. Natl. Acad. Sci. USA* 87, 3410-3414 (1990). For review of gene marking and gene therapy protocols see Anderson et al., *Science* 256, 808-813 (1992).

The IL-11p polypeptides of the present invention can be formulated according to known methods to prepare pharmaceutically useful compositions, whereby the IL-11p product hereof is combined in admixture with a pharmaceutically acceptable carrier vehicle. Therapeutic formulations are prepared for storage by mixing the active ingredient having the desired degree of purity with optional physiologically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or PEG.

The formulations to be used for in vivo administration must be sterile. This is readily accomplished by filtration through sterile filtration membranes, prior to or following lyophilization and reconstitution.

Therapeutic compositions herein generally are placed into a container having a sterile access port, for example, an intravenous solution bag or vial having a stopper pierceable by a hypodermic injection needle.

The route of administration is in accord with known methods, e.g. injection or infusion by intravenous, intraperitoneal, intracerebral, intramuscular, intraocular, intraarterial or intralesional routes, topical administration, or by sustained release systems.

Dosages and desired drug concentrations of pharmaceutical compositions of the present invention may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42-96.

An "effective amount" of the IL-1lp to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. Typically, the clinician will administer the IL-1lp until a dosage is reached that achieves the desired effect. The progress of this therapy is easily monitored by conventional assays.

In one embodiment, the invention provides a method for treating an IL-1-mediated disorder comprising administering to a mammal, such as human, in need of such treatment an effective amount of an IL-1lp, such as a native sequence IL-1lp.

In another embodiment, the invention provides a method for treating an IL-1-mediated disorder comprising administering to a mammal, such as human, in need of such treatment an effective amount of an IL-1lp selected from the group consisting of hIL-1Ra1, hIL-1Ra1L, hIL-1Ra1V, hIL-1Ra1S, hIL-1Ra2, hIL-1Ra3, and mIL-1Ra3.

In another embodiment, the invention provides a method for treating an IL-1-mediated disorder comprising administering to a mammal, such as human, in need of such treatment an effective amount of an hIL-1lp, such as a native sequence hIL-1lp, e.g. native sequence hIL-1Ra3.

In another embodiment, the invention provides a method for treating an IL-18-mediated disorder comprising administering to a mammal, such as human, in need of such treatment an effective amount of an IL-1lp, such as a native sequence IL-1lp.

In another embodiment, the invention provides a method for treating an IL-18-mediated disorder comprising administering to a mammal, such as human, in need of such treatment an effective amount of an IL-1lp selected from the group consisting of hIL-1Ra1, hIL-1Ra1L, hIL-1Ra1V, hIL-1Ra1S, hIL-1Ra2, hIL-1Ra3, and mIL-1Ra3.

In another embodiment, the invention provides a method for treating an IL-18-mediated disorder comprising administering to a mammal, such as human, in need of such treatment an effective amount of an hIL-1lp, such as a native sequence hIL-1lp, e.g. native sequence hIL-1Ra1.

In another embodiment, the invention provides a method for treating an IL-18-mediated disorder comprising administering to a mammal, such as human, in need of such treatment an effective amount of an hIL-1Ra1L, such as a native sequence hIL-1Ra1L, or an effective amount of an hIL-1Ra1V, such as a native sequence hIL-1Ra1V, or an effective amount of an hIL-1Ra1S, such as a native sequence hIL-1Ra1S.

In one embodiment, the invention provides a method for treating an inflammatory disorder comprising administering to a mammal, such as human, in need of such treatment an effective amount of an IL-1lp, such as a native sequence IL-1lp.

In another embodiment, the invention provides a method for treating an inflammatory disorder comprising administering to a mammal, such as human, in need of such treatment an effective amount of an IL-1lp selected from the group consisting of hIL-1Ra1, hIL-1Ra1L, hIL-1Ra1V, hIL-1Ra1S, hIL-1Ra2, hIL-1Ra3, and mIL-1Ra3.

In another embodiment, the invention provides a method for treating an inflammatory disorder comprising administering to a mammal, such as human, in need of such treatment an effective amount of an hIL-1lp, such as a native sequence hIL-1lp, e.g. native sequence hIL-1Ra1 or hIL-1Ra3.

In another embodiment, the invention provides a method for treating an inflammatory disorder comprising administering to a mammal, such as human, in need of such treatment an effective amount of an hIL-1Ra1L, such as a native sequence hIL-1Ra1L, or an effective amount of an hIL-1Ra1V, such as a native sequence hIL-1Ra1V, or an effective amount of an hIL-1Ra1S, such as a native sequence hIL-1Ra1S.

In another embodiment, the invention provides a method for treating asthma comprising administering to a mammal, such as human, in need of such treatment an effective amount of an IL-1lp, such as a native sequence IL-1lp.

In another embodiment, the invention provides a method for treating asthma comprising administering to a mammal, such as human, in need of such treatment an effective amount of an IL-1lp selected from the group consisting of hIL-1Ra1, hIL-1Ra1L, hIL-1Ra1V, hIL-1Ra1S, hIL-1Ra2, hIL-1Ra3, and mIL-1Ra3.

In another embodiment, the invention provides a method for treating asthma comprising administering to a mammal, such as human, in need of such treatment an effective amount of an hIL-1lp, such as a native sequence hIL-1lp, e.g. native sequence hIL-1Ra1 or hIL-1Ra3.

In another embodiment, the invention provides a method for treating asthma comprising administering to a mammal, such as human, in need of such treatment an effective amount of an hIL-1Ra1L, such as a native sequence hIL-1Ra1L, or an effective amount of an hIL-1Ra1V, such as a native sequence hIL-1Ra1V, or an effective amount of an hIL-1Ra1S, such as a native sequence hIL-1Ra1S.

In another embodiment, the invention provides a method for treating rheumatoid arthritis comprising administering to a mammal, such as human, in need of such treatment an effective amount of an IL-1lp, such as a native sequence IL-1lp.

In another embodiment, the invention provides a method for treating rheumatoid arthritis comprising administering to a mammal, such as human, in need of such treatment an effective amount of an IL-1lp selected from the group consisting of hIL-1Ra1, hIL-1Ra1L, hIL-1Ra1V, hIL-1Ra1S, hIL-1Ra2, hIL-1Ra3, and mIL-1Ra3.

In another embodiment, the invention provides a method for treating rheumatoid arthritis comprising administering to a mammal, such as human, in need of such treatment an effective amount of an hIL-1lp, such as a native sequence hIL-1lp, e.g. native sequence hIL-1Ra1 or hIL-1Ra3.

In another embodiment, the invention provides a method for treating rheumatoid arthritis comprising administering to a mammal, such as human, in need of such treatment an effective amount of an hIL-1Ra1L, such as a native sequence hIL-1Ra1L, or an effective amount of an hIL-1Ra1V, such as a native sequence hIL-1Ra1V, or an effective amount of an hIL-1Ra1S, such as a native sequence hIL-1Ra1S.

In another embodiment, the invention provides a method for treating osteoarthritis comprising administering to a mammal, such as human, in need of such treatment an effective amount of an IL-1lp, such as a native sequence IL-1lp.

In another embodiment, the invention provides a method for treating osteoarthritis comprising administering to a mammal, such as human, in need of such treatment an effective amount of an IL-1lp selected from the group consisting of hIL-1Ra1, hIL-1Ra1L, hIL-1Ra1V, hIL-1Ra1S, hIL-1Ra2, hIL-1Ra3, and mIL-1Ra3.

In another embodiment, the invention provides a method for treating osteoarthritis comprising administering to a mammal, such as human, in need of such treatment an effective amount of an hIL-1lp, such as a native sequence hIL-1lp, e.g. native sequence hIL-1Ra1 or hIL-1Ra3.

In another embodiment, the invention provides a method for treating osteoarthritis comprising administering to a mammal, such as human, in need of such treatment an effective amount of an hIL-1Ra1L, such as a native sequence hIL-1Ra1L, or an effective amount of an hIL-1Ra1V, such as a native sequence hIL-1Ra1V, or an effective amount of an hIL-1Ra1S, such as a native sequence hIL-1Ra1S.

In another embodiment, the invention provides a method for treating sepsis comprising administering to a mammal, such as human, in need of such treatment an effective amount of an IL-1lp, such as a native sequence IL-1lp.

In another embodiment, the invention provides a method for treating sepsis comprising administering to a mammal, such as human, in need of such treatment an effective amount of an IL-1lp selected from the group consisting of hIL-1Ra1, hIL-1Ra1L, hIL-1Ra1V, hIL-1Ra1S, hIL-1Ra2, hIL-1Ra3, and mIL-1Ra3.

In another embodiment, the invention provides a method for treating sepsis comprising administering to a mammal, such as human, in need of such treatment an effective amount of an hIL-1lp, such as a native sequence hIL-1lp, e.g. native sequence hIL-1Ra1 or hIL-1Ra3.

In another embodiment, the invention provides a method for treating sepsis comprising administering to a mammal, such as human, in need of such treatment an effective amount of an hIL-1Ra1L, such as a native sequence hIL-1Ra1L, or an effective amount of an hIL-1Ra1V, such as a native sequence hIL-1Ra1V, or an effective amount of an hIL-1Ra1S, such as a native sequence hIL-1Ra1S.

In another embodiment, the invention provides a method for treating acute lung injury comprising administering to a mammal, such as human, in need of such treatment an effective amount of an IL-1lp, such as a native sequence IL-1lp.

In another embodiment, the invention provides a method for treating acute lung injury comprising administering to a mammal, such as human, in need of such treatment an effective amount of an IL-1lp selected from the group consisting of hIL-1Ra1, hIL-1Ra1L, hIL-1Ra1V, hIL-1Ra1S, hIL-1Ra2, hIL-1Ra3, and mIL-1Ra3.

In another embodiment, the invention provides a method for treating acute lung injury comprising administering to a mammal, such as human, in need of such treatment an effective amount of an hIL-1lp, such as a native sequence hIL-1lp, e.g. native sequence hIL-1Ra1 or hIL-1Ra3.

In another embodiment, the invention provides a method for treating acute lung injury comprising administering to a mammal, such as human, in need of such treatment an effective amount of an hIL-1Ra1L, such as a native sequence hIL-1Ra1L, or an effective amount of an hIL-1Ra1V, such as a native sequence hIL-1Ra1V, or an effective amount of an hIL-1Ra1S, such as a native sequence hIL-1Ra1S.

In another embodiment, the invention provides a method for treating adult respiratory distress syndrome comprising administering to a mammal, such as human, in need of such treatment an effective amount of an IL-1lp, such as a native sequence IL-1lp.

In another embodiment, the invention provides a method for treating adult respiratory distress syndrome comprising administering to a mammal, such as human, in need of such treatment an effective amount of an IL-1lp selected from the group consisting of hIL-1Ra1, hIL-1Ra1L, hIL-1Ra1V, hIL-1Ra1S, hIL-1Ra2, hIL-1Ra3, and mIL-1Ra3.

In another embodiment, the invention provides a method for treating adult respiratory distress syndrome comprising administering to a mammal, such as human, in need of such treatment an effective amount of an hIL-1lp, such as a native sequence hIL-1lp, e.g. native sequence hIL-1Ra1 or hIL-1Ra3.

In another embodiment, the invention provides a method for treating adult respiratory distress syndrome comprising administering to a mammal, such as human, in need of such treatment an effective amount of an hIL-1Ra1L, such as a native sequence hIL-1Ra1L, or an effective amount of an hIL-1Ra1V, such as a native sequence hIL-1Ra1V, or an effective amount of an hIL-1Ra1S, such as a native sequence hIL-1Ra1S.

In another embodiment, the invention provides a method for treating idiopathic pulmonary fibrosis comprising administering to a mammal, such as human, in need of such treatment an effective amount of an IL-1lp, such as a native sequence IL-1lp.

In another embodiment, the invention provides a method for treating idiopathic pulmonary fibrosis comprising administering to a mammal, such as human, in need of such treatment an effective amount of an IL-1lp selected from the group consisting of hIL-1Ra1, hIL-1Ra1L, hIL-1Ra1V, hIL-1Ra1S, hIL-1Ra2, hIL-1Ra3, and mIL-1Ra3.

In another embodiment, the invention provides a method for treating idiopathic pulmonary fibrosis comprising administering to a mammal, such as human, in need of such treatment an effective amount of an hIL-1lp, such as a native sequence hIL-1lp, e.g. native sequence hIL-1Ra1 or hIL-1Ra3.

In another embodiment, the invention provides a method for treating idiopathic pulmonary fibrosis comprising administering to a mammal, such as human, in need of such treatment an effective amount of an hIL-1Ra1L, such as a native sequence hIL-1Ra1L, or an effective amount of an hIL-1Ra1V, such as a native sequence hIL-1Ra1V, or an effective amount of an hIL-1Ra1S, such as a native sequence hIL-1Ra1S.

In another embodiment, the invention provides a method for treating an ischemic reperfusion disease, such as surgical tissue reperfusion injury, stroke, myocardial ischemia, or acute myocardial infarction, comprising administering to a mammal, such as human, in need of such treatment an effective amount of an IL-1lp, such as a native sequence IL-1lp.

In another embodiment, the invention provides a method for treating an ischemic reperfusion disease, such as surgical tissue reperfusion injury, stroke, myocardial ischemia, or acute myocardial infarction, comprising administering to a mammal, such as human, in need of such treatment an effective amount of an IL-1lp selected from the group consisting of hIL-1Ra1, hIL-1Ra1L, hIL-1Ra1V, hIL-1Ra1S, hIL-1Ra2, hIL-1Ra3, and mIL-1Ra3.

In another embodiment, the invention provides a method for treating an ischemic reperfusion disease, such as surgical tissue reperfusion injury, stroke, myocardial ischemia, or acute myocardial infarction, comprising administering to a mammal, such as human, in need of such treatment an effective amount of an hIL-11p, such as a native sequence hIL-11p, e.g. native sequence hIL-1Ra1 or hIL-1Ra3.

In another embodiment, the invention provides a method for treating an ischemic reperfusion disease, such as surgical tissue reperfusion injury, stroke, myocardial ischemia, or acute myocardial infarction, comprising administering to a mammal, such as human, in need of such treatment an effective amount of an hIL-1Ra1L, such as a native sequence hIL-1Ra1L, or an effective amount of an hIL-1Ra1V, such as a native sequence hIL-1Ra1V, or an effective amount of an hIL-1Ra1S, such as a native sequence hIL-1Ra1S.

In another embodiment, the invention provides a method for treating psoriasis comprising administering to a mammal, such as human, in need of such treatment an effective amount of an IL-11p, such as a native sequence IL-11p.

In another embodiment, the invention provides a method for treating psoriasis comprising administering to a mammal, such as human, in need of such treatment an effective amount of an IL-11p selected from the group consisting of hIL-1Ra1, hIL-1Ra1L, hIL-1Ra1V, hIL-1Ra1S, hIL-1Ra2, hIL-1Ra3, and mIL-1Ra3.

In another embodiment, the invention provides a method for treating psoriasis comprising administering to a mammal, such as human, in need of such treatment an effective amount of an hIL-11p, such as a native sequence hIL-11p, e.g. native sequence hIL-1Ra1 or hIL-1Ra3.

In another embodiment, the invention provides a method for treating psoriasis comprising administering to a mammal, such as human, in need of such treatment an effective amount of an hIL-1Ra1L, such as a native sequence hIL-1Ra1L, or an effective amount of an hIL-1Ra1V, such as a native sequence hIL-1Ra1V, or an effective amount of an hIL-1Ra1S, such as a native sequence hIL-1Ra1S.

In another embodiment, the invention provides a method for treating graft-versus-host disease (GVHD) comprising administering to a mammal, such as human, in need of such treatment an effective amount of an IL-11p, such as a native sequence IL-11p.

In another embodiment, the invention provides a method for treating graft-versus-host disease (GVHD) comprising administering to a mammal, such as human, in need of such treatment an effective amount of an IL-11p selected from the group consisting of hIL-1Ra1, hIL-1Ra1L, hIL-1Ra1V, hIL-1Ra1S, hIL-1Ra2, hIL-1Ra3, and mIL-1Ra3.

In another embodiment, the invention provides a method for treating graft-versus-host disease (GVHD) comprising administering to a mammal, such as human, in need of such treatment an effective amount of an hIL-11p, such as a native sequence hIL-11p, e.g. native sequence hIL-1Ra1 or hIL-1Ra3.

In another embodiment, the invention provides a method for treating graft-versus-host disease (GVHD) comprising administering to a mammal, such as human, in need of such treatment an effective amount of an hIL-1Ra1L, such as a native sequence hIL-1Ra1L, or an effective amount of an hIL-1Ra1V, such as a native sequence hIL-1Ra1V, or an effective amount of an hIL-1Ra1S, such as a native sequence hIL-1Ra1S.

In another embodiment, the invention provides a method for treating an inflammatory bowel disease such as ulcerative colitis, comprising administering to a mammal, such as human, in need of such treatment an effective amount of an IL-11p, such as a native sequence IL-11p.

In another embodiment, the invention provides a method for treating an inflammatory bowel disease such as ulcerative colitis, comprising administering to a mammal, such as human, in need of such treatment an effective amount of an IL-11p selected from the group consisting of hIL-1Ra1, hIL-1Ra1L, hIL-1Ra1V, hIL-1Ra1S, hIL-1Ra2, hIL-1Ra3, and mIL-1Ra3.

In another embodiment, the invention provides a method for treating an inflammatory bowel disease such as ulcerative colitis, comprising administering to a mammal, such as human, in need of such treatment an effective amount of an hIL-11p, such as a native sequence hIL-11p, e.g. native sequence hIL-1Ra1 or hIL-1Ra3.

In another embodiment, the invention provides a method for treating an inflammatory bowel disease such as ulcerative colitis, comprising administering to a mammal, such as human, in need of such treatment an effective amount of an hIL-1Ra1L, such as a native sequence hIL-1Ra1L, or an effective amount of an hIL-1Ra1V, such as a native sequence hIL-1Ra1V, or an effective amount of an hIL-1Ra1S, such as a native sequence hIL-1Ra1S.

D. Anti-IL-11p Antibodies

The present invention further provides anti-IL-11p antibodies. Exemplary antibodies include polyclonal, monoclonal, humanized, bispecific, and heteroconjugate antibodies.

1. Polyclonal Antibodies

The anti-IL-11p antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the IL-11p polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

2. Monoclonal Antibodies

The anti-IL-11p antibodies may, alternatively, be monoclonal antibodies. Monoclonal antibodies may be prepared using hybridoma methods, such as those described by Kohler and Milstein, *Nature,* 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the IL-11p polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice,* Academic Press, (1986) pp. 59-103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51-63].

The culture medium in which the hybridoma cells are cultured can then be assayed for the presence of monoclonal antibodies directed against IL-11p. Preferably, the binding specificity of monoclonal antibodies produced by the hybridoma cells is determined by immunoprecipitation or by an in vitro binding assay, such as radioimmunoassay (RIA) or enzyme-linked immunosorbant assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

3. Human and Humanized Antibodies

The anti-IL-11p antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321: 522-525 (1986); Riechmann et al., *Nature*, 332: 323-329 (1988); and Presta, *Curr. Op. Struct. Biol.*, 2: 593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature*, 321: 522-525 (1986); Riechmann et al., *Nature*, 332: 323-327 (1988); Verhoeyen et al., *Science*, 239: 1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.*, 227: 381 (1991);

Marks et al., *J. Mol. Biol.*, 222: 581 (1991)]. The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et a., *J. Immunol.*, 147(1): 86-95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10, 779-783 (1992); Lonberg et al., *Nature* 368: 856-859 (1994); Morrison, *Nature* 368, 812-13 (1994); Fishwild et al., *Nature Biotechnology* 14, 845-51 (1996); Neuberger, *Nature Biotechnology* 14, 826 (1996); Lonberg and Huszar, *Intern. Rev. Immunol.* 13 65-93 (1995).

4. Bispecific Antibodies

Bispecific antibodies are monoclonal, preferably human or humanized, antibodies that have binding specificities for at least two different antigens. In the present case, one of the binding specificities is for the IL-1lp, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, *Nature*, 305:537-539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., *EMBO J.*, 10: 3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology*, 121:210 (1986).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

E. Uses for Anti-IL-1lp Antibodies

The anti-IL-1lp antibodies of the invention have various utilities. For example, anti-IL-1lp antibodies may be used in diagnostic assays for IL-1lp, e.g., detecting its expression in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: A Manual of Techniques*, CRC Press, Inc. (1987) pp. 147-158]. The antibodies used in the diagnostic assays can be labeled with a detectable moiety. The detectable moiety should be capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature*, 144: 945 (1962); David et al., *Biochemistry*, 13: 1014 (1974); Pain et al., *J. Immunol. Meth.*, 40: 219 (1981); and Nygren, *J. Histochem. and Cytochem.*, 30: 407 (1982).

Anti-IL-1lp antibodies also are useful for the affinity purification of IL-1lp from recombinant cell culture or natural sources. In this process, the antibodies against IL-1lp are immobilized on a suitable support, such a Sephadex resin or filter paper, using methods well known in the art. The immobilized antibody then is contacted with a sample containing the IL-1lp to be purified, and thereafter the support is washed with a suitable solvent that will remove substantially all the material in the sample except the IL-1lp, which is bound to the immobilized antibody. Finally, the support is washed with another suitable solvent that will release the IL-1lp from the antibody.

In addition, anti-IL-1lp antibodies are useful as therapeutic agents for targeting of native IL-1lp in IL-1lp-mediated disease conditions, e.g. disease states characterized by pathologic IL-1 or IL-18 agonist or agonist-like activity of the native IL-1lp. In the treatment and prevention of a native IL-1lp-mediated disorder with the anti-IL-1lp antibody of the invention, the antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the antibody, the particular type of antibody, the method of administration, the scheduling of administration, and other factors known to medical practitioners. The "effective amount" or "therapeutically effective amount" of antibody to be administered will be governed by such considerations, and is the minimum amount necessary to prevent, ameliorate, or treat the native IL-1lp-mediated disorder, including treating inflammatory diseases and reducing inflammatory responses. Such amount is preferably below the amount that is toxic to the host or renders the host significantly more susceptible to infections.

As a general proposition, the initial pharmaceutically effective amount of the antibody or antibody fragment administered parenterally per dose will be in the range of about 0.1 to 50 mg/kg of patient body weight per day, with the typical initial range of antibody used being 0.3 to 20 mg/kg/day, more preferably 0.3 to 15 mg/kg/day.

In one embodiment, using systemic administration, the initial pharmaceutically effective amount will be in the range of about 2 to 5 mg/kg/day.

For methods of the invention using administration by inhalation, the initial pharmaceutically effective amount will be in the range of about 1 microgram (µg)/kg/day to 100 mg/kg/day.

In one embodiment, the invention provides a method for treating an IL-1lp-mediated inflammatory disorder comprising administering to a mammal, such as human, in need of such treatment an effective amount of an anti-IL-1lp antibody.

In another embodiment, the invention provides a method for treating an hIL-1lp-mediated asthmatic disorder comprising administering to a human in need of such treatment an effective amount of an anti-hIL-1lp antibody.

In another embodiment, the invention provides a method for treating an hIL-1Ra1-mediated asthmatic disorder comprising administering to a human in need of such treatment an effective amount of an anti-hIL-1Ra1 antibody.

In another embodiment, the invention provides a method for treating an IL-1lp-mediated rheumatoid arthritic disorder comprising administering to a mammal, such as human, in need of such treatment an effective amount of an anti-IL-1lp antibody.

In another embodiment, the invention provides a method for treating an hIL-1lp-mediated rheumatoid arthritic disorder comprising administering to a human in need of such treatment an effective amount of an anti-hIL-1lp antibody.

In another embodiment, the invention provides a method for treating an hIL-1Ra1-mediated rheumatoid arthritic disorder comprising administering to a human in need of such treatment an effective amount of an anti-hIL-1Ra1 antibody.

In another embodiment, the invention provides a method for treating an IL-1lp-mediated osteoarthritic disorder comprising administering to a mammal, such as human, in need of such treatment an effective amount of an anti-IL-1lp antibody.

In another embodiment, the invention provides a method for treating an hIL-1lp-mediated osteoarthritic disorder comprising administering to a human in need of such treatment an effective amount of an anti-hIL-1lp antibody.

In another embodiment, the invention provides a method for treating an hIL-1Ra1-mediated osteoarthritic disorder comprising administering to a human in need of such treatment an effective amount of an anti-hIL-1Ra1 antibody.

In another embodiment, the invention provides a method for treating an IL-1lp-mediated septic disorder comprising administering to a mammal, such as human, in need of such treatment an effective amount of an anti-IL-1lp antibody.

In another embodiment, the invention provides a method for treating an hIL-1lp-mediated septic disorder comprising administering to a human in need of such treatment an effective amount of an anti-hIL-1lp antibody.

In another embodiment, the invention provides a method for treating an hIL-1Ra1-mediated septic disorder comprising administering to a human in need of such treatment an effective amount of an anti-hIL-1Ra1 antibody.

In another embodiment, the invention provides a method for treating IL-1lp-mediated acute lung injury comprising administering to a mammal, such as human, in need of such treatment an effective amount of an anti-IL-1lp antibody.

In another embodiment, the invention provides a method for treating hIL-1lp-mediated acute lung injury comprising administering to a human in need of such treatment an effective amount of an anti-hIL-1lp antibody.

In another embodiment, the invention provides a method for treating hIL-1Ra1-mediated acute lung injury comprising administering to a human in need of such treatment an effective amount of an anti-hIL-1Ra1 antibody.

In another embodiment, the invention provides a method for treating IL-1lp-mediated adult respiratory distress syndrome comprising administering to a mammal, such as human, in need of such treatment an effective amount of an anti-IL-1lp antibody.

In another embodiment, the invention provides a method for treating hIL-1lp-mediated adult respiratory distress syndrome comprising administering to a human in need of such treatment an effective amount of an anti-hIL-1lp antibody.

In another embodiment, the invention provides a method for treating hIL-1Ra1-mediated adult respiratory distress syndrome comprising administering to a human in need of such treatment an effective amount of an anti-hIL-1Ra1 antibody.

In another embodiment, the invention provides a method for treating IL-1lp-mediated idiopathic pulmonary fibrosis comprising administering to a mammal, such as human, in need of such treatment an effective amount of an anti-IL-1lp antibody.

In another embodiment, the invention provides a method for treating hIL-1lp-mediated idiopathic pulmonary fibrosis comprising administering to a human in need of such treatment an effective amount of an anti-hIL-1lp antibody.

In another embodiment, the invention provides a method for treating hIL-1Ra1-mediated idiopathic pulmonary fibrosis comprising administering to a human in need of such treatment an effective amount of an anti-hIL-1Ra1 antibody.

In another embodiment, the invention provides a method for treating an IL-1lp-mediated ischemic reperfusion disease, such as surgical tissue reperfusion injury, stroke, myocardial ischemia, or acute myocardial infarction, comprising administering to a mammal, such as human, in need of such treatment an effective amount of an anti-IL-1lp antibody.

In another embodiment, the invention provides a method for treating an hIL-1lp-mediated ischemic reperfusion disease, such as surgical tissue reperfusion injury, stroke, myocardial ischemia, or acute myocardial infarction, comprising administering to a human in need of such treatment an effective amount of an anti-hIL-1lp antibody.

In another embodiment, the invention provides a method for treating an hIL-1Ra1-mediated ischemic reperfusion disease, such as surgical tissue reperfusion injury, stroke, myocardial ischemia, or acute myocardial infarction, comprising administering to a human in need of such treatment an effective amount of an anti-hIL-1Ra1 antibody.

In another embodiment, the invention provides a method for treating an IL-1lp-mediated psoriatic disorder comprising administering to a mammal, such as human, in need of such treatment an effective amount of an anti-IL-1lp antibody.

In another embodiment, the invention provides a method for treating an hIL-1lp-mediated psoriatic disorder comprising administering to a human in need of such treatment an effective amount of an anti-hIL-1lp antibody.

In another embodiment, the invention provides a method for treating an hIL-1Ra1-mediated psoriatic disorder comprising administering to a human in need of such treatment an effective amount of an anti-hIL-1Ra1 antibody.

In another embodiment, the invention provides a method for treating an IL-1lp-mediated graft-versus-host disease (GVHD) comprising administering to a mammal, such as human, in need of such treatment an effective amount of an anti-IL-1lp antibody.

In another embodiment, the invention provides a method for treating an hIL-1lp-mediated graft-versus-host disease (GVHD) comprising administering to a human in need of such treatment an effective amount of an anti-hIL-1lp antibody.

In another embodiment, the invention provides a method for treating an hIL-1Ra1-mediated graft-versus-host disease (GVHD) comprising administering to a human in need of such treatment an effective amount of an anti-hIL-1Ra1 antibody.

In another embodiment, the invention provides a method for treating an IL-1lp-mediated inflammatory bowel disease such as ulcerative colitis, comprising administering to a mammal, such as human, in need of such treatment an effective amount of an anti-IL-1lp antibody.

In another embodiment, the invention provides a method for treating an hIL-1lp-mediated inflammatory bowel disease such as ulcerative colitis, comprising administering to a human in need of such treatment an effective amount of an anti-hIL-1lp antibody.

In another embodiment, the invention provides a method for treating an hIL-1Ra1-mediated inflammatory bowel disease such as ulcerative colitis, comprising administering to a human in need of such treatment an effective amount of an anti-hIL-1Ra1 antibody.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va.

Example 1

Isolation of DNA Encoding hIL-1Ra1 and mIL-1Ra3

A public expressed sequence tag (EST) DNA database (Genbank) was searched with human interleukin-1 receptor antagonist (hIL-1Ra) sequence, also known as secretory human interleukin-1 receptor antagonist ("sIL-1Ra") sequence, and a human EST designated AI014548 (which corresponds to nucleotides 145-629 of FIG. 4, SEQ ID NO:8), and a murine EST designated W08205 (FIG. 10, SEQ ID NO:17), were identified, which showed homology with the known protein hIL-1Ra (sIL-1Ra).

EST clones AI014548 and W08205 were purchased from Research Genetics (Huntsville, Ala.) and the cDNA inserts were obtained and sequenced in their entireties.

The entire nucleotide sequence of the clone AI014548, designated DNA85066, is shown in FIG. 1 (SEQ ID NO:1). Clone DNA85066 contains a single open reading frame that is interrupted by an apparent intronic sequence. The intron is bounded by splice junctions at nucleotide positions 181 to 186 (splice donor site) and nucleotide positions 430 to 432 (splice acceptor site) (FIG. 1; SEQ ID NO:1).

A virtual processed nucleotide sequence (FIG. 3; SEQ ID NO:6), designated DNA94618, was derived by removing the apparent intronic sequence from clone DNA85066. Clone DNA94618 contains a single open reading frame with an apparent translational initiation site at nucleotide positions 103-105, and a stop codon at nucleotide positions 682-684 (FIG. 3; SEQ ID NO:6). The predicted polypeptide precursor (hIL-1Ra1) (FIG. 3; SEQ ID NO:7) is 193 amino acids long. The putative signal sequence extends from amino acid positions 1 to 14. A putative cAMP- and cGMP-dependent protein kinase phosphorylation site is located at amino acid positions 33-36. Putative N-myristoylation sites are located at amino acid positions 50-55 and 87-92.

Clone DNA85066 (designated as DNA85066-2534) has been deposited with ATCC and was assigned ATCC deposit no. 203588. The full-length hIL-1Ra1 protein shown in FIG. 3 (SEQ ID NO:7) has an estimated molecular weight of about 21,822 daltons and a pI of about 8.9.

Based on a sequence alignment analysis of the full-length sequence (SEQ ID NO:7), hIL-1Ra1 shows significant amino acid sequence identity to hIL-1Ra (sIL-1Ra) and hIL-1Raβ proteins.

The entire nucleotide sequence of the clone W08205, designated DNA92505, is shown in FIG. 9 (SEQ ID NO:15). Clone DNA92505 contains a single open reading frame with an apparent translational initiation site at nucleotide positions 145-147, and a stop codon at nucleotide positions 610-612 (FIG. 9; SEQ ID NO:15). The predicted polypeptide precursor (mIL-1Ra3) (FIG. 9; SEQ ID NO:16) is 155 amino acids long. The putative signal sequence extends from amino acid positions 1-33. Putative N-myristoylation sites are located at amino acid positions 29-34, 60-65, 63-68, 91-96 and 106-111. An interleukin-1-like sequence is located at amino acid positions 111-131.

Clone DNA92505 (designated as DNA92505-2534) was deposited with ATCC and was assigned ATCC deposit no. 203590. The full length mIL-1Ra3 protein shown in FIG. 9 (SEQ ID NO:16) has an estimated molecular weight of about 17,134 daltons and a pI of about 4.8.

Based on a sequence alignment analysis of the full-length sequence (SEQ ID NO:16), mIL-1Ra3 shows significant amino acid sequence identity to mIL-1Ra, hicIL-1Ra, hIL-1Ra (sIL-1Ra) and hIL-1Raβ proteins.

Example 2

Isolation of DNA Encoding hIL-1ra2 and hIL-1Ra3

A expressed sequence tag (EST) DNA database (LIFESEQ®, Incyte Pharmaceuticals, Palo Alto, Calif.) was searched with human interleukin-1 receptor antagonist (hIL-1Ra) sequence, also known as secretory human interleukin-1 receptor antagonist ("sIL-1Ra") sequence, and the ESTs, designated 1433156 (FIG. 5, SEQ ID NO:11) and 5120028 (FIG. 8, SEQ ID NO:14), were identified, which showed homology with the hIL-1Ra known protein.

EST clones 1433156 and 5120028 were purchased from Incyte Pharmaceuticals (Palo Alto, Calif.) and the cDNA inserts were obtained and sequenced in their entireties.

The entire nucleotide sequence of the clone 1433156, designated DNA92929, is shown in FIG. 5 (SEQ ID NO:9). Clone DNA92929 contains a single open reading frame with an apparent translational initiation site at nucleotide positions 96-98, and a stop codon at nucleotide positions 498-500 (FIG. 5; SEQ ID NO:9). The predicted polypeptide precursor (hIL- 1Ra2) (FIG. 5; SEQ ID NO:10) is 134 amino acids long. A putative signal sequence extends from amino acid positions 1-26.

Clone DNA92929 (designated as DNA92929-2534) was deposited with ATCC and was assigned ATCC deposit no. 203586. The full-length hIL-1Ra2 protein shown in FIG. 5 (SEQ ID NO:10) has an estimated molecular weight of about 14,927 daltons and a pI of about 4.8.

Based on a sequence alignment analysis of the full-length sequence (SEQ ID NO:10), hIL-1Ra2 shows significant amino acid sequence identity to hIL-1Raβ protein. hIL-1Ra2 is believed to be a splice variant of hIL-1Raβ.

The entire nucleotide sequence of the clone 5120028, designated DNA96787, is shown in FIG. 7 (SEQ ID NO:12). Clone DNA96787 contains a single open reading frame with an apparent translational initiation site at nucleotide positions 1-3, and a stop codon at nucleotide positions 466-468 (FIG. 7; SEQ ID NO:12). The predicted polypeptide precursor (hIL-1Ra3) (FIG. 7; SEQ ID NO:13) is 155 amino acids long. A putative signal sequence extends from amino acid positions 1-33. Putative N-myristoylation sites are located at amino acid positions 29-34, 60-65, 63-68, 73-78, 91-96 and 106-111. An interleukin-1-like sequence is located at amino acid positions 111-131.

It is believed that the predicted 155 amino acid polypeptide of hIL-1Ra3 behaves as a mature sequence (without a presequence that is removed in post-translational processing) in certain animal cells. It is also believed that other animal cells recognize and remove one or more signal peptide(s) extending from amino acid positions 1 to about 33. As shown in Example 14 below, transiently transfected CHO host cells secrete a form of hIL-1Ra3 that only lacks the N-terminal methionine in the sequence of FIG. 7 (SEQ ID NO:13).

Clone DNA96787 (designated as DNA96787-2534) was deposited with ATCC and was assigned ATCC deposit no. 203589. The full length hIL-1Ra3 protein shown in FIG. 7 (SEQ ID NO:13) has an estimated molecular weight of about 16,961 daltons and a pI of about 4.9.

Based on a sequence alignment analysis of the full-length sequence (SEQ ID NO:13), hIL-1Ra3 shows significant amino acid sequence identity to hicIL-1Ra and hIL-1Ra (sIL-1Ra) proteins.

Example 3

Northern Blot Analysis

Expression of hIL-1Ra3 mRNA in human tissues and mIL-1Ra3 mRNA in mouse tissues was examined by Northern blot analysis. Human and mouse multiple tissue northern (RNA) blots and mouse embryo blots were purchased from Clontech and probed with corresponding cDNA according to the manufacturer's instructions.

Figure 11B:
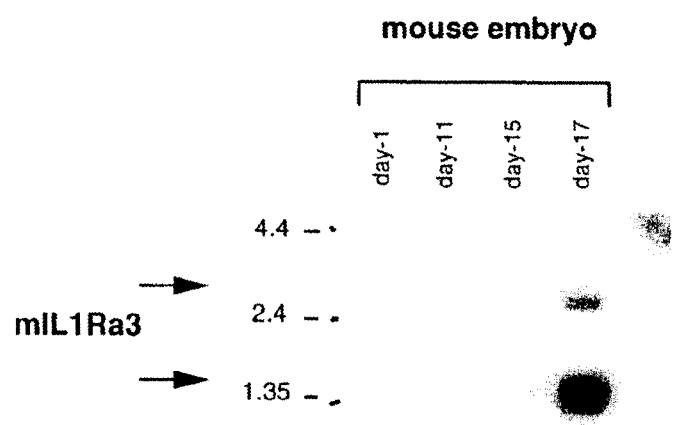

As shown in FIG. 11, hIL-1Ra3 mRNA (2.7 kb) were detected only in human placenta and mIL-1Ra3 mRNA transcripts (1.4 kb and 2.5 kb) were detected only in the day-17 mouse embryo.

Example 4

Use of IL-1lp as a Hybridization Probe

The following method describes use of a nucleotide sequence encoding IL-1lp as a hybridization probe.

DNA comprising the coding sequence of full-length IL-1lp (as shown in FIGS. 3, 5, 7, 9, 15, 16 and 19; SEQ ID NOS:6, 9, 12, 15, 18, 20 and 24) is employed as a probe to screen for homologous DNAs (such as those encoding naturally-occurring variants of IL-1lp) in human tissue cDNA libraries or human tissue genomic libraries.

Hybridization and washing of filters containing either library DNAs is performed under the following high stringency conditions. Hybridization of radiolabeled IL-1lp-derived probe to the filters is performed in a solution of 50% formamide, 5×SSC, 0.1% SDS, 0.1% sodium pyrophosphate, 50 mM sodium phosphate, pH 6.8, 2×Denhardt's solution, and 10% dextran sulfate at 42° C. for 20 hours. Washing of the filters is performed in an aqueous solution of 0.1×SSC and 0.1% SDS at 42° C.

DNAs having a desired sequence identity with the DNA encoding full-length native sequence IL-1lp can then be identified using standard techniques known in the art.

Example 5

Expression of IL-1lp in *E. coli*

This example illustrates preparation of an unglycosylated form of IL-1lp by recombinant expression in *E. coli*.

The DNA sequence encoding an IL-1lp is initially amplified using selected PCR primers. The primers should contain restriction enzyme sites which correspond to the restriction enzyme sites on the selected expression vector. A variety of expression vectors may be employed. An example of a suitable vector is pBR322 (derived from *E. coli*; see Bolivar et al., *Gene*, 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the IL-1lp coding region, lambda transcriptional terminator, and an argU gene.

The ligation mixture is then used to transform a selected *E. coli* strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized IL-1lp protein can then be purified using a metal chelating column under conditions that allow tight binding of the protein.

Example 6

Expression of IL-1lp in Mammalian Cells

This example illustrates preparation of a potentially glycosylated form of IL-1lp by recombinant expression in mammalian cells.

The vector, pRK5 (see EP 307,247, published Mar. 15, 1989), is employed as the expression vector. Optionally, the IL-1lp DNA is ligated into pRK5 with selected restriction enzymes to allow insertion of the IL-1lp DNA using ligation methods such as described in Sambrook et al., supra. The resulting vector is called pRK5-IL-11p.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 μg pRK5-IL-11p DNA is mixed with about 1 μg DNA encoding the VA RNA gene [Thimmappaya et al., *Cell,* 31:543 (1982)] and dissolved in 500 μl of 1 mM Tris-HCl, 0.1 mM EDTA, 0.227 M $CaCl_2$. To this mixture is added, dropwise, 500 μl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 μCi/ml $^{35}$S-cysteine and 200 μCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of IL-11p polypeptide. The cultures containing transfected cells may undergo further incubation (in serum free medium) and the medium is tested in selected bioassays.

In an alternative technique, IL-11p may be introduced into 293 cells transiently using the dextran sulfate method described by Somparyrac et al., *ProC. Natl. Acad. Sci. USA,* 12: 7575 (1981). 293 cells are grown to maximal density in a spinner flask and 700 μg pRK5-IL-11p DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 μg/ml bovine insulin and 0.1 μg/ml bovine transferrin. After about four days, the conditioned media is centrifuged and filtered to remove cells and debris. The sample containing expressed IL-11p can then be concentrated and purified by any selected method, such as by dialysis and/or column chromatography.

In another embodiment, IL-11p can be expressed in CHO cells. The pRK5-IL-11p can be transfected into CHO cells using known reagents such as $CaPO_4$ or DEAE-dextran. As described above, the cell cultures can be incubated, and the medium replaced with culture medium (alone) or medium containing a radiolabel such as $^{35}$S-methionine. After determining the presence of IL-11p polypeptide, the culture medium may be replaced with serum free medium. Preferably, the cultures are incubated for about 6 days, and then the conditioned medium is harvested. The medium containing the expressed IL-11p can then be concentrated and purified by any selected method.

Epitope-tagged IL-11p may also be expressed in host CHO cells. The IL-11p may be subcloned out of the pRK5 vector. The subclone insert can undergo PCR to fuse in frame with a selected epitope tag such as a poly-his tag into a Baculovirus expression vector. The poly-his tagged IL-11p insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged IL-11p can then be concentrated and purified by any selected method, such as by $Ni^{2+}$-chelate affinity chromatography.

Example 7

Expression of IL-11p in Yeast

The following method describes recombinant expression of IL-11p in yeast.

First, yeast expression vectors are constructed for intracellular production or secretion of IL-11p from the ADH2/GAPDH promoter. DNA encoding IL-11p and the promoter is inserted into suitable restriction enzyme sites in the selected plasmid to direct intracellular expression of IL-11p. For secretion, DNA encoding IL-11p can be cloned into the selected plasmid, together with DNA encoding the ADH2/GAPDH promoter, a native IL-11p signal peptide or other mammalian signal peptide, or, for example, a yeast alpha-factor or invertase secretory signal/leader sequence, and linker sequences (if needed) for expression of IL-11p.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant IL-11p can subsequently be isolated and purified by removing the yeast cells from the fermentation medium by centrifugation and then concentrating the medium using selected cartridge filters. The concentrate containing IL-11p may further be purified using selected column chromatography resins.

Example 8

Expression of IL-11p in Baculovirus-Infected Insect Cells

The following method describes recombinant expression of IL-11p in Baculovirus-infected insect cells.

The sequence coding for IL-11p is fused upstream of an epitope tag contained within a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the sequence encoding IL-11p or the desired portion of the coding sequence of IL-11p (such as the sequence encoding the mature protein) is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGold™ virus DNA (Pharmingen) into *Spodoptera frugiperda* ("Sf9") cells (ATCC CRL 1711) using lipofectin (commercially available from GIBCO-BRL). After 4-5 days of incubation at 28° C., the released viruses are harvested and used for further amplifications. Viral infection and protein expression are performed as described by O'Reilley et al., *Baculovirus expression vectors: A Laboratory Manual*, Oxford: Oxford University Press (1994).

Expressed poly-his tagged IL-11p can then be purified, for example, by $Ni^{2+}$-chelate affinity chromatography as follows.

Extracts are prepared from recombinant virus-infected Sf9 cells as described by Rupert et al., Nature, 362: 175-179 (1993). Briefly, Sf9 cells are washed, resuspended in sonication buffer (25 mL Hepes, pH 7.9; 12.5 mM $MgCl_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% glycerol, pH 7.8) and filtered through a 0.45 μm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or Western blot with $Ni^{2+}$-NTA-conjugated to alkaline phosphatase (Qiagen). Fractions containing the eluted $His_{10}$-tagged IL-1lp are pooled and dialyzed against loading buffer.

Alternatively, purification of the IgG tagged (or Fc tagged) IL-1lp can be performed using known chromatography techniques, including for instance, Protein A or protein G column chromatography.

Example 9

IL-18 Receptor and IL-1 Receptor Binding of hIL-1Ra1

To facilitate the characterization of hIL-1Ra1, a PCR fragment containing the partial ORF of clone DNA85066 (FIG. 1; SEQ ID NO:3) was cloned into pCMV1FLAG (IBI Kodak, described in Pan et al., Science, 276: 111-113) as an in-frame fusion to a $NH_2$-terminal preprotrypsin leader sequence and FLAG tag encoded by the vector. The entire cDNA insert of the recombinant pCMV1FLAG vector clone (designated clone DNA96786) was sequenced (FIG. 2; SEQ ID NO:4). The cDNAs encoding the extracellular domain of hIL1R and hIL18R (formerly known as hIL1Rrp) were obtained by polymerase chain reaction (PCR) and cloned into a modified pCMV1FLAG vector that allowed for in-frame fusion with the Fc portion of human immunoglobulin G.

Human embryonic kidney 293 cells were grown in high glucose DMEM (Genentech, Inc). The cells were seeded at $3-4\times10^6$ per plate (100 mm) and co-transfected with pCMV1FLAG-hIL-1Ra1 and pCMV1FLAG-IL1R-ECD-Fc or pCMV1FLAG-IL18R-ECD-Fc by means of calcium phosphate precipitation. The media were changed 12 hours post transfection. The resultant conditioned media (10 ml each) were harvested after a further 70-74 hour incubation, clarified by centrifugation, aliquoted and stored at −70° C. The receptor-Fc and ligand complex from 1.5 ml conditioned medium was immunoprecipitated with protein G-Sepharose, washed three times with buffer containing 50 mM Hepes, pH7.0, 150 mM NaCl, 1 mM EDTA, 1% NP-40, and a protease inhibitor cocktail (BMB) and resolved on a 10-20% SDS-PAGE gel. The bound ligand was identified by immunoblotting using anti-FLAG monoclonal antibody (BMB).

Figure 13A:
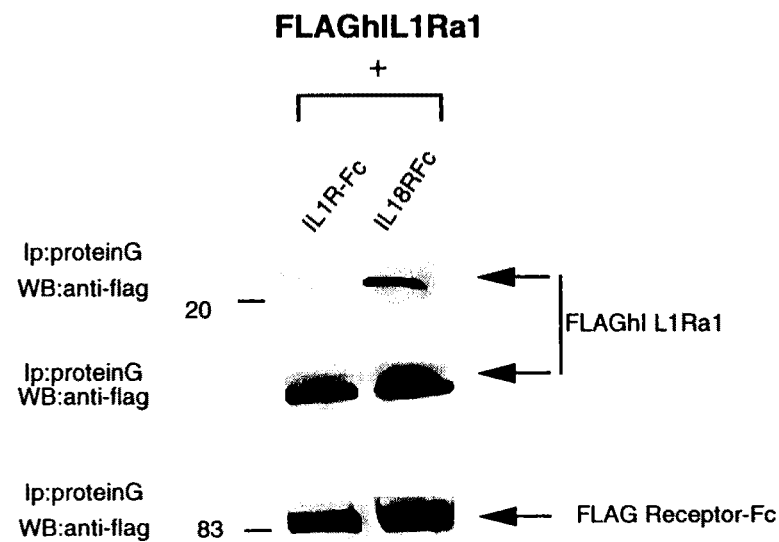
FIG. 13A is a Western blot depicting the interleukin-18 receptor (IL-18R) binding activity of hIL-1Ra1. In the top panel (depicting a protein band at approximately 22 kD), a conditioned medium containing FLAGhIL-1Ra1 and FLAGIL-1R-ECD-Fc (shown in the left lane) and a conditioned medium containing FLAGhIL-1Ra1 and FLAGIL-18R-ECD-Fc (shown in the right lane) were each immunoprecipitated with protein G-sepharose, and the resulting precipitates were resolved by gel electrophoresis and Western blotting with anti-FLAG monoclonal antibody. In the middle and bottom panels (depicting protein bands at approximately 22 kD and 85 kD), a second aliquot from the FLAGhIL-1Ra1 and FLAGIL-1R-ECD-Fc conditioned medium used in the top panel (shown in the left lane) and a second aliquot from the FLAGhIL-1Ra1 and FLAGIL-18R-ECD-Fc conditioned medium used in the top panel (shown in the right lane) were each immunoprecipitated with anti-FLAG monoclonal antibody, and the resulting precipitates were resolved by gel electrophoresis and Western blotting with anti-FLAG monoclonal antibody.

As shown in FIG. 13A, the secreted FLAGhIL-1Ra1 fusion protein bound to IL-18R ECD and did not bind to IL-1R ECD, which indicates that hIL-1Ra1 could be an agonist or antagonist of IL-18R.

Example 10

IL-1 Receptor and IL-18 Receptor Binding of mIL-1Ra3 and hIL-1Ra3 cDNA encoding mIL-1Ra3 (DNA92505 shown in FIG. 9; SEQ ID NO:15) was cloned into pRK7 with a carboxy-terminal FLAG-tag. The resulting expression construct was transfected into human embryonic kidney 293 cells by means of calcium phosphate precipitation. 84-90 hours post transfection, the conditioned media containing secreted FLAG-mIL-1Ra3 fusion protein was harvested. Conditioned media containing secreted IL-18R-Fc and IL-1R-Fc proteins were prepared as described in Example 9 above, with the exception that the 293 cells were transfected with either pCMV1FLAG-IL1R-ECD-Fc or pCMV1FLAG-IL18R-ECD-Fc alone (without pCMV1FLAG-IL-1Ra1 cotransfection).

For in vitro binding assays, IL-1R-Fc or IL-18R-Fc from 0.5 ml of the conditioned medium was immobilized to protein G-agarose and then mixed with 1.2 ml conditioned medium containing FLAGmIL-1Ra3. The receptor-ligand complexes were washed and resolved on an 10-20% SDS-PAGE gel and the bound ligand was detected by immunoblotting using anti-FLAG monoclonal antibody (Boehringer Mannheim).

Figure 14:
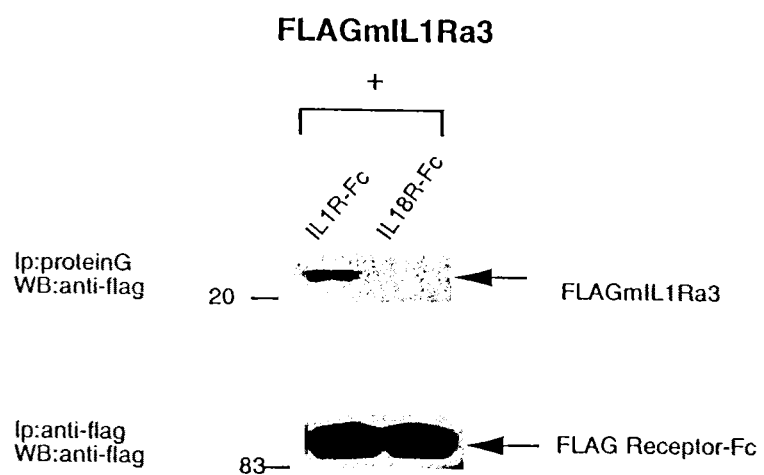
FIG. 14 is a Western blot depicting the interleukin-1 receptor (IL-1R) binding activity of mIL-1Ra3. In the top panel (depicting a protein band at approximately 21 kD) and the bottom panel (depicting protein bands at approximately 85 kD) the FLAGIL-1R-ECD-Fc in conditioned medium (shown in the left lane) and the FLAGIL-18R-ECD-Fc in conditioned medium (shown in the right lane) were immobilized with protein G-agarose, the resulting solid phase was contacted with conditioned medium containing FLAGmIL-1Ra3, and the resulting bound complexes were resolved by gel electrophoresis and Western blotting with anti-FLAG monoclonal antibody.

As shown in FIG. 14, FLAGmIL-1Ra3 fusion protein bound to IL-1R ECD and did not bind to IL-18R ECD. Since the amino acid sequence of mIL-1Ra3 is related to that of the known interleukin-1 receptor antagonist protein (IL-1Ra), mIL-3Ra3 is believed to be a novel IL-1 receptor antagonist.

cDNA encoding hIL-1Ra3 (DNA96787 shown in FIG. 7; SEQ ID NO:12) was cloned into pRK7 with a carboxy-terminal FLAG tag to form pRK7hIL-1Ra3-FLAG. pCMV1FLAG-IL1R-ECD-Fc and pCMV1FLAG-IL18R-ECD-Fc were obtained as described in Example 9 above. Similarly, cDNA encoding DR6 was cloned into the modified pCMV1FLAG vector of Example 9 to form pCMV1FLAG-DR6-Fc, encoding DR6 fused to the Fc portion of human immunoglobulin G. Conditioned media containing (1) a combination of secreted FLAGhIL-1Ra3 and FLAG-DR6-Fc (2) a combination of secreted FLAGhIL-1Ra3 and FLAG-IL1R-ECD-Fc or (3) a combination of secreted FLAGhIL-1Ra3 and FLAG-IL18R-ECD-Fc were prepared by cotransfecting Human 293 cells with (1) pRK7hIL-1Ra3-FLAG and pCMV1FLAG-DR6-Fc (2) pRK7hIL-1Ra3-FLAG and pCMV1FLAG-IL1R-ECD-Fc or (3) pRK7hIL-1Ra3-FLAG and pCMV1FLAG-IL18R-ECD-Fc, culturing the transfectant cells and harvesting culture media essentially as described in Example 9 above. The receptor-Fc and ligand complex from each conditioned medium was immunoprecipitated with protein G-Sepharose or anti-FLAG monoclonal antibody, and immunoprecipitates were resolved by gel electrophoresis and immunoblotting with anti-FLAG monoclonal antibody essentially as described in Example 9 above.

Figure 13B:
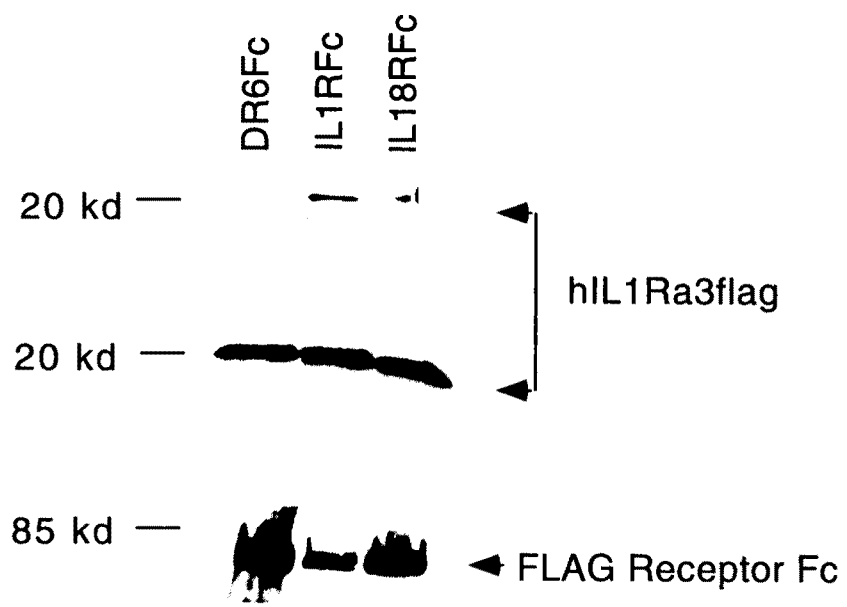
FIG. 13B is a Western blot depicting the IL-1R binding activity of hIL-1Ra3. In the top panel (depicting a protein band at approximately 20 kD), a conditioned medium containing hIL-1Ra3-FLAG and FLAGDR6-Fc (shown in the left lane), a conditioned medium containing hIL-1Ra3-FLAG and FLAGIL-1R-ECD-Fc (shown in the middle lane), and conditioned medium containing hIL-1Ra3-FLAG and FLAGIL-18R-ECD-Fc (shown in the right lane) were each immunoprecipitated with protein G sepharose, and the resulting precipitates were resolved by gel electrophoresis and Western blotting with anti-FLAG monoclonal antibody. In the middle and bottom panels (depicting protein bands at approximately 20 kD and 85 kD), a second aliquot from the hIL-1Ra3-FLAG and FLAGDR6-Fc conditioned medium used in the top panel (shown in the left lane), a second aliquot from the hIL-1Ra3-FLAG and FLAGIL-1R-ECD-Fc conditioned medium used in the top panel (shown in the middle lane) and a second aliquot from the hIL-1Ra3-FLAG and FLAGIL-18R-ECD-Fc conditioned medium used in the top panel (shown in the right lane) were each immunoprecipitated with anti-FLAG monoclonal antibody, and the resulting precipitates were resolved by gel electrophoresis and Western blotting with anti-FLAG monoclonal antibody.

As shown in FIG. 13B, FLAGhIL-1Ra3 fusion protein bound to IL-1R-ECD-Fc and did not bind to IL-18R-ECD-Fc or DR6-Fc. Since the amino acid sequence of hIL-1Ra3 is related to that of the known interleukin-1 receptor antagonist protein (IL-1Ra), hIL-3Ra3 is believed to be a novel IL-1 receptor antagonist.

Example 11

Preparation of Antibodies that Bind IL-1lp

This example illustrates preparation of monoclonal antibodies which can specifically bind IL-1lp.

Techniques for producing the monoclonal antibodies are known in the art and are described, for instance, in Goding, supra. Immunogens that may be employed include purified IL-1lp, fusion proteins containing IL-1lp, and cells expressing recombinant IL-1lp on the cell surface. Selection of the immunogen can be made by the skilled artisan without undue experimentation.

Mice, such as Balb/c, are immunized with the IL-1lp immunogen emulsified in complete Freund's adjuvant and injected subcutaneously or intraperitoneally in an amount from 1-100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect anti-IL-1lp antibodies.

After a suitable antibody titer has been detected, the animals "positive" for antibodies can be injected with a final intravenous injection of IL-1lp. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against IL-1lp. Determination of "positive" hybridoma cells secreting the desired monoclonal antibodies against IL-1lp is within the skill in the art.

The positive hybridoma cells can be injected intraperitoneally into syngeneic Balb/c mice to produce ascites containing the anti-IL-1lp monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Example 12

Isolation of DNA Encoding hIL-1Ra1L, hIL-1Ra1V and hIL-1Ra1S

Several intron-containing cDNA clones related to the hIL-1Ra1 intron-containing clone DNA85066 (FIG. 2) (SEQ ID NO:4) were isolated from a human testis cDNA library and fully sequenced. The intron-containing cDNA sequences were used to determine a full-length open reading frame (ORF) with the GENESCAN program (http://CCR-081.mit.edu/GENESCAN.html) The ORF-encoding sequence was used to design two DNA primers, ggc gga tcc aaa atg ggc tct gag gac tgg g (SEQ ID NO:29) (1Ra1016) and gcg gaa ttc taa tcg ctg acc tca ctg ggg (SEQ ID NO:30) (1Ra1017). The 1Ra1016 and 1Ra1017 primers were synthesized and used to clone cDNA from human fetal skin and SK-lu-1 cell cDNA libraries using polymerase chain reaction (PCR). Several PCR products were isolated and sequenced. Two full length cDNA clones (designated DNA102043 and DNA102044) from PCR products were found to encode hIL-1Ra1 isoforms.

The entire nucleotide sequence of clone DNA102043 is shown in FIG. 15 (SEQ ID NO:18). Clone DNA102043 contains a single open reading frame with an apparent translational initiation site at nucleotide positions 4-6, and a stop codon at nucleotide positions 625-627 (FIG. 15; SEQ ID NO:18). The predicted polypeptide precursor (designated hIL-1Ra1L) (FIG. 15; SEQ ID NO:19) is 207 amino acids long. The putative signal sequence extends from amino acid positions 1-34.

Clone DNA102043 (designated DNA102043-2534) was deposited with ATCC and was assigned ATCC deposit no. 203846. The full-length hIL-1Ra1L protein shown in FIG. 15 (SEQ ID NO:19) has an estimated molecular weight of about 23,000 daltons and a pI of about 6.08.

Based on a sequence alignment analysis of the full length sequence (SEQ ID NO:19), hIL-1Ra1L shows significant amino acid sequence identity to hIL-1Raβ and TANGO-77 protein. In addition, a portion of the DNA sequence of clone DNA102043 (FIG. 15) (SEQ ID NO:18) was found to coincide with the DNA sequence of EST AI014548 (FIG. 4) (SEQ ID NO:8) and with the complement of the DNA sequence of EST AI343258 (FIG. 17) (SEQ ID NO:23).

The entire nucleotide sequence of clone DNA102044 is shown in FIG. 16 (SEQ ID NO:20). Clone DNA102044 contains a single open reading frame with an apparent translational initiation site at nucleotide positions 4-6, and a stop codon at nucleotide positions 505-507 (FIG. 16; SEQ ID NO:20). The predicted polypeptide (designated hIL-1Ra1S) (FIG. 16; SEQ ID NO:21) is 167 amino acids long, and it is believed to behave as a mature sequence (without a presequence that is removed in post-translational processing) in certain animal cells. In addition, it is believed that other animal cells recognize and remove in post-translational processing one or more signal peptide(s) contained in the sequence extending from amino acid positions 1 to about 46.

Clone DNA102044 (designated DNA102044-2534) was deposited with ATCC and was assigned ATCC deposit no. 203855. The full-length hIL-1Ra1S protein shown in FIG. 16 (SEQ ID NO:21) has an estimated molecular weight of about 18,478 daltons and a pI of about 5.5.

Based on a sequence alignment analysis of the full length sequence (SEQ ID NO:21), hIL-1Ra1S appears to be an allelic variant of TANGO-77 protein and also shows significant amino acid sequence identity to hIL-1Raβ. In addition, a portion of the DNA sequence of clone DNA102044 (FIG. 16) (SEQ ID NO:20) was found to coincide with the DNA sequence of EST AI014548 (FIG. 4) (SEQ ID NO:8) and with the complement of the DNA sequence of EST AI343258 (FIG. 17) (SEQ ID NO:23).

EST clone AI343258 was purchased from Research Genetics (Huntsville, Ala.) and the cDNA insert was obtained and sequenced in its entirety. The entire sequence of the clone AI343258, designated DNA114876, is shown in FIG. 19 (SEQ ID NO:24). Clone DNA114876 contains a single open reading frame (ORF) with an apparent translation initiation site at nucleotide positions 73-75 and a stop codon at nucleotide positions 726-728 (FIG. 19; SEQ ID NO:24), encoding a predicted polypeptide precursor (hIL-1Ra1V) (FIG. 19; SEQ ID NO:25) that is 218 amino acids long. In addition, the ORF contains an alternate translation initiation site at nucleotide positions 106-108. The predicted polypeptide (also designated hIL-1Ra1V) for translation initiated at the alternate start codon is 207 amino acids in length (lacking the first eleven residues at the N-terminus of the 218 amino acid polypeptide). It is believed that the predicted 218 amino acid and 207 amino acid polypeptides behave as mature sequences (without a presequence that is removed in post-translational processing) in certain animal cells. It is also believed that other animal cells recognize and remove one or more signal peptide(s) extending from amino acid positions 1 to about 48

(a putative leader sequence in the 218 amino acid polypeptide) or from amino acid positions 12 to 36 (a putative leader sequence in the 207 amino acid polypeptide) in the amino acid sequence of FIG. 19 (SEQ ID NO:25). As shown in Example 14 below, transiently transfected CHO host cells secrete unprocessed forms of hIL-1Ra1V and hIL-1Ra1L and a single processed form that results from the removal of a signal peptide extending from amino acid positions 1 to 45 in FIG. 19 (SEQ ID NO:25) or the removal of a signal peptide extending from amino acid positions 1 to 34 of FIG. 15 (SEQ ID NO:19). The processed form of hIL-1Ra1V and hIL-1Ra1L secreted by transiently transfected CHO host cells has the amino acid sequence of amino acid residues 35 to 207 of FIG. 15 (SEQ ID NO:19) and amino acid residues 46 to 218 of FIG. 19 (SEQ ID NO:25).

Clone DNA114876 (designated DNA114876-2534) was deposited with ATCC and was assigned ATCC deposit no. 203973. The full length hIL-1Ra1V protein shown in FIG. 19 (SEQ ID NO:25) has an estimated molecular weight of about 24,124 and a pI of about 6.1.

Based on a sequence alignment analysis of the full length sequence (SEQ ID NO:25), hIL-1Ra1V shows significant amino acid sequence identity to hIL-1Raβ. hIL-1Ra1V is believed to be an allelic variant of hIL-1Ra1L.

Example 13

IL-18 Receptor and IL-1 Receptor Binding of hIL-1Ra1S

To facilitate the characterization of hIL-1Ra1S, a PCR fragment encoding amino acid residues 39-167 in the ORF of clone DNA102044 (FIG. 16; SEQ ID NO:21) was cloned into pCMV1FLAG (IBI Kodak, described in Pan et al., *Science*, 276: 111-113) as an in-frame fusion to a $NH_2$-terminal pre-protrypsin leader sequence and FLAG tag encoded by the vector to form plasmid pCMV1FLAG-IL-1Ra1S. Plasmid pCMV1FLAG-IL18R-ECD-Fc was obtained as described in Example 9 above.

Human embryonic kidney 293 cells were grown in high glucose DMEM (Genentech, Inc). The cells were seeded at $3\text{-}4\times10^6$ per plate (100 mm) and co-transfected with pCMV1FLAG-hIL-1Ra1S and pCMV1FLAG-IL18R-ECD-Fc by means of calcium phosphate precipitation. The media were changed 12 hours post transfection. The resultant conditioned media (10 ml each) were harvested after a further 70-74 hour incubation, clarified by centrifugation, aliquoted and stored at −70° C. The receptor-Fc and ligand complex from 1.5 ml conditioned medium was immunoprecipitated with protein G-Sepharose, washed three times with buffer containing 50 mM Hepes, pH7.0, 150 mM NaCl, 1 mM EDTA, 1% NP-40, and a protease inhibitor cocktail (BMB) and resolved on a 10-20% SDS-PAGE gel. The bound ligand was identified by immunoblotting using anti-FLAG monoclonal antibody (BMB).

The immunoblotting results indicated that the secreted FLAGhIL-1Ra1S fusion protein bound to IL-18R ECD. These data show that hIL-1Ra1S could be an agonist or antagonist of IL-18R.

Example 14 hIL-1Ra1V, hIL-1Ra1L and hIL-1Ra3 Processing cDNAs encoding full-length hIL-1Ra1V (amino acids 1-218 in the ORF of clone DNA114876 shown in FIG. 19 (SEQ ID NO:25)), full length hIL-1Ra1L (amino acids 1-207 in the ORF of clone DNA102043 shown in FIG. 15 (SEQ ID NO:19)), and full length hIL-1Ra3 (amino acids 1-155 in the ORF of clone DNA96787 shown in FIG. 7 (SEQ ID NO:13)) were each cloned into a pRK7 expression vector as an in-frame fusion with a carboxy-terminal FLAG-tag sequence. In preparation for mammalian cell transient transfections, CHO DP12 cells were seeded at $4\times10^6$ cells per plate (100 mm petri dish) in growth medium (PS20, 5% FBS, 1× GHT, 1× pen/strep, 1× L-glutamine) the day before transfection. On the day of transfection, cells were washed with PBS and fed with 10 ml serum-free transfection medium (PS20, 1× GHT). DNA-lipid transfection mixtures were prepared by adding stepwise into eppendorf tubes (1) 400 µl transfection medium (PS20, 1×GHT); (2) 12 µg DNA; (3) 10 µg poly-lysine; and (4) 50 µl Dosper liposomal transfection reagent (Boehringer Mannheim). The DNA-lipid mixtures were incubated for 15 minutes at room temperature and then added dropwise to cell culture plates. Cells were incubated overnight at 37° C. On the day after transfection, cells were washed with PBS, fed with 10 ml serum-free production medium (PS24, 10 mg/L insulin, 1× trace elements, 1.4 mg/L lipid EtOH), and placed in a 32° C. incubator. After 5 days, the culture media containing the expressed proteins were harvested and cleared by centrifugation. For peptide sequencing of each expressed protein, 5-10 ml of the conditioned medium containing the expressed protein was incubated with monoclonal anti-FLAG antibody (Boehringer Mannheim) coupled to agarose beads. The immunoprecipitated FLAG-tag proteins were extensively washed with 1% NP-40 buffer (125 mM NaCl, 1 mM EDTA and 50 mM Tris-HCl, pH 7.4). The immunoprecipitates were run on a SDS polyacrylamide gel, the separated polypeptides on the gel were transferred to a PVDF membrane, the PVDF membrane was stained with Coomassie blue, and the corresponding protein bands were excised from the membrane. The amino-terminal protein sequences were obtained by conventional methods.

The processed N-terminal sequence of both of the hIL-1Ra1L and hIL-1Ra1V polypeptides was determined to be VHTSPKVKN (SEQ ID NO:31). Approximately 50% of hIL-1Ra1L and hIL-1Ra1V material recovered from conditioned media exhibited the processed N-terminal sequence, indicating that the CHO host cells secreted a processed form corresponding to amino acid residues 35 to 207 in the amino acid sequence of FIG. 15 (SEQ ID NO:19) and amino acid residues 46 to 218 in the amino acid sequence of FIG. 19 (SEQ ID NO:25). The remaining 50% of the hIL-1Ra1L and hIL-1Ra1V material recovered from conditioned media exhibited an unprocessed N-terminus, indicating that the CHO host cells also secreted unprocessed forms of hIL-1Ra1L and hIL-1Ra1V corresponding to amino acid residues 1 to 207 in the amino acid sequence of FIG. 15 (SEQ ID NO:19) and to amino acid residues 1 to 218 in the amino acid sequence of FIG. 19 (SEQ ID NO:25), respectively.

The processed N-terminal sequence of both of the hIL-1Ra3 and mIL-1Ra3 polypeptides was determined to be VLS-GALCFRM (SEQ ID NO:32). Approximately 100% of the hIL-1Ra3 and mIL-1Ra3 material recovered from conditioned media exhibited the processed N-terminal sequence, indicating that the CHO host cells secreted processed forms of hIL-1Ra3 and mIL-1Ra3 that lack the N-terminal methionine and correspond to amino acid residues 2 to 155 in the amino acid sequence of FIG. 7 (SEQ ID NO:13) and amino acid residues 2 to 155 in the amino acid sequence of FIG. 9 (SEQ ID NO:16), respectively.

Deposit of Material

The following materials have been deposited with the American Type Culture Collection, 10801 University Blvd., Manassas, Va. 20110-2209, USA (ATCC):

| Material | ATCC Dep. No. | Deposit Date |
|---|---|---|
| pSPORT1-based plasmid DNA92929-2534 | 203586 | Jan. 12, 1999 |
| pCMV-1Flag-pcmv5 plasmid DNA96786-2534 | 203587 | Jan. 12, 1999 |
| pT7T3D-Pac plasmid DNA85066-2534 | 203588 | Jan. 12, 1999 |
| pINCY-based plasmid DNA96787-2534 | 203589 | Jan. 12, 1999 |
| pT7T3D-Pac plasmid DNA92505-2534 | 203590 | Jan. 12, 1999 |
| pRK7-based plasmid DNA102043-2534 | 203846 | Mar. 16, 1999 |
| pRK7-based plasmid DNA102044-2534 | 203855 | Mar. 16, 1999 |
| pRK7-based plasmid DNA114876-2534 | 203973 | Apr. 27, 1999 |

These deposits were made under the provisions of the Budapest Treaty on the International Recognition of the Deposit of Microorganisms for the Purpose of Patent Procedure and the Regulations thereunder (Budapest Treaty). This assures maintenance of viable cultures of the deposits for 30 years from the date of deposit. The deposits will be made available by ATCC under the terms of the Budapest Treaty, and subject to an agreement between Genentech, Inc. and ATCC, which assures permanent and unrestricted availability of the progeny of the cultures of the deposits to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the constructs deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

TABLE 2A

| PRO | XXXXXXXXXXXXXXX | (Length = 15 amino acids) |
|---|---|---|
| Comparison Protein | XXXXXYYYYYYY | (Length = 12 amino acids) |

% amino acid sequence identity = (the number of identically matching amino acid residues between the two polypeptide sequences as determined by ALIGN-2) divided by (the total number of amino acid residues of the PRO polypeptide) = 5 divided by 15 = 33.3%

TABLE 2B

| PRO | XXXXXXXXXX | (Length = 10 amino acids) |
|---|---|---|
| Comparison Protein | XXXXXYYYYYYZZYZ | (Length = 15 amino acids) |

% amino acid sequence identity = (the number of identically matching amino acid residues between the two polypeptide sequences as determined by ALIGN-2) divided by (the total number of amino acid residues of the PRO polypeptide) = 5 divided by 10 = 50%

TABLE 2C

| PRO-DNA | NNNNNNNNNNNNNN | (Length = 14 nucleotides) |
|---|---|---|
| Comparison DNA | NNNNNNLLLLLLLLLL | (Length = 16 nucleotides) |

% nucleic acid sequence identity = (the number of identically matching nucleotides between the two nucleic acid sequences as determined by ALIGN-2) divided by (the total number of nucleotides of the PRO-DNA nucleic acid sequence) = 6 divided by 14 = 42.9%

TABLE 2D

| PRO-DNA | NNNNNNNNNNNN | (Length = 12 nucleotides) |
|---|---|---|
| Comparison DNA | NNNNLLLVV | (Length = 9 nucleotides) |

% nucleic acid sequence identity = (the number of identically matching nucleotides between the two nucleic acid sequences as determined by ALIGN-2) divided by (the total number of nucleotides of the PRO-DNA nucleic acid sequence) = 4 divided by 12 = 33.3%

TABLE 3A

```
/*
*
* C-C increased from 12 to 15
* Z is average of EQ
* B is average of ND
* match with stop is _M; stop-stop = 0; J (joker) match = 0
*/
#define   _M    -8    /* value of a match with a stop */
int    _day[26][26] = {
/*      A  B  C  D  E  F  G  H  I  J  K  L  M  N  O  P  Q  R  S  T  U  V  W  X  Y  Z */
/* A */  { 2, 0,-2, 0, 0,-4, 1,-1,-1, 0,-1,-2,-1, 0,_M, 1, 0,-2, 1, 1, 0, 0,-6, 0,-3, 0},
/* B */  { 0, 3,-4, 3, 2,-5, 0, 1,-2, 0, 0,-3,-2, 2,_M,-1, 1, 0, 0, 0,-2,-5, 0,-3, 1},
/* C */  {-2,-4,15,-5,-5,-4,-3,-3,-2, 0,-5,-6,-5,-4,_M,-3,-5,-4, 0,-2, 0,-2,-8, 0, 0,-5},
/* D */  { 0, 3,-5, 4, 3,-6, 1, 1,-2, 0, 0,-4,-3, 2,_M,-1, 2,-1, 0, 0, 0,-2,-7, 0,-4, 2},
/* E */  { 0, 2,-5, 3, 4,-5, 0, 1,-2, 0, 0,-3,-2, 1,_M,-1, 2,-1, 0, 0, 0,-2,-7, 0,-4, 3},
/* F */  {-4,-5,-4,-6,-5, 9,-5,-2, 1, 0,-5, 2, 0,-4,_M,-5,-5,-4,-3,-3, 0,-1, 0, 0, 7,-5},
/* G */  { 1, 0,-3, 1, 0,-5, 5,-2,-3, 0,-2,-4,-3, 0,_M,-1,-1,-3, 1, 0, 0,-1,-7, 0,-5, 0},
```

TABLE 3A-continued

```
/* H */    {-1, 1,-3, 1, 1,-2,-2, 6,-2, 0, 0,-2,-2, 2,_M, 0, 3, 2,-1,-1, 0,-2,-3, 0, 0, 2},
/* I */    {-1,-2,-2,-2,-2, 1,-3,-2, 5, 0,-2, 2, 2,-2,_M,-2,-2,-2,-1, 0, 0, 4,-5, 0,-1,-2},
/* J */    { 0, 0, 0, 0, 0, 0, 0, 0, 0, 0, 0, 0, 0, 0,_M, 0, 0, 0, 0, 0, 0, 0, 0, 0, 0, 0},
/* K */    {-1, 0,-5, 0, 0,-5,-2, 0,-2, 0, 5,-3, 0, 1,_M,-1, 1, 3, 0, 0, 0,-2,-3, 0,-4, 0},
/* L */    {-2,-3,-6,-4,-3, 2,-4,-2, 2, 0,-3, 6, 4,-3,_M,-3,-2,-3,-3,-1, 0, 2,-2, 0,-1,-2},
/* M */    {-1,-2,-5,-3,-2, 0,-3,-2, 2, 0, 0, 4, 6,-2,_M,-2,-1, 0,-2,-1, 0, 2,-4, 0,-2,-1},
/* N */    { 0, 2,-4, 2, 1,-4, 0, 2,-2, 0, 1,-3,-2, 2,_M,-1, 1, 0, 1, 0, 0,-2,-4, 0,-2, 1},
/* O */    {_M,_M,_M,_M,_M,_M,_M,_M,_M,_M,_M,_M,_M,_M, 0,_M,_M,_M,_M,_M,_M,_M,_M,_M,_M,_M},
/* P */    { 1,-1,-3,-1,-1,-5,-1, 0,-2, 0,-1,-3,-2,-1,_M, 6, 0, 0, 1, 0, 0,-1,-6, 0,-5, 0},
/* Q */    { 0, 1,-5, 2, 2,-5,-1, 3,-2, 0, 1,-2,-1, 1,_M, 0, 4, 1,-1,-1, 0,-2,-5, 0,-4, 3},
/* R */    {-2, 0,-4,-1,-1,-4,-3, 2,-2, 0, 3,-3, 0, 0,_M, 0, 1, 6, 0,-1, 0,-2, 2, 0,-4, 0},
/* S */    { 1, 0, 0, 0, 0,-3, 1,-1,-1, 0, 0,-3,-2, 1,_M, 1,-1, 0, 2, 1, 0,-1,-2, 0,-3, 0},
/* T */    { 1, 0,-2, 0, 0,-3, 0,-1, 0, 0, 0,-1,-1, 0,_M, 0,-1,-1, 1, 3, 0, 0,-5, 0,-3, 0},
/* U */    { 0, 0, 0, 0, 0, 0, 0, 0, 0, 0, 0, 0, 0, 0,_M, 0, 0, 0, 0, 0, 0, 0, 0, 0, 0, 0},
/* V */    { 0,-2,-2,-2,-2,-1,-1,-2, 4, 0,-2, 2, 2,-2,_M,-1,-2,-2,-1, 0, 0, 4,-6, 0,-2,-2},
/* W */    {-6,-5,-8,-7,-7, 0,-7,-3,-5, 0,-3,-2,-4,-4,_M,-6,-5, 2,-2,-5, 0,-6,17, 0, 0,-6},
/* X */    { 0, 0, 0, 0, 0, 0, 0, 0, 0, 0, 0, 0, 0, 0,_M, 0, 0, 0, 0, 0, 0, 0, 0, 0, 0, 0},
/* Y */    {-3,-3, 0,-4,-4, 7,-5, 0,-1, 0,-4,-1,-2,-2,_M,-5,-4,-4,-3,-3, 0,-2, 0, 0,10,-4},
/* Z */    { 0, 1,-5, 2, 3,-5, 0, 2,-2, 0, 0,-2,-1, 1,_M, 0, 3, 0, 0, 0, 0,-2,-6, 0,-4, 4}
};
```

TABLE 3B

```
/*
*/
#include <stdio.h>
#include <ctype.h>
#define    MAXJMP    16      /* max jumps in a diag */
#define    MAXGAP    24      /* don't continue to penalize gaps larger than this */
#define    JMPS      1024    /* max jmps in an path */
#define    MX        4       /* save if there's at least MX-1 bases since last jmp */
#define    DMAT      3       /* value of matching bases */
#define    DMIS      0       /* penalty for mismatched bases */
#define    DINS0     8       /* penalty for a gap */
#define    DINS1     1       /* penalty per base */
#define    PINS0     8       /* penalty for a gap */
#define    PINS1     4       /* penalty per residue */
struct jmp {
        short            n[MAXJMP];        /* size of jmp (neg for dely) */
        unsigned short   x[MAXJMP];        /* base no. of jmp in seq x */
};                                         /* limits seq to 2^16 -1 */
struct diag {
        int              score;            /* score at last jmp */
        long             offset;           /* offset of prev block */
        short            ijmp;             /* current jmp index */
        struct jmp       jp;               /* list of jmps */
};
struct path {
        int              spc;              /* number of leading spaces */
        short            n[JMPS];          /* size of jmp (gap) */
        int              x[JMPS];          /* loc of jmp (last elem before gap) */
};
char              *ofile;                  /* output file name */
char              *namex[2];               /* seq names: getseqs( ) */
char              *prog;                   /* prog name for err msgs */
char              *seqx[2];                /* seqs: getseqs( ) */
int               dmax;                    /* best diag: nw( ) */
int               dmax0;                   /* final diag */
int               dna;                     /* set if dna: main( ) */
int               endgaps;                 /* set if penalizing end gaps */
int               gapx, gapy;              /* total gaps in seqs */
int               len0, len1;              /* seq lens */
int               ngapx, ngapy;            /* total size of gaps */
int               smax;                    /* max score: nw( ) */
int               *xbm;                    /* bitmap for matching */
long              offset;                  /* current offset in jmp file */
struct  diag      *dx;                     /* holds diagonals */
struct  path      pp[2];                   /* holds path for seqs */
char              *calloc( ), *malloc( ), *index( ), *strcpy( );
char              *getseq( ), *g_calloc( );
```

TABLE 3C

```
/* Needleman-Wunsch alignment program
*
* usage: progs file1 file2
*   where file1 and file2 are two dna or two protein sequences.
*   The sequences can be in upper- or lower-case an may contain ambiguity
*   Any lines beginning with ';', '>' or '<' are ignored
*   Max file length is 65535 (limited by unsigned short x in the jmp struct)
*   A sequence with 1/3 or more of its elements ACGTU is assumed to be
*   DNA Output is in the file "align.out"
*
* The program may create a tmp file in /tmp to hold info about traceback.
* Original version developed under BSD 4.3 on a vax 8650
*/
#include "nw.h"
#include "day.h"
static   _dbval[26] = {
    1,14,2,13,0,0,4,11,0,0,12,0,3,15,0,0,0,5,6,8,8,7,9,0,10,0
};
static   _pbval[26] = {
    1, 2|(1 << ('D'-'A'))|(1 << ('N'-'A')), 4, 8, 16, 32, 64, 128,
    256, 0xFFFFFFF, 1 << 10, 1 << 11, 1 << 12, 1 << 13,
    1 << 14, 1 << 15, 1 << 16, 1 << 17, 1 << 18, 1 << 19,
    1 << 20, 1 << 21, 1 << 22, 1 << 23, 1 << 24, 1 << 25|
    (1 << ('E'-'A'))|(1 << ('Q'-'A'))
};
main(ac, av)                                                           main
        int      ac;
        char     *av[ ];
{
        prog = av[0];
        if (ac != 3) {
                fprintf(stderr,"usage: %s file1 file2\n", prog);
                fprintf(stderr,"where file1 and file2 are two dna or
                two protein sequences.\n");
                fprintf(stderr,"The sequences can be in upper- or
                lower-case\n");
                fprintf(stderr,"Any lines beginning with ';' or '<'
                are ignored\n");
                fprintf(stderr,"Output is in the file \"align.out\"\n");
                exit(1);
        }
        namex[0] = av[1];
        namex[1] = av[2];
        seqx[0] = getseq(namex[0], &len0);
        seqx[1] = getseq(namex[1], &len1);
        xbm = (dna)? _dbval : _pbval;
        endgaps = 0;          /* 1 to penalize endgaps */
        ofile = "align.out";  /* output file */
        nw( );                /* fill in the matrix, get the possible jmps */
        readjmps( );          /* get the actual jmps */
        print( );             /* print stats, alignment */
        cleanup(0);           /* unlink any tmp files */
}
```

TABLE 3D

```
/* do the alignment, return best score: main( )
* dna: values in Fitch and Smith, PNAS, 80, 1382-1386, 1983
* pro: PAM 250 values
* When scores are equal, we prefer mismatches to any gap, prefer
* a new gap to extending an ongoing gap, and prefer a gap in seqx
* to a gap in seq y.
*/
nw( )                                                                  nw
{
        char     *px, *py;         /* seqs and ptrs */
        int      *ndely, *dely;    /* keep track of dely */
        int      ndelx, delx;      /* keep track of delx */
        int      *tmp;             /* for swapping row0, row1 */
        int      mis;              /* score for each type */
        int      ins0, ins1;       /* insertion penalties */
        register id;               /* diagonal index */
        register ij;               /* jmp index */
        register *col0, *col1;     /* score for curr, last row */
        register xx, yy;           /* index into seqs */
        dx = (struct diag *)g_calloc("to get diags", len0+len1+1,
        sizeof(struct diag));
```

TABLE 3D-continued

```
        ndely = (int *)g_calloc("to get ndely", len1+1, sizeof(int));
        dely = (int *)g_calloc("to get dely", len1+1, sizeof(int));
        col0 = (int *)g_calloc("to get col0", len1+1, sizeof(int));
        col1 = (int *)g_calloc("to get col1", len1+1, sizeof(int));
        ins0 = (dna)? DINS0 : PINS0;
        ins1 = (dna)? DINS1 : PINS1;
        smax = -10000;
        if (endgaps) {
                for (col0[0] = dely[0] = -ins0, yy = 1; yy <= len1;
                yy++) {
                        col0[yy] = dely[yy] = col0[yy-1] - ins1;
                        ndely[yy] = yy;
                }
                col0[0] = 0;     /* Waterman Bull Math Biol 84 */
        }
        else
                for (yy = 1; yy <= len1; yy++)
                        dely[yy] = -ins0;
/* fill in match matrix
*/
for (px = seqx[0], xx = 1; xx <= len0; px++, xx++) {
        /* initialize first entry in col
        */
        if (endgaps) {
                if (xx == 1)
                        col1[0] = delx = -(ins0+ins1);
                else
                        col1[0] = delx = col0[0] - ins1;
                ndelx = xx;
        }
        else {
                col1[0] = 0;
                delx = -ins0;
                ndelx = 0;
        }
```

TABLE 3E

```
                                                                      ...nw
for (py = seqx[1], yy = 1; yy <= len1; py++, yy++) {
        mis = col0[yy-1];
        if (dna)
                mis += (xbm[*px-'A']&xbm[*py-'A'])? DMAT :
                DMIS;
        else
                mis += _day[*px-'A'][*py-'A'];
/* update penalty for del in x seq;
* favor new del over ongong del
* ignore MAXGAP if weighting endgaps
*/
if (endgaps || ndely[yy] < MAXGAP) {
        if (col0[yy] - ins0 >= dely[yy]) {
                dely[yy] = col0[yy] - (ins0+ins1);
                ndely[yy] = 1;
        } else {
                dely[yy] -= ins1;
                ndely[yy]++;
        }
} else {
        if (col0[yy] - (ins0+ins1) >= dely[yy]) {
                dely[yy] = col0[yy] - (ins0+ins1);
                ndely[yy] = 1;
        } else
                ndely[yy]++;
}
/* update penalty for del in y seq;
* favor new del over ongong del
*/
if (endgaps || ndelx < MAXGAP) {
        if (col1[yy-1] - ins0 >= delx) {
                delx = col1[yy-1] - (ins0+ins1);
                ndelx = 1;
        } else {
                delx -= ins1;
                ndelx++;
        }
```

TABLE 3E-continued

```
        } else {
                if (col1[yy−1] − (ins0+ins1) >= delx) {
                        delx = col1[yy−1] − (ins0+ins1);
                        ndelx = 1;
                } else
                        ndelx++;
        }
/* pick the maximum score; we're favoring
 * mis over any del and delx over dely
 */
```

TABLE 3F

```
                                                                    ...nw
id = xx − yy + len1 − 1;
if (mis >= delx && mis >= dely[yy])
        col1[yy] = mis;
else if (delx >= dely[yy]) {
        col1[yy] = delx;
        ij = dx[id].ijmp;
        if (dx[id].jp.n[0] && (!dna || (ndelx >= MAXJMP
                && xx > dx[id].jp.x[ij]+MX) || mis > dx[id].score+DINS0)) {
                dx[id].ijmp++;
                if (++ij >= MAXJMP) {
                                        writejmps(id);
                                        ij = dx[id].ijmp = 0;
                                        dx[id].offset = offset;
                                        offset += sizeof(struct jmp) +
                                                sizeof(offset);
                }
        }
        dx[id].jp.n[ij] = ndelx;
        dx[id].jp.x[ij] = xx;
        dx[id].score = delx;
}
else {
        col1[yy] = dely[yy];
        ij = dx[id].ijmp;
        if (dx[id].jp.n[0] && (!dna || (ndely[yy] >= MAXJMP
                && xx > dx[id].jp.x[ij]+MX) || mis
                > dx[id].score+DINS0)) {
                dx[id].ijmp++;
                if (++ij >= MAXJMP) {
                                        writejmps(id);
                                        ij = dx[id].ijmp = 0;
                                        dx[id].offset = offset;
                                        offset += sizeof(struct jmp) +
                                                sizeof(offset);
                }
        }
        dx[id].jp.n[ij] = −ndely[yy];
        dx[id].jp.x[ij] = xx;
        dx[id].score = dely[yy];
}
if (xx == len0 && yy < len1) {
        /* last col
         */
        if (endgaps)
                col1[yy] −= ins0+ins1*(len1−yy);
        if (col1[yy] > smax) {
                smax = col1[yy];
                dmax = id;
        }
    }
}
if (endgaps && xx < len0)
        col1[yy−1] −= ins0+ins1*(len0−xx);
if (col1[yy−1] > smax) {
        smax = col1[yy−1];
        dmax = id;
}
tmp = col0; col0 = col1; col1 = tmp;
```

TABLE 3F-continued

```
}
(void) free((char *)ndely);
(void) free((char *)dely);
(void) free((char *)col0);
(void) free((char *)col1);
}
```

TABLE 3G

```
/*
 *
 * print( ) -- only routine visible outside this module
 *
 * static:
 * getmat( ) -- trace back best path, count matches: print( )
 * pr_align( ) -- print alignment of described in array p[ ]: print( )
 * dumpblock( ) -- dump a block of lines with numbers, stars: pr_align( )
 * nums( ) -- put out a number line: dumpblock( )
 * putline( ) -- put out a line (name, [num], seq, [num]): dumpblock( )
 * stars( ) --put a line of stars: dumpblock( )
 * stripname( ) -- strip any path and prefix from a seqname
 */
#include "nw.h"
#define SPC       3
#define P_LINE    256    /* maximum output line */
#define P_SPC     3      /* space between name or num and seq */
extern    _day[26][26];
int       olen;          /* set output line length */
FILE      *fx;           /* output file */
print( )                                                         print
{
        int    lx, ly, firstgap, lastgap;   /* overlap */
        if ((fx = fopen(ofile, "w")) == 0) {
                fprintf(stderr,"%s: can't write %s\n", prog, ofile);
                cleanup(1);
        }
        fprintf(fx, "<first sequence: %s (length = %d)\n",
                namex[0], len0);
        fprintf(fx, "<second sequence: %s (length = %d)\n",
                namex[1], len1);
        olen = 60;
        lx = len0;
        ly = len1;
        firstgap = lastgap = 0;
        if (dmax < len1 − 1) {         /* leading gap in x */
                pp[0].spc = firstgap = len1 − dmax − 1;
                ly −= pp[0].spc;
        }
        else if (dmax > len1 − 1) {    /* leading gap in y */
                pp[1].spc = firstgap = dmax − (len1 − 1);
                lx −= pp[1].spc;
        }
        if (dmax0 < len0 − 1) {        /* trailing gap in x */
                lastgap = len0 − dmax0 −1;
                lx −= lastgap;
        }
        else if (dmax0 > len0 − 1) { /* trailing gap in y */
                lastgap = dmax0 − (len0 − 1);
                ly −= lastgap;
        }
        getmat(lx, ly, firstgap, lastgap);
        pr_align( );
}
```

TABLE 3H

```
/*
 * trace back the best path, count matches
 */
static
getmat(lx, ly, firstgap, lastgap)                                 getmat
        int    lx, ly;               /* "core" (minus endgaps) */
        int    firstgap, lastgap;    /* leading trailing overlap */
{
```

TABLE 3H-continued

```
int         nm, i0, i1, siz0, siz1;
char        outx[32];
double      pct;
register    n0, n1;
register char *p0, *p1;
/* get total matches, score
 */
i0 = i1 = siz0 = siz1 = 0;
p0 = seqx[0] + pp[1].spc;
p1 = seqx[1] + pp[0].spc;
n0 = pp[1].spc + 1;
n1 = pp[0].spc + 1;
nm = 0;
while ( *p0 && *p1 ) {
        if (siz0) {
                p1++;
                n1++;
                siz0--;
        }
        else if (siz1) {
                p0++;
                n0++;
                siz1--;
        }
```

TABLE 3H-continued

```
        else {
                if (xbm[*p0-'A']&xbm[*p1-'A'])
                        nm++;
                if (n0++ == pp[0].x[i0])
                        siz0 = pp[0].n[i0++];
                if (n1++ == pp[1].x[i1])
                        siz1 = pp[1].n[i1++];
                p0++;
                p1++;
        }
}
/* pct homology:
 * if penalizing endgaps, base is the shorter seq
 * else, knock off overhangs and take shorter core
 */
if (endgaps)
        lx = (len0 < len1)? len0 : len1;
else
        lx = (lx < ly)? lx : ly;
pct = 100.*(double)nm/(double)lx;
fprintf(fx, "\n");
fprintf(fx, "<%d match%s in an overlap of %d: %.2f percent
        similarity\n", nm, (nm == 1)? "" : "es", lx, pct);
```

TABLE 3I

```
fprintf(fx, "<gaps in first sequence: %d", gapx);                              ...getmat
if (gapx) {
        (void) sprintf(outx, " (%d %s%s)",
                ngapx, (dna)? "base":"residue", (ngapx == 1)? "":"s");
        fprintf(fx,"%s", outx);
}
fprintf(fx, ", gaps in second sequence: %d", gapy);
if (gapy) {
        (void) sprintf(outx, " (%d %s%s)",
                ngapy, (dna)? "base":"residue", (ngapy == 1)? "":"s");
        fprintf(fx,"%s", outx);
}
if (dna)
        fprintf(fx,
        "\n<score: %d (match = %d, mismatch = %d, gap penalty = %d + %d per
        base)\n", smax, DMAT, DMIS, DINS0, DINS1);
else
        fprintf(fx,
        "\n<score: %d (Dayhoff PAM 250 matrix, gap penalty = %d + %d per residue)\n",
        smax, PINS0, PINS1);
if (endgaps)
        fprintf(fx,
        "<endgaps penalized. left endgap: %d %s%s, right endgap: %d %s%s\n",
        firstgap, (dna)? "base" : "residue", (firstgap == 1)? "" : "s",
        lastgap, (dna)? "base" : "residue", (lastgap == 1)? "" : "s");
else
        fprintf(fx, "<endgaps not penalized\n");
}
static          nm;             /* matches in core -- for checking */
static          lmax;           /* lengths of stripped file names */
static          ij[2];          /* jmp index for a path */
static          nc[2];          /* number at start of current line */
static          ni[2];          /* current elem number -- for gapping */
static          siz[2];
static char     *ps[2];         /* ptr to current element */
static char     *po[2];         /* ptr to next output char slot */
static char     out[2][P_LINE]; /* output line */
static char     star[P_LINE];   /* set by stars( ) */
/*
 * print alignment of described in struct path pp[ ]
 */
static
pr_align( )                                                                    pr_align
{
        int             nn;     /* char count */
        int             more;
        register        i;
```

TABLE 3I-continued

```
for (i = 0, lmax = 0; i < 2; i++) {
        nn = stripname(namex[i]);
        if (nn > lmax)
                lmax = nn;
        nc[i] = 1;
        ni[i] = 1;
        siz[i] = ij[i] = 0;
        ps[i] = seqx[i];
        po[i] = out[i];
```

TABLE 3J

```
for (nn = nm = 0, more = 1; more; ) {              ...pr_align
        for (i = more = 0; i < 2; i++) {
                /*
                 * do we have more of this sequence?
                 */
                if (!*ps[i])
                        continue;
                more++;
                if (pp[i].spc) {     /* leading space */
                        *po[i]++ = ' ';
                        pp[i].spc--;
                }
                else if (siz[i]) {   /* in a gap */
                        *po[i]++ = '-';
                        siz[i]--;
                }
                else {               /* we're putting a seq element
                                      */
                        *po[i] = *ps[i];
                        if (islower(*ps[i]))
                                *ps[i] = toupper(*ps[i]);
                        po[i]++;
                        ps[i]++;
                        /*
                         * are we at next gap for this seq?
                         */
                        if (ni[i] == pp[i].x[ij[i]]) {
                                /*
                                 * we need to merge all gaps
                                 * at this location
                                 */
                                siz[i] = pp[i].n[ij[i]++];
                                while (ni[i] == pp[i].x[ij[i]])
                                        siz[i] +=
                                                pp[i].n[ij[i]++];
                        }
                        ni[i]++;
                }
        }
        if (++nn == olen || !more && nn) {
                dumpblock( );
                for (i = 0; i < 2; i++)
                        po[i] = out[i];
                nn = 0;
        }
    }
}
/*
 * dump a block of lines, including numbers, stars: pr_align( )
 */
static
dumpblock( )                                        dumpblock
{
        register i;
        for (i = 0; i < 2; i++)
                *po[i]-- = '\0';
```

TABLE 3K

```
                                                    ...dumpblock
        (void) putc('\n', fx);
        for (i = 0; i < 2; i++) {
                if (*out[i] && (*out[i] != ' ' || *(po[i]) != ' ')) {
                        if (i == 0)
                                nums(i);
                        if (i == 0 && *out[1])
                                stars( );
                        putline(i);
                        if (i == 0 && *out[1])
                                fprintf(fx, star);
                        if (i == 1)
                                nums(i);
                }
        }
}
/*
 * put out a number line: dumpblock( )
 */
static
nums(ix)                                                nums
        int        ix;      /* index in out[ ] holding seq line */
{
        char       nline[P_LINE];
        register   i, j;
        register char    *pn, *px, *py;
        for (pn = nline, i = 0; i < lmax+P_SPC; i++, pn++)
                *pn = ' ';
        for (i = nc[ix], py = out[ix]; *py; py++, pn++) {
                if (*py == ' ' || *py == '-')
                        *pn = ' ';
                else {
                        if (i%10 == 0 || (i == 1 && nc[ix] != 1)) {
                                j = (i < 0)? -i : i;
                                for (px = pn; j; j /= 10, px--)
                                        *px = j%10 + '0';
                                if (i < 0)
                                        *px = '-';
                        }
                        else
                                *pn = ' ';
                        i++;
                }
        }
        *pn = '\0';
        nc[ix] = i;
        for (pn = nline; *pn; pn++)
                (void) putc(*pn, fx);
        (void) putc('\n', fx);
}
/*
 * put out a line (name, [num], seq, [num]): dumpblock( )
 */
static
putline(ix)                                             putline
        int        ix;
{
```

TABLE 3L

```
                                                        ...putline
        int             i;
        register char   *px;
        for (px = namex[ix], i = 0; *px && *px != ':'; px++, i++)
                (void) putc(*px, fx);
        for (; i < lmax+P_SPC; i++)
                (void) putc(' ', fx);
        /* these count from 1:
         * ni[ ] is current element (from 1)
         * nc[ ] is number at start of current line
         */
        for (px = out[ix]; *px; px++)
                (void) putc(*px&0x7F, fx);
        (void) putc('\n', fx);
}
/*
 * put a line of stars (seqs always in out[0], out[1]): dumpblock( )
 */
static
stars( )                                                        stars
{
        int             i;
        register char   *p0, *p1, cx, *px;
        if (!*out[0] || (*out[0] == ' ' && *(po[0]) == ' ') ||
            !*out[1] || (*out[1] == ' ' && *(po[1]) == ' '))
                return;
        px = star;
        for (i = lmax+P_SPC; i; i--)
                *px++ = ' ';
        for (p0 = out[0], p1 = out[1]; *p0 && *p1; p0++, p1++) {
                if (isalpha(*p0) && isalpha(*p1)) {
                        if (xbm[*p0-'A']&xbm[*p1-'A']) {
                                cx = '*';
                                nm++;
                        }
                        else if (!dna && _day[*p0-'A'][*p1-'A']
                                > 0)
                                cx = '.';
                        else
                                cx = ' ';
                }
                else
                        cx = ' ';
                *px++ = cx;
        }
        *px++ = '\n';
        *px = '\0';
}
```

TABLE 3M

```
/*
 * strip path or prefix from pn, return len: pr_align( )
 */
static
stripname(pn)                                                   stripname
        char            *pn;    /* file name (may be path) */
{
        register char   *px, *py;
        py = 0;
        for (px = pn; *px; px++)
                if (*px == '/')
                        py = px + 1;
        if (py)
                (void) strcpy(pn, py);
        return(strlen(pn));
}
```

TABLE 3N

```
/*
 * cleanup( ) -- cleanup any tmp file
 * getseq( ) -- read in seq, set dna, len, maxlen
 * g_calloc( ) -- calloc( ) with error checkin
 * readjmps( ) -- get the good jmps, from tmp file if necessary
 * writejmps( ) -- write a filled array of jmps to a tmp file: nw( )
 */
#include "nw.h"
#include <sys/file.h>
char    *jname = "/tmp/homgXXXXXX";     /* tmp file for jmps */
FILE    *fj;
int     cleanup( );                     /* cleanup tmp file */
long    lseek( );
/*
 * remove any tmp file if we blow
 */
cleanup(i)                                                      cleanup
        int             i;
{
        if (fj)
                (void) unlink(jname);
        exit(i);
}
/*
 * read, return ptr to seq, set dna, len, maxlen
 * skip lines starting with ';', '<', or '>'
 * seq in upper or lower case
 */
char    *
getseq(file, len)                                               getseq
        char            *file;  /* file name */
        int             *len;   /* seq len */
{
        char            line[1024], *pseq;
        register char   *px, *py;
        int             natgc, tlen;
        FILE            *fp;
        if ((fp = fopen(file,"r")) == 0) {
                fprintf(stderr,"%s: can't read %s\n", prog, file);
                exit(1);
        }
        tlen = natgc = 0;
        while (fgets(line, 1024, fp)) {
                if (*line == ';' || *line == '<' || *line == '>')
                        continue;
                for (px = line; *px != '\n'; px++)
                        if (isupper(*px) || islower(*px))
                                tlen++;
        }
        if ((pseq = malloc((unsigned)(tlen+6))) == 0) {
                fprintf(stderr,"%s: malloc( ) failed to get %d
                bytes for %s\n", prog, tlen+6, file);
                exit(1);
        }
        pseq[0] = pseq[1] = pseq[2] = pseq[3] = '\0';
```

TABLE 3O

```
                                                                ...getseq
        py = pseq + 4;
        *len = tlen;
        rewind(fp);
        while (fgets(line, 1024, fp)) {
                if (*line == ';' || *line == '<' || *line == '>')
                        continue;
                for (px = line; *px != '\n'; px++) {
                        if (isupper(*px))
                                *py++ = *px;
                        else if (islower(*px))
                                *py++ = toupper(*px);
                        if (index("ATGCU",*(py-1)))
                                natgc++;
                }
        }
        *py++ = '\0';
        *py = '\0';
        (void) fclose(fp);
```

TABLE 3O-continued

```
            dna = natgc > (tlen/3);
            return(pseq+4);
}
char    *
g_calloc(msg, nx, sz)                                           g_calloc
        char        *msg;           /* program, calling routine */
        int         nx, sz;         /* number and size of elements */
{
        char            *px, *calloc( );
        if ((px = calloc((unsigned)nx, (unsigned)sz)) == 0) {
                if (*msg) {
                        fprintf(stderr, "%s: g_calloc( ) failed %s
                                (n=%d, sz=%d)\n", prog, msg, nx, sz);
                        exit(1);
                }
        }
        return(px);
}
/*
* get final jmps from dx[ ] or tmp file, set pp[ ], reset dmax: main( )
```

TABLE 3O-continued

```
*/
readjmps( )                                                     readjmps
{
        int             fd = -1;
        int             siz, i0, i1;
        register i, j, xx;
        if (fj) {
                (void) fclose(fj);
                if ((fd = open(jname, O_RDONLY, 0)) < 0) {
                        fprintf(stderr, "%s: can't open( )
                                %s\n", prog, jname);
                        cleanup(1);
                }
        }
        for (i = i0 = i1 = 0, dmax0 = dmax, xx = len0; ; i++) {
                while (1) {
                        for (j = dx[dmax].ijmp; j >= 0 &&
                                dx[dmax].jp.x[j] >= xx; j--)
                                ;
```

TABLE 3P

```
                                                                ...readjmps
        if (j < 0 && dx[dmax].offset && fj) {
                (void) lseek(fd, dx[dmax].offset, 0);
                (void) read(fd, (char *)&dx[dmax].jp, sizeof(struct jmp));
                (void) read(fd, (char *)&dx[dmax].offset, sizeof(dx[dmax].offset));
                dx[dmax].ijmp = MAXJMP-1;
        }
        else
                break;
}
if (i >= JMPS) {
        fprintf(stderr, "%s: too many gaps in alignment\n", prog);
        cleanup(1);
}
if (j >= 0) {
        siz = dx[dmax].jp.n[j];
        xx = dx[dmax].jp.x[j];
        dmax += siz;
        if (siz < 0) {                  /* gap in second seq */
                pp[1].n[i1] = -siz;
                xx += siz;
                /* id = xx - yy + len1 - 1
                 */
                pp[1].x[i1] = xx - dmax + len1 - 1;
                gapy++;
                ngapy -= siz;
/* ignore MAXGAP when doing endgaps */
                siz = (-siz < MAXGAP || endgaps)? -siz : MAXGAP;
                i1++;
        }
        else if (siz > 0) {  /* gap in first seq */
                pp[0].n[i0] = siz;
                pp[0].x[i0] = xx;
                gapx++;
                ngapx += siz;
/* ignore MAXGAP when doing endgaps */
                siz = (siz < MAXGAP || endgaps)? siz : MAXGAP;
                i0++;
        }
}
else
        break;
}
/* reverse the order of jmps
 */
for (j = 0, i0--; j < i0; j++, i0--) {
        i = pp[0].n[j]; pp[0].n[j] = pp[0].n[i0]; pp[0].n[i0] = i;
        i = pp[0].x[j]; pp[0].x[j] = pp[0].x[i0]; pp[0].x[i0] = i;
}
for (j = 0, i1--; j < i1; j++, i1--) {
        i = pp[1].n[j]; pp[1].n[j] = pp[1].n[i1]; pp[1].n[i1] = i;
        i = pp[1].x[j]; pp[1].x[j] = pp[1].x[i1]; pp[1].x[i1] = i;
```

TABLE 3P-continued

```
        }
    if (fd >= 0)
        (void) close(fd);
    if (fj) {
        (void) unlink(jname);
        fj = 0;
        offset = 0;
    }
```

TABLE 3Q

```
/*
 * write a filled jmp struct offset of the prev one (if any): nw( )
 */
writejmps(ix)                                    writejmps
        int     ix;
{
        char    *mktemp( );
        if (!fj) {
                if (mktemp(jname) < 0) {
                        fprintf(stderr, "%s: can't mktemp( )
                        %s\n", prog, jname);
                        cleanup(1);
```

TABLE 3Q-continued

```
                }
                if ((fj = fopen(jname, "w")) == 0) {
                        fprintf(stderr, "%s: can't write %s\n",
                                prog, jname);
                        exit(1);
                }
        }
        (void) fwrite((char *)&dx[ix].jp, sizeof(struct jmp), 1, fj);
        (void) fwrite((char *)&dx[ix].offset, sizeof(dx[ix].offset),
                1, fj);
}
```

What is claimed is:

1. An isolated monoclonal antibody which specifically binds to residues 15 to 25 of the N-terminal region of the IL-1lp polypeptide of FIG. 3 (SEQ ID NO:7).

2. A composition comprising the antibody of claim 1 and a pharmaceutically acceptable carrier.

3. An isolated monoclonal antibody which specifically binds to residues 2 to 25 of the N-terminal region of the IL-1lp polypeptide encoded by the human cDNA insert of ATCC Deposit No. 203587.

4. A composition comprising the antibody of claim 3 and a pharmaceutically acceptable carrier.

* * * * *

SEQUENCE LISTING

<160> NUMBER OF SEQ ID NOS: 32

<210> SEQ ID NO 1
<211> LENGTH: 1006
<212> TYPE: DNA
<213> ORGANISM: Homo sapiens

<400> SEQUENCE: 1

| | | | | | |
|---|---|---|---|---|---|
| ggcacgaggc | aagccttcca | ggttatcgtg | acgcaccttg | aaagtctgag | 50 |
| agctactgcc | ctacagaaag | ttactagtgc | cctaaagctg | gcgctggcac | 100 |
| tgatgttact | gctgctgttg | gagtacaact | tccctataga | aaacaactgc | 150 |
| cagcacctta | agaccactca | caccttcaga | gtggccttga | gaaagatttg | 200 |
| gggtcaagga | tcatgagcga | gaacaccact | taagaggata | gtgaactagt | 250 |
| ctgcatgtga | gacgctgaga | tcctatgtca | ggctgtgata | ggagggaaac | 300 |
| agaaaccaaa | ggaaagaaca | gctttaagaa | gcgcttaaga | gccacccacc | 350 |
| cattcttgac | agtcactggc | ccagcctggg | ggcccctgtt | ctttatcaaa | 400 |
| caagtgcctg | agctctttgc | agaggtccaa | aggtgaagaa | cttaaacccg | 450 |
| aagaaattca | gcattcatga | ccaggatcac | aaagtactgg | tcctggactc | 500 |
| tgggaatctc | atagcagttc | cagataaaaa | ctacatacgc | ccagagatct | 550 |
| tctttgcatt | agcctcatcc | ttgagctcag | cctctgcgga | gaaaggaagt | 600 |
| ccgattctcc | tggggtctc | taaaggggag | ttttgtctct | actgtgacaa | 650 |
| ggataaagga | caaagtcatc | catcccttca | gctgaagaag | gagaaactga | 700 |
| tgaagctggc | tgcccaaaag | gaatcagcac | gccggccctt | catcttttat | 750 |
| agggctcagg | tgggctcctg | gaacatgctg | gagtcggcgg | ctcaccccgg | 800 |
| atggttcatc | tgcacctcct | gcaattgtaa | tgagcctgtt | ggggtgacag | 850 |
| ataaatttga | gaacaggaaa | cacattgaat | tttcatttca | accagtttgc | 900 |
| aaagctgaaa | tgagccccag | tgaggtcagc | gattaggaaa | ctgccccatt | 950 |
| gaacgccttc | ctcgctaatt | tgaactaatt | gtataaaaac | accaaacctg | 1000 |

```
ctcact                                                              1006
```

<210> SEQ ID NO 2
<211> LENGTH: 26
<212> TYPE: PRT
<213> ORGANISM: Homo sapiens

<400> SEQUENCE: 2

Met Leu Leu Leu Leu Leu Glu Tyr Asn Phe Pro Ile Glu Asn Asn
 1               5                  10                  15

Cys Gln His Leu Lys Thr Thr His Thr Phe Arg
                20                  25

<210> SEQ ID NO 3
<211> LENGTH: 167
<212> TYPE: PRT
<213> ORGANISM: Homo sapiens

<400> SEQUENCE: 3

Val Lys Asn Leu Asn Pro Lys Lys Phe Ser Ile His Asp Gln Asp
 1               5                  10                  15

His Lys Val Leu Val Leu Asp Ser Gly Asn Leu Ile Ala Val Pro
                20                  25                  30

Asp Lys Asn Tyr Ile Arg Pro Glu Ile Phe Phe Ala Leu Ala Ser
                35                  40                  45

Ser Leu Ser Ser Ala Ser Ala Glu Lys Gly Ser Pro Ile Leu Leu
                50                  55                  60

Gly Val Ser Lys Gly Glu Phe Cys Leu Tyr Cys Asp Lys Asp Lys
                65                  70                  75

Gly Gln Ser His Pro Ser Leu Gln Leu Lys Lys Glu Lys Leu Met
                80                  85                  90

Lys Leu Ala Ala Gln Lys Glu Ser Ala Arg Arg Pro Phe Ile Phe
                95                 100                 105

Tyr Arg Ala Gln Val Gly Ser Trp Asn Met Leu Glu Ser Ala Ala
               110                 115                 120

His Pro Gly Trp Phe Ile Cys Thr Ser Cys Asn Cys Asn Glu Pro
               125                 130                 135

Val Gly Val Thr Asp Lys Phe Glu Asn Arg Lys His Ile Glu Phe
               140                 145                 150

Ser Phe Gln Pro Val Cys Lys Ala Glu Met Ser Pro Ser Glu Val
               155                 160                 165

Ser Asp

<210> SEQ ID NO 4
<211> LENGTH: 650
<212> TYPE: DNA
<213> ORGANISM: Artificial Sequence
<220> FEATURE:
<223> OTHER INFORMATION: recombinant DNA

<400> SEQUENCE: 4

```
taattcacca tgtctgcact tctgatccta gctcttgttg gagctgcagt          50
tgctgactac aaagacgatg acgacaagct tgcggccgcg aattcagctc         100
tttgcagagg tccaaaggtg aagaacttaa acccgaagaa attcagcatt         150
catgaccagg atcacaaagt actggtcctg gactctggga atctcatagc         200
agttccagat aaaaactaca tacgcccaga gatcttcttt gcattagcct         250
```

```
catccttgag ctcagcctct gcggagaaag gaagtccgat tctcctgggg         300
gtctctaaag gggagttttg tctctactgt gacaaggata aaggacaaag         350
tcatccatcc cttcagctga agaaggagaa actgatgaag ctggctgccc         400
aaaaggaatc agcacgccgg cccttcatct tttataggggc tcaggtgggc        450 tcctggaaca tgctggagtc ggcggctcac cccggatggt tcatctgcac         500
ctcctgcaat gtaatgagc ctgttggggt gacagataaa tttgagaaca          550
ggaaacacat tgaattttca tttcaaccag tttgcaaagc tgaaatgagc         600
cccagtgagg tcagcgatta gggtaccagt cgactctaga ggatcccggg         650
```

<210> SEQ ID NO 5
<211> LENGTH: 203
<212> TYPE: PRT
<213> ORGANISM: Artificial Sequence
<220> FEATURE:
<223> OTHER INFORMATION: recombinant protein

<400> SEQUENCE: 5

```
Met Ser Ala Leu Leu Ile Leu Ala Leu Val Gly Ala Ala Val Ala
 1               5                  10                  15

Asp Tyr Lys Asp Asp Asp Lys Leu Ala Ala Ala Asn Ser Ala
                20                  25                  30

Leu Cys Arg Gly Pro Lys Val Lys Asn Leu Asn Pro Lys Lys Phe
                35                  40                  45

Ser Ile His Asp Gln Asp His Lys Val Leu Val Leu Asp Ser Gly
                50                  55                  60

Asn Leu Ile Ala Val Pro Asp Lys Asn Tyr Ile Arg Pro Glu Ile
                65                  70                  75

Phe Phe Ala Leu Ala Ser Ser Leu Ser Ser Ala Ser Ala Glu Lys
                80                  85                  90

Gly Ser Pro Ile Leu Leu Gly Val Ser Lys Gly Glu Phe Cys Leu
                95                 100                 105

Tyr Cys Asp Lys Asp Lys Gly Gln Ser His Pro Ser Leu Gln Leu
               110                 115                 120

Lys Lys Glu Lys Leu Met Lys Leu Ala Ala Gln Lys Glu Ser Ala
               125                 130                 135

Arg Arg Pro Phe Ile Phe Tyr Arg Ala Gln Val Gly Ser Trp Asn
               140                 145                 150

Met Leu Glu Ser Ala Ala His Pro Gly Trp Phe Ile Cys Thr Ser
               155                 160                 165

Cys Asn Cys Asn Glu Pro Val Gly Val Thr Asp Lys Phe Glu Asn
               170                 175                 180

Arg Lys His Ile Glu Phe Ser Phe Gln Pro Val Cys Lys Ala Glu
               185                 190                 195

Met Ser Pro Ser Glu Val Ser Asp
               200
```

<210> SEQ ID NO 6
<211> LENGTH: 754
<212> TYPE: DNA
<213> ORGANISM: Homo sapiens

<400> SEQUENCE: 6

```
ggcacgaggc aagccttcca ggttatcgtg acgcaccttg aaagtctgag          50
agctactgcc ctacagaaag ttactagtgc cctaaagctg cgctggcac          100
```

```
tgatgttact gctgctgttg gagtacaact tccctataga aaacaactgc      150
cagcacctta agaccactca caccttcaga gtgaagaact taaacccgaa      200
gaaattcagc attcatgacc aggatcacaa agtactggtc ctggactctg      250
ggaatctcat agcagttcca gataaaaact acatacgccc agagatcttc      300
tttgcattag cctcatcctt gagctcagcc tctgcggaga aaggaagtcc      350
gattctcctg ggggtctcta aaggggagtt ttgtctctac tgtgacaagg      400
ataaaggaca aagtcatcca tcccttcagc tgaagaagga gaaactgatg      450
aagctggctg cccaaaagga atcagcacgc cggccccttca tcttttatag     500 ggctcaggtg ggctcctgga acatgctgga gtcggcggct caccccggat      550
ggttcatctg cacctcctgc aattgtaatg agcctgttgg ggtgacagat      600
aaatttgaga acaggaaaca cattgaattt tcatttcaac cagttttgcaa     650 agctgaaatg agccccagtg aggtcagcga ttaggaaact gccccattga      700
acgccttcct cgctaatttg aactaattgt ataaaaacac caaacctgct      750
cact                                                       754
```

<210> SEQ ID NO 7
<211> LENGTH: 193
<212> TYPE: PRT
<213> ORGANISM: Homo sapiens

<400> SEQUENCE: 7

```
Met Leu Leu Leu Leu Glu Tyr Asn Phe Pro Ile Glu Asn Asn
  1               5                  10                  15

Cys Gln His Leu Lys Thr Thr His Thr Phe Arg Val Lys Asn Leu
                 20                  25                  30

Asn Pro Lys Lys Phe Ser Ile His Asp Gln Asp His Lys Val Leu
                 35                  40                  45

Val Leu Asp Ser Gly Asn Leu Ile Ala Val Pro Asp Lys Asn Tyr
                 50                  55                  60

Ile Arg Pro Glu Ile Phe Phe Ala Leu Ala Ser Ser Leu Ser Ser
                 65                  70                  75

Ala Ser Ala Glu Lys Gly Ser Pro Ile Leu Leu Gly Val Ser Lys
                 80                  85                  90

Gly Glu Phe Cys Leu Tyr Cys Asp Lys Asp Lys Gly Gln Ser His
                 95                 100                 105

Pro Ser Leu Gln Leu Lys Lys Glu Lys Leu Met Lys Leu Ala Ala
                110                 115                 120

Gln Lys Glu Ser Ala Arg Arg Pro Phe Ile Phe Tyr Arg Ala Gln
                125                 130                 135

Val Gly Ser Trp Asn Met Leu Glu Ser Ala Ala His Pro Gly Trp
                140                 145                 150

Phe Ile Cys Thr Ser Cys Asn Cys Asn Glu Pro Val Gly Val Thr
                155                 160                 165

Asp Lys Phe Glu Asn Arg Lys His Ile Glu Phe Ser Phe Gln Pro
                170                 175                 180

Val Cys Lys Ala Glu Met Ser Pro Ser Glu Val Ser Asp
                185                 190
```

<210> SEQ ID NO 8
<211> LENGTH: 629
<212> TYPE: DNA
<213> ORGANISM: Homo sapiens

```
<220> FEATURE:
<221> NAME/KEY: Unsure
<222> LOCATION: 13
<223> OTHER INFORMATION: Unknown base

<400> SEQUENCE: 8
ccaggcccaa gcntccccac catgaatttt gttcacacaa gtcgaaaggt          50
gaagagctta aacccgaaga aattcagcat tcatgaccag gatcacaaag         100
tactggcctg gactctggga atctcatagc agttccagat aaaaactaca         150
tacgcccaga gatcttcttt gcattagcct catccttgag ctcagcctct         200
gcggagaaag gaagtccgat tctcctgggg gtctctaaag gggagttttg         250
tctctactgt gacaaggata aaggacaaag tcatccatcc cttcagctga         300
agaaggagaa actgatgaag ctggctgccc aaaaggaatc agcacgccgg         350
cccttcatct tttatagggc tcaggtgggc tcctggaaca tgctggagtc         400
ggcggctcac cccggatggt tcatctgcac ctcctgcaat tgtaatgagc         450
ctgttggggt gacagataaa tttgagaaca ggaaacacat tgaattttca         500
tttcaaccag tttgcaaagc tgaaatgagc cccagtgagg tcagcgatta         550
ggaaactgcc ccattgaacg ccttcctcgc taatttgaac taattgtata         600
aaaaccccaa acctgctcac  taaaaaaaa                               629

<210> SEQ ID NO 9
<211> LENGTH: 1321
<212> TYPE: DNA
<213> ORGANISM: Homo sapiens

<400> SEQUENCE: 9
gtcgacccac gcgtccgaag ctgctggagc cacgattcag tcccctggac          50
tgtagataaa gacccttcct tgccaggtgc tgagacaacc acactatgag         100
aggcactcca ggagacgctg atggtggagg aagggccgtc tatcaatcaa         150
tcactgttgc tgttatcaca tgcaagtatc cagaggctct tgagcaaggc         200 agagggggatc ccatttattt gggaatccag aatccagaaa tgtgtttgta         250
ttgtgagaag gttggagaac agcccacatt gcagctaaaa gagcagaaga         300
tcatggatct gtatggccaa cccgagcccg tgaaacccct cctttctac          350 cgtgccaaga ctggtaggac ctccacccctt gagtctgtgg ccttcccgga         400
ctggttcatt gcctcctcca agagagacca gcccatcatt ctgacttcag         450
aacttgggaa gtcatacaac actgcctttg aattaaatat aaatgactga         500
actcagccta gaggtggcag cttggtcttt gtcttaaagt ttctggttcc         550
caatgtgttt tcgtctacat tttcttagtg tcattttcac gctggtgctg         600
agacaggagc aaggctgctg ttatcatctc attttataat gaagaagaag         650
caattacttc atagcaactg aagaacagga tgtggcctca gaagcaggag         700
agctgggtgg tataaggctg tcctctcaag ctggtgctgt gtaggccaca         750
aggcatctgc atgagtgact ttaagactca aagaccaaac actgagcttt         800
cttctagggg tgggtatgaa gatgcttcag agctcatgcg cgttaccac          850 gatggcatga ctagcacaga gctgatctct gtttctgttt tgctttattc         900
cctcttggga tgatatcatc cagtctttat atgttgccaa tatacctcat         950
tgtgtgtaat agaaccttct tagcattaag accttgtaaa caaaaataat        1000
```

```
tcttggggtg ggtatgaaga tgcttcagag ctcatgcgcg ttacccacga          1050
tggcatgact agcacagagc tgatctctgt ttctgttttg ctttattccc          1100
tcttgggatg atatcatcca gtctttatat gttgccaata tacctcattg          1150
tgtgtaatag aaccttctta gcattaagac cttgtaaaca aaaataattc          1200
ttgtgttaag ttaaatcatt tttgtcctaa ttgtaatgtg taatcttaaa          1250
gttaaataaa ctttgtgtat ttatataata ataaagctaa aactgatata          1300
aaataaagaa agagtaaact g                                         1321
```

<210> SEQ ID NO 10
<211> LENGTH: 134
<212> TYPE: PRT
<213> ORGANISM: Homo sapiens

<400> SEQUENCE: 10

```
Met Arg Gly Thr Pro Gly Asp Ala Asp Gly Gly Gly Arg Ala Val
 1               5                  10                  15

Tyr Gln Ser Ile Thr Val Ala Val Ile Thr Cys Lys Tyr Pro Glu
                20                  25                  30

Ala Leu Glu Gln Gly Arg Gly Asp Pro Ile Tyr Leu Gly Ile Gln
                35                  40                  45

Asn Pro Glu Met Cys Leu Tyr Cys Glu Lys Val Gly Glu Gln Pro
                50                  55                  60

Thr Leu Gln Leu Lys Glu Gln Lys Ile Met Asp Leu Tyr Gly Gln
                65                  70                  75

Pro Glu Pro Val Lys Pro Phe Leu Phe Tyr Arg Ala Lys Thr Gly
                80                  85                  90

Arg Thr Ser Thr Leu Glu Ser Val Ala Phe Pro Asp Trp Phe Ile
                95                  100                 105

Ala Ser Ser Lys Arg Asp Gln Pro Ile Ile Leu Thr Ser Glu Leu
                110                 115                 120

Gly Lys Ser Tyr Asn Thr Ala Phe Glu Leu Asn Ile Asn Asp
                125                 130
```

<210> SEQ ID NO 11
<211> LENGTH: 249
<212> TYPE: DNA
<213> ORGANISM: Homo sapiens

<400> SEQUENCE: 11

```
aagctgctgg agccacgatt cagtcccctg gactgtagat aaagacccctt         50 tcttgccagg tgctgagaca accacactat gagaggcact ccaggagacg          100
ctgatggtgg aggaagggcc gtctatcaat caatcactgt tgctgttatc          150
acatgcaagt atccgagagc tcttgagcaa ggcagagggg atcccattta          200
tttgggaatc cagaatccag aaatgtgttt gtattgtgag aaggttgga           249
```

<210> SEQ ID NO 12
<211> LENGTH: 468
<212> TYPE: DNA
<213> ORGANISM: Homo sapiens

<400> SEQUENCE: 12

```
atggtcctga gtggggcgct gtgcttccga atgaaggact cggcattgaa          50
ggtgctttat ctgcataata accagcttct agctggaggg ctgcatgcag          100
```

```
ggaaggtcat taaaggtgaa gagatcagcg tggtccccaa tcggtggctg        150
gatgccagcc tgtcccccgt catcctgggt gtccagggtg gaagccagtg        200
cctgtcatgt ggggtggggc aggagccgac tctaacacta gagccagtga        250
acatcatgga gctctatctt ggtgccaagg aatccaagag cttcaccttc        300
taccggcggg acatggggct cacctccagc ttcgagtcgg ctgcctaccc        350
gggctggttc ctgtgcacgg tgcctgaagc cgatcagcct gtcagactca        400
cccagcttcc cgagaatggt ggctggaatg cccccatcac agacttctac        450
ttccagcagt gtgactag                                           468
```

```
<210> SEQ ID NO 13
<211> LENGTH: 155
<212> TYPE: PRT
<213> ORGANISM: Homo sapiens

<400> SEQUENCE: 13

Met Val Leu Ser Gly Ala Leu Cys Phe Arg Met Lys Asp Ser Ala
 1               5                   10                  15

Leu Lys Val Leu Tyr Leu His Asn Asn Gln Leu Leu Ala Gly Gly
            20                  25                  30

Leu His Ala Gly Lys Val Ile Lys Gly Glu Glu Ile Ser Val Val
            35                  40                  45

Pro Asn Arg Trp Leu Asp Ala Ser Leu Ser Pro Val Ile Leu Gly
            50                  55                  60

Val Gln Gly Gly Ser Gln Cys Leu Ser Cys Gly Val Gly Gln Glu
        65                  70                      75

Pro Thr Leu Thr Leu Glu Pro Val Asn Ile Met Glu Leu Tyr Leu
            80                  85                  90

Gly Ala Lys Glu Ser Lys Ser Phe Thr Phe Tyr Arg Arg Asp Met
            95                  100                 105

Gly Leu Thr Ser Ser Phe Glu Ser Ala Ala Tyr Pro Gly Trp Phe
            110                 115                 120

Leu Cys Thr Val Pro Glu Ala Asp Gln Pro Val Arg Leu Thr Gln
            125                 130                 135

Leu Pro Glu Asn Gly Gly Trp Asn Ala Pro Ile Thr Asp Phe Tyr
            140                 145                 150

Phe Gln Gln Cys Asp
            155
```

```
<210> SEQ ID NO 14
<211> LENGTH: 295
<212> TYPE: DNA
<213> ORGANISM: Homo sapiens
<220> FEATURE:
<221> NAME/KEY: Unsure
<222> LOCATION: 283
<223> OTHER INFORMATION: Unknown base

<400> SEQUENCE: 14
gctcccgcca ggagaaagga acattctgag gggagtctac accctgtgga         50
gctcaagatg gtcctgagtg gggcgctgtg cttccgaatg aaggactcgg        100
cattgaaggt gctttatctg cataataacc agcttctagc tggagggctg        150
catgcaggga aggtcattaa aggtgaagag atcagcgtgg tccccaatcg        200
gtggctggat gccagcctgt cccccgtcat cctgggtgtc cagggtggaa        250
gccagtgcct gtcatgtggg gtggggcagg agncgactct aacat            295
```

<210> SEQ ID NO 15
<211> LENGTH: 1385
<212> TYPE: DNA
<213> ORGANISM: Mus musculus

<400> SEQUENCE: 15

| | |
|---|---|
| atagggaatt tggccctcga ggccaagaat tcggcacgag gggagcctgc | 50 |
| tttctactta ggtctcaaat tttccagcct tgtctttgcc taaaatttcc | 100 |
| tgctgtttat ttcaaaatag ggtctacata ctgtggagct catgatggtt | 150 |
| ctgagtgggg cactatgctt ccgaatgaag gattcagcct tgaaggtact | 200 |
| gtatctgcac aataaccagc tgctggctgg aggactgcac gcagagaagg | 250 |
| tcattaaagg tgaggagatc agtgttgtcc caaatcgggc actggatgcc | 300 |
| agtctgtccc ctgtcatcct gggcgttcaa ggaggaagcc agtgcctatc | 350 |
| ttgtgggaca gagaaagggc caattctgaa acttgagcca gtgaacatca | 400 |
| tggagctcta cctcggggcc aaggaatcaa agagcttcac cttctaccgg | 450 |
| cgggatatgg gtcttacctc cagcttcgaa tccgctgcct acccaggctg | 500 |
| gttcctctgc acctcaccgg aagctgacca gcctgtcagg ctcactcaga | 550 |
| tccctgagga ccccgcctgg gatgctccca tcacagactt ctactttcag | 600 |
| cagtgtgact agggctgcgt ggtccccaaa actccataag cagaggcaga | 650 |
| gtaggcagtg gcggctcctg atagaggata gagagacaga ggagctccac | 700 |
| agtaggtggc ttactcctct ccttccctac tggactcccg cttctgacct | 750 |
| aaggcacaca gacactctct tctcctgcat cccagtgctg gtaaatcttc | 800 |
| tggtatttgg agctcaatgt gtagattctt tcagattgga tggtactacc | 850 |
| tctggtgtgg aacccaatag aaaccacgta ggaccaacaa agagcaacat | 900 |
| aaaagattct tgggtgaaga agaggtggga actgttcata catagtaaga | 950 |
| tctgacacag tacctcagaa gtcctgccat tccttatgtt ctggagaaag | 1000 |
| tggaggggggg gtcaccaaga cttttctctgg ctggctgggc cctttccctc | 1050 |
| aaccttctg acatctgcag cctctctcat tcttgccttc attctctggc | 1100 |
| cctgaaccga gagggtgata tcaggatagc tgacagaaga tgaccaggca | 1150 |
| cactgtcctg gtttgaaacc agaggggaca ataaaaaacc ctgattctgg | 1200 |
| tctctactca cataaaaaga agcttgtgaa cattaagtgg gaagagattg | 1250 |
| ctactaaata acataccttg taatttcatc ttaattaaaa tatacttctc | 1300 |
| tatattatat attttaaaaa aaaaaaaaaa aaaaaaaaa aaaaaaaaa | 1350 |
| aaaaacatgc ggccgcaagc ttattccatt tagga | 1385 |

<210> SEQ ID NO 16
<211> LENGTH: 155
<212> TYPE: PRT
<213> ORGANISM: Mus musculus

<400> SEQUENCE: 16

Met Val Leu Ser Gly Ala Leu Cys Phe Arg Met Lys Asp Ser Ala
1               5                   10                  15

Leu Lys Val Leu Tyr Leu His Asn Asn Gln Leu Leu Ala Gly Gly
            20                  25                  30

Leu His Ala Glu Lys Val Ile Lys Gly Glu Glu Ile Ser Val Val

```
                35                  40                  45
Pro Asn Arg Ala Leu Asp Ala Ser Leu Ser Pro Val Ile Leu Gly
                50                  55                  60
Val Gln Gly Gly Ser Gln Cys Leu Ser Cys Gly Thr Glu Lys Gly
                65                  70                  75
Pro Ile Leu Lys Leu Glu Pro Val Asn Ile Met Glu Leu Tyr Leu
                80                  85                  90
Gly Ala Lys Glu Ser Lys Ser Phe Thr Phe Tyr Arg Arg Asp Met
                95                 100                 105
Gly Leu Thr Ser Ser Phe Glu Ser Ala Ala Tyr Pro Gly Trp Phe
               110                 115                 120
Leu Cys Thr Ser Pro Glu Ala Asp Gln Pro Val Arg Leu Thr Gln
               125                 130                 135
Ile Pro Glu Asp Pro Ala Trp Asp Ala Pro Ile Thr Asp Phe Tyr
               140                 145                 150
Phe Gln Gln Cys Asp
               155

<210> SEQ ID NO 17
<211> LENGTH: 382
<212> TYPE: DNA
<213> ORGANISM: Mus musculus

<400> SEQUENCE: 17
ggagcctgct ttctacttag gtctcaaatt ttccagcctt gtctttgcct              50
aaaatttcct gctgtttatt tcaaaatagg gtctacatac tgtggagctc             100
atgatggttc tgagtggggc actatgcttc cgaatgaagg attcagcctt             150
gaaggtactg tatctgcaca ataaccagct gctggctgga ggactgcacg             200
cagagaaggt cattaaaggt gaggagatca gtgttgtccc aaatcgggca             250
ctggatgcca gtctgtcccc tgtcatcctg ggcgttcaag gaggaagcca             300
gtgcctatct tgtgggacag agaaagggcc aattctgaaa cttgagccag             350
tgaacatcat ggagctctac ctcggggcca ag                                382

<210> SEQ ID NO 18
<211> LENGTH: 626
<212> TYPE: DNA
<213> ORGANISM: Homo sapiens

<400> SEQUENCE: 18
aaaatgggct ctgaggactg ggaaaaagat gaaccccagt gctgcttaga              50
agacccggct gtaagccccc tggaaccagg cccaagcctc cccgccatga             100 atttttgttca cacaagtcca aggtgaaga acttaaaccc gaagaaattc             150
agcattcatg accaggatca caaagtactg gtcctggact ctgggaatct             200
catagcagtt ccagataaaa actacatacg cccagagatc ttctttgcat             250
tagcctcatc cttgagctca gcctctgcgg agaaaggaag tccgattctc             300 ctggggtct ctaaagggga gttttgtctc tactgtgaca aggataaagg             350
acaaagtcat ccatcccttc agctgaagaa ggagaaactg atgaagctgg             400
ctgcccaaaa ggaatcagca cgccggccct tcatctttta tagggctcag             450
gtgggctcct ggaacatgct ggagtcggcg gctcaccccg atggttcat              500 ctgcacctcc tgcaattgta atgagcctgt tggggtgaca gataaatttg             550
```

```
agaacaggaa acacattgaa ttttcatttc aaccagtttg caaagctgaa        600
atgagcccca gtgaggtcag cgatta                                  626
```

<210> SEQ ID NO 19
<211> LENGTH: 207
<212> TYPE: PRT
<213> ORGANISM: Homo sapiens

<400> SEQUENCE: 19

```
Met Gly Ser Glu Asp Trp Glu Lys Asp Glu Pro Gln Cys Cys Leu
  1               5                  10                  15

Glu Asp Pro Ala Val Ser Pro Leu Glu Pro Gly Pro Ser Leu Pro
             20                  25                  30

Ala Met Asn Phe Val His Thr Ser Pro Lys Val Lys Asn Leu Asn
             35                  40                  45

Pro Lys Lys Phe Ser Ile His Asp Gln Asp His Lys Val Leu Val
             50                  55                  60

Leu Asp Ser Gly Asn Leu Ile Ala Val Pro Asp Lys Asn Tyr Ile
 65                  70                  75

Arg Pro Glu Ile Phe Phe Ala Leu Ala Ser Ser Leu Ser Ser Ala
             80                  85                  90

Ser Ala Glu Lys Gly Ser Pro Ile Leu Leu Gly Val Ser Lys Gly
             95                 100                 105

Glu Phe Cys Leu Tyr Cys Asp Lys Asp Lys Gly Gln Ser His Pro
            110                 115                 120

Ser Leu Gln Leu Lys Lys Glu Lys Leu Met Lys Leu Ala Ala Gln
            125                 130                 135

Lys Glu Ser Ala Arg Arg Pro Phe Ile Phe Tyr Arg Ala Gln Val
            140                 145                 150

Gly Ser Trp Asn Met Leu Glu Ser Ala Ala His Pro Gly Trp Phe
            155                 160                 165

Ile Cys Thr Ser Cys Asn Cys Asn Glu Pro Val Gly Val Thr Asp
            170                 175                 180

Lys Phe Glu Asn Arg Lys His Ile Glu Phe Ser Phe Gln Pro Val
            185                 190                 195

Cys Lys Ala Glu Met Ser Pro Ser Glu Val Ser Asp
            200                 205
```

<210> SEQ ID NO 20
<211> LENGTH: 506
<212> TYPE: DNA
<213> ORGANISM: Homo sapiens

<400> SEQUENCE: 20

```
aaaatgggct ctgaggactg ggaaaaagat gaaccccagt gctgcttaga         50
agacccggct gtaagccccc tggaaccagg cccaagcctc cccgccatga        100
attttgttca cacaaagatc ttctttgcat tagcctcatc cttgagctca        150
gcctctgcgg agaaaggaag tccgattctc ctgggggtct ctaaagggaa        200
gttttgtctc tactgtgaca aggataaagg acaaagtcat ccatcccttc        250
agctgaagaa ggagaaactg atgaagctgg ctgcccaaaa ggaatcagca        300
cgccggccct tcatctttta tagggctcag gtgggctcct ggaacatgct        350
ggagtcggcg gctcaccccg gatggttcat ctgcacctcc tgcaattgta        400
atgagcctgt tggggtgaca gataaatttg agaacaggaa acacattgaa        450
```

```
ttttcatttc aaccagtttg caaagctgaa atgagcccca gtgaggtcag        500
cgatta                                                       506
```

<210> SEQ ID NO 21
<211> LENGTH: 167
<212> TYPE: PRT
<213> ORGANISM: Homo sapiens

<400> SEQUENCE: 21

```
Met Gly Ser Glu Asp Trp Glu Lys Asp Glu Pro Gln Cys Cys Leu
 1               5                  10                  15

Glu Asp Pro Ala Val Ser Pro Leu Glu Pro Gly Pro Ser Leu Pro
                20                  25                  30

Ala Met Asn Phe Val His Thr Lys Ile Phe Phe Ala Leu Ala Ser
                35                  40                  45

Ser Leu Ser Ser Ala Ser Ala Glu Lys Gly Ser Pro Ile Leu Leu
            50                  55                  60

Gly Val Ser Lys Gly Glu Phe Cys Leu Tyr Cys Asp Lys Asp Lys
        65                  70                  75

Gly Gln Ser His Pro Ser Leu Gln Leu Lys Lys Glu Lys Leu Met
    80                  85                  90

Lys Leu Ala Ala Gln Lys Glu Ser Ala Arg Arg Pro Phe Ile Phe
        95                 100                 105

Tyr Arg Ala Gln Val Gly Ser Trp Asn Met Leu Glu Ser Ala Ala
       110                 115                 120

His Pro Gly Trp Phe Ile Cys Thr Ser Cys Asn Cys Asn Glu Pro
       125                 130                 135

Val Gly Val Thr Asp Lys Phe Glu Asn Arg Lys His Ile Glu Phe
       140                 145                 150

Ser Phe Gln Pro Val Cys Lys Ala Glu Met Ser Pro Ser Glu Val
       155                 160                 165

Ser Asp
```

<210> SEQ ID NO 22
<211> LENGTH: 561
<212> TYPE: DNA
<213> ORGANISM: Homo sapiens

<400> SEQUENCE: 22

```
aacccgaaga aattcagcat tcatgaccag gatcacaaag tactggtcct         50
ggactctggg aatctcatag cagttccaga taaaaactac atacgcccag        100
agatcttctt tgcattagcc tcatccttga gctcagcctc tgcggagaaa        150
ggaagtccga ttctcctggg ggtctctaaa ggggagtttt gtctctactg        200
tgacaaggat aaaggacaaa gtcatccatc ccttcagctg aagaaggaga        250
aactgatgaa gctggctgcc caaaaggaat cagcacgccg gcccttcatc        300
ttttataggg ctcaggtggg ctcctggaac atgctggagt cggcggctca        350 cccccggatgg ttcatctgca cctcctgcaa ttgtaatgag cctgttgggg       400
tgacagataa atttgagaac aggaaacaca ttgaattttc atttcaacca        450
gtttgcaaag ctgaaatgag ccccagtgag gtcagcgatt aggaaactgc        500
cccattgaac gccttcctcg ctaatttgaa ctaattgtat aaaaacacca        550
aacctgctca c                                                  561
```

<210> SEQ ID NO 23
<211> LENGTH: 561
<212> TYPE: DNA
<213> ORGANISM: Homo sapiens

<400> SEQUENCE: 23

| ttgggcttct | ttaagtcgta | agtactggtc | ctagtgtttc | atgaccagga | 50 |
| cctgagaccc | ttagagtatc | gtcaaggtct | atttttgatg | tatgcgggtc | 100 |
| tctagaagaa | acgtaatcgg | agtaggaact | cgagtcggag | acgcctcttt | 150 |
| ccttcaggct | aagaggaccc | ccagagattt | cccctcaaaa | cagagatgac | 200 |
| actgttccta | tttcctgttt | cagtaggtag | ggaagtcgac | ttcttcctct | 250 |
| ttgactactt | cgaccgacgg | gttttcctta | gtcgtgcggc | cgggaagtag | 300 |
| aaaatatccc | gagtccaccc | gaggacccttg | tacgacctca | gccgccgagt | 350 |
| ggggcctacc | aagtagacgt | ggaggacgtt | aacattactc | ggacaacccc | 400 |
| actgtctatt | taaactcttg | tcctttgtgt | aacttaaaag | taaagttggt | 450 |
| caaacgtttc | gactttactc | ggggtcactc | cagtcgctaa | tcctttgacg | 500 |
| gggtaacttg | cggaaggagc | gattaaactt | gattaacata | ttttgtggt | 550 |
| ttggacgagt | g | | | | 561 |

<210> SEQ ID NO 24
<211> LENGTH: 839
<212> TYPE: DNA
<213> ORGANISM: Homo sapiens

<400> SEQUENCE: 24

| ggccctcgag | gccaagaatt | cggcacgagg | cttcattcca | ttttctgttg | 50 |
| agtaataaac | tcaacgttga | aaatgtcctt | tgtggggag | aactcaggag | 100 |
| tgaaaatggg | ctctgaggac | tgggaaaaag | atgaacccca | gtgctgctta | 150 |
| gaagacccgg | ctggaagccc | cctggaacca | ggcccaagcc | tccccaccat | 200 |
| gaattttgtt | cacacaagtc | caaaggtgaa | gaacttaaac | ccgaagaaat | 250 |
| tcagcattca | tgaccaggat | cacaaagtac | tggtcctgga | ctctgggaat | 300 |
| ctcatagcag | ttccagataa | aaactacata | cgcccagaga | tcttctttgc | 350 |
| attagcctca | tccttgagct | cagcctctgc | ggagaaagga | agtccgattc | 400 |
| tcctggggt | ctctaaaggg | gagttttgtc | tctactgtga | caaggataaa | 450 |
| ggacaaagtc | atccatccct | tcagctgaag | aaggagaaac | tgatgaagct | 500 |
| ggctgcccaa | aaggaatcag | cacgccggcc | cttcatcttt | tatagggctc | 550 |
| aggtgggctc | ctggaacatg | ctggagtcgg | cggctcaccc | cggatggttc | 600 |
| atctgcacct | cctgcaattg | taatgagcct | gttggggtga | cagataaatt | 650 |
| tgagaacagg | aaacacattg | aatttttcatt | tcaaccagtt | tgcaaagctg | 700 |
| aaatgagccc | cagtgaggtc | agcgattagg | aaactgcccc | attgaacgcc | 750 |
| ttcctcgcta | atttgaacta | attgtataaa | aacaccaaac | ctgctcacta | 800 |
| aaaaaaaaaa | aaaaaaacgt | ttgcggccgc | aagcttatt | | 839 |

<210> SEQ ID NO 25
<211> LENGTH: 218
<212> TYPE: PRT
<213> ORGANISM: Homo sapiens

<400> SEQUENCE: 25

```
Met Ser Phe Val Gly Glu Asn Ser Gly Val Lys Met Gly Ser Glu
  1               5                  10                  15

Asp Trp Glu Lys Asp Glu Pro Gln Cys Cys Leu Glu Asp Pro Ala
                 20                  25                  30

Gly Ser Pro Leu Glu Pro Gly Pro Ser Leu Pro Thr Met Asn Phe
                 35                  40                  45

Val His Thr Ser Pro Lys Val Lys Asn Leu Asn Pro Lys Lys Phe
                 50                  55                  60

Ser Ile His Asp Gln Asp His Lys Val Leu Val Leu Asp Ser Gly
                 65                  70                  75

Asn Leu Ile Ala Val Pro Asp Lys Asn Tyr Ile Arg Pro Glu Ile
                 80                  85                  90

Phe Phe Ala Leu Ala Ser Ser Leu Ser Ser Ala Ser Ala Glu Lys
                 95                 100                 105

Gly Ser Pro Ile Leu Leu Gly Val Ser Lys Gly Glu Phe Cys Leu
                110                 115                 120

Tyr Cys Asp Lys Asp Lys Gly Gln Ser His Pro Ser Leu Gln Leu
                125                 130                 135

Lys Lys Glu Lys Leu Met Lys Leu Ala Ala Gln Lys Glu Ser Ala
                140                 145                 150

Arg Arg Pro Phe Ile Phe Tyr Arg Ala Gln Val Gly Ser Trp Asn
                155                 160                 165

Met Leu Glu Ser Ala Ala His Pro Gly Trp Phe Ile Cys Thr Ser
                170                 175                 180

Cys Asn Cys Asn Glu Pro Val Gly Val Thr Asp Lys Phe Glu Asn
                185                 190                 195

Arg Lys His Ile Glu Phe Ser Phe Gln Pro Val Cys Lys Ala Glu
                200                 205                 210

Met Ser Pro Ser Glu Val Ser Asp
                215

<210> SEQ ID NO 26
<211> LENGTH: 177
<212> TYPE: PRT
<213> ORGANISM: Homo sapiens

<400> SEQUENCE: 26

Met Glu Ile Cys Arg Gly Leu Arg Ser His Leu Ile Thr Leu Leu
  1               5                  10                  15

Leu Phe Leu Phe His Ser Glu Thr Ile Cys Arg Pro Ser Gly Arg
                 20                  25                  30

Lys Ser Ser Lys Met Gln Ala Phe Arg Ile Trp Asp Val Asn Gln
                 35                  40                  45

Lys Thr Phe Tyr Leu Arg Asn Asn Gln Leu Val Ala Gly Tyr Leu
                 50                  55                  60

Gln Gly Pro Asn Val Asn Leu Glu Glu Lys Ile Asp Val Val Pro
                 65                  70                  75

Ile Glu Pro His Ala Leu Phe Leu Gly Ile His Gly Gly Lys Met
                 80                  85                  90

Cys Leu Ser Cys Val Lys Ser Gly Asp Glu Thr Arg Leu Gln Leu
                 95                 100                 105

Glu Ala Val Asn Ile Thr Asp Leu Ser Glu Asn Arg Lys Gln Asp
                110                 115                 120

Lys Arg Phe Ala Phe Ile Arg Ser Asp Ser Gly Pro Thr Thr Ser
                125                 130                 135
```

```
Phe Glu Ser Ala Ala Cys Pro Gly Trp Phe Leu Cys Thr Ala Met
                140                 145                 150

Glu Ala Asp Gln Pro Val Ser Leu Thr Asn Met Pro Asp Glu Gly
                155                 160                 165

Val Met Val Thr Lys Phe Tyr Phe Gln Glu Asp Glu
                170                 175

<210> SEQ ID NO 27
<211> LENGTH: 169
<212> TYPE: PRT
<213> ORGANISM: Homo sapiens

<400> SEQUENCE: 27

Met Arg Gly Thr Pro Gly Asp Ala Asp Gly Gly Gly Arg Ala Val
  1               5                  10                  15

Tyr Gln Ser Met Cys Lys Pro Ile Thr Gly Thr Ile Asn Asp Leu
                 20                  25                  30

Asn Gln Gln Val Trp Thr Leu Gln Gly Gln Asn Leu Val Ala Val
                 35                  40                  45

Pro Arg Ser Asp Ser Val Thr Pro Val Thr Val Ala Val Ile Thr
                 50                  55                  60

Cys Lys Tyr Pro Glu Ala Leu Glu Gln Gly Arg Gly Asp Pro Ile
                 65                  70                  75

Tyr Leu Gly Ile Gln Asn Pro Glu Met Cys Leu Tyr Cys Glu Lys
                 80                  85                  90

Val Gly Glu Gln Pro Thr Leu Gln Leu Lys Gln Lys Ile Met
                 95                 100                 105

Asp Leu Tyr Gly Gln Pro Glu Pro Val Lys Pro Phe Leu Phe Tyr
                110                 115                 120

Arg Ala Lys Thr Gly Arg Thr Ser Thr Leu Glu Ser Val Ala Phe
                125                 130                 135

Pro Asp Trp Phe Ile Ala Ser Ser Lys Arg Asp Gln Pro Ile Ile
                140                 145                 150

Leu Thr Ser Glu Leu Gly Lys Ser Tyr Asn Thr Ala Phe Glu Leu
                155                 160                 165

Asn Ile Asn Asp

<210> SEQ ID NO 28
<211> LENGTH: 167
<212> TYPE: PRT
<213> ORGANISM: Homo sapiens

<400> SEQUENCE: 28

Met Gly Ser Glu Asp Trp Glu Lys Asp Glu Pro Gln Cys Cys Leu
  1               5                  10                  15

Glu Asp Pro Ala Gly Ser Pro Leu Glu Pro Gly Pro Ser Leu Pro
                 20                  25                  30

Thr Met Asn Phe Val His Thr Lys Ile Phe Phe Ala Leu Ala Ser
                 35                  40                  45

Ser Leu Ser Ser Ala Ser Ala Glu Lys Gly Ser Pro Ile Leu Leu
                 50                  55                  60

Gly Val Ser Lys Gly Glu Phe Cys Leu Tyr Cys Asp Lys Asp Lys
                 65                  70                  75

Gly Gln Ser His Pro Ser Leu Gln Leu Lys Lys Glu Lys Leu Met
                 80                  85                  90

Lys Leu Ala Ala Gln Lys Glu Ser Ala Arg Arg Pro Phe Ile Phe
```

```
                        95                  100                 105
Tyr Arg Ala Gln Val Gly Ser Trp Asn Met Leu Glu Ser Ala Ala
                    110                 115                 120
His Pro Gly Trp Phe Ile Cys Thr Ser Cys Asn Cys Asn Glu Pro
                    125                 130                 135
Val Gly Val Thr Asp Lys Phe Glu Asn Arg Lys His Ile Glu Phe
                    140                 145                 150
Ser Phe Gln Pro Val Cys Lys Ala Glu Met Ser Pro Ser Glu Val
                    155                 160                 165
Ser Asp

<210> SEQ ID NO 29
<211> LENGTH: 31
<212> TYPE: DNA
<213> ORGANISM: Homo sapiens

<400> SEQUENCE: 29
ggcggatcca aaatgggctc tgaggactgg  g                              31

<210> SEQ ID NO 30
<211> LENGTH: 30
<212> TYPE: DNA
<213> ORGANISM: Homo sapiens

<400> SEQUENCE: 30
gcggaattct aatcgctgac ctcactgggg                                 30

<210> SEQ ID NO 31
<211> LENGTH: 9
<212> TYPE: PRT
<213> ORGANISM: Homo sapiens

<400> SEQUENCE: 31

Val His Thr Ser Pro Lys Val Lys Asn
 5

<210> SEQ ID NO 32
<211> LENGTH: 10
<212> TYPE: PRT
<213> ORGANISM: Homo sapiens

<400> SEQUENCE: 32

Val Leu Ser Gly Ala Leu Cys Phe Arg Met
 5                  10
```